US009434734B2

(12) United States Patent
Mayer et al.

(10) Patent No.: US 9,434,734 B2
(45) Date of Patent: Sep. 6, 2016

(54) SUBSTITUTED PYRAZOLOQUINAZOLINONES AND PYRROLOQUINAZOLINONES AS ALLOSTERIC MODULATORS OF GROUP II METABOTROPIC GLUTAMATE RECEPTORS

(71) Applicant: Domain Therapeutics, Illkirch Graffenstaden (FR)

(72) Inventors: Stanislas Mayer, Eschau (FR); Stephan Schann, Illkirch Graffenstaden (FR)

(73) Assignee: DOMAIN THERAPEUTICS, Illkirch-Graffenstaden (FR)

( * ) Notice: Subject to any disclaimer, the term of this patent is extended or adjusted under 35 U.S.C. 154(b) by 0 days.

(21) Appl. No.: 14/403,070

(22) PCT Filed: May 21, 2013

(86) PCT No.: PCT/EP2013/060426
§ 371 (c)(1),
(2) Date: Nov. 21, 2014

(87) PCT Pub. No.: WO2013/174822
PCT Pub. Date: Nov. 28, 2013

(65) Prior Publication Data
US 2015/0105381 A1    Apr. 16, 2015

(30) Foreign Application Priority Data
May 21, 2012  (EP) .................................... 12360043

(51) Int. Cl.
C07D 487/04  (2006.01)
G01N 33/566  (2006.01)
G01N 33/94  (2006.01)

(52) U.S. Cl.
CPC ........... *C07D 487/04* (2013.01); *G01N 33/566* (2013.01); *G01N 33/9406* (2013.01); *G01N 2333/726* (2013.01); *G01N 2500/04* (2013.01); *G01N 2500/10* (2013.01)

(58) Field of Classification Search
CPC .................................................. C07D 487/04
See application file for complete search history.

(56) References Cited

U.S. PATENT DOCUMENTS

| 4,105,764 | A | 8/1978 | Alexander |
|---|---|---|---|
| 4,105,766 | A | 8/1978 | Alexander |
| 4,485,045 | A | 11/1984 | Regen |
| 4,544,545 | A | 10/1985 | Ryan et al. |
| 5,061,613 | A | 10/1991 | Kaneko |
| 2008/0015182 | A1 | 1/2008 | Penning et al. |
| 2009/0298858 | A1 | 12/2009 | Penning et al. |
| 2012/0004240 | A1 | 1/2012 | Fan et al. |

FOREIGN PATENT DOCUMENTS

| CN | 101506214 A | 8/2009 |
|---|---|---|
| EP | 0 036 676 A1 | 9/1981 |
| EP | 0 052 322 A2 | 5/1982 |
| EP | 0 088 046 A2 | 9/1983 |
| EP | 0 102 324 A2 | 3/1984 |
| EP | 0 142 641 A2 | 5/1985 |
| EP | 0 149 949 A1 | 6/1985 |
| EP | 0 374 781 A2 | 6/1990 |
| JP | 4003154 B2 | 11/2007 |
| JP | 4003155 B2 | 11/2007 |
| JP | 4009050 B2 | 11/2007 |
| JP | 4037741 B2 | 11/2007 |
| JP | 4037748 B2 | 11/2007 |
| JP | 4039656 B2 | 1/2008 |
| WO | WO 2006/084634 A1 | 8/2006 |
| WO | WO 2006/099072 A2 | 9/2006 |
| WO | WO 2007/039439 A1 | 4/2007 |
| WO | WO 2007/110337 A1 | 10/2007 |
| WO | WO 2007/119689 A1 | 10/2007 |
| WO | WO 2007/144669 A1 | 12/2007 |
| WO | WO 2007/149907 A2 | 12/2007 |
| WO | WO 2008/090379 A1 | 7/2008 |
| WO | 2010104933 A1 | 9/2010 |
| WO | WO 2012/020820 A1 | 2/2012 |

OTHER PUBLICATIONS

Orvieto, Federica, et al., "Identification of substituted pyrazolo[1,5-a]quinazolin-5(4H)-one as potent poly(ADP-ribose)polymeraze-1 (PARP-1) inhibitors," Bioorganic & Medicinal Chemistry Letters, vol. 19, No. 15 (Jun. 2, 2009) pp. 4196-4200, XP-002681549.

Lipunova, G.N., et al., "Fluorine-Containing Heterocycles: XLI. Fluorine-Containing Quinazolin-4-ones and Azolo[a]quinazolinone Derivatives," Russian Journal of Organic Chemistry, vol. 41, No. 7, (2005), pp. 1071-1080, XP-002681550.

International Search Report (PCT/ISA/210) mailed on Jun. 17, 2013, by the European Patent Office as the International Searching Authority for International Application No. PCT/EP2013/060426.

*Primary Examiner* — Rebecca Anderson
(74) *Attorney, Agent, or Firm* — Buchanan Ingersoll & Rooney PC

(57) ABSTRACT

The present invention relates to the pyrazoloquinazolinone and pyrroloquinazolinone derivatives of the general formula (I), as well as pharmaceutical compositions containing them, and their use in the treatment and/or prophylaxis of conditions associated with altered glutamatergic signalling and/or functions, and/or conditions which can be affected by alteration of glutamate level or signalling in mammals, in particular their use in the treatment and/or prophylaxis of acute and chronic neurological and/or psychiatric disorders.

15 Claims, No Drawings

SUBSTITUTED PYRAZOLOQUINAZOLINONES AND PYRROLOQUINAZOLINONES AS ALLOSTERIC MODULATORS OF GROUP II METABOTROPIC GLUTAMATE RECEPTORS

The present invention provides new pyrazoloquinazolinone and new pyrroloquinazolinone derivatives of the general formula (I) and pharmaceutical compositions containing them. Moreover, the compounds of formula (I) and the compositions containing them are provided for use in the treatment and/or prophylaxis of conditions associated with altered glutamatergic signalling and/or functions, and/or conditions which can be affected by alteration of glutamate level or signalling in mammals. These pyrazoloquinazolinone and pyrroloquinazolinone derivatives of the general formula (I) can act as modulators of nervous system receptors sensitive to glutamate, which makes them particularly suitable for the treatment and/or prophylaxis of acute and chronic neurological and/or psychiatric disorders. In particular embodiments, the new pyrazoloquinazolinone and new pyrroloquinazolinone derivatives of the invention are modulators of metabotropic glutamate receptors (mGluRs). The invention further provides negative allosteric modulators of mGluRs and more specifically negative allosteric modulators of mGluR2.

Glutamatergic pathways have been shown to be clearly involved in the physiopathology of a number of neuronal damages and injuries. Many nervous system disorders including epilepsy and chronic or acute degenerative processes, such as for example Alzheimer's disease, Huntington's disease, Parkinson's disease and amyotrophic lateral sclerosis (Mattson M P., Neuromolecular Med., 3(2), 65-94, 2003), but also AIDS-induced dementia, multiple sclerosis, spinal muscular atrophy, retinopathy, stroke, ischemia, hypoxia, hypoglycaemia and various traumatic brain injuries, involve neuronal cell death caused by imbalanced levels of glutamate. It has also been shown that drug-induced neurotoxicity, for example neurotoxic effects of methamphetamine (METH) on striatal dopaminergic neurons, could actually be mediated by over-stimulation of the glutamate receptors (Stephans S E and Yamamoto B K, Synapse 17(3), 203-9, 1994). Antidepressant and anxiolytic-like effects of compounds acting on glutamate have also been observed on mice, suggesting that glutamatergic transmission is implicated in the pathophysiology of affective disorders such as major depression, schizophrenia and anxiety (Palucha A et al., Pharmacol. Ther. 115(1), 116-47, 2007; Cryan J F et al., Eur. J. Neurosc. 17(11), 2409-17, 2003; Conn P J et al., Trends Pharmacol. Sci. 30(1), 25-31, 2009). Consequently, any compound able to modulate glutamatergic signalling or function would constitute a promising therapeutic compound for many disorders of the nervous system.

Moreover, compounds modulating glutamate level or signalling may be of great therapeutic value for diseases and/or disorders not directly mediated by glutamate levels and/or glutamate receptors malfunctioning, but which could be affected by alteration of glutamate levels or signaling.

In the central nervous system (CNS), L-glutamate (Glu) is the main excitatory neurotransmitter and is referred to as an excitatory amino-acid (EAA), and gamma-aminobutyric acid (GABA) is the main inhibitory neurotransmitter. The balance between excitation and inhibition is of utmost importance to CNS functions, and dysfunctions of either of the two can be related to various neurodegenerative or neurological disorders.

Glutamate is ubiquitously distributed in the nervous system in high concentrations, especially in the brain and spinal cord of mammals, where it is working at a variety of excitatory synapses being thereby involved in virtually all physiological functions such as motor control, vision, central control of heart, processes of learning and memory. However, a large number of studies have established that cellular communication involving glutamate can also lead to a mechanism of cell destruction. This combination of neuroexcitatory activities and neurotoxic properties is called excitotoxicity.

Glutamate operates through two classes of receptors (Bräuner-Osborne H et al., J. Med. Chem. 43(14), 2609-45, 2000). The first class of glutamate receptors is directly coupled to the opening of cation channels in the cellular membrane of the neurons. Therefore they are called ionotropic glutamate receptors (IGluRs). The IGluRs are divided in three subtypes, which are named according to the depolarizing action of their selective agonists: N-methyl-D-aspartate (NMDA), α-amino-3-hydroxy-5-methylisoxazole-4-propionic acid (AMPA), and kainic acid (KA). The second class of glutamate receptor consists of G-protein coupled receptors (GPCRs) called metabotropic glutamate receptors (mGluRs). These mGluRs are localized both pre- and post-synaptically. They are coupled to multiple second messenger systems and their role is to regulate the activity of the ionic channels or enzymes producing second messengers via G-proteins binding the GTP (Nicoletti F et al.; Neuropharmacol., 60(7-8), 1017-41, 2011). Although they are generally not directly involved in rapid synaptic transmission, the mGluRs modulate the efficacy of the synapses by regulating either the post-synaptic channels and their receptors, or the pre-synaptic release or recapture of glutamate. Therefore, mGluRs play an important role in a variety of physiological processes such as long-term potentiation and long-term depression of synaptic transmission, regulation of baroreceptive reflexes, spatial learning, motor learning, and postural and kinetic integration.

To date, eight mGluRs have been cloned and classified in three groups according to their sequence homologies, pharmacological properties and signal transduction mechanisms. Group I is constituted of mGluR1 and mGluR5, group II of mGluR2 and mGluR3 and group III of mGluR4, mGluR6, mGluR7 and mGluR8 (Schoepp D D et al., Neuropharmacology, 38(10), 1431-76, 1999).

mGluRs modulators can be classified in two families depending on their site of interaction with the receptor (see Bräuner-Osborne H et al., J. Med. Chem. 43(14), 2609-45, 2000 for review). The first family consists in orthosteric modulators (or competitive modulators) able to interact with the glutamate binding-site of the mGluRs, which is localized in the large extra-cellular N-terminal part of the receptor (about 560 amino acids). Therefore, they are glutamate analogs and constitute a highly polar family of ligand. Examples of orthosteric modulators are S-DHPG or LY-367385 for group I mGluRs, LY-354740 or LY-379268 for group II mGluRs and ACPT-I or L-AP4 for group III mGluRs. The second family of mGluRs modulators consists in allosteric modulators that interact with a different site from the extracellular active site of the receptor (see Bridges T M et al., ACS Chem Biol, 3(9), 530-41, 2008 for review). Their action results in a modulation of the effects induced by the endogenous ligand glutamate. Examples of such allosteric modulators are Ro-674853, MPEP or JNJ16259685 for group I mGluRs and CBiPES, BINA or LY487379 for group II mGluRs and PHCCC, VU0155041 or VU0359516 for group III mGluRs.

By interacting with allosteric binding sites, mGluR allosteric modulators stabilize a receptor conformation and equilibrium shift that increases or decreases the affinity and/or efficacy of an orthosteric agonist of the receptor, without activating the receptor on its own (Bridges T M et al., *ACS Chem Biol*, 3(9), 530-41, 2008). Such modulators are respectively termed positive allosteric modulators (PAMs) and negative allosteric modulators (NAMs).

Numerous examples of group II mGluR PAMs have already been described in research articles and patent literature (see Trabanco A A, et al.; *Curr Med Chem*, 18(1), 47-68, 2011 for review). However, less information is available regarding group II mGluR NAMs. Benzodiazepinone derivatives (Woltering T J, et al.; *Bioorg Med Chem Lett*, 17, 6811-5, 2007—Woltering T J, et al.; *Bioorg Med Chem Lett*, 18, 1091-5, 2008—Woltering T J, et al.; *Bioorg Med Chem Lett*, 18, 2725-9, 2008—Woltering T J, et al.; *Bioorg Med Chem Lett*, 20, 6969-74, 2010), pyrazolopyrimidine derivatives (WO2006/084634-WO2006/099072-WO2007/039439), pyridine/pyrimidine derivatives (WO2007/110337-WO2007/119689) and heteroaryl-pyrazole (WO2012/020820) have been disclosed as group II mGluR NAMs. The presently claimed compounds have not been previously suggested in this context.

Group II mGluR activation or potentiation has been shown to be associated with positive effects in animal models of anxiety (Swanson C J.; *Nat Rev Drug Discov*, 4, 131-44, 2005), schizophrenia (Conn P J et al.; *Trends in Pharmacol Sci*, 30, 25-31, 2009), drug-addiction (Adewale A S et al.; *J Pharmacol Exp Ther*, 318, 922-31, 2006) or chronic pain (Jones C K et al.; *Neuropharmacology*, 49 (Suppl 1), 206-18, 2005).

Antagonists and NAMs of group II mGluRs have been shown to exert antidepressant-like and cognitive enhancing properties (Chaki S et al.; *Neuropharmacology*, 46, 457-67, 2004—Higgins G A et al.; *Neuropharmacology*, 46, 907-17, 2004—Yoshimizu T and Shaki S.; *Biochem Biophys Res Commun*, 315, 493-6, 2004—Knoflach F et al.; 5$^{th}$ *International Meeting on Metabotropic Glutamate Receptors*, Taormina Italy, 2005—Yoshimizu T et al.; *Psychopharmacology (Berl)*, 183, 587-93, 2006—Campo B et al.; *Annual Meeting of the Society for Neuroscience*, Chicago Ill., 2009, 343.8—Kalinichev M et al.; *Annual Meeting of the Society for Neuroscience*, San Diego Calif., 2010, 406.9—Kalinichev M et al.; *Annual Meeting of the Society for Neuroscience*, San Diego Calif., 2010, 886.14—Lambeng N et al.; *Annual Meeting of the Society for Neuroscience*, San Diego Calif., 2010, 651.15—Lambeng N et al.; 3$^{rd}$ *RSC/SCI Symposium on GPCRs in Medicinal Chemistry*, Oss The Netherlands, 2010—Woltering T J, et al.; *Bioorg Med Chem Lett*, 20, 6969-74, 2010) or cytotoxic properties against colorectal cancer cell lines and human glioblastoma stem cells (Mosillo P et al.; *Annual Meeting of the Society for Neuroscience*, San Diego Calif., 2010, 642.28—Bonelli M et al.; *Annual Meeting of the Society for Neuroscience*, San Diego Calif., 2010, 642.29).

Pyrazoloquinazolinone structures are described as poly (ADP-ribose)polymerase (PARP) inhibitors in Orvieto F, et al., *Bioorg Med Chem Lett*, 2009, 19(15):4196-4200 and also in the patent applications WO2007/144669, WO2007/149907 and WO2008/090379. These pyrazoloquinazolinones mimick the nicotinamide moiety of NAD$^+$, the cofactor of PARP, and therefore invariably comprise an unsubstituted lactam nitrogen, i.e. a hydrogen in position 4 of the pyrazoloquinazolinone scaffold, as an essential feature. In contrast thereto, the compounds of the present invention are substituted at position 4 of the pyrazoloquinazolinone ring and thus form a different class of therapeutic agents. Moreover, the mGluR2 negative allosteric modulator compounds of the present invention are particularly effective due to their substituted lactam nitrogen (i.e., R$^4$ in formula (I)). As an illustration, the N-methylated compounds Example 38 and Example 1 according to the invention show an IC$_{50}$<30 nM for mGluR2 whereas their analogs bearing a hydrogen on the lactam nitrogen are at least 50 times less active.

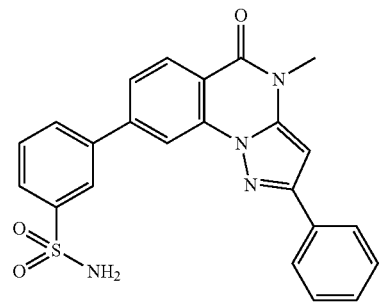 [SMILES: Cn1c(=O)c2ccc(-c3cccc(S(N)(=O)=O)c3)cc2n2nc(-c3ccccc3)cc12]

Example 1
(IC$_{50}$ for mGluR2 < 30 nM)

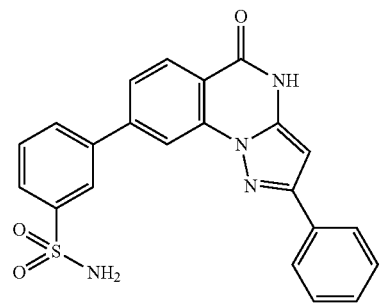

Example 1 NH analog
(IC$_{50}$ for mGluR2 > 1500 nM)

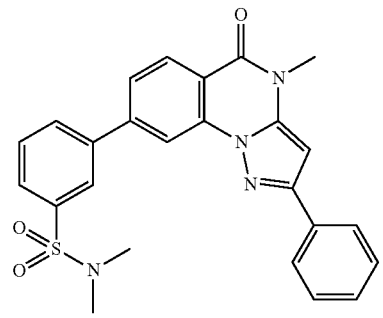

Example 38
(IC$_{50}$ for mGluR2 < 30 nM)

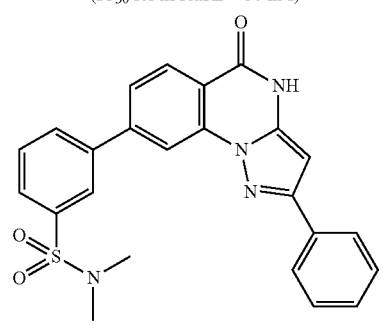

Example 38 NH analog
(IC$_{50}$ for mGluR2 > 1500 nM)

Pyrazoloquinazolinone compounds and their microwave-assisted preparations were described in Vasquez T E et al., *Mol Divers*, 7(2-4), 161-4, 2003. However, all the compounds disclosed in this publication differ structurally from those of the present invention, e.g., due to a hydrogen atom on position 4 of the pyrazoloquinazolinone scaffold and due to the lack of an aromatic ring group in position 8 of the pyrazoloquinazolinone scaffold.

Pyrazoloquinazolinone structures were also described as anti-secretory, anti-inflammatory, anti-allergic and anti-parasitic agents in patent documents U.S. Pat. Nos. 4,105,764 and 4,105,766 or as photographic material in patent applications such as EP0374781, JP4003154, JP4003155, JP4009050, JP4039656, JP4037741 or JP4037748.

Pyrroloquinazolinone compounds and their preparations were described in Volovenko Y M et al., *Chemistry of Heterocyclic Compounds*, 38(3), 324-30, 2002. The pyrroloquinazolin-2,5-diones disclosed in this publication differ structurally from the compounds of the present invention, e.g., since they have a carbonyl on position 2, a thiazole substituent in position 3, and an unsubstituted lactam nitrogen in position 4.

The present invention thus solves the problem of providing improved and/or alternative means and methods for the medical intervention in diseases, disorders and conditions associated with altered glutamatergic signalling and/or functions as well as conditions which can be affected by alteration of glutamate level or signalling in mammals, in particular for the treatment and/or prophylaxis of acute and chronic neurological and/or psychiatric disorders.

Accordingly, the present invention relates to a compound of the general formula (I):

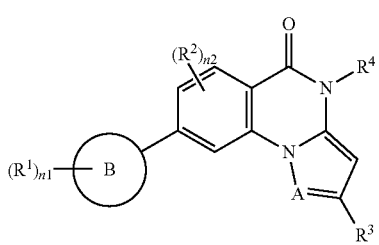

and pharmaceutically acceptable salts, solvates and prodrugs thereof.

In formula (I), A represents N or C(H).
B represents aryl or heteroaryl.
Each $R^1$ is independently selected from $R^5$, halogen, —$CF_3$, —CN, —$OR^5$, —$OCF_3$, —$NR^5R^6$, —$COOR^5$, tetrazolyl, —$SO_3H$, —$B(OH)_2$, —$CONR^5R^6$, —$COR^5$, —$SR^5$, —$SOR^5$, —$SO_2R^5$, —$SO_2NR^5R^6$, —$NR^5COR^6$, —$NR^5SO_2R^6$ or —$OCOR^5$.
n1 is 1, 2 or 3.
Each $R^2$ is independently selected from $R^5$, halogen, —$CF_3$, —CN, —$OR^5$, —$OCF_3$, —$NR^5R^6$, —$COOR^5$, —$CONR^5R^6$, —$COR^5$, —$SR^5$, —$SOR^5$, —$SO_2R^5$, —$SO_2NR^5R^6$, —$NR^5COR^6$, —$NR^5SO_2R^6$, or —$OCOR^5$.
n2 is 1, 2 or 3.
$R^3$ represents a -L-$R^7$ group, wherein:
  L represents a bond or a $C_1$-$C_4$ alkylene, wherein one or more —$CH_2$— units comprised in said alkylene are each optionally replaced by a group independently selected from —O—, —$NR^5$—, —CO—, —S—, —SO—, or —$SO_2$—; and $R^7$ is selected from hydrogen, halogen, —$CF_3$, —CN, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups independently selected from $R^5$, halogen, —$CF_3$, —CN, —$NR^5R^6$, —$CONR^5R^6$, —$COR^5$, —$OR^5$, —$SR^5$, —$SOR^5$, —$SO_2R^5$, —$SO_2NR^5R^6$, —$NR^5COR^6$, —$NR^5SO_2R^6$, —$OCOR^5$, —$COOR^5$, tetrazolyl, —$SO_3H$, or —$B(OH)_2$.

$R^4$ is selected from an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups independently selected from cycloalkyl, halogen, —$CF_3$, —CN, —OH or —O($C_1$-$C_4$ alkyl), and further wherein said cycloalkyl or said heterocycloalkyl is optionally substituted with one or more groups independently selected from $C_1$-$C_4$ alkyl, cycloalkyl, halogen, —$CF_3$, —CN, —OH or —O($C_1$-$C_4$ alkyl).

Each $R^5$ and each $R^6$ is independently selected from hydrogen, an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl).

The present invention relates to the compounds of the general formula (I) as described and defined herein, which represent new pyrazoloquinazolinone or new pyrroloquinazolinone derivatives, and to pharmaceutically acceptable salts, solvates and prodrugs thereof (which may be collectively referred to herein as the compounds of/in accordance with the invention). It also relates to pharmaceutical compositions containing any of the aforementioned entities and optionally a pharmaceutically acceptable excipient. Furthermore, the invention relates to the compounds of the general formula (I) as well as their pharmaceutically acceptable salts, solvates and prodrugs for use as medicaments, in particular for use in the treatment and/or prophylaxis of conditions associated with altered glutamatergic signalling and/or functions, and/or conditions which can be affected by alteration of glutamate level or signalling in mammals.

It further relates to a method of treating and/or preventing conditions associated with altered glutamatergic signalling and/or functions, and/or conditions which can be affected by alteration of glutamate level or signalling in a mammal. Accordingly, the present invention provides a method of treating and/or preventing a disease or disorder, in particular a condition associated with altered glutamatergic signalling and/or functions, and/or a condition which can be affected by alteration of glutamate level or signalling, the method comprising the administration of a compound of the general formula (I) as described and defined herein, or a pharmaceutically acceptable salt, solvate or prodrug thereof, or a pharmaceutical composition comprising any of the aforementioned entities, to a subject (preferably, a mammal; more preferably, a human) in need of such treatment or prevention.

In further embodiments the compounds of the general formula (I) are modulators of mGluRs of the nervous system. In preferred embodiments the compounds of the invention are allosteric modulators of the mGluRs and in a most preferred embodiment they are negative allosteric modulators of group II mGluRs.

As noted above, the invention also relates to the compounds of general formula (I), as well as their pharmaceutically acceptable salts, solvates and prodrugs, for use in medicine. In particular, it relates to the compounds of general formula (I), their pharmaceutically acceptable salts, solvates and prodrugs, as well as pharmaceutical compositions comprising any of the aforementioned entities and optionally a pharmaceutically acceptable excipient, for use in the treatment and/or prophylaxis of conditions associated with altered glutamatergic signalling and/or functions, and/or conditions which can be affected by alteration of glutamate level or signalling in mammals.

The conditions associated with altered glutamatergic signalling and/or functions, and/or conditions which can be affected by alteration of glutamate level or signalling, to be treated and/or prevented with the compounds or the pharmaceutical compositions according to the invention, include in particular: epilepsy, including newborn, infantile, childhood and adult syndromes, partial (localization-related) and generalized epilepsies, with partial and generalized, convulsive and non-convulsive seizures, with and without impairment of consciousness, and status epilepticus; Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Motor neuron disease or amyotrophic lateral sclerosis (ALS); Other neurodegenerative and/or hereditary disorders of the nervous system, including spinocerebrellar degenerations such as Friedrich's ataxia and other hereditary cerebellar ataxias, predominantly spinal muscular atrophies, hereditary neuropathies, and phakomatoses; Disorders of the peripheral nervous system, including trigeminal neuralgia, facial nerve disorders, disorders of the other cranial nerves, nerve root and plexus disorders, mononeuritis such as carpal tunnel syndrome and sciatica, hereditary and idiopathic peripheral neuropathies, inflammatory and toxic neuropathies; Multiple sclerosis and other demyelinating diseases of the nervous system; Infantile cerebral palsy (spastic), monoplegic, paraplegic or tetraplegic; Hemiplegia and hemiparesis, flaccid or spastic, and other paralytic syndromes; Cerebrovascular disorders, including subarachnoid hemorrhage, intracerebral hemorrhage, occlusion and stenosis of precerebral arteries, occlusion of cerebral arteries including thrombosis and embolism, brain ischemia, stroke, transient ischemic attacks, atherosclerosis, cerebrovascular dementias, aneurysms, cerebral deficits due to cardiac bypass surgery and grafting; Migraine, including classical migraine and variants such as cluster headache; Headache; Myoneural disorders including myasthenia gravis, acute muscle spasms, myopathies including muscular dystrophies, mytotonias and familial periodic paralysis; Disorders of the eye and visual pathways, including retinal disorders, and visual disturbances; Intracranial trauma/injury and their sequels; Trauma/Injury to nerves and spinal cord and their sequels; Poisoning and toxic effects of nonmedicinal substances; Accidental poisoning by drugs, medicinal substances and biologicals acting on the central, peripheral and autonomic system; Neurological and psychiatric adverse effects of drugs, medicinal and biological substances; Disturbance of sphincter control and sexual function; Mental disorders usually diagnosed in infancy, childhood or adolescence, including: mental retardation, learning disorders, motor skill disorders, communication disorders, pervasive developmental disorders, attention deficit and disruptive behaviour disorders, feeding and eating disorders, TIC disorders, elimination disorders; Delirium and other cognitive disorders; Substance related disorders including: alcohol-related disorders, nicotine-related disorders, disorders related to cocaine, opioids, cannabis, hallucinogens and other drugs; Schizophrenia and other psychotic disorders; Mood disorders, including depressive disorders and bipolar disorders; Anxiety disorders, including panic disorders, phobias, obsessive-compulsive disorders, stress disorders, generalized anxiety disorders; Eating disorders, including anorexia and bulimia; Sleep disorders, including dyssomnias (insomnia, hypersomnia, narcolepsy, breathing related sleep disorder) and parasomnias; Medication-induced movement disorders (including neuroleptic-induced parkinsonism and tardive dyskinesia); Endocrine and metabolic diseases including diabetes, disorders of the endocrine glands, hypoglycaemia; Acute and chronic pain; Nausea and vomiting; Irritable bowel syndrome; or cancers, including gliomas, colorectal cancer, melanoma, prostate cancer. Accordingly, the present invention relates to the compounds of formula (I), as described and defined herein, and pharmaceutically acceptable salts, solvates and prodrugs thereof, as well as pharmaceutical compositions containing any of the aforementioned entities, for use in the treatment and/or prophylaxis of any of the above-mentioned diseases, disorders or conditions. The invention also encompasses methods for the treatment and/or prophylaxis of any of the above-mentioned diseases, disorders or conditions, comprising administering an effective amount of any the compounds of formula (I), as described and defined herein, or of a pharmaceutically acceptable salt, solvate or prodrug thereof, or of a pharmaceutical composition comprising a compound of formula (I) or a pharmaceutically acceptable salt, solvate or prodrug thereof in combination with a pharmaceutically acceptable excipient, to a subject in need thereof (preferably a mammal, more preferably a human).

In particular, the conditions associated with altered glutamatergic signalling and/or functions, and/or conditions which can be affected by alteration of glutamate level or signalling, to be treated and/or prevented by the compounds or the pharmaceutical compositions according to the invention, include: Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Acute and chronic pain; Anxiety disorders, including panic disorders, phobias, obsessive-compulsive disorders, stress disorders and generalized anxiety disorders; Schizophrenia and other psychotic disorders; Mood disorders, including depressive disorders and bipolar disorders; Endocrine and metabolic diseases including diabetes, disorders of the endocrine glands and hypoglycaemia; or cancers, including gliomas, colorectal cancer, melanoma, prostate cancer.

In the context of the present invention, the compounds and the pharmaceutical compositions according to the invention are envisaged to be used particularly in the treatment or prevention/prophylaxis of the following conditions/diseases/disorders: Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Mood disorders, including depressive disorders and bipolar disorders; Endocrine and metabolic diseases including diabetes, disorders of the endocrine glands and hypoglycaemia; or cancers, including gliomas, colorectal cancer, melanoma, prostate cancer. Accordingly, the present invention relates to the compounds of formula (I), their pharmaceutically acceptable salts, solvates and prodrugs, as well as pharmaceutical compositions comprising any of the aforementioned entities and optionally a pharmaceutically acceptable excipient, for use in the treatment or prevention/prophylaxis of any of the above-mentioned conditions/diseases/disorders.

Some of the compounds of the present invention were furthermore found to have negative allosteric modulator activity on human mGluR3 (hmGluR3). For instance, Examples 1, 34 and 69 were found to have mGluR3 negative allosteric modulator activity with an $IC_{50}$<1 µM.

The present invention furthermore provides a method for identifying an agent that binds to metabotropic glutamate receptor 2 (mGluR2) or to metabotropic glutamate receptor 3 (mGluR3), or in other words for determining the capability of one or more test agent(s) to bind to these receptors, comprising the following steps: (a) contacting mGluR2 or mGluR3 with a compound of the present invention which is labeled, preferably radio-labeled or fluorescence-labeled, under conditions that permit binding of the compound to mGluR2 or mGluR3, thereby generating a bound, labeled compound; (b) detecting a signal that corresponds to the amount of the bound, labeled compound in the absence of test agent; (c) contacting the bound, labeled compound with a test agent; (d) detecting a signal that corresponds to the amount of the bound labeled compound in the presence of test agent; and (e) comparing the signal detected in step (d) to the signal detected in step (b) to determine whether the test agent binds to mGluR2 or mGluR3. As will be understood, a substantially unchanged signal detected in step (d) in comparison with the signal detected in step (b) indicates that the test agent does not bind to the receptor, or binds to the receptor less strongly than the compounds according to the invention. A decreased or increased signal detected in step (d) in comparison with the signal detected in step (b) indicates that the test agent binds to the receptor. Thus, agents that bind to mGluR2 or mGluR3 can be identified among the test agents employed in this method. It will further be understood that it is preferred to remove unbound labeled compounds, e.g. in a washing step, before carrying out steps (b) and (d). In this method, either mGluR2 or mGluR3 can be employed. Accordingly, the above references to "mGluR2 or mGluR3" should be understood either as referring all to mGluR2 or as referring all to mGluR3.

The mGluR2 or the mGluR3 which is used in the above method may be a human form (Flor P J, et al. *Eur J Neurosci.* 1995. 7(4):622-629), e.g., a protein of the accession number NP_000830.2 or a protein of the accession number NP_000831.2 respectively, or a protein having at least 80% (preferably, at least 90%; more preferably, at least 95%; even more preferably, at least 99%) amino acid identity to said protein of the accession number NP_000830.2 or said protein of the accession number NP_000831.2, or a non-human form, including e.g. a mouse form or a homolog thereof found in a different species (e.g. in a different mammalian species), or a mutein of any of the aforementioned entities wherein the mutein retains the mGluR2 or mGluR3 activity. Said mutein can preferably be obtained by substitution, insertion, addition and/or deletion of one or more (such as, e.g., 1 to 20, including 1 to 10 or 1 to 3) amino acid residues of said aforementioned entities. The mGluR2 or mGluR3 used in the above method may also be a functional fragment of any of the aforementioned entities (including said muteins), i.e. a fragment which retains the mGluR2 or mGluR3 activity of the respective aforementioned entity or, in other words, a fragment having essentially the same biological activity (i.e., at least about 60% activity, preferably at least about 70% activity, more preferably at least about 80% activity, even more preferably at least about 90% activity) as the respective aforementioned entity. A person skilled in the art is readily in a position to determine whether mGluR2 or mGluR3 activity is retained using techniques known in the art, e.g. knock-out and rescue experiments. Furthermore, the mGluR2 or mGluR3 used in the above method may also be a compound comprising any one or more of the aforementioned entities (including, without limitation, a protein of the accession number NP_000830.2 or a protein of the accession number NP_000831.2, a protein having at least 80% amino acid identity to said protein of the accession number NP_000830.2 or to said protein of the accession number NP_000831.2, or a functional fragment thereof), wherein the mGluR2 or mGluR3 activity is retained. Preferably, the mGluR2 or the mGluR3 used in the above method is a human form.

The compounds of the general formula (I) will be described in more detail in the following:

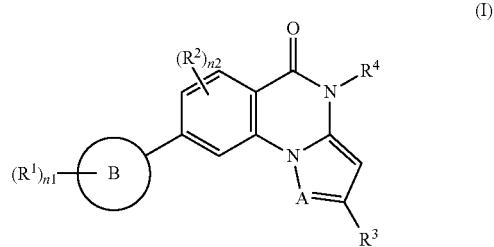

(I)

A represents N or C(H).
B represents aryl or heteroaryl. Said aryl is preferably an aryl having 6 to 10 ring members, and more preferably said aryl is phenyl. Said heteroaryl is preferably a heteroaryl having 5 to 14 ring members and comprising one or more (particularly one, two, or three) ring heteroatoms independently selected from O, S, or N. More preferably, said heteroaryl is a heteroaryl having 5 or 6 ring members and comprising one or more (particularly one, two, or three) ring heteroatoms independently selected from O, S, or N. Even more preferably, said heteroaryl is selected from pyridinyl (such as, e.g., pyridin-3-yl or pyridin-4-yl), pyrazolyl (such as, e.g., 1H-pyrazol-4-yl or 1H-pyrazol-3-yl), oxazolyl (such as, e.g., oxazol-2-yl or oxazol-5-yl), tetrazolyl (such as, e.g., 2H-tetrazol-5-yl), pyrimidinyl (such as, e.g., pyrimidin-5-yl), pyridazinyl (such as, e.g., pyridazin-3-yl), or pyrazinyl (such as, e.g., pyrazin-2-yl). Yet even more preferably, said heteroaryl is pyridinyl (such as, e.g., pyridin-3-yl or pyridin-4-yl).

Accordingly, it is preferred that B represents phenyl or heteroaryl. More preferably, B represents phenyl or a heteroaryl having 5 or 6 ring members and comprising one or more (particularly one, two, or three) ring heteroatoms independently selected from O, S, or N. Even more preferably, B represents a heteroaryl having 5 or 6 ring members and comprising one or more (particularly one, two, or three) ring heteroatoms independently selected from O, S, or N. Yet even more preferably, B represents a heteroaryl selected from pyridinyl (such as, e.g., pyridin-3-yl or pyridin-4-yl), pyrazolyl (such as, e.g., 1H-pyrazol-4-yl or 1H-pyrazol-3-yl), oxazolyl (such as, e.g., oxazol-2-yl or oxazol-5-yl), tetrazolyl (such as, e.g., 2H-tetrazol-5-yl), pyrimidinyl (such as, e.g., pyrimidin-5-yl), pyridazinyl (such as, e.g., pyridazin-3-yl), or pyrazinyl (such as, e.g., pyrazin-2-yl), and most preferably B represents pyridinyl (such as, e.g., pyridin-3-yl or pyridin-4-yl).

Each $R^1$ is independently selected from $R^5$, halogen, —$CF_3$, —CN, —$OCF_3$, —$NR^5R^6$, —$COOR^5$, tetrazolyl (particularly tetrazol-5-yl), —$SO_3H$, —$B(OH)_2$, —$CONR^5R^6$, —$COR^5$, —$SR^5$, —$SOR^5$, —$SO_2R^5$, —$SO_2NR^5R^6$, —$NR^5COR^6$, —$NR^5SO_2R^6$ or —$OCOR^5$. Preferably, each $R^1$ is independently selected from $R^5$, halogen, —$CF_3$, —CN, —$OR^5$, —$NR^5R^6$, —$COOR^5$, tetrazolyl (particularly tetrazol-5-yl), —$SO_3H$, —$B(OH)_2$, —$CONR^5R^6$, —$COR^5$, —$SO_2R^5$, or —$SO_2NR^5R^6$. More preferably, each $R^1$ is independently selected from $R^5$, halogen, —$CF_3$, —CN, —$OR^5$, —$NR^5R^6$, —$COOR^5$, tetrazolyl (particularly tetrazol-5-yl), —$SO_3H$, —$COR^5$, —$SO_2NR^5R^6$, or —$SO_2R^5$, accordingly, in a preferred embodiment, each $R^1$ is independently selected from $C_1$-$C_4$ alkyl (particularly methyl), halogen (particularly fluoro), —$CF_3$, —CN, —$NH_2$, —$NH(C_1$-$C_4$ alkyl), —$N(C_1$-$C_4$ alkyl)($C_1$-$C_4$ alkyl), —COOH, —COO($C_1$-$C_4$ alkyl), tetrazol-5-yl, —$SO_3H$, —CO($C_1$-$C_4$ alkyl), —$SO_2$($C_1$-$C_4$ alkyl), —$SO_2NH_2$, —$SO_2NH(C_1$-$C_4$ alkyl), or —$SO_2N(C_1$-$C_4$ alkyl)($C_1$-$C_4$ alkyl); and in a particularly preferred embodiment, each $R^1$ is independently selected from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$. Even more preferably, each $R^1$ is independently selected from $R^5$, halogen, —$NR^5R^6$, or —$SO_2NR^5R^6$. Yet even more preferably, each $R^1$ is independently selected from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$.

n1 is 1, 2 or 3. Preferably, n1 is 1 or 2.

In accordance with the above definitions of B, $R^1$ and n1, it is particularly preferred that the entire moiety —(B)—($R^1$)$_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with one, two or three groups (preferably one or two groups) selected independently from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$; preferably, the one, two or three substituting groups are selected independently from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$. It is even more preferred that the moiety —(B)—($R^1$)$_{n1}$ is pyridinyl (such as, e.g., pyridin-3-yl or pyridin-4-yl) substituted with one, two or three groups (preferably one or two groups) selected independently from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$, and preferably selected independently from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$.

Each $R^2$ is independently selected from $R^5$, halogen, —$CF_3$, —CN, —$OR^5$, —$OCF_3$, —$NR^5R^6$, —$COOR^5$, —$CONR^5R^6$, —$COR^5$, —$SR^5$, —$SOR^5$, —$SO_2R^5$, —$SO_2NR^5R^6$, —$NR^5COR^6$, —$NR^5SO_2R^6$, or —$OCOR^5$. Preferably, each $R^2$ is independently selected from $R^5$, halogen, —$CF_3$, —CN, —$OR^5$, —$OCF_3$, —$NR^5R^6$, —$CONR^5R^6$ or —$COR^5$. More preferably, each $R^2$ is independently selected from $R^5$, halogen, —$CF_3$, —CN, —$OR^5$, —$OCF_3$ or —$NR^5R^6$. Even more preferably, each $R^2$ is independently selected from hydrogen, $C_1$-$C_4$ alkyl (particularly methyl), halogen, —$CF_3$, —CN, —$OCF_3$, —$NH_2$, —$NH(C_1$-$C_4$ alkyl), or —$N(C_1$-$C_4$ alkyl)($C_1$-$C_4$ alkyl). Most preferably, each $R^2$ is hydrogen.

n2 is 1, 2 or 3. Preferably, n2 is 1 or 2. More preferably, n2 is 1. Accordingly, it is most preferred that n2 is 1 and $R^2$ is hydrogen.

$R^3$ represents a -L-$R^7$ group.

L represents a bond or a $C_1$-$C_4$ alkylene, wherein one or more —$CH_2$— units (e.g., one, two or three —$CH_2$— units; preferably one or two —$CH_2$— units; more preferably one —$CH_2$— unit) comprised in said alkylene are each optionally replaced by a group independently selected from —O—, —$NR^5$—, —CO—, —S—, —SO—, or —$SO_2$— Preferably, L represents a bond or a $C_1$-$C_4$ alkylene, wherein one or two —$CH_2$— units (preferably one —$CH_2$— unit) comprised in said alkylene are each optionally replaced by a group independently selected from —O—, —NH—, —$N(CH_3)$—, —CO—, —S—, —SO—, or —$SO_2$—. More preferably, L represents a bond or a $C_1$-$C_4$ alkylene, wherein one —$CH_2$— unit comprised in said alkylene is optionally replaced by —O—. Exemplary preferred L groups include, in particular, a bond, methylene, ethylene, propylene, butylene, —$CH_2$—$CH_2$—O—$CH_2$— and —$CH_2$—O—$CH_2$—. It is particularly preferred that L is a bond.

$R^7$ is selected from hydrogen, halogen, —$CF_3$, —CN, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $R^5$, halogen, —$CF_3$, —CN, —$NR^5R^6$, —$CONR^5R^6$, —COR$^5$, —OR$^5$, —SR$^5$, —SOR$^5$, —SO$_2$R$^5$, —SO$_2$NR$^5$R$^6$, —NR$^5$COR$^6$, —NR$^5$SO$_2$R$^6$, —OCOR$^5$, —OCOR$^5$, tetrazolyl, —SO$_3$H, or —B(OH)$_2$. Preferably, R$^7$ is selected from hydrogen, an optionally substituted C$_1$-C$_4$ alkyl, an optionally substituted cycloalkyl, an optionally substituted heterocycloalkyl, an optionally substituted aryl, or an optionally substituted heteroaryl, wherein said optionally substituted C$_1$-C$_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from C$_1$-C$_4$ alkyl, halogen, —CF$_3$, —CN, —NH$_2$, —NH(C$_1$-C$_4$ alkyl), —N(C$_1$-C$_4$ alkyl)(C$_1$-C$_4$ alkyl), —CONH$_2$, —CONH(C$_1$-C$_4$ alkyl), —CON(C$_1$-C$_4$ alkyl)(C$_1$-C$_4$ alkyl), —COH, —CO(C$_1$-C$_4$ alkyl), —OH, —O(C$_1$-C$_4$ alkyl), —SH, —S(C$_1$-C$_4$ alkyl), —SO(C$_1$-C$_4$ alkyl), —SO$_2$(C$_1$-C$_4$ alkyl), —SO$_2$NH$_2$, —SO$_2$NH(C$_1$-C$_4$ alkyl), —SO$_2$N(C$_1$-C$_4$ alkyl)(C$_1$-C$_4$ alkyl), —NHCO(C$_1$-C$_4$ alkyl), —N(C$_1$-C$_4$ alkyl)CO(C$_1$-C$_4$ alkyl), —NHSO$_2$(C$_1$-C$_4$ alkyl), —NHSO$_2$(C$_1$-C$_4$ alkyl), —N(C$_1$-C$_4$ alkyl)SO$_2$(C$_1$-C$_4$ alkyl), —OCO(C$_1$-C$_4$ alkyl), —COOH, —COO(C$_1$-C$_4$ alkyl), tetrazolyl, or —SO$_3$H. More preferably, R$^7$ is selected from hydrogen, an optionally substituted C$_1$-C$_4$ alkyl, an optionally substituted cycloalkyl, an optionally substituted heterocycloalkyl, an optionally substituted aryl, or an optionally substituted heteroaryl, wherein said C$_1$-C$_4$ alkyl may be substituted with one or more groups (e.g., one, two or three groups) independently selected from halogen, —CF$_3$, —CN, —NH$_2$, —NH(C$_1$-C$_4$ alkyl), —N(C$_1$-C$_4$ alkyl)(C$_1$-C$_4$ alkyl), —COH, —CO(C$_1$-C$_4$ alkyl), —OH, —O(C$_1$-C$_4$ alkyl), —SH, —S(C$_1$-C$_4$ alkyl), —SO(C$_1$-C$_4$ alkyl), or —SO$_2$(C$_1$-C$_4$ alkyl), and further wherein said cycloalkyl, said heterocycloalkyl, said aryl or said heteroaryl may be substituted with one or more groups (e.g., one, two or three groups) independently selected from C$_1$-C$_4$ alkyl, halogen, —CF$_3$, —CN, —NH$_2$, —NH(C$_1$-C$_4$ alkyl), —N(C$_1$-C$_4$ alkyl)(C$_1$-C$_4$ alkyl), —COH, —CO(C$_1$-C$_4$ alkyl), —OH, —O(C$_1$-C$_4$ alkyl), —SH, —S(C$_1$-C$_4$ alkyl), —SO(C$_1$-C$_4$ alkyl), or —SO$_2$(C$_1$-C$_4$ alkyl). Even more preferably, R$^7$ is selected from hydrogen, an optionally substituted C$_1$-C$_4$ alkyl, an optionally substituted cycloalkyl, an optionally substituted heterocycloalkyl, an optionally substituted aryl, or an optionally substituted heteroaryl, wherein said C$_1$-C$_4$ alkyl may be substituted with one or more groups (e.g., one, two or three groups) independently selected from halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl), and further wherein said cycloalkyl, said heterocycloalkyl, said aryl or said heteroaryl may be substituted with one or more groups (e.g., one, two or three groups) independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl). Yet even more preferably, R$^7$ is selected from hydrogen, an optionally substituted cycloalkyl, an optionally substituted heterocycloalkyl, an optionally substituted aryl, or an optionally substituted heteroaryl, wherein said cycloalkyl, said heterocycloalkyl, said aryl or said heteroaryl may be substituted with one or more groups (e.g., one, two or three groups; preferably one or two groups; more preferably one group) independently selected from C$_1$-C$_4$ alkyl, halogen, —CF$_3$, —CN, —OH, or —O(C$_1$-C$_4$ alkyl). It is particularly preferred that the above-mentioned groups R$^7$ are not substituted with any optional substituent groups. In the above-mentioned definitions of R$^7$, said cycloalkyl is preferably selected from cyclopropyl, cyclobutyl, cyclopentyl, cyclohexyl or cycloheptyl; said heterocycloalkyl is preferably selected from tetrahydrofuranyl, tetrahydropyran or tetrahydrothiopyran; said aryl is preferably phenyl; and/or said heteroaryl is preferably selected from pyridinyl, pyrazolyl or furanyl. Most preferably, R$^7$ is selected from hydrogen, cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), aryl (e.g., phenyl), or heteroaryl (e.g., pyridinyl, pyrazolyl or furanyl).

In accordance with the above definitions of L and R$^7$, it is particularly preferred that R$^3$ is selected from C$_1$-C$_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —(C$_1$-C$_4$ alkylene)-phenyl (e.g., benzyl), —(C$_1$-C$_4$ alkylene)-heteroaryl, —(C$_1$-C$_4$ alkylene)-cycloalkyl, or —(C$_1$-C$_4$ alkylene)-heterocycloalkyl, wherein said C$_1$-C$_4$ alkyl, said phenyl, said heteroaryl, said cycloalkyl, said heterocycloalkyl, the phenyl moiety of said —(C$_1$-C$_4$ alkylene)-phenyl, the heteroaryl moiety of said —(C$_1$-C$_4$ alkylene)-heteroaryl, the cycloalkyl moiety of said —(C$_1$-C$_4$ alkylene)-cycloalkyl, or the heterocycloalkyl moiety of said —(C$_1$-C$_4$ alkylene)-heterocycloalkyl is optionally substituted with one or two groups (preferably one group) independently selected from C$_1$-C$_4$ alkyl, halogen, —CF$_3$, —CN, —OH or —O(C$_1$-C$_4$ alkyl). It is even more preferred that R$^3$ is selected from C$_1$-C$_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —(C$_1$-C$_4$ alkylene)-phenyl (e.g., benzyl), —(C$_1$-C$_4$ alkylene)-heteroaryl, —(C$_1$-C$_4$ alkylene)-cycloalkyl, or —(C$_1$-C$_4$ alkylene)-heterocycloalkyl.

R$^4$ is selected from an optionally substituted C$_1$-C$_4$ alkyl, an optionally substituted cycloalkyl, or an optionally substituted heterocycloalkyl, wherein said C$_1$-C$_4$ alkyl is optionally substituted with one or more groups (e.g., one, two or three groups) independently selected from cycloalkyl, halogen, —CF$_3$, —CN, —OH or —O(C$_1$-C$_4$ alkyl), and further wherein said cycloalkyl or said heterocycloalkyl is optionally substituted with one or more groups (e.g., one, two or three groups) independently selected from C$_1$-C$_4$ alkyl, cycloalkyl, halogen, —CF$_3$, —CN, —OH or —O(C$_1$-C$_4$ alkyl). Preferably, R$^4$ is selected from an optionally substituted C$_1$-C$_4$ alkyl, a cycloalkyl, or a heterocycloalkyl, wherein said C$_1$-C$_4$ alkyl is optionally substituted with one or more groups (e.g., one, two or three groups) independently selected from cycloalkyl, halogen, —CF$_3$, —CN, —OH or —O(C$_1$-C$_4$ alkyl). More preferably, R$^4$ is selected from an optionally substituted C$_1$-C$_4$ alkyl, a cycloalkyl, or a heterocycloalkyl, wherein said C$_1$-C$_4$ alkyl is optionally substituted with one or more groups (e.g., one, two or three groups) independently selected from cycloalkyl, halogen or —CF$_3$. Even more preferably, R$^4$ is selected from an optionally substituted C$_1$-C$_4$ alkyl or a cycloalkyl, wherein said C$_1$-C$_4$ alkyl is optionally substituted with one or more groups (e.g., one, two or three groups) independently selected from cycloalkyl, halogen or —CF$_3$. It is furthermore preferred that the optionally substituted C$_1$-C$_4$ alkyl referred to in the above definitions of $R^4$ is unsubstituted or is substituted with one of the above-defined groups, and it is more preferred that the optionally substituted $C_1$-$C_4$ alkyl referred to in the above definitions of $R^4$ is unsubstituted. Yet even more preferably, $R^4$ is selected from methyl, ethyl, propyl (in particular, n-propyl or isopropyl), —$CH_2$-cycloalkyl (such as, e.g., —$CH_2$-cyclopropyl), cycloalkyl (such as, e.g., cylopropyl or cyclobutyl), —$CH_2$—$CF_3$, or —$CH_2$—$CHF_2$.

Each $R^5$ and each $R^6$ is independently selected from hydrogen, an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups (e.g., one, two or three groups) independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Preferably, each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said heterocycloalkyl is optionally substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). More preferably, each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen or —$CF_3$, and further wherein said heterocycloalkyl is optionally substituted with one or more groups (e.g., one, two or three groups) independently selected from $C_1$-$C_4$ alkyl, halogen, or —$CF_3$. Even more preferably, each $R^5$ and each $R^6$ is independently selected from hydrogen or an optionally substituted $C_1$-$C_4$ alkyl, wherein said $C_1$-$C_4$ alkyl is optionally substituted with one or more groups (e.g., one, two or three groups) independently selected from halogen or —$CF_3$. Yet even more preferably, each $R^5$ and each $R^6$ is independently selected from hydrogen or $C_1$-$C_4$ alkyl.

Compounds of general formula (I) may exist in the form of different isomers, in particular stereoisomers (including geometric isomers (or cis-trans isomers), enantiomers and diastereomers) or tautomers. All such isomers of the compounds according to the invention are contemplated as being part of the present invention, either in admixture or in pure or substantially pure form. As for stereoisomers, the invention embraces mixtures (such as racemic forms) and the isolated optical isomers of the compounds according to the invention. The racemic forms can be resolved by physical methods, such as, e.g., fractional crystallization, separation or crystallization of diastereomeric derivatives or separation by chiral column chromatography.

For a person skilled in the field of synthetic chemistry, various ways for the preparation of the compounds of general formula (I) will be readily apparent. For example, the compounds of the invention can be prepared in accordance with or in analogy to the synthetic routes described in detail in the examples section. In particular, the compounds of formula (I) can be synthesized in accordance with the methods described in the following schemes (the substituent groups and variables shown in schemes 1 to 3 have the same meanings as the corresponding groups and variables in general formula (I)).

Compounds of formula (I) can be obtained via a cross coupling reaction from the intermediates F where $X^1$ is an halide or a pseudo halide, and a metallic species G such as boronic derivatives, tin derivatives or zinc derivatives (in the formula G, M represents a group such as, e.g., $B(OH)_2$, B(pinacol), $BF_3^-K^+$, $SnBu_3$ or ZnI) in presence of a catalytic amount of transition metal like palladium or Nickel (*Metal-Catalyzed cross-coupling reactions*; Diederich, F., Stang, P. J., Eds.; VCH: Weinheim, Germany, 1998). Compounds of formula I can also be obtained from the same intermediates F via a CH activation (Liégauld B., et al, *Journal of organic chemistry*, 74 (5), 1826-34, 2009). An alternative method to generate compounds of formula I could be to convert intermediates F in boronates J in presence of bispinacolatodiborane via a catalytic amount of palladium (Ishiyama, T., et Al, *Journal of organic chemistry*, 60 (23), 7508-10, 1995) and then via a cross coupling reaction with intermediates K where $X^3$ is an halide or a pseudo halide.

Intermediates F can be obtained from the pyrazolo[1,5-a]quinazolin-5-ones D in presence of a base such as NaH or $K_2CO_3$ and the electrophiles E where $X^2$ is an halide or a pseudo halide.

Intermediates D can be obtained in one step in presence of the hydrazines B and the β-ketonitriles C under acidic conditions (Vasquez T E et al., *Mol Divers*, 7(2-4), 161-4, 2003). A way to generate hydrazines B is to convert the amino group in a diazonium salt in a presence of sodium nitrite under aqueous acidic conditions and to reduce it with tin chloride (II) for example. β-ketonitriles C can be generated from an activated acid such as an acid chloride or an ester in presence of the acetonile anion formed from the acetonitrile and buthyl lithium for example.

Scheme 1:

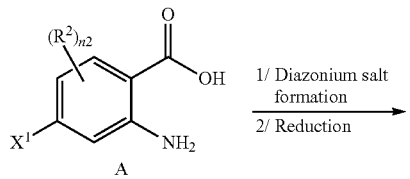

1/ Diazonium salt formation
2/ Reduction

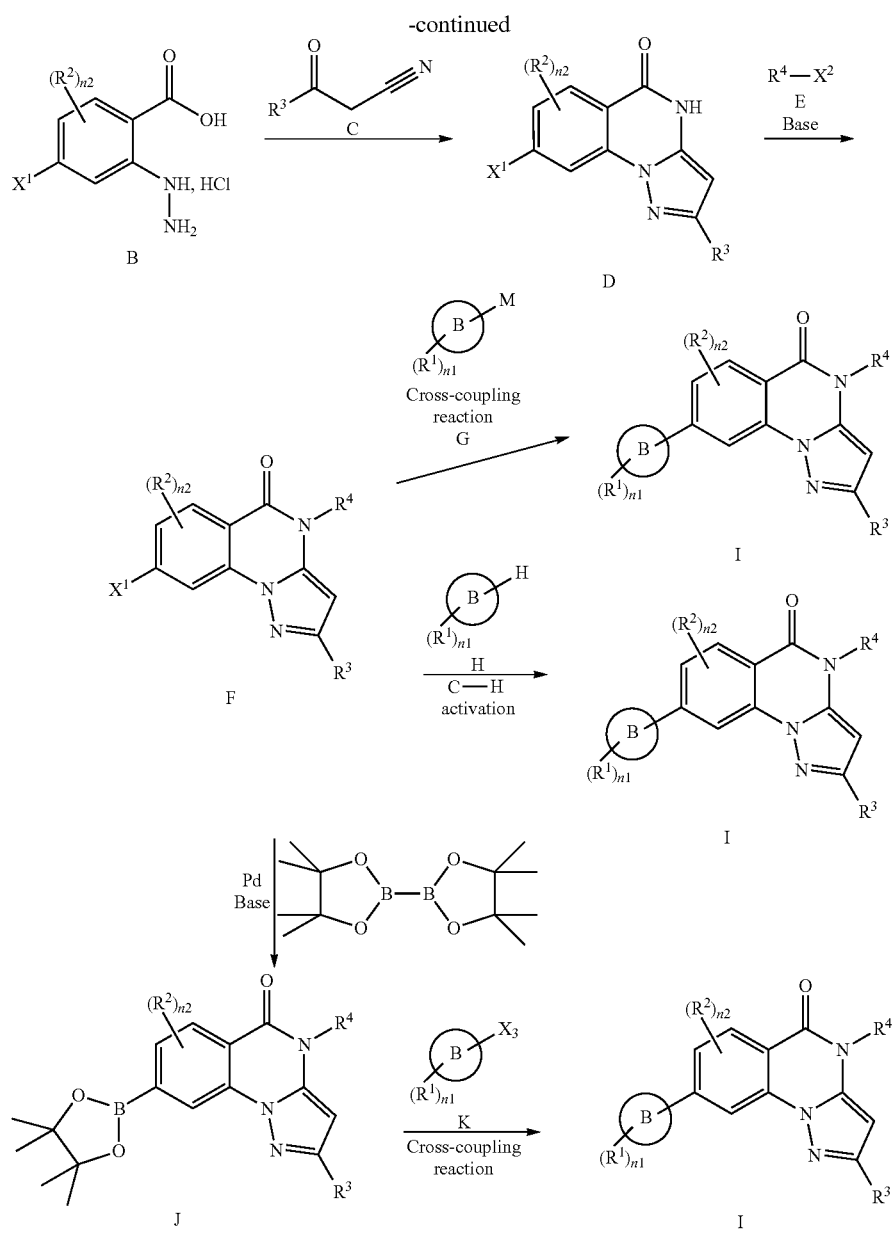
In an alternative method, the cross-coupling reaction can be performed before the N-alkylation, as shown in the following scheme 2.
Scheme 2:
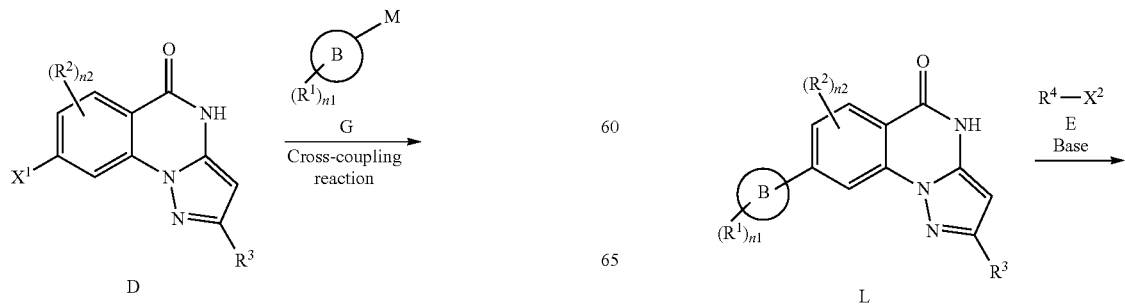
-continued

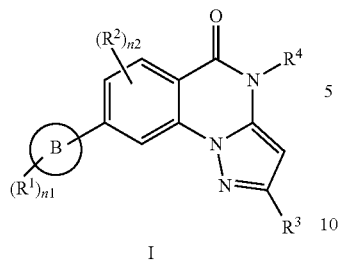

I

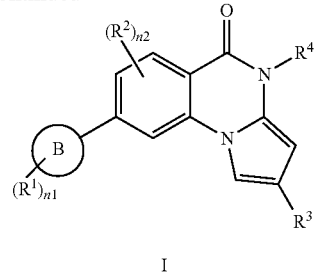

I

The pyrroloquinazolinone scaffold can be obtained in 2 steps, as shown in scheme 3 below. The dicyanide M is prepared according to procedures well known in the art. This compound reacts with 2-amino benzoic acid derivatives to give the cyanide derivatives N. Then, the cyanide moiety can be removed under acidic conditions or other conditions such as basic hydrolysis followed by thermal decarboxylation.

From the intermediates O, the same chemistry described from D (scheme 1) can be applied. For example, O can be alkylated and then coupled with a boronic acid to give examples Q.

Scheme 3:

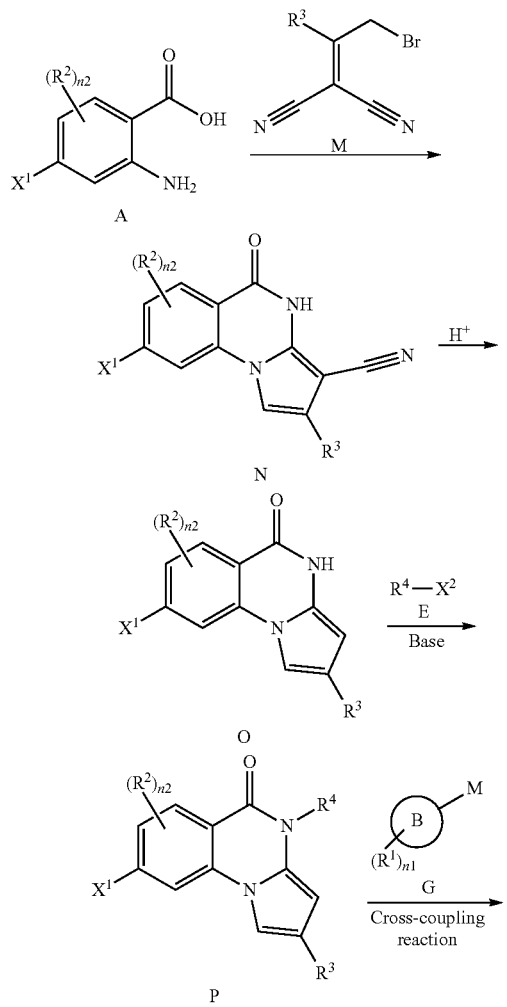

As used herein, "alkyl" represents a straight or branched chain saturated hydrocarbon residue which does not comprise any carbon-to-carbon double bonds or carbon-to-carbon triple bonds. As exemplary groups, methyl, ethyl, propyl and butyl are mentioned.

As used herein, "alkenyl" represents a straight or branched chain unsaturated hydrocarbon residue comprising one or more than one (such as two or three) carbon-to-carbon double bond(s) which does not comprise any carbon-to-carbon triple bonds.

As used herein, "alkynyl" represents a straight or branched chain unsaturated hydrocarbon residue comprising one or more than one (such as two or three) carbon-to-carbon triple bond(s). It will be understood that an "alkynyl" may also comprise one or more than one (such as two or three) carbon-to-carbon double bonds.

As used herein, "alkylene" represents a straight or branched chain alkanediyl group which does not comprise any carbon-to-carbon double bonds or carbon-to-carbon triple bonds.

As used herein, "alkynylene" represents a straight or branched chain alkenediyl group comprising at least one carbon-to-carbon double bond which does not comprise any carbon-to-carbon triple bonds.

As used herein, "alkynylene" represents a straight or branched chain alkenediyl group comprising at least one carbon-to-carbon triple bond and optionally comprising one or more carbon-to-carbon double bonds.

As used herein, "aryl" represents an aromatic hydrocarbon ring, in particular a 6 to 10 membered ring, including bridged ring or fused ring systems containing at least one aromatic ring. "Aryl" may, for example, refer to phenyl or naphthyl.

As used herein, "heteroaryl" represents an aromatic ring, in particular a 5-14 membered ring, including bridged ring or fused ring systems containing at least one aromatic ring, comprising one or more (such as, e.g., one, two, or three) ring heteroatoms independently selected from O, S, or N, wherein one or more of said S ring atoms (if present) and/or one or more of said N ring atoms (if present) may optionally be oxidized. A "heteroaryl", as defined herein above, preferably represents a 5-14 membered aromatic ring, including bridged ring or fused ring systems containing at least one aromatic ring, comprising one or more (such as, e.g., one, two, or three) ring heteroatoms independently selected from O, S, or N. "Heteroaryl" may, for example, refer to thienyl (thiophenyl), benzo[b]thienyl, naphtho[2,3-b]thienyl, thianthrenyl, furyl (furanyl), isobenzofuranyl, chromenyl, xanthenyl, phenoxathiinyl, pyrrolyl (including, without limitation, 2H-pyrrolyl), imidazolyl, pyrazolyl, pyridyl (pyridinyl; including, without limitation, 2-pyridyl, 3-pyridyl, and 4-pyridyl), pyrazinyl, pyrimidinyl, pyridazinyl, indolizinyl, isoindolyl, indolyl (including, without limitation, 3H-indolyl), indazolyl, purinyl, isoquinolyl, quinolyl, phthalazinyl, naphthyridinyl, quinoxalinyl, cinnolinyl, pteridinyl, carbazolyl, beta-carbolinyl, phenanthridinyl, acridinyl, perimidinyl, phenanthrolinyl (including, without limitation, [1,10]phenanthrolinyl, [1,7]phenanthro-linyl, and [4,7]phenanthrolinyl), phenazinyl, isothiazolyl, phenothiazinyl, oxazolyl, isoxazolyl, furazanyl, phenoxazinyl, pyrazolo[1,5-a]pyrimidinyl (including, without limitation, pyrazolo[1,5-a]pyrimidin-3-yl), 1,2-benzoisoxazol-3-yl, or benzimidazolyl.

As used herein, "cycloalkyl" represents a saturated hydrocarbon ring, in particular a 3-11 membered ring, including bridged ring, Spiro ring or fused ring systems. "Cycloalkyl" may, for example, refer to cyclopropyl, cyclobutyl, cyclopentyl, cyclohexyl, or cycloheptyl.

As used herein, "heterocycloalkyl" represents a saturated ring, in particular a 3-11 membered ring, including bridged ring, spiro ring or fused ring systems, containing one or more (such as, e.g., one, two, or three) ring heteroatoms independently selected from O, S, or N, wherein one or more of said S ring atoms (if present) and/or one or more of said N ring atoms (if present) may optionally be oxidized. A "heterocycloalkyl", as defined herein above, preferably represents a 3-11 membered saturated ring, including bridged ring or fused ring systems, containing one or more (such as, e.g., one, two, or three) ring heteroatoms independently selected from O, S, or N. "Heterocycloalkyl" may, for example, refer to oxetanyl, tetrahydrofuranyl, piperidinyl, piperazinyl, aziridinyl, azetidinyl, pyrrolidinyl, imidazolidinyl, morpholinyl, pyrazolidinyl, tetrahydrothienyl, octahydroquinolinyl, octahydroisoquinolinyl, oxazolidinyl, isoxazolidinyl, azepanyl, diazepanyl, oxazepanyl or 2-oxa-5-aza-bicyclo[2.2.1]hept-5-yl.

As used herein, "arylene" represents an aryl group, as defined herein above, which is divalent (i.e., has two points of attachment to the remainder of the molecule). "Arylene" may, for example, refer to phenylene (i.e., a —$C_6H_4$— group; including, e.g., phen-1,2-diyl, phen-1,3-diyl, and phen-1,4-diyl).

As used herein, "heteroarylene" represents a heteroaryl group, as defined herein above, which is divalent (i.e., has two points of attachment to the remainder of the molecule).

As used herein, "cycloalkylene" represents a cycloalkyl group, as defined herein above, which is divalent (i.e., has two points of attachment to the remainder of the molecule).

As used herein, "heterocycloalkylene" represents a heterocycloalkyl group, as defined herein above, which is divalent (i.e., has two points of attachment to the remainder of the molecule).

As used herein, "halogen" represents fluoro, chloro, bromo, or iodo.

Various groups are referred to as being "optionally substituted" in the context of this description. Generally, these groups may carry one or more than one, such as e.g. one, two, three or four substituents. It will be understood that the maximum number of substitutents is limited by the number of attachment sites available on the substituted moiety. Unless defined otherwise in the specific context, these groups carry preferably not more than two substituents and may, in particular, carry only one substituent. Moreover, unless specifically defined otherwise, it is preferred that the optional substituents are absent.

In one specific embodiment, the invention relates to a compound of formula (I), wherein A is N and the further groups and variables in formula (I) have the meanings or preferred meanings described and defined herein above for the compound of formula (I).

In a further specific embodiment, the invention relates to a compound of formula (I), wherein A is C(H) and the further groups and variables in formula (I) have the meanings or preferred meanings described and defined herein above for the compound of formula (I).

In a further specific embodiment, the invention relates to a compound of formula (I), wherein n1 is 1 and the further groups and variables in formula (I) have the meanings or preferred meanings described and defined herein above for the compound of formula (I).

In a further specific embodiment, the invention relates to a compound of formula (I), wherein n1 is 2 and the further groups and variables in formula (I) have the meanings or preferred meanings described and defined herein above for the compound of formula (I).

In a further specific embodiment, the invention relates to a compound of formula (I), wherein A is N, n1 is 1, and the further groups and variables in formula (I) have the meanings or preferred meanings described and defined herein above for the compound of formula (I).

In a further specific embodiment, the invention relates to a compound of formula (I), wherein A is N, n1 is 2, and the further groups and variables in formula (I) have the meanings or preferred meanings described and defined herein above for the compound of formula (I).

In a further specific embodiment, the invention relates to a compound of formula (I), wherein A is C(H), n1 is 1, and the further groups and variables in formula (I) have the meanings or preferred meanings described and defined herein above for the compound of formula (I).

In a further specific embodiment, the invention relates to a compound of formula (I), wherein A is C(H), n1 is 2, and the further groups and variables in formula (I) have the meanings or preferred meanings described and defined herein above for the compound of formula (I).

In a further specific embodiment, the invention relates to a compound of formula (I), wherein the groups and variables in formula (I) have the following meanings and preferred meanings:

A is N.

B represents phenyl or a heteroaryl having 5 or 6 ring members and comprising one or more (particularly one, two, or three) ring heteroatoms independently selected from O, S, or N. Preferably, B represents a heteroaryl having 5 or 6 ring members and comprising one or more (particularly one, two, or three) ring heteroatoms independently selected from O, S, or N. More preferably, B represents a heteroaryl selected from pyridinyl (such as, e.g., pyridin-3-yl or pyridin-4-yl), pyrazolyl (such as, e.g., 1H-pyrazol-4-yl or 1H-pyrazol-3-yl), oxazolyl (such as, e.g., oxazol-2-yl or oxazol-5-yl), tetrazolyl (such as, e.g., 2H-tetrazol-5-yl), pyrimidinyl (such as, e.g., pyrimidin-5-yl), pyridazinyl (such as, e.g., pyridazin-3-yl), or pyrazinyl (such as, e.g., pyrazin-2-yl), and even more preferably B represents pyridinyl (such as, e.g., pyridin-3-yl or pyridin-4-yl).

Each $R^1$ is independently selected from $R^5$, halogen, —$CF_3$, —CN, —$OR^5$, —$NR^5R^6$, —$OCOR^5$, tetrazolyl (particularly tetrazol-5-yl), —$SO_3H$, —$B(OH)_2$, —$CONR^5R^6$, —$COR^5$, —$SO_2R^5$, or —$SO_2NR^5R^6$. Preferably, each $R^1$ is independently selected from $R^5$, halogen, —$CF_3$, —CN, —$OR^5$, —$NR^5R^6$, —$COOR^5$, tetrazolyl (particularly tetrazol-5-yl), —$SO_3H$, —$COR^5$, —$SO_2NR^5R^6$, or —$SO_2R^5$; accordingly, in a preferred embodiment, each $R^1$ is independently selected from $C_1$-$C_4$ alkyl (particularly methyl), halogen (particularly fluoro), —$CF_3$, —CN, —$NH_2$, —$NH(C_1$-$C_4$ alkyl), —$N(C_1$-$C_4$ alkyl)($C_1$-$C_4$ alkyl), —COOH, —COO($C_1$-$C_4$ alkyl), tetrazol-5-yl, —$SO_3H$, —CO($C_1$-$C_4$ alkyl), —$SO_2$($C_1$-$C_4$ alkyl), —$SO_2NH_2$, —$SO_2NH$($C_1$-$C_4$ alkyl), or —$SO_2N$($C_1$-$C_4$ alkyl)($C_1$-$C_4$ alkyl); and in a particularly preferred embodiment, each $R^1$ is independently selected from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$. More preferably, each $R^1$ is independently selected from $R^5$, halogen, —$NR^5R^6$, or —$SO_2NR^5R^6$. Even more preferably, each $R^1$ is independently selected from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$.

n1 is 1, 2 or 3. Preferably, n1 is 1 or 2.

In accordance with the above definitions of B, $R^1$ and n1, it is particularly preferred that the entire moiety —(B)—$(R^1)_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with one, two or three groups (preferably one or two groups) selected independently from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$; preferably, the one, two or three substituting groups are selected independently from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$. It is even more preferred that the moiety —(B)—$(R^1)_{n1}$ is pyridinyl (such as, e.g., pyridin-3-yl or pyridin-4-yl) substituted with one, two or three groups (preferably one or two groups) selected independently from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$, and preferably selected independently from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$.

Each $R^2$ is independently selected from $R^5$, halogen, —$CF_3$, —CN, —$OR^5$, —$OCF_3$ or —$NR^5R^6$. Preferably, each $R^2$ is independently selected from hydrogen, $C_1$-$C_4$ alkyl (particularly methyl), halogen, —$CF_3$, —CN, —$OCF_3$, —$NH_2$, —$NH(C_1$-$C_4$ alkyl), or —$N(C_1$-$C_4$ alkyl)($C_1$-$C_4$ alkyl). More preferably, each $R^2$ is hydrogen.

n2 is 1, 2 or 3. Preferably, n2 is 1 or 2. More preferably, n2 is 1. Accordingly, it is most preferred that n2 is 1 and $R^2$ is hydrogen.

$R^3$ represents a -L-$R^7$ group.

L represents a bond or a $C_1$-$C_4$ alkylene, wherein one or two —$CH_2$— units (preferably one —$CH_2$— unit) comprised in said alkylene are each optionally replaced by a group independently selected from —O—, —NH—, —$N(CH_3)$—, —CO—, —S—, —SO—, or —$SO_2$—. Preferably, L represents a bond or a $C_1$-$C_4$ alkylene, wherein one —$CH_2$— unit comprised in said alkylene is optionally replaced by —O—. Exemplary preferred L groups include, in particular, a bond, methylene, ethylene, propylene, butylene, —$CH_2$—$CH_2$—O—$CH_2$— and —$CH_2$—O—$CH_2$—. It is particularly preferred that L is a bond.

$R^7$ is selected from hydrogen, —$CF_3$, —CN, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $R^5$, halogen, —$CF_3$, —CN, —$NR^5R^6$, —$CONR^5R^6$, —$COR^5$, —$OR^5$, —$SR^5$, —$SOR^5$, —$SO_2R^5$, —$SO_2NR^5R^6$, —$NR^5COR^6$, —$NR^5SO_2R^6$, —$OCOR^5$, —$COOR^5$, tetrazolyl, —$SO_3H$, or —$B(OH)_2$. Preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $C_1$-$C_4$ alkyl, halogen, —$CF_3$, —CN, —$NH_2$, —$NH(C_1$-$C_4$ alkyl), —$N(C_1$-$C_4$ alkyl)($C_1$-$C_4$ alkyl), —$CONH_2$, —$CONH(C_1$-$C_4$ alkyl), —CON($C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), —$SO_2$($C_1$-$C_4$ alkyl), —$SO_2NH_2$, —$SO_2NH(C_1$-$C_4$ alkyl), —$SO_2N(C_1$-$C_4$ alkyl)($C_1$-$C_4$ alkyl), —NHCO($C_1$-$C_4$ alkyl), —N($C_1$-$C_4$ alkyl)CO($C_1$-$C_4$ alkyl), —$NHSO_2$($C_1$-$C_4$ alkyl), —$NHSO_2$($C_1$-$C_4$ alkyl), —N($C_1$-$C_4$ alkyl)$SO_2$($C_1$-$C_4$ alkyl), —OCO($C_1$-$C_4$ alkyl), —COOH, —COO($C_1$-$C_4$ alkyl), tetrazolyl, or —$SO_3H$. More preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —$CF_3$, —CN, —$NH_2$, —$NH(C_1$-$C_4$ alkyl), —$N(C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), or —$SO_2$($C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —$CF_3$, —CN, —$NH_2$, —$NH(C_1$-$C_4$ alkyl), —$N(C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), or —$SO_2$($C_1$-$C_4$ alkyl). Even more preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Yet even more preferably, $R^7$ is selected from hydrogen, an optionally substituted cycloalkyl, an optionally substituted heterocycloalkyl, an optionally substituted aryl, or an optionally substituted heteroaryl, wherein said cycloalkyl, said heterocycloalkyl, said aryl or said heteroaryl may be substituted with one or more groups (e.g., one, two or three groups;

preferably one or two groups; more preferably one group) independently selected from $C_1$-$C_4$ alkyl, halogen, —$CF_3$, —CN, —OH, or —O($C_1$-$C_4$ alkyl). It is particularly preferred that the above-mentioned groups $R^7$ are not substituted with any optional substituent groups. In the above-mentioned definitions of $R^7$, said cycloalkyl is preferably selected from cyclopropyl, cyclobutyl, cyclopentyl, cyclohexyl or cycloheptyl; said heterocycloalkyl is preferably selected from tetrahydrofuranyl, tetrahydropyran or tetrahydrothiopyran; said aryl is preferably phenyl; and/or said heteroaryl is preferably selected from pyridinyl, pyrazolyl or furanyl. Most preferably, $R^7$ is selected from hydrogen, cycloalkyl (e.g., cyclopropyl, cyclobutyl, cyclopentyl, cyclohexyl or cycloheptyl), heterocycloalkyl (e.g., tetra hydrofuranyl, tetrahydropyran or tetrahydrothiopyran), aryl (e.g., phenyl), or heteroaryl (e.g., pyridinyl, pyrazolyl or furanyl).

In accordance with the above definitions of L and $R^7$, it is particularly preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl, wherein said $C_1$-$C_4$ alkyl, said phenyl, said heteroaryl, said cycloalkyl, said heterocycloalkyl, the phenyl moiety of said —($C_1$-$C_4$ alkylene)-phenyl, the heteroaryl moiety of said —($C_1$-$C_4$ alkylene)-heteroaryl, the cycloalkyl moiety of said —($C_1$-$C_4$ alkylene)-cycloalkyl, or the heterocycloalkyl moiety of said —($C_1$-$C_4$ alkylene)-heterocycloalkyl is optionally substituted with one or two groups (preferably one group) independently selected from $C_1$-$C_4$ alkyl, halogen, —$CF_3$, —CN, —OH or —O($C_1$-$C_4$ alkyl). It is even more preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl.

$R^4$ is selected from an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups (e.g., one, two or three groups) independently selected from cycloalkyl, halogen, —$CF_3$, —CN, —OH or —O($C_1$-$C_4$ alkyl), and further wherein said cycloalkyl or said heterocycloalkyl is optionally substituted with one or more groups (e.g., one, two or three groups) independently selected from $C_1$-$C_4$ alkyl, cycloalkyl, halogen, —$CF_3$, —CN, —OH or —O($C_1$-$C_4$ alkyl). Preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen, —$CF_3$, —CN, —OH or —O($C_1$-$C_4$ alkyl). More preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen or —$CF_3$. Even more preferably, $R^4$ is selected from an optionally substituted $C_1$-$C_4$ alkyl or a cycloalkyl, wherein said $C_1$-$C_4$ alkyl is optionally substituted with one or more groups (e.g., one, two or three groups) independently selected from cycloalkyl, halogen or —$CF_3$. It is furthermore preferred that the optionally substituted $C_1$-$C_4$ alkyl referred to in the above definitions of $R^4$ is unsubstituted or is substituted with one of the above-defined groups, and it is more preferred that the optionally substituted $C_1$-$C_4$ alkyl referred to in the above definitions of $R^4$ is unsubstituted. Yet even more preferably, $R^4$ is selected from methyl, ethyl, propyl (in particular, n-propyl or isopropyl), —$CH_2$-cycloalkyl (such as, e.g., —$CH_2$-cyclopropyl), cycloalkyl (such as, e.g., cylopropyl or cyclobutyl), —$CH_2$—$CF_3$, or —$CH_2$—$CHF_2$.

Each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said heterocycloalkyl is optionally substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Preferably, each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen or —$CF_3$, and further wherein said heterocycloalkyl is optionally substituted with one or more groups (e.g., one, two or three groups) independently selected from $C_1$-$C_4$ alkyl, halogen, or —$CF_3$. More preferably, each $R^5$ and each $R^6$ is independently selected from hydrogen or an optionally substituted $C_1$-$C_4$ alkyl, wherein said $C_1$-$C_4$ alkyl is optionally substituted with one or more groups (e.g., one, two or three groups) independently selected from halogen or —$CF_3$. Yet even more preferably, each $R^5$ and each $R^6$ is independently selected from hydrogen or $C_1$-$C_4$ alkyl.

In a further specific embodiment, the invention relates to a compound of formula (I), wherein the groups and variables in formula (I) have the following meanings and preferred meanings:

A is C(H).

B represents phenyl or a heteroaryl having 5 or 6 ring members and comprising one or more (particularly one, two, or three) ring heteroatoms independently selected from O, S, or N. Preferably, B represents a heteroaryl having 5 or 6 ring members and comprising one or more (particularly one, two, or three) ring heteroatoms independently selected from O, S, or N. More preferably, B represents a heteroaryl selected from pyridinyl (such as, e.g., pyridin-3-yl or pyridin-4-yl), pyrazolyl (such as, e.g., 1H-pyrazol-4-yl or 1H-pyrazol-3-yl), oxazolyl (such as, e.g., oxazol-2-yl or oxazol-5-yl), tetrazolyl (such as, e.g., 2H-tetrazol-5-yl), pyrimidinyl (such as, e.g., pyrimidin-5-yl), pyridazinyl (such as, e.g., pyridazin-3-yl), or pyrazinyl (such as, e.g., pyrazin-2-yl), and even more preferably B represents pyridinyl (such as, e.g., pyridin-3-yl or pyridin-4-yl).

Each $R^1$ is independently selected from $R^5$, halogen, —$CF_3$, —CN, —$OR^5$, —$NR^5R^6$, —$COOR^5$, tetrazolyl (particularly tetrazol-5-yl), —$SO_3H$, —$B(OH)_2$, —$CONR^5R^6$, —$COR^5$, —$SO_2R^5$, or —$SO_2NR^5R^6$. Preferably, each $R^1$ is independently selected from $R^5$, halogen, —$CF_3$, —CN, —$OR^5$, —$NR^5R^6$, —$COOR^5$, tetrazolyl (particularly tetrazol-5-yl), —$SO_3H$, —$COR^5$, —$SO_2NR^5R^6$, or —$SO_2R^5$; accordingly, in a preferred embodiment, each $R^1$ is independently selected from $C_1$-$C_4$ alkyl (particularly methyl), halogen (particularly fluoro), —$CF_3$, —CN, —$NH_2$, —$NH(C_1$-$C_4$ alkyl), —$N(C_1$-$C_4$ alkyl)($C_1$-$C_4$ alkyl), —COOH, —$COO(C_1$-$C_4$ alkyl), tetrazol-5-yl, —$SO_3H$, —$CO(C_1$-$C_4$ alkyl), —$SO_2(C_1$-$C_4$ alkyl), —$SO_2NH_2$, —$SO_2NH(C_1$-$C_4$ alkyl), or —$SO_2N(C_1$-$C_4$ alkyl)($C_1$-$C_4$ alkyl); and in a particularly preferred embodiment, each $R^1$ is independently selected from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$. More preferably, each $R^1$ is independently selected from $R^5$, halogen, —$NR^5R^6$, or —$SO_2NR^5R^6$. Even more preferably, each $R^1$ is independently selected from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$.

n1 is 1, 2 or 3. Preferably, n1 is 1 or 2.

In accordance with the above definitions of B, $R^1$ and n1, it is particularly preferred that the entire moiety —(B)—($R^1$)$_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with one, two or three groups (preferably one or two groups) selected independently from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$; preferably, the one, two or three substituting groups are selected independently from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$. It is even more preferred that the moiety —(B)—($R^1$)$_{n1}$ is pyridinyl (such as, e.g., pyridin-3-yl or pyridin-4-yl) substituted with one, two or three groups (preferably one or two groups) selected independently from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$, and preferably selected independently from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$.

Each $R^2$ is independently selected from $R^5$, halogen, —$CF_3$, —CN, —$OR^5$, —$OCF_3$ or —$NR^5R^6$. Preferably, each $R^2$ is independently selected from hydrogen, $C_1$-$C_4$ alkyl (particularly methyl), halogen, —$CF_3$, —CN, —$OCF_3$, —$NH_2$, —$NH(C_1$-$C_4$ alkyl), or —$N(C_1$-$C_4$ alkyl)($C_1$-$C_4$ alkyl). More preferably, each $R^2$ is hydrogen.

n2 is 1, 2 or 3. Preferably, n2 is 1 or 2. More preferably, n2 is 1. Accordingly, it is most preferred that n2 is 1 and $R^2$ is hydrogen.

$R^3$ represents a -L-$R^7$ group.

L represents a bond or a $C_1$-$C_4$ alkylene, wherein one or two —$CH_2$— units (preferably one —$CH_2$— unit) comprised in said alkylene are each optionally replaced by a group independently selected from —O—, —NH—, —N($CH_3$)—, —CO—, —S—, —SO—, or —$SO_2$—. Preferably, L represents a bond or a $C_1$-$C_4$ alkylene, wherein one —$CH_2$— unit comprised in said alkylene Is optionally replaced by —O—. Exemplary preferred L groups include, in particular, a bond, methylene, ethylene, propylene, butylene, —$CH_2$—$CH_2$—O—$CH_2$— and —$CH_2$—O—$CH_2$—. It is particularly preferred that L is a bond.

$R^7$ is selected from hydrogen, halogen, —$CF_3$, —CN, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $R^5$, halogen, —$CF_3$, —CN, —$NR^5R^6$, —$CONR^5R^6$, —$COR^5$, —$OR^5$, —$SR^5$, —$SOR^5$, —$SO_2R^5$, —$SO_2NR^5R^6$, —$NR^5COR^6$, —$NR^5SO_2R^6$, —$OCOR^5$, —$COOR^5$, tetrazolyl, —$SO_3H$, or —$B(OH)_2$. Preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $C_1$-$C_4$ alkyl, halogen, —$CF_3$, —CN, —$NH_2$, —$NH(C_1$-$C_4$ alkyl), —$N(C_1$-$C_4$ alkyl)($C_1$-$C_4$ alkyl), —$CONH_2$, —$CONH(C_1$-$C_4$ alkyl), —$CON(C_1$-$C_4$ alkyl)($C_1$-$C_4$ alkyl), —COH, —$CO(C_1$-$C_4$ alkyl), —OH, —$O(C_1$-$C_4$ alkyl), —SH, —$S(C_1$-$C_4$ alkyl), —$SO(C_1$-$C_4$ alkyl), —$SO_2(C_1$-$C_4$ alkyl), —$SO_2NH_2$, —$SO_2NH(C_1$-$C_4$ alkyl), —$SO_2N(C_1$-$C_4$ alkyl)($C_1$-$C_4$ alkyl), —$NHCO(C_1$-$C_4$ alkyl), —$N(C_1$-$C_4$ alkyl)$CO(C_1$-$C_4$ alkyl), —$NHSO_2(C_1$-$C_4$ alkyl), —$NHSO_2(C_1$-$C_4$ alkyl), —$N(C_1$-$C_4$ alkyl)$SO_2(C_1$-$C_4$ alkyl), —$OCO(C_1$-$C_4$ alkyl), —COOH, —$COO(C_1$-$C_4$ alkyl), tetrazolyl, or —$SO_3H$. More preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —$CF_3$, —CN, —$NH_2$, —$NH(C_1$-$C_4$ alkyl), —$N(C_1$-$C_4$ alkyl)($C_1$-$C_4$ alkyl), —COH, —$CO(C_1$-$C_4$ alkyl), —OH, —$O(C_1$-$C_4$ alkyl), —SH, —$S(C_1$-$C_4$ alkyl), —$SO(C_1$-$C_4$ alkyl), or —$SO_2(C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —$CF_3$, —CN, —$NH_2$, —$NH(C_1$-$C_4$ alkyl), —$N(C_1$-$C_4$ alkyl)($C_1$-$C_4$ alkyl), —COH, —$CO(C_1$-$C_4$ alkyl), —OH, —$O(C_1$-$C_4$ alkyl), —SH, —$S(C_1$-$C_4$ alkyl), —$SO(C_1$-$C_4$ alkyl), or —$SO_2(C_1$-$C_4$ alkyl). Even more preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —$CF_3$, —CN, —OH, —$O(C_1$-$C_4$ alkyl), —$NH_2$, —NH($C_1$-$C_4$ alkyl) or —$N(C_1$-$C_4$ alkyl)($C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Yet even more preferably, $R^7$ is selected from hydrogen, an optionally substituted cycloalkyl, an optionally substituted heterocycloalkyl, an optionally substituted aryl, or an optionally substituted heteroaryl, wherein said cycloalkyl, said heterocycloalkyl, said aryl or said heteroaryl may be substituted with one or more groups (e.g., one, two or three groups; preferably one or two groups; more preferably one group) independently selected from $C_1$-$C_4$ alkyl, halogen, —$CF_3$, —CN, —OH, or —O($C_1$-$C_4$ alkyl). It is particularly preferred that the above-mentioned groups $R^7$ are not substituted with any optional substituent groups. In the above-mentioned definitions of $R^7$, said cycloalkyl is preferably selected from cyclopropyl, cyclobutyl, cyclopentyl, cyclohexyl or cycloheptyl; said heterocycloalkyl is preferably selected from tetrahydrofuranyl, tetrahydropyran or tetrahydrothiopyran; said aryl is preferably phenyl; and/or said heteroaryl is preferably selected from pyridinyl, pyrazolyl or furanyl. Most preferably, $R^7$ is selected from hydrogen, cycloalkyl (e.g., cyclopropyl, cyclobutyl, cyclopentyl, cyclohexyl or cycloheptyl), heterocycloalkyl (e.g., tetra hydrofuranyl, tetrahydropyran or tetrahydrothiopyran), aryl (e.g., phenyl), or heteroaryl (e.g., pyridinyl, pyrazolyl or furanyl).

In accordance with the above definitions of L and $R^7$, it is particularly preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl, wherein said $C_1$-$C_4$ alkyl, said phenyl, said heteroaryl, said cycloalkyl, said heterocycloalkyl, the phenyl moiety of said —($C_1$-$C_4$ alkylene)-phenyl, the heteroaryl moiety of said —($C_1$-$C_4$ alkylene)-heteroaryl, the cycloalkyl moiety of said —($C_1$-$C_4$ alkylene)-cycloalkyl, or the heterocycloalkyl moiety of said —($C_1$-$C_4$ alkylene)-heterocycloalkyl is optionally substituted with one or two groups (preferably one group) independently selected from $C_1$-$C_4$ alkyl, halogen, —$CF_3$, —CN, —OH or —O($C_1$-$C_4$ alkyl). It is even more preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl.

$R^4$ is selected from an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups (e.g., one, two or three groups) independently selected from cycloalkyl, halogen, —$CF_3$, —CN, —OH or —O($C_1$-$C_4$ alkyl), and further wherein said cycloalkyl or said heterocycloalkyl is optionally substituted with one or more groups (e.g., one, two or three groups) independently selected from $C_1$-$C_4$ alkyl, cycloalkyl, halogen, —$CF_3$, —CN, —OH or —O($C_1$-$C_4$ alkyl). Preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups independently selected from cycloalkyl, halogen, —$CF_3$, —CN, —OH or —O($C_1$-$C_4$ alkyl). More preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen or —$CF_3$. Even more preferably, $R^4$ is selected from an optionally substituted $C_1$-$C_4$ alkyl or a cycloalkyl, wherein said $C_1$-$C_4$ alkyl is optionally substituted with one or more groups (e.g., one, two or three groups) independently selected from cycloalkyl, halogen or —$CF_3$. It is furthermore preferred that the optionally substituted $C_1$-$C_4$ alkyl referred to in the above definitions of $R^4$ is unsubstituted or is substituted with one of the above-defined groups, and it is more preferred that the optionally substituted $C_1$-$C_4$ alkyl referred to in the above definitions of $R^4$ is unsubstituted. Yet even more preferably, $R^4$ is selected from methyl, ethyl, propyl (in particular, n-propyl or isopropyl), —$CH_2$-cycloalkyl (such as, e.g., —$CH_2$-cyclopropyl), cycloalkyl (such as, e.g., cylopropyl or cyclobutyl), —$CH_2$—$CF_3$, or —$CH_2$—$CHF_2$.

Each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said heterocycloalkyl is optionally substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Preferably, each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen or —$CF_3$, and further wherein said heterocycloalkyl is optionally substituted with one or more groups (e.g., one, two or three groups) independently selected from $C_1$-$C_4$ alkyl, halogen, or —$CF_3$. More preferably, each $R^5$ and each $R^6$ is independently selected from hydrogen or an optionally substituted $C_1$-$C_4$ alkyl, wherein said $C_1$-$C_4$ alkyl is optionally substituted with one or more groups (e.g., one, two or three groups) independently selected from halogen or —$CF_3$. Yet even more preferably, each $R^5$ and each $R^6$ is independently selected from hydrogen or $C_1$-$C_4$ alkyl.

In a further specific embodiment, the invention relates to a compound of formula (I), wherein the groups and variables in formula (I) have the following meanings and preferred meanings:

A is N.

B represents phenyl or a heteroaryl having 5 or 6 ring members and comprising one or more (particularly one, two, or three) ring heteroatoms independently selected from O, S, or N. Preferably, B represents a heteroaryl having 5 or 6 ring members and comprising one or more (particularly one, two, or three) ring heteroatoms independently selected from O, S, or N. More preferably, B represents a heteroaryl selected from pyridinyl (such as, e.g., pyridin-3-yl or pyridin-4-yl), pyrazolyl (such as, e.g., 1H-pyrazol-4-yl or 1H-pyrazol-3-yl), oxazolyl (such as, e.g., oxazol-2-yl or oxazol-5-yl), tetrazolyl (such as, e.g., 2H-tetrazol-5-yl), pyrimidinyl (such as, e.g., pyrimidin-5-yl), pyridazinyl (such as, e.g., pyridazin-3-yl), or pyrazinyl (such as, e.g., pyrazin-2-yl), and even more preferably B represents pyridinyl (such as, e.g., pyridin-3-yl or pyridin-4-yl).

n1 is 1.

$R^1$ is selected from $R^5$, halogen, $-CF_3$, $-CN$, $-OR^5$, $-NR^5R^6$, $-COOR^5$, tetrazolyl (particularly tetrazol-5-yl), $-SO_3H$, $-B(OH)_2$, $-CONR^5R^6$, $-COR^5$, $-SO_2R^5$, or $-SO_2NR^5R^6$. Preferably, $R^1$ is selected from $R^5$, halogen, $-CF_3$, $-CN$, $-OR^5$, $-NR^5R^6$, $-COOR^5$, tetrazolyl (particularly tetrazol-5-yl), $-SO_3H$, $-COR^5$, $-SO_2NR^5R^6$, or $-SO_2R^5$; accordingly, in a preferred embodiment, $R^1$ is selected from $C_1$-$C_4$ alkyl (particularly methyl), halogen (particularly fluoro), $-CF_3$, $-CN$, $-NH_2$, $-NH(C_1$-$C_4$ alkyl), $-N(C_1$-$C_4$ alkyl)($C_1$-$C_4$ alkyl), $-COOH$, $-COO(C_1$-$C_4$ alkyl), tetrazol-5-yl, $-SO_3H$, $-CO(C_1$-$C_4$ alkyl), $-SO_2$($C_1$-$C_4$ alkyl), $-SO_2NH_2$, $-SO_2NH(C_1$-$C_4$ alkyl), or $-SO_2N(C_1$-$C_4$ alkyl)($C_1$-$C_4$ alkyl); and in a particularly preferred embodiment, $R^1$ is selected from methyl, ethyl, halogen (particularly fluoro), $-CF_3$, $-CN$, $-NH_2$, $-NH(CH_3)$, $-N(CH_3)_2$, $-COOH$, tetrazol-5-yl, $-COCH_3$, $-SO_2NH_2$, $-SO_2NH(CH_3)$, or $-SO_2N(CH_3)_2$. More preferably, $R^1$ is selected from $R^5$, halogen, $-NR^5R^6$, or $-SO_2NR^5R^6$. Even more preferably, $R^1$ is selected from methyl, ethyl, fluoro, $-CF_3$, $-NH_2$, $-NH(CH_3)$, $-N(CH_3)_2$, $-SO_2NH_2$, $-SO_2NH(CH_3)$, or $-SO_2N(CH_3)_2$.

In accordance with the above definitions of B, $R^1$ and n1, it is particularly preferred that the entire moiety $-(B)-(R^1)_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with one group selected from methyl, ethyl, halogen (particularly fluoro), $-CF_3$, $-CN$, $-NH_2$, $-NH(CH_3)$, $-N(CH_3)_2$, $-COOH$, tetrazol-5-yl, $-COCH_3$, $-SO_2NH_2$, $-SO_2NH(CH_3)$, or $-SO_2N(CH_3)_2$; preferably, the one substituting group is selected from methyl, ethyl, fluoro, $-CF_3$, $-NH_2$, $-NH(CH_3)$, $-N(CH_3)_2$, $-SO_2NH_2$, $-SO_2NH(CH_3)$, or $-SO_2N(CH_3)_2$. It is even more preferred that the moiety $-(B)-(R^1)_{n1}$ is pyridinyl (such as, e.g., pyridin-3-yl or pyridin-4-yl) substituted with one group selected from methyl, ethyl, halogen (particularly fluoro), $-CF_3$, $-CN$, $-NH_2$, $-NH(CH_3)$, $-N(CH_3)_2$, $-COOH$, tetrazol-5-yl, $-COCH_3$, $-SO_2NH_2$, $-SO_2NH(CH_3)$, or $-SO_2N(CH_3)_2$, and preferably selected from methyl, ethyl, fluoro, $-CF_3$, $-NH_2$, $-NH(CH_3)$, $-N(CH_3)_2$, $-SO_2NH_2$, $-SO_2NH(CH_3)$, or $-SO_2N(CH_3)_2$.

Each $R^2$ is independently selected from $R^5$, halogen, $-CF_3$, $-CN$, $-OR^5$, $-OCF_3$ or $-NR^5R^6$. Preferably, each $R^2$ is independently selected from hydrogen, $C_1$-$C_4$ alkyl (particularly methyl), halogen, $-CF_3$, $-CN$, $-OCF_3$, $-NH_2$, $-NH(C_1$-$C_4$ alkyl), or $-N(C_1$-$C_4$ alkyl)($C_1$-$C_4$ alkyl). More preferably, each $R^2$ is hydrogen.

n2 is 1, 2 or 3. Preferably, n2 is 1 or 2. More preferably, n2 is 1. Accordingly, it is most preferred that n2 is 1 and $R^2$ is hydrogen.

$R^3$ represents a -L-$R^7$ group.

L represents a bond or a $C_1$-$C_4$ alkylene, wherein one or two $-CH_2-$ units (preferably one $-CH_2-$ unit) comprised in said alkylene are each optionally replaced by a group independently selected from $-O-$, $-NH-$, $-N(CH_3)-$, $-CO-$, $-S-$, $-SO-$, or $-SO_2-$. Preferably, L represents a bond or a $C_1$-$C_4$ alkylene, wherein one $-CH_2-$ unit comprised in said alkylene is optionally replaced by $-O-$. Exemplary preferred L groups include, in particular, a bond, methylene, ethylene, propylene, butylene, $-CH_2-CH_2-O-CH_2-$ and $-CH_2-O-CH_2-$. It is particularly preferred that L is a bond.

$R^7$ is selected from hydrogen, halogen, $-CF_3$, $-CN$, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $R^5$, halogen, $-CF_3$, $-CN$, $-NR^5R^6$, $-CONR^5R^6$, $-COR^5$, $-OR^5$, $-SR^5$, $-SOR^5$, $-SO_2R^5$, $-SO_2NR^5R^6$, $-NR^5COR^8$, $-NR^5SO_2R^6$, $-OCOR^5$, $-COOR^5$, tetrazolyl, $-SO_3H$, or $-B(OH)_2$. Preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $C_1$-$C_4$ alkyl, halogen, $-CF_3$, $-CN$, $-NH_2$, $-NH(C_1$-$C_4$ alkyl), $-N(C_1$-$C_4$ alkyl)($C_1$-$C_4$ alkyl), $-CONH_2$, $-CONH(C_1$-$C_4$ alkyl), $-CON(C_1$-$C_4$ alkyl)($C_1$-$C_4$ alkyl), $-COH$, $-CO(C_1$-$C_4$ alkyl), $-OH$, $-O(C_1$-$C_4$ alkyl), $-SH$, $-S(C_1$-$C_4$ alkyl), $-SO(C_1$-$C_4$ alkyl), $-SO_2(C_1$-$C_4$ alkyl), $-SO_2NH_2$, $-SO_2NH(C_1$-$C_4$ alkyl), $-SO_2N(C_1$-$C_4$ alkyl)($C_1$-$C_4$ alkyl), $-NHCO(C_1$-$C_4$ alkyl), $-N(C_1$-$C_4$ alkyl)CO($C_1$-$C_4$ alkyl), $-NHSO_2(C_1$-$C_4$ alkyl), $-NHSO_2(C_1$-$C_4$ alkyl), $-N(C_1$-$C_4$ alkyl)SO_2(C_1$-$C_4$ alkyl), $-OCO(C_1$-$C_4$ alkyl), $-COOH$, $-COO(C_1$-$C_4$ alkyl), tetrazolyl, or $-SO_3H$. More preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, $-CF_3$, $-CN$, $-NH_2$, $-NH(C_1$-$C_4$ alkyl), $-N(C_1$-$C_4$ alkyl)($C_1$-$C_4$ alkyl), $-COH$, $-CO(C_1$-$C_4$ alkyl), $-OH$, $-O(C_1$-$C_4$ alkyl), $-SH$, $-S(C_1$-$C_4$ alkyl), $-SO(C_1$-$C_4$ alkyl), or $-SO_2(C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, $-CF_3$, $-CN$, $-NH_2$, $-NH(C_1$-$C_4$ alkyl), $-N(C_1$-$C_4$ alkyl)($C_1$-$C_4$ alkyl), $-COH$, $-CO(C_1$-$C_4$ alkyl), $-OH$, $-O(C_1$-$C_4$ alkyl), $-SH$, $-S(C_1$-$C_4$ alkyl), $-SO(C_1$-$C_4$ alkyl), or $-SO_2(C_1$-$C_4$ alkyl). Even more preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, $-CF_3$, $-CN$, $-OH$, $-O(C_1$-$C_4$ alkyl), $-NH_2$, $-NH(C_1$-$C_4$ alkyl) or $-N(C_1$-$C_4$ alkyl)($C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Yet even more preferably, $R^7$ is selected from hydrogen, an optionally substituted cycloalkyl, an optionally substituted heterocycloalkyl, an optionally substituted aryl, or an optionally substituted heteroaryl, wherein said cycloalkyl, said heterocycloalkyl, said aryl or said heteroaryl may be substituted with one or more groups (e.g., one, two or three groups; preferably one or two groups; more preferably one group) independently selected from $C_1$-$C_4$ alkyl, halogen, —$CF_3$, —CN, —OH, or —O($C_1$-$C_4$ alkyl). It is particularly preferred that the above-mentioned groups $R^7$ are not substituted with any optional substituent groups. In the above-mentioned definitions of $R^7$, said cycloalkyl is preferably selected from cyclopropyl, cyclobutyl, cyclopentyl, cyclohexyl or cycloheptyl; said heterocycloalkyl is preferably selected from tetrahydrofuranyl, tetrahydropyran or tetrahydrothiopyran; said aryl is preferably phenyl; and/or said heteroaryl is preferably selected from pyridinyl, pyrazolyl or furanyl. Most preferably, $R^7$ is selected from hydrogen, cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), aryl (e.g., phenyl), or heteroaryl (e.g., pyridinyl, pyrazolyl or furanyl).

In accordance with the above definitions of L and $R^7$, it is particularly preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetra hydrofuranyl, tetra hydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl, wherein said $C_1$-$C_4$ alkyl, said phenyl, said heteroaryl, said cycloalkyl, said heterocycloalkyl, the phenyl moiety of said —($C_1$-$C_4$ alkylene)-phenyl, the heteroaryl moiety of said —($C_1$-$C_4$ alkylene)-heteroaryl, the cycloalkyl moiety of said —($C_1$-$C_4$ alkylene)-cycloalkyl, or the heterocycloalkyl moiety of said —($C_1$-$C_4$ alkylene)-heterocycloalkyl is optionally substituted with one or two groups (preferably one group) independently selected from $C_1$-$C_4$ alkyl, halogen, —$CF_3$, —CN, —OH or —O($C_1$-$C_4$ alkyl). It is even more preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl.

$R^4$ is selected from an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups (e.g., one, two or three groups) independently selected from cycloalkyl, halogen, —$CF_3$, —CN, —OH or —O($C_1$-$C_4$ alkyl), and further wherein said cycloalkyl or said heterocycloalkyl is optionally substituted with one or more groups (e.g., one, two or three groups) independently selected from $C_1$-$C_4$ alkyl, cycloalkyl, halogen, —$CF_3$, —CN, —OH or —O($C_1$-$C_4$ alkyl). Preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen, —$CF_3$, —CN, —OH or —O($C_1$-$C_4$ alkyl). More preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen or —$CF_3$. Even more preferably, $R^4$ is selected from an optionally substituted $C_1$-$C_4$ alkyl or a cycloalkyl, wherein said $C_1$-$C_4$ alkyl is optionally substituted with one or more groups (e.g., one, two or three groups) independently selected from cycloalkyl, halogen or —$CF_3$. It is furthermore preferred that the optionally substituted $C_1$-$C_4$ alkyl referred to in the above definitions of $R^4$ is unsubstituted or is substituted with one of the above-defined groups, and it is more preferred that the optionally substituted $C_1$-$C_4$ alkyl referred to in the above definitions of $R^4$ is unsubstituted. Yet even more preferably, $R^4$ is selected from methyl, ethyl, propyl (in particular, n-propyl or isopropyl), —$CH_2$-cycloalkyl (such as, e.g., —$CH_2$-cyclopropyl), cycloalkyl (such as, e.g., cylopropyl or cyclobutyl), —$CH_2$—$CF_3$, or —$CH_2$—$CHF_2$.

Each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said heterocycloalkyl is optionally substituted with one or more groups (e.g., one, two or three groups) independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl). Preferably, each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen or —$CF_3$, and further wherein said heterocycloalkyl is optionally substituted with one or more groups (e.g., one, two or three groups) independently selected from $C_1$-$C_4$ alkyl, halogen, or —$CF_3$. More preferably, each $R^5$ and each $R^6$ is independently selected from hydrogen or an optionally substituted $C_1$-$C_4$ alkyl, wherein said $C_1$-$C_4$ alkyl is optionally substituted with one or more groups (e.g., one, two or three groups) independently selected from halogen or —$CF_3$. Yet even more preferably, each $R^5$ and each $R^6$ is independently selected from hydrogen or $C_1$-$C_4$ alkyl.

In a further specific embodiment, the invention relates to a compound of formula (I), wherein the groups and variables in formula (I) have the following meanings and preferred meanings:

A is C(H).

B represents phenyl or a heteroaryl having 5 or 6 ring members and comprising one or more (particularly one, two, or three) ring heteroatoms independently selected from O, S, or N. Preferably, B represents a heteroaryl having 5 or 6 ring members and comprising one or more (particularly one, two, or three) ring heteroatoms independently selected from O, S, or N. More preferably, B represents a heteroaryl selected from pyridinyl (such as, e.g., pyridin-3-yl or pyridin-4-yl), pyrazolyl (such as, e.g., 1H-pyrazol-4-yl or 1H-pyrazol-3-yl), oxazolyl (such as, e.g., oxazol-2-yl or oxazol-5-yl), tetrazolyl (such as, e.g., 2H-tetrazol-5-yl), pyrimidinyl (such as, e.g., pyrimidin-5-yl), pyridazinyl (such as, e.g., pyridazin-3-yl), or pyrazinyl (such as, e.g., pyrazin-2-yl), and even more preferably B represents pyridinyl (such as, e.g., pyridin-3-yl or pyridin-4-yl).

n1 is 1.

$R^1$ is selected from $R^5$, halogen, —$CF_3$, —CN, —$OR^5$, —$NR^5R^6$, —$COOR^5$, tetrazolyl (particularly tetrazol-5-yl), —$SO_3H$, —$B(OH)_2$, —$CONR^5R^6$, —$COR^5$, —$SO_2R^5$, or —$SO_2NR^5R^6$. Preferably, $R^1$ is selected from $R^5$, halogen, —$CF_3$, —CN, —$NR^5R^6$, —$COOR^5$, tetrazolyl (particularly tetrazol-5-yl), —$SO_3H$, —$COR^5$, —$SO_2NR^5R^6$, or —$SO_2R^5$; accordingly, in a preferred embodiment, $R^1$ is selected from $C_1$-$C_4$ alkyl (particularly methyl), halogen (particularly fluoro), —$CF_3$, —CN, —$NH_2$, —NH($C_1$-$C_4$ alkyl), —N($C_1$-$C_4$ alkyl)($C_1$-$C_4$ alkyl), —COOH, —COO($C_1$-$C_4$ alkyl), tetrazol-5-yl, —$SO_3H$, —CO($C_1$-$C_4$ alkyl), —$SO_2$($C_1$-$C_4$ alkyl), —$SO_2NH_2$, —$SO_2NH$($C_1$-$C_4$ alkyl), or —$SO_2N$($C_1$-$C_4$ alkyl)($C_1$-$C_4$ alkyl); and in a particularly preferred embodiment, $R^1$ is selected from methyl, ethyl, halogen (particularly fluoro), —$CF_3$, —CN, —$NH_2$, —NH($CH_3$), —N($CH_3$)$_2$, —COOH, tetrazol-5-yl, —$COCH_3$, —$SO_2NH_2$, —$SO_2NH(CH_3)$, or —$SO_2N(CH_3)_2$. More preferably, $R^1$ is selected from $R^5$, halogen, —$NR^5R^6$, or —$SO_2NR^5R^6$. Even more preferably, $R^1$ is selected from methyl, ethyl, fluoro, —$CF_3$, —$NH_2$, —NH($CH_3$), —N($CH_3$)$_2$, —$SO_2NH_2$, —$SO_2NH(CH_3)$, or —$SO_2N(CH_3)_2$.

In accordance with the above definitions of B, $R^1$ and n1, it is particularly preferred that the entire moiety —(B)—$(R^1)_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with one group selected from methyl, ethyl, halogen (particularly fluoro), —$CF_3$, —CN, —$NH_2$, —NH($CH_3$), —N($CH_3$)$_2$, —COOH, tetrazol-5-yl, —$COCH_3$, —$SO_2NH_2$, —$SO_2NH(CH_3)$, or —$SO_2N(CH_3)_2$; preferably, the one substituting group is selected from methyl, ethyl, fluoro, —$CF_3$, —$NH_2$, —NH($CH_3$), —N($CH_3$)$_2$, —$SO_2NH_2$, —$SO_2NH(CH_3)$, or —$SO_2N(CH_3)_2$. It is even more preferred that the moiety —(B)—$(R^1)_{n1}$ is pyridinyl (such as, e.g., pyridin-3-yl or pyridin-4-yl) substituted with one group selected from methyl, ethyl, halogen (particularly fluoro), —$CF_3$, —CN, —$NH_2$, —NH($CH_3$), —N($CH_3$)$_2$, —COOH, tetrazol-5-yl, —$COCH_3$, —$SO_2NH_2$, —$SO_2NH(CH_3)$, or —$SO_2N(CH_3)_2$, and preferably selected from methyl, ethyl, fluoro, —$CF_3$, —$NH_2$, —NH($CH_3$), —N($CH_3$)$_2$, —$SO_2NH_2$, —$SO_2NH(CH_3)$, or —$SO_2N(CH_3)_2$.

Each $R^2$ is independently selected from $R^5$, halogen, —$CF_3$, —CN, —$OR^5$, —$OCF_3$ or —$NR^5R^6$. Preferably, each $R^2$ is independently selected from hydrogen, $C_1$-$C_4$ alkyl (particularly methyl), halogen, —$CF_3$, —CN, —$OCF_3$, —$NH_2$, —NH($C_1$-$C_4$ alkyl), or —N($C_1$-$C_4$ alkyl)($C_1$-$C_4$ alkyl). More preferably, each $R^2$ is hydrogen.

n2 is 1, 2 or 3. Preferably, n2 is 1 or 2. More preferably, n2 is 1. Accordingly, it is most preferred that n2 is 1 and $R^2$ is hydrogen.

$R^3$ represents a -L-$R^7$ group.

L represents a bond or a $C_1$-$C_4$ alkylene, wherein one or two —$CH_2$— units (preferably one —$CH_2$— unit) comprised in said alkylene are each optionally replaced by a group independently selected from —O—, —NH—, —N($CH_3$)—, —CO—, —S—, —SO—, or —$SO_2$—. Preferably, L represents a bond or a $C_1$-$C_4$ alkylene, wherein one —$CH_2$— unit comprised in said alkylene is optionally replaced by —O—. Exemplary preferred L groups include, in particular, a bond, methylene, ethylene, propylene, butylene, —$CH_2$—$CH_2$—O—$CH_2$— and —$CH_2$—O—$CH_2$—. It is particularly preferred that L is a bond.

$R^7$ is selected from hydrogen, halogen, —$CF_3$, —CN, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $R^5$, halogen, —$CF_3$, —CN, —$NR^5R^6$, —$CONR^5R^6$, —$COR^5$, —$OR^5$, —$SR^5$, —$SOR^5$, —$SO_2R^5$, —$SO_2NR^5R^6$, —$NR^5COR^6$, —$NR^5SO_2R^6$, —$OCOR^5$, —$COOR^5$, tetrazolyl, —$SO_3H$, or —$B(OH)_2$. Preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $C_1$-$C_4$ alkyl, halogen, —$CF_3$, —CN, —$NH_2$, —NH($C_1$-$C_4$ alkyl), —N($C_1$-$C_4$ alkyl)($C_1$-$C_4$ alkyl), —$CONH_2$, —$CONH(C_1$-$C_4$ alkyl), —$CON(C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), —$SO_2$($C_1$-$C_4$ alkyl), —$SO_2NH_2$, —$SO_2NH(C_1$-$C_4$ alkyl), —$SO_2N(C_1$-$C_4$ alkyl)($C_1$-$C_4$ alkyl), —NHCO($C_1$-$C_4$ alkyl), —N($C_1$-$C_4$ alkyl)CO($C_1$-$C_4$ alkyl), —$NHSO_2$($C_1$-$C_4$ alkyl), —$NHSO_2$($C_1$-$C_4$ alkyl), —N($C_1$-$C_4$ alkyl)$SO_2$($C_1$-$C_4$ alkyl), —OCO($C_1$-$C_4$ alkyl), —COOH, —COO($C_1$-$C_4$ alkyl), tetrazolyl, or —$SO_3H$. More preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —$CF_3$, —CN, —$NH_2$, —NH($C_1$-$C_4$ alkyl), —N($C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), or —$SO_2$($C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —$CF_3$, —CN, —$NH_2$, —NH($C_1$-$C_4$ alkyl), —N($C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), or —$SO_2$($C_1$-$C_4$ alkyl). Even more preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl), and further wherein said cycloalkyl, said heterocycloalkyl, said aryl or said heteroaryl may be substituted with one or more groups (e.g., one, two or three groups) independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl). Yet even more preferably, R$^7$ is selected from hydrogen, an optionally substituted cycloalkyl, an optionally substituted heterocycloalkyl, an optionally substituted aryl, or an optionally substituted heteroaryl, wherein said cycloalkyl, said heterocycloalkyl, said aryl or said heteroaryl may be substituted with one or more groups (e.g., one, two or three groups; preferably one or two groups; more preferably one group) independently selected from C$_1$-C$_4$ alkyl, halogen, —CF$_3$, —CN, —OH, or —O(C$_1$-C$_4$ alkyl). It is particularly preferred that the above-mentioned groups R$^7$ are not substituted with any optional substituent groups. In the above-mentioned definitions of R$^7$, said cycloalkyl is preferably selected from cyclopropyl, cyclobutyl, cyclopentyl, cyclohexyl or cycloheptyl; said heterocycloalkyl is preferably selected from tetrahydrofuranyl, tetrahydropyran or tetrahydrothiopyran; said aryl is preferably phenyl; and/or said heteroaryl is preferably selected from pyridinyl, pyrazolyl or furanyl. Most preferably, R$^7$ is selected from hydrogen, cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), aryl (e.g., phenyl), or heteroaryl (e.g., pyridinyl, pyrazolyl or furanyl).

In accordance with the above definitions of L and R$^7$, it is particularly preferred that R$^3$ is selected from C$_1$-C$_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetra hydrofuranyl, tetrahydropyran or tetrahydrothiopyran), —(C$_1$-C$_4$ alkylene)-phenyl (e.g., benzyl), —(C$_1$-C$_4$ alkylene)-heteroaryl, —(C$_1$-C$_4$ alkylene)-cycloalkyl, or —(C$_1$-C$_4$ alkylene)-heterocycloalkyl, wherein said C$_1$-C$_4$ alkyl, said phenyl, said heteroaryl, said cycloalkyl, said heterocycloalkyl, the phenyl moiety of said —(C$_1$-C$_4$ alkylene)-phenyl, the heteroaryl moiety of said —(C$_1$-C$_4$ alkylene)-heteroaryl, the cycloalkyl moiety of said —(C$_1$-C$_4$ alkylene)-cycloalkyl, or the heterocycloalkyl moiety of said —(C$_1$-C$_4$ alkylene)-heterocycloalkyl is optionally substituted with one or two groups (preferably one group) independently selected from C$_1$-C$_4$ alkyl, halogen, —CF$_3$, —CN, —OH or —O(C$_1$-C$_4$ alkyl). It is even more preferred that R$^3$ is selected from C$_1$-C$_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —(C$_1$-C$_4$ alkylene)-phenyl (e.g., benzyl), —(C$_1$-C$_4$ alkylene)-heteroaryl, —(C$_1$-C$_4$ alkylene)-cycloalkyl, or —(C$_1$-C$_4$ alkylene)-heterocycloalkyl.

R$^4$ is selected from an optionally substituted C$_1$-C$_4$ alkyl, an optionally substituted cycloalkyl, or an optionally substituted heterocycloalkyl, wherein said C$_1$-C$_4$ alkyl is optionally substituted with one or more groups (e.g., one, two or three groups) independently selected from cycloalkyl, halogen, —CF$_3$, —CN, —OH or —O(C$_1$-C$_4$ alkyl), and further wherein said cycloalkyl or said heterocycloalkyl is optionally substituted with one or more groups (e.g., one, two or three groups) independently selected from C$_1$-C$_4$ alkyl, cycloalkyl, halogen, —CF$_3$, —CN, —OH or —O(C$_1$-C$_4$ alkyl). Preferably, R$^4$ is selected from an optionally substituted C$_1$-C$_4$ alkyl, a cycloalkyl, or a heterocycloalkyl, wherein said C$_1$-C$_4$ alkyl is optionally substituted with one or more groups (e.g., one, two or three groups) independently selected from cycloalkyl, halogen, —CF$_3$, —CN, —OH or —O(C$_1$-C$_4$ alkyl). More preferably, R$^4$ is selected from an optionally substituted C$_1$-C$_4$ alkyl, a cycloalkyl, or a heterocycloalkyl, wherein said C$_1$-C$_4$ alkyl is optionally substituted with one or more groups (e.g., one, two or three groups) independently selected from cycloalkyl, halogen or —CF$_3$. Even more preferably, R$^4$ is selected from an optionally substituted C$_1$-C$_4$ alkyl or a cycloalkyl, wherein said C$_1$-C$_4$ alkyl is optionally substituted with one or more groups (e.g., one, two or three groups) independently selected from cycloalkyl, halogen or —CF$_3$. It is furthermore preferred that the optionally substituted C$_1$-C$_4$ alkyl referred to in the above definitions of R$^4$ is unsubstituted or is substituted with one of the above-defined groups, and it is more preferred that the optionally substituted C$_1$-C$_4$ alkyl referred to in the above definitions of R$^4$ is unsubstituted. Yet even more preferably, R$^4$ is selected from methyl, ethyl, propyl (in particular, n-propyl or isopropyl), —CH$_2$-cycloalkyl (such as, e.g., —CH$_2$-cyclopropyl), cycloalkyl (such as, e.g., cylopropyl or cyclobutyl), —CH$_2$—CF$_3$, or —CH$_2$—CHF$_2$.

Each R$^5$ and each R$^6$ is independently selected from hydrogen, an optionally substituted C$_1$-C$_4$ alkyl or an optionally substituted heterocycloalkyl, wherein said C$_1$-C$_4$ alkyl is optionally substituted with one or more groups (e.g., one, two or three groups) independently selected from halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl), and further wherein said heterocycloalkyl is optionally substituted with one or more groups (e.g., one, two or three groups) independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl). Preferably, each R$^5$ and each R$^6$ is independently selected from hydrogen, an optionally substituted C$_1$-C$_4$ alkyl or an optionally substituted heterocycloalkyl, wherein said C$_1$-C$_4$ alkyl is optionally substituted with one or more groups (e.g., one, two or three groups) independently selected from halogen or —CF$_3$, and further wherein said heterocycloalkyl is optionally substituted with one or more groups (e.g., one, two or three groups) independently selected from C$_1$-C$_4$ alkyl, halogen, or —CF$_3$. More preferably, each R$^5$ and each R$^6$ is independently selected from hydrogen or an optionally substituted C$_1$-C$_4$ alkyl, wherein said C$_1$-C$_4$ alkyl is optionally substituted with one or more groups (e.g., one, two or three groups) independently selected from halogen or —CF$_3$. Yet even more preferably, each R$^5$ and each R$^6$ is independently selected from hydrogen or C$_1$-C$_4$ alkyl.

In a further specific embodiment, the invention relates to a compound of formula (I), wherein the groups and variables in formula (I) have the following meanings and preferred meanings:

A is N.

B represents phenyl or a heteroaryl having 5 or 6 ring members and comprising one or more (particularly one, two, or three) ring heteroatoms independently selected from O, S, or N. Preferably, B represents a heteroaryl having 5 or 6 ring members and comprising one or more (particularly one, two, or three) ring heteroatoms independently selected from O, S, or N. More preferably, B represents a heteroaryl selected from pyridinyl (such as, e.g., pyridin-3-yl or pyridin-4-yl), pyrazolyl (such as, e.g., 1H-pyrazol-4-yl or 1H-pyrazol-3-yl), oxazolyl (such as, e.g., oxazol-2-yl or oxazol-5-yl), tetrazolyl (such as, e.g., 2H-tetrazol-5-yl), pyrimidinyl (such as, e.g., pyrimidin-5-yl), pyridazinyl (such as, e.g., pyridazin-3-yl), or pyrazinyl (such as, e.g., pyrazin-2-yl), and even more preferably B represents pyridinyl (such as, e.g., pyridin-3-yl or pyridin-4-yl).

Each $R^1$ is independently selected from $R^5$, halogen, $-CF_3$, $-CN$, $-OR^5$, $-NR^5R^6$, $-COOR^5$, tetrazolyl (particularly tetrazol-5-yl), $-SO_3H$, $-B(OH)_2$, $-CONR^5R^6$, $-COR^5$, $-SO_2R^5$, or $-SO_2NR^5R^6$. Preferably, each $R^1$ is independently selected from $R^5$, halogen, $-CF_3$, $-CN$, $-OR^5$, $-NR^5R^6$, $-COOR^5$, tetrazolyl (particularly tetrazol-5-yl), $-SO_3H$, $-COR^5$, $-SO_2NR^5R^6$, or $-SO_2R^5$; accordingly, in a preferred embodiment, each $R^1$ is independently selected from $C_1$-$C_4$ alkyl (particularly methyl), halogen (particularly fluoro), $-CF_3$, $-CN$, $-NH_2$, $-NH(C_1$-$C_4$ alkyl), $-N(C_1$-$C_4$ alkyl)($C_1$-$C_4$ alkyl), $-COOH$, $-COO(C_1$-$C_4$ alkyl), tetrazol-5-yl, $-SO_3H$, $-CO(C_1$-$C_4$ alkyl), $-SO_2(C_1$-$C_4$ alkyl), $-SO_2NH_2$, $-SO_2NH(C_1$-$C_4$ alkyl), or $-SO_2N(C_1$-$C_4$ alkyl)($C_1$-$C_4$ alkyl); and in a particularly preferred embodiment, each $R^1$ is independently selected from methyl, ethyl, halogen (particularly fluoro), $-CF_3$, $-CN$, $-NH_2$, $-NH(CH_3)$, $-N(CH_3)_2$, $-COOH$, tetrazol-5-yl, $-COCH_3$, $-SO_2NH_2$, $-SO_2NH(CH_3)$, or $-SO_2N(CH_3)_2$. More preferably, each $R^1$ is independently selected from $R^5$, halogen, $-NR^5R^6$, or $-SO_2NR^5R^6$. Even more preferably, each $R^1$ is independently selected from methyl, ethyl, fluoro, $-CF_3$, $-NH_2$, $-NH(CH_3)$, $-N(CH_3)_2$, $-SO_2NH_2$, $-SO_2NH(CH_3)$, or $-SO_2N(CH_3)_2$.

n1 is 2.

In accordance with the above definitions of B, $R^1$ and n1, it is particularly preferred that the entire moiety $-(B)-(R^1)_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with two groups selected independently from methyl, ethyl, halogen (particularly fluoro), $-CF_3$, $-CN$, $-NH_2$, $-NH(CH_3)$, $-N(CH_3)_2$, $-COOH$, tetrazol-5-yl, $-COCH_3$, $-SO_2NH_2$, $-SO_2NH(CH_3)$, or $-SO_2N(CH_3)_2$; preferably, the two substituting groups are selected independently from methyl, ethyl, fluoro, $-CF_3$, $-NH_2$, $-NH(CH_3)$, $-N(CH_3)_2$, $-SO_2NH_2$, $-SO_2NH(CH_3)$, or $-SO_2N(CH_3)_2$. It is even more preferred that the moiety $-(B)-(R^1)_{n1}$ is pyridinyl (such as, e.g., pyridin-3-yl or pyridin-4-yl) substituted with two groups selected independently from methyl, ethyl, halogen (particularly fluoro), $-CF_3$, $-CN$, $-NH_2$, $-NH(CH_3)$, $-N(CH_3)_2$, $-COOH$, tetrazol-5-yl, $-COCH_3$, $-SO_2NH_2$, $-SO_2NH(CH_3)$, or $-SO_2N(CH_3)_2$, and preferably selected independently from methyl, ethyl, fluoro, $-CF_3$, $-NH_2$, $-NH(CH_3)$, $-N(CH_3)_2$, $-SO_2NH_2$, $-SO_2NH(CH_3)$, or $-SO_2N(CH_3)_2$.

Each $R^2$ is independently selected from $R^5$, halogen, $-CF_3$, $-CN$, $-OR^5$, $-OCF_3$ or $-NR^5R^6$. Preferably, each $R^2$ is independently selected from hydrogen, $C_1$-$C_4$ alkyl (particularly methyl), halogen, $-CF_3$, $-CN$, $-OCF_3$, $-NH_2$, $-NH(C_1$-$C_4$ alkyl), or $-N(C_1$-$C_4$ alkyl)($C_1$-$C_4$ alkyl). More preferably, each $R^2$ is hydrogen.

n2 is 1, 2 or 3. Preferably, n2 is 1 or 2. More preferably, n2 is 1. Accordingly, it is most preferred that n2 is 1 and $R^2$ is hydrogen.

$R^3$ represents a -L-$R^7$ group.

L represents a bond or a $C_1$-$C_4$ alkylene, wherein one or two $-CH_2-$ units (preferably one $-CH_2-$ unit) comprised in said alkylene are each optionally replaced by a group independently selected from $-O-$, $-NH-$, $-N(CH_3)-$, $-CO-$, $-S-$, $-SO-$, or $-SO_2-$. Preferably, L represents a bond or a $C_1$-$C_4$ alkylene, wherein one $-CH_2-$ unit comprised in said alkylene is optionally replaced by $-O-$. Exemplary preferred L groups include, in particular, a bond, methylene, ethylene, propylene, butylene, $-CH_2-CH_2-O-CH_2-$ and $-CH_2-O-CH_2-$. It is particularly preferred that L is a bond.

$R^7$ is selected from hydrogen, halogen, $-CF_3$, $-CN$, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $R^5$, halogen, $-CF_3$, $-CN$, $-NR^5R^6$, $-CONR^5R^6$, $-COR^5$, $-OR^5$, $-SR^5$, $-SOR^5$, $-SO_2R^5$, $-SO_2NR^5R^6$, $-NR^5COR^6$, $-NR^5SO_2R^6$, $-OCOR^5$, $-COOR^5$, tetrazolyl, $-SO_3H$, or $-B(OH)_2$. Preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $C_1$-$C_4$ alkyl, halogen, $-CF_3$, $-CN$, $-NH_2$, $-NH(C_1$-$C_4$ alkyl), $-N(C_1$-$C_4$ alkyl)($C_1$-$C_4$ alkyl), $-CONH_2$, $-CONH(C_1$-$C_4$ alkyl), $-CON(C_1$-$C_4$ alkyl)($C_1$-$C_4$ alkyl), $-COH$, $-CO(C_1$-$C_4$ alkyl), $-OH$, $-O(C_1$-$C_4$ alkyl), $-SH$, $-S(C_1$-$C_4$ alkyl), $-SO(C_1$-$C_4$ alkyl), $-SO_2(C_1$-$C_4$ alkyl), $-SO_2NH_2$, $-SO_2NH(C_1$-$C_4$ alkyl), $-SO_2N(C_1$-$C_4$ alkyl)($C_1$-$C_4$ alkyl), $-NHCO(C_1$-$C_4$ alkyl), $-N(C_1$-$C_4$ alkyl)CO($C_1$-$C_4$ alkyl), $-NHSO_2(C_1$-$C_4$ alkyl), $-NHSO_2(C_1$-$C_4$ alkyl), $-N(C_1$-$C_4$ alkyl)SO$_2$($C_1$-$C_4$ alkyl), $-OCO(C_1$-$C_4$ alkyl), $-COOH$, $-COO(C_1$-$C_4$ alkyl), tetrazolyl, or $-SO_3H$. More preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, $-CF_3$, $-CN$, $-NH_2$, $-NH(C_1$-$C_4$ alkyl), $-N(C_1$-$C_4$ alkyl)($C_1$-$C_4$ alkyl), $-COH$, $-CO(C_1$-$C_4$ alkyl), $-OH$, $-O(C_1$-$C_4$ alkyl), $-SH$, $-S(C_1$-$C_4$ alkyl), $-SO(C_1$-$C_4$ alkyl), or $-SO_2(C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, $-CF_3$, $-CN$, $-NH_2$, $-NH(C_1$-$C_4$ alkyl), $-N(C_1$-$C_4$ alkyl)($C_1$-$C_4$ alkyl), $-COH$, $-CO($C_1$-$C_4$ alkyl), $-OH$, $-O(C_1$-$C_4$ alkyl), $-SH$, $-S($C_1$-

$C_4$ alkyl), —SO($C_1$-$C_4$ alkyl), or —SO$_2$($C_1$-$C_4$ alkyl). Even more preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl). Yet even more preferably, $R^7$ is selected from hydrogen, an optionally substituted cycloalkyl, an optionally substituted heterocycloalkyl, an optionally substituted aryl, or an optionally substituted heteroaryl, wherein said cycloalkyl, said heterocycloalkyl, said aryl or said heteroaryl may be substituted with one or more groups (e.g., one, two or three groups; preferably one or two groups; more preferably one group) independently selected from $C_1$-$C_4$ alkyl, halogen, —CF$_3$, —CN, —OH, or —O($C_1$-$C_4$ alkyl). It is particularly preferred that the above-mentioned groups $R^7$ are not substituted with any optional substituent groups. In the above-mentioned definitions of $R^7$, said cycloalkyl is preferably selected from cyclopropyl, cyclobutyl, cyclopentyl, cyclohexyl or cycloheptyl; said heterocycloalkyl is preferably selected from tetrahydrofuranyl, tetrahydropyran or tetrahydrothiopyran; said aryl is preferably phenyl; and/or said heteroaryl is preferably selected from pyridinyl, pyrazolyl or furanyl. Most preferably, $R^7$ is selected from hydrogen, cycloalkyl (e.g., cyclopropyl, cyclobutyl, cyclopentyl, cyclohexyl or cycloheptyl), heterocycloalkyl (e.g., tetra hydrofuranyl, tetrahydropyran or tetrahydrothiopyran), aryl (e.g., phenyl), or heteroaryl (e.g., pyridinyl, pyrazolyl or furanyl).

In accordance with the above definitions of L and $R^7$, it is particularly preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetra hydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl, wherein said $C_1$-$C_4$ alkyl, said phenyl, said heteroaryl, said cycloalkyl, said heterocycloalkyl, the phenyl moiety of said —($C_1$-$C_4$ alkylene)-phenyl, the heteroaryl moiety of said —($C_1$-$C_4$ alkylene)-heteroaryl, the cycloalkyl moiety of said —($C_1$-$C_4$ alkylene)-cycloalkyl, or the heterocycloalkyl moiety of said —($C_1$-$C_4$ alkylene)-heterocycloalkyl is optionally substituted with one or two groups (preferably one group) independently selected from $C_1$-$C_4$ alkyl, halogen, —CF$_3$, —CN, —OH or —O($C_1$-$C_4$ alkyl). It is even more preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl.

$R^4$ is selected from an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups (e.g., one, two or three groups) independently selected from cycloalkyl, halogen, —CF$_3$, —CN, —OH or —O($C_1$-$C_4$ alkyl), and further wherein said cycloalkyl or said heterocycloalkyl is optionally substituted with one or more groups (e.g., one, two or three groups) independently selected from $C_1$-$C_4$ alkyl, cycloalkyl, halogen, —CF$_3$, —CN, —OH or —O($C_1$-$C_4$ alkyl). Preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen, —CF$_3$, —CN, —OH or —O($C_1$-$C_4$ alkyl). More preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen or —CF$_3$. Even more preferably, $R^4$ is selected from an optionally substituted $C_1$-$C_4$ alkyl or a cycloalkyl, wherein said $C_1$-$C_4$ alkyl is optionally substituted with one or more groups (e.g., one, two or three groups) independently selected from cycloalkyl, halogen or —CF$_3$. It is furthermore preferred that the optionally substituted $C_1$-$C_4$ alkyl referred to in the above definitions of $R^4$ is unsubstituted or is substituted with one of the above-defined groups, and it is more preferred that the optionally substituted $C_1$-$C_4$ alkyl referred to in the above definitions of $R^4$ is unsubstituted. Yet even more preferably, $R^4$ is selected from methyl, ethyl, propyl (in particular, n-propyl or isopropyl), —CH$_2$-cycloalkyl (such as, e.g., —CH$_2$-cyclopropyl), cycloalkyl (such as, e.g., cylopropyl or cyclobutyl), —CH$_2$—CF$_3$, or —CH$_2$—CHF$_2$.

Each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein said heterocycloalkyl is optionally substituted with one or more groups (e.g., one, two or three groups) independently selected from $C_1$-$C_4$ alkyl, halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl). Preferably, each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen or —CF$_3$, and further wherein said heterocycloalkyl is optionally substituted with one or more groups (e.g., one, two or three groups) independently selected from $C_1$-$C_4$ alkyl, halogen, or —CF$_3$. More preferably, each $R^5$ and each $R^6$ is independently selected from hydrogen or an optionally substituted $C_1$-$C_4$ alkyl, wherein said $C_1$-$C_4$ alkyl is optionally substituted with one or more groups (e.g., one, two or three groups) independently selected from halogen or —CF$_3$. Yet even more preferably, each $R^5$ and each $R^6$ is independently selected from hydrogen or $C_1$-$C_4$ alkyl.

In a further specific embodiment, the invention relates to a compound of formula (I), wherein the groups and variables in formula (I) have the following meanings and preferred meanings:

A is C(H).

B represents phenyl or a heteroaryl having 5 or 6 ring members and comprising one or more (particularly one, two, or three) ring heteroatoms independently selected from O, S, or N. Preferably, B represents a heteroaryl having 5 or 6 ring members and comprising one or more (particularly one, two, or three) ring heteroatoms independently selected from O, S, or N. More preferably, B represents a heteroaryl selected from pyridinyl (such as, e.g., pyridin-3-yl or pyridin-4-yl), pyrazolyl (such as, e.g., 1H-pyrazol-4-yl or 1H-pyrazol-3-yl), oxazolyl (such as, e.g., oxazol-2-yl or oxazol-5-yl), tetrazolyl (such as, e.g., 2H-tetrazol-5-yl), pyrimidinyl (such as, e.g., pyrimidin-5-yl), pyridazinyl (such as, e.g., pyridazin-3-yl), or pyrazinyl (such as, e.g., pyrazin-2-yl), and even more preferably B represents pyridinyl (such as, e.g., pyridin-3-yl or pyridin-4-yl).

Each $R^1$ is independently selected from $R^5$, halogen, —$CF_3$, —CN, —$OR^5$, —$NR^5R^6$, —$COOR^5$, tetrazolyl (particularly tetrazol-5-yl), —$SO_3H$, —$B(OH)_2$, —$CONR^5R^6$, —$COR^5$, —$SO_2R^5$, or —$SO_2NR^5R^6$. Preferably, each $R^1$ is independently selected from $R^5$, halogen, —$CF_3$, —CN, —$OR^5$, —$NR^5R^6$, —$COOR^5$, tetrazolyl (particularly tetrazol-5-yl), —$SO_3H$, —$COR^5$, —$SO_2NR^5R^6$, or —$SO_2R^5$; accordingly, in a preferred embodiment, each $R^1$ is independently selected from $C_1$-$C_4$ alkyl (particularly methyl), halogen (particularly fluoro), —$CF_3$, —CN, —$NH_2$, —$NH(C_1$-$C_4$ alkyl), —$N(C_1$-$C_4$ alkyl)($C_1$-$C_4$ alkyl), —COOH, —COO($C_1$-$C_4$ alkyl), tetrazol-5-yl, —$SO_3H$, —CO($C_1$-$C_4$ alkyl), —$SO_2$($C_1$-$C_4$ alkyl), —$SO_2NH_2$, —$SO_2NH(C_1$-$C_4$ alkyl), or —$SO_2N(C_1$-$C_4$ alkyl)($C_1$-$C_4$ alkyl); and in a particularly preferred embodiment, each $R^1$ is independently selected from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$. More preferably, each $R^1$ is independently selected from $R^5$, halogen, —$NR^5R^6$, or —$SO_2NR^5R^6$. Even more preferably, each $R^1$ is independently selected from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$.

n1 is 2.

In accordance with the above definitions of B, $R^1$ and n1, it is particularly preferred that the entire moiety —(B)—$(R^1)_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with two groups selected independently from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$; preferably, the two substituting groups are selected independently from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$. It is even more preferred that the moiety —(B)—$(R^1)_{n1}$ is pyridinyl (such as, e.g., pyridin-3-yl or pyridin-4-yl) substituted with two groups selected independently from methyl, ethyl, halogen (particularly fluoro), —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$, and preferably selected independently from methyl, ethyl, fluoro, —$CF_3$, —$NH_2$, —$NH(CH_3)$, —$N(CH_3)_2$, —$SO_2NH_2$, —$SO_2NH(CH_3)$, or —$SO_2N(CH_3)_2$.

Each $R^2$ is independently selected from $R^5$, halogen, —$CF_3$, —CN, —$OR^5$, —$OCF_3$ or —$NR^5R^6$. Preferably, each $R^2$ is independently selected from hydrogen, $C_1$-$C_4$ alkyl (particularly methyl), halogen, —$CF_3$, —CN, —$OCF_3$, —$NH_2$, —$NH(C_1$-$C_4$ alkyl), or —$N(C_1$-$C_4$ alkyl)($C_1$-$C_4$ alkyl). More preferably, each $R^2$ is hydrogen.

n2 is 1, 2 or 3. Preferably, n2 is 1 or 2. More preferably, n2 is 1. Accordingly, it is most preferred that n2 is 1 and $R^2$ is hydrogen.

$R^3$ represents a -L-$R^7$ group.

L represents a bond or a $C_1$-$C_4$ alkylene, wherein one or two —$CH_2$— units (preferably one —$CH_2$— unit) comprised in said alkylene are each optionally replaced by a group independently selected from —O—, —NH—, —N($CH_3$)—, —CO—, —S—, —SO—, or —$SO_2$—. Preferably, L represents a bond or a $C_1$-$C_4$ alkylene, wherein one —$CH_2$— unit comprised in said alkylene is optionally replaced by —O—. Exemplary preferred L groups include, in particular, a bond, methylene, ethylene, propylene, butylene, —$CH_2$—$CH_2$—O—$CH_2$— and —$CH_2$—O—$CH_2$—. It is particularly preferred that L is a bond.

$R^7$ is selected from hydrogen, halogen, —$CF_3$, —CN, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $R^5$, halogen, —$CF_3$, —CN, —$NR^5R^6$, —$CONR^5R^6$, —$COR^5$, —$OR^5$, —$SR^5$, —$SOR^5$, —$SO_2R^5$, —$SO_2NR^5R^6$, —$NR^5COR^6$, —$NR^5SO_2R^6$, —$OCOR^5$, —$COOR^5$, tetrazolyl, —$SO_3H$, or —$B(OH)_2$. Preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said optionally substituted $C_1$-$C_4$ alkyl, said optionally substituted cycloalkyl, said optionally substituted heterocycloalkyl, said optionally substituted aryl or said optionally substituted heteroaryl may be substituted with one or more groups (e.g., one, two or three groups) independently selected from $C_1$-$C_4$ alkyl, halogen, —$CF_3$, —CN, —$NH_2$, —$NH(C_1$-$C_4$ alkyl), —$N(C_1$-$C_4$ alkyl)($C_1$-$C_4$ alkyl), —$CONH_2$, —$CONH(C_1$-$C_4$ alkyl), —$CON(C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), —$SO_2$($C_1$-$C_4$ alkyl), —$SO_2NH_2$, —$SO_2NH(C_1$-$C_4$ alkyl), —$SO_2N(C_1$-$C_4$ alkyl)($C_1$-$C_4$ alkyl), —NHCO($C_1$-$C_4$ alkyl), —N($C_1$-$C_4$ alkyl)CO($C_1$-$C_4$ alkyl), —$NHSO_2$($C_1$-$C_4$ alkyl), —$NHSO_2$($C_1$-$C_4$ alkyl), —N($C_1$-$C_4$ alkyl)$SO_2$($C_1$-$C_4$ alkyl), —OCO($C_1$-$C_4$ alkyl), —COOH, —COO($C_1$-$C_4$ alkyl), tetrazolyl, or —$SO_3H$. More preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —$CF_3$, —CN, —$NH_2$, —$NH(C_1$-$C_4$ alkyl), —$N(C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), or —SO$_2$($C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —CF$_3$, —CN, —NH$_2$, —NH($C_1$-$C_4$ alkyl), —N($C_1$-$C_4$ alkyl)($C_1$-$C_4$ alkyl), —COH, —CO($C_1$-$C_4$ alkyl), —OH, —O($C_1$-$C_4$ alkyl), —SH, —S($C_1$-$C_4$ alkyl), —SO($C_1$-$C_4$ alkyl), or —SO$_2$($C_1$-$C_4$ alkyl). Even more preferably, $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl may be substituted with one or more groups (e.g., one, two or three groups) independently selected from halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein said cycloalkyl, said heterocycloalkyl, said aryl or said heteroaryl may be substituted with one or more groups (e.g., one, two or three groups) independently selected from $C_1$-$C_4$ alkyl, halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl). Yet even more preferably, $R^7$ is selected from hydrogen, an optionally substituted cycloalkyl, an optionally substituted heterocycloalkyl, an optionally substituted aryl, or an optionally substituted heteroaryl, wherein said cycloalkyl, said heterocycloalkyl, said aryl or said heteroaryl may be substituted with one or more groups (e.g., one, two or three groups; preferably one or two groups; more preferably one group) independently selected from $C_1$-$C_4$ alkyl, halogen, —CF$_3$, —CN, —OH, or —O($C_1$-$C_4$ alkyl). It is particularly preferred that the above-mentioned groups $R^7$ are not substituted with any optional substituent groups. In the above-mentioned definitions of $R^7$, said cycloalkyl is preferably selected from cyclopropyl, cyclobutyl, cyclopentyl, cyclohexyl or cycloheptyl; said heterocycloalkyl is preferably selected from tetrahydrofuranyl, tetrahydropyran or tetrahydrothiopyran; said aryl is preferably phenyl; and/or said heteroaryl is preferably selected from pyridinyl, pyrazolyl or furanyl. Most preferably, $R^7$ is selected from hydrogen, cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), aryl (e.g., phenyl), or heteroaryl (e.g., pyridinyl, pyrazolyl or furanyl).

In accordance with the above definitions of L and $R^7$, it is particularly preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetra hydrofuranyl, tetrahydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl, wherein said $C_1$-$C_4$ alkyl, said phenyl, said heteroaryl, said cycloalkyl, said heterocycloalkyl, the phenyl moiety of said —($C_1$-$C_4$ alkylene)-phenyl, the heteroaryl moiety of said —($C_1$-$C_4$ alkylene)-heteroaryl, the cycloalkyl moiety of said —($C_1$-$C_4$ alkylene)-cycloalkyl, or the heterocycloalkyl moiety of said —($C_1$-$C_4$ alkylene)-heterocycloalkyl is optionally substituted with one or two groups (preferably one group) independently selected from $C_1$-$C_4$ alkyl, halogen, —CF$_3$, —CN, —OH or —O($C_1$-$C_4$ alkyl). It is even more preferred that $R^3$ is selected from $C_1$-$C_4$ alkyl (e.g., methyl, ethyl, propyl or butyl), phenyl, heteroaryl (e.g., pyridinyl, pyrazolyl or furanyl), cycloalkyl (e.g., cyclopropyl, cyclobutyl, cyclopentyl, cyclohexyl or cycloheptyl), heterocycloalkyl (e.g., tetrahydrofuranyl, tetrahydropyran or tetrahydrothiopyran), —($C_1$-$C_4$ alkylene)-phenyl (e.g., benzyl), —($C_1$-$C_4$ alkylene)-heteroaryl, —($C_1$-$C_4$ alkylene)-cycloalkyl, or —($C_1$-$C_4$ alkylene)-heterocycloalkyl.

$R^4$ is selected from an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups (e.g., one, two or three groups) independently selected from cycloalkyl, halogen, —CF$_3$, —CN, —OH or —O($C_1$-$C_4$ alkyl), and further wherein said cycloalkyl or said heterocycloalkyl is optionally substituted with one or more groups (e.g., one, two or three groups) independently selected from $C_1$-$C_4$ alkyl, cycloalkyl, halogen, —CF$_3$, —CN, —OH or —O($C_1$-$C_4$ alkyl). Preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen, —CF$_3$, —CN, —OH or —O($C_1$-$C_4$ alkyl). More preferably, $R^4$ is selected from an optionally substituted $C_1$-$C_4$ alkyl, a cycloalkyl, or a heterocycloalkyl, wherein said $C_1$-$C_4$ alkyl is optionally substituted with one or more groups (e.g., one, two or three groups) independently selected from cycloalkyl, halogen or —CF$_3$. Even more preferably, $R^4$ is selected from an optionally substituted $C_1$-$C_4$ alkyl or a cycloalkyl, wherein said $C_1$-$C_4$ alkyl is optionally substituted with one or more groups (e.g., one, two or three groups) independently selected from cycloalkyl, halogen or —CF$_3$. It is furthermore preferred that the optionally substituted $C_1$-$C_4$ alkyl referred to in the above definitions of $R^4$ is unsubstituted or is substituted with one of the above-defined groups, and it is more preferred that the optionally substituted $C_1$-$C_4$ alkyl referred to in the above definitions of $R^4$ is unsubstituted. Yet even more preferably, $R^4$ is selected from methyl, ethyl, propyl (in particular, n-propyl or isopropyl), —CH$_2$-cycloalkyl (such as, e.g., —CH$_2$-cyclopropyl), cycloalkyl (such as, e.g., cylopropyl or cyclobutyl), —CH$_2$—CF$_3$, or —CH$_2$—CHF$_2$.

Each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl), and further wherein said heterocycloalkyl is optionally substituted with one or more groups (e.g., one, two or three groups) independently selected from $C_1$-$C_4$ alkyl, halogen, —CF$_3$, —CN, —OH, —O($C_1$-$C_4$ alkyl), —NH$_2$, —NH($C_1$-$C_4$ alkyl) or —N($C_1$-$C_4$ alkyl)($C_1$-$C_4$ alkyl). Preferably, each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups (e.g., one, two or three groups) independently selected from halogen or —CF$_3$, and further wherein said heterocycloalkyl is optionally substituted with one or more groups (e.g., one, two or three groups) independently selected from $C_1$-$C_4$ alkyl, halogen, or —CF$_3$. More preferably, each $R^5$ and each $R^6$ is independently selected from hydrogen or an optionally substituted $C_1$-$C_4$ alkyl, wherein said $C_1$-$C_4$ alkyl is optionally substituted with one or more groups (e.g., one, two or three groups) independently selected from halogen or —$CF_3$. Yet even more preferably, each $R^5$ and each $R^6$ is independently selected from hydrogen or $C_1$-$C_4$ alkyl.

The scope of the invention also embraces compounds of the general formula (I), in which one or more atoms are replaced by a specific isotope of the corresponding atom. For example, the invention encompasses compounds of formula (I), in which one or more hydrogen atoms (e.g., all hydrogen atoms) are replaced by deuterium atoms (i.e., $^2$H; also referred to as "D"), although the presence of naturally occurring hydrogen atoms or $^1$H hydrogen atoms in the compounds of formula (I) is preferred. In general, it is preferred that none of the atoms in the compounds of formula (I) is replaced by a specific isotope.

The scope of the invention embraces all pharmaceutically acceptable salt forms of the compounds of the general formula (I) which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention embraces solid forms of the compounds of the general formula (I) in any solvated form, including e.g. solvates with water, for example hydrates, or with organic solvents such as, e.g., methanol, ethanol or acetonitrile, i.e. as a methanolate, ethanolate or acetonitralate, respectively; or in the form of any polymorph.

Pharmaceutically acceptable prodrugs of compounds that can be used in the present invention, in particular the compounds of the general formula (I), are derivatives which have chemically or metabolically cleavable groups and become, by solvolysis or under physiological conditions, the compounds used in the present invention which are pharmaceutically active in vivo. Prodrugs of compounds that can be used in the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound employed in the present invention, in particular a compound of the general formula (I), has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester or N,N-diethylglycolamidoester. When a compound employed in the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—$CH_3$, —OC(=O)—$C_2H_5$, —OC(=O)—$C_3H_7$, —OC(=O)-(tert-butyl), —OC(=O)—$C_{15}H_{31}$, —OC(=O)—$CH_2CH_2$COONa, —O(C=O)—CH($NH_2$)$CH_3$ or —OC(=O)—$CH_2$—N($CH_3$)$_2$. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—($CH_2$)$_2$$OCH_3$ or —NHC(=O)—CH($NH_2$)$CH_3$.

The compounds of general formula (I) or pharmaceutically acceptable salts, solvates or prodrugs thereof, may be administered as compounds per se or may be formulated as medicaments. Within the scope of the present invention are pharmaceutical compositions comprising as an active ingredient one or more compounds of the general formula (I), or pharmaceutically acceptable salts, solvates or prodrugs thereof. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions may also comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds in accordance with the invention, encompassing compounds of the general formula (I) and pharmaceutically acceptable salts, solvates and prodrugs thereof, or the above described pharmaceutical compositions may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (U.S. Pat. No. 3,773,919), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; Japanese Pat. Appl. 83-118008; U.S. Pat. Nos. 4,485,045 and 4,544,545; and EP0102324.

Alternatively, said compounds or pharmaceutical compositions can be administered in the form of a suppository or pessary, or may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of the general formula (I) for administration to a human (of approximately 70 kg body weight) may be 0.05 to 2000 mg, preferably 0.1 mg to 1000 mg, of the active ingredient per unit dose. The unit dose may be administered, for example, 1 to 4 times per day. The unit dose may also be administered 1 to 7 times per week, e.g., with not more than one administration per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The subject or patient, such as the subject in need of treatment or prophylaxis, may be a eukaryote, an animal, a vertebrate animal, a mammal, a rodent (e.g., a guinea pig, a hamster, a rat, a mouse), a murine (e.g., a mouse), a canine (e.g., a dog), a feline (e.g., a cat), an equine (e.g., a horse), a primate, a simian (e.g., a monkey or ape), a monkey (e.g., a marmoset, a baboon), an ape (e.g., a gorilla, chimpanzee, orang-utan, gibbon), or a human. The meaning of the terms "eukaryote", "animal", "mammal", etc. is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal; more preferably, the subject/patient is a human.

The term "treatment" of a condition, disorder or disease as used herein is well known in the art. "Treatment" of a condition, disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e. diagnose a disorder or disease).

The treatment of a condition, disorder or disease may, for example, lead to a halt in the progression of the condition, disorder or disease (e.g. no deterioration of symptoms) or a delay in the progression of the disorder or disease (in case the halt In progression is of a transient nature only). Treatment may also lead to a partial response (e.g. amelioration of symptoms) or complete response (e.g. disappearance of symptoms) of the subject/patient suffering from the condition, disorder or disease. Amelioration of a condition, disorder or disease may, for example, lead to a halt in the progression of the disorder or disease or a delay in the progresssion of the disorder or disease. Such a partial or complete response may be followed by a relapse. It is to be understood that a subject/patient may experience a broad range of responses to a treatment (e.g. the exemplary responses as described herein above).

Treatment of a condition, disorder or disease may, inter alia, comprise curative treatment (preferably leading to a complete response and eventually to healing of the disorder or disease) and palliative treatment (including symptomatic relief).

Also the term "prophylaxis" or "prevention" of a condition, disorder or disease as used herein is well known in the art. For example, a patient/subject suspected of being prone to suffer from a condition, disorder or disease as defined herein may, in particular, benefit from a prophylaxis of the disorder or disease. Said subject/patient may have a susceptibility or predisposition for a condition, disorder or disease, including but not limited to hereditary predisposition. Such a predisposition can be determined by standard assays, using, for example, genetic markers or phenotypic indicators. It is to be understood that a condition, disorder or disease to be prevented in accordance with the present invention has not been diagnosed or cannot be diagnosed in said patient/subject (for example, said patient/subject does not show any clinical or pathological symptoms). Thus, the term "prophylaxis" comprises the use of compounds of the present invention before any clinical and/or pathological symptoms are diagnosed or determined or can be diagnosed or determined by the attending physician. The terms "prophylaxis" and "prevention" are used herein interchangeably.

In the method for identifying an agent that binds to group II metabotropic glutamate receptor (mGluR2) or to group III metabotropic glutamate receptor (mGluR3) described herein above, the test agent may, for example, be selected from nucleic acids, DNA, RNA, PNA, oligonucleotides, aptamers (Gold, Ann. Rev. Biochem. 64 (1995), 763-797)), aptazymes, RNAzymes, ribozymes (see e.g., EP-B1 0 291 533, EP-A1 0 321 201, EP-B1 0 360 257), antisense DNA, antisense oligonucleotides, antisense RNA, siRNA, RNAi, shRNA, amino acids, peptides, polypeptides, proteins, glycoproteins, lipoproteins, nucleoproteins, antibodies (Harlow and Lane "Antibodies, A Laboratory Manual", CSH Press, Cold Spring Harbor, 1988), monoclonal antibodies, polyclonal antibodies, immunoglobulins, affibodies (Hansson, Immunotechnology 4 (1999), 237-252; Henning, Hum Gene Ther. 13 (2000), 1427-1439), immunoreactive fragments, immunoreactive derivatives, antigens, epitopes, haptens, cell-surface molecules, cofactors, ligands, small organic molecules, lectins or derivatives thereof, lectin fragments, trinectins (Phylos Inc., Lexington, Mass., USA; Xu, Chem. Biol. 9 (2002), 933), anticalins (EP-B-1 1 017 814), hormones, peptide and protein hormones, non-peptide hormones, steroids, interleukins, interferons, cytokines, neurotransmitters, toxins, enzymes, polysaccharides, carbohydrates, lipids, lipopolysaccharides, vitamins, crown ethers, cyclodextrins, cryptands, calixarenes, aldehydes, thiols, amines, drugs, drugs of abuse, therapeutic agents, medicaments, pharmaceuticals, substrates, fragments, portions, components or products of microorganisms, metabolites of or antibodies to any of the above substances and the like.

In this specification, a number of documents including patent applications and manufacturer's manuals are cited.

The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention particularly relates to a compound of formula (I):

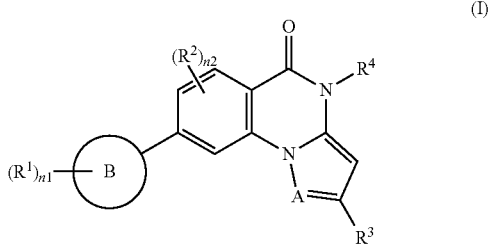

wherein:
- A is N or C(H);
- B is aryl or heteroaryl;
- each $R^1$ is independently selected from $R^5$, halogen, —$CF_3$, —CN, —$OR^5$, —$OCF_3$, —$NR^5R^6$, —$COOR^5$, tetrazolyl, —$SO_3H$, —$B(OH)_2$, —$CONR^5R^6$, —$COR^5$, —$SR^5$, —$SOR^5$, —$SO_2R^5$, —$SO_2NR^5R^6$, —$NR^5COR^6$, —$NR^5SO_2R^6$ or —$OCOR^5$;
- n1 is 1, 2 or 3;
- each $R^2$ is independently selected from $R^5$, halogen, —$CF_3$, —CN, —$OR^5$, —$OCF_3$, —$NR^5R^6$, —$COOR^5$, —$CONR^5R^6$, —$COR^5$, —$SR^5$, —$SOR^5$, —$SO_2R^5$, —$SO_2NR^5R^6$, —$NR^5COR^6$, —$NR^5SO_2R^6$, or —$OCOR^5$;
- n2 is 1, 2 or 3;
- $R^3$ is a -L-$R^7$ group, wherein:
  - L is a bond or $C_1$-$C_4$ alkylene, wherein one or more —$CH_2$— units comprised in said alkylene are each optionally replaced by a group independently selected from —O—, —$NR^5$—, —CO—, —S—, —SO—, or —$SO_2$—; and
  - $R^7$ is selected from hydrogen, halogen, —$CF_3$, —CN, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl, said cycloalkyl, said heterocycloalkyl, said aryl or said heteroaryl is optionally substituted with one or more groups independently selected from $R^5$, halogen, —$CF_3$, —CN, —$NR^5R^6$, —$CONR^5R^6$, —$COR^5$, —$OR^5$, —$SR^5$, —$SOR^5$, —$SO_2R^5$, —$SO_2NR^5R^6$, —$NR^5COR^6$, —$NR^5SO_2R^6$, —$OCOR^5$, —$OCOR^5$, tetrazolyl, —$SO_3H$, or —$B(OH)_2$;
- $R^4$ is selected from an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups independently selected from cycloalkyl, halogen, —$CF_3$, —CN, —OH or —O($C_1$-$C_4$ alkyl), and further wherein said cycloalkyl or said heterocycloalkyl is optionally substituted with one or more groups independently selected from $C_1$-$C_4$ alkyl, cycloalkyl, halogen, —$CF_3$, —CN, —OH or —O($C_1$-$C_4$ alkyl); and
- each $R^5$ and each $R^6$ is independently selected from hydrogen, an optionally substituted $C_1$-$C_4$ alkyl, an optionally substituted cycloalkyl, or an optionally substituted heterocycloalkyl, wherein said $C_1$-$C_4$ alkyl is optionally substituted with one or more groups independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said cycloalkyl and said heterocycloalkyl are each optionally substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl);

or a pharmaceutically acceptable salt, solvate or prodrug thereof.

In a first particular embodiment, the invention relates to a compound according to formula (I) above, wherein A is N.

In a second particular embodiment, the invention relates to a compound according to formula (I) above, wherein A is C(H).

In another embodiment, the invention relates to a compound according to formula (I) above, wherein B is phenyl or B is a heteroaryl group having 5 or 6 ring members and comprising one or more ring heteroatoms independently selected from O, S, or N. In a preferred embodiment, the invention relates to a compound according to formula (I) above, wherein B is a heteroaryl group selected from pyridinyl, pyrazolyl, oxazolyl, tetrazolyl, pyrimidinyl, pyridazinyl, or pyrazinyl.

In a particular embodiment, the invention relates to a compound according to formula (I) above, wherein each $R^1$ is independently selected from $R^5$, halogen, —$CF_3$, —CN, —$OR^5$, —$NR^5R^6$, —$COOR^5$, tetrazolyl, —$SO_3H$, —$COR^5$, —$SO_2NR^5R^6$, or —$SO_2R^5$. In a preferred embodiment, the invention relates to a compound according to formula (I) above, wherein each $R^1$ is independently selected from $C_1$-$C_4$ alkyl, halogen, —$CF_3$, —CN, —$NH_2$, —NH($C_1$-$C_4$ alkyl), —N($C_1$-$C_4$ alkyl)($C_1$-$C_4$ alkyl), —COOH, —COO($C_1$-$C_4$ alkyl), tetrazol-5-yl, —$SO_3H$, —CO($C_1$-$C_4$ alkyl), —$SO_2$($C_1$-$C_4$ alkyl), —$SO_2NH_2$, —$SO_2NH$($C_1$-$C_4$ alkyl), or —$SO_2N$($C_1$-$C_4$ alkyl)($C_1$-$C_4$ alkyl).

In a first particular embodiment, the invention relates to a compound according to formula (I) above, wherein n1 is 1. In a second particular embodiment, the invention relates to a compound according to formula (I) above, wherein n1 is 2.

In one embodiment the invention relates to a compound according to formula (I) above, wherein the moiety —(B)—$(R^1)_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with one, two or three groups selected independently from methyl, ethyl, halogen, —$CF_3$, —CN, —$NH_2$, —$NH(CH_3)$, —$N(CH_3)_2$, —COOH, tetrazol-5-yl, —$COCH_3$, —$SO_2NH_2$, —$SO_2NH(CH_3)$, or —$SO_2N(CH_3)_2$.

In another embodiment, the invention relates to a compound according to formula (I) above, wherein each $R^2$ is independently selected from hydrogen, $C_1$-$C_4$ alkyl, halogen, —$CF_3$, —CN, —$OCF_3$, —$NH_2$, —NH($C_1$-$C_4$ alkyl), or —N($C_1$-$C_4$ alkyl)($C_1$-$C_4$ alkyl).

In another embodiment, the invention relates to a compound according to formula (I) above, wherein n2 is 1 and $R^2$ is hydrogen.

In another embodiment, the invention relates to a compound according to formula (I) above, wherein L is a bond or $C_1$-$C_4$ alkylene, wherein one —$CH_2$— unit comprised in said alkylene is optionally replaced by —O—.

In yet another embodiment, the invention relates to a compound according to formula (I) above, wherein $R^7$ is selected from hydrogen, an optionally substituted $C_1$-$C_4$ alkyl, an optionally substituted cycloalkyl, an optionally substituted heterocycloalkyl, an optionally substituted aryl, or an optionally substituted heteroaryl, wherein said $C_1$-$C_4$ alkyl is optionally substituted with one or more groups independently selected from halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl), and further wherein said cycloalkyl, said heterocycloalkyl, said aryl or said heteroaryl is optionally substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl) or —N($C_1$-$C_4$ alkyl)($C_1$-$C_4$ alkyl).

In another embodiment, the invention relates to a compound according to formula (I) above, wherein $R^3$ is selected from $C_1$-$C_4$ alkyl, phenyl, heteroaryl, cycloalkyl, heterocycloalkyl, —($C_1$-$C_4$ alkylene)-phenyl, —($C_1$-$C_4$ alkylene)-heteroaryl, —($C_1$-$C_4$ alkylene)-cycloalkyl, or —($C_1$-$C_4$ alkylene)-heterocycloalkyl, wherein said $C_1$-$C_4$ alkyl, said phenyl, said heteroaryl, said cycloalkyl, said heterocycloalkyl, the phenyl moiety of said —($C_1$-$C_4$ alkylene)-phenyl, the heteroaryl moiety of said —($C_1$-$C_4$ alkylene)-heteroaryl, the cycloalkyl moiety of said —($C_1$-$C_4$ alkylene)-cycloalkyl, or the heterocycloalkyl moiety of said —($C_1$-$C_4$ alkylene)-heterocycloalkyl is optionally substituted with one or two groups independently selected from $C_1$-$C_4$ alkyl, halogen, —$CF_3$, —CN, —OH or —O($C_1$-$C_4$ alkyl).

In another embodiment, the invention relates to a compound according to formula (I) above, wherein $R^4$ is selected from an optionally substituted $C_1$-$C_4$ alkyl, a cycloalkyl, or a heterocycloalkyl, wherein said $C_1$-$C_4$ alkyl is optionally substituted with one or more groups independently selected from cycloalkyl, halogen, —$CF_3$, —CN, —OH or —O($C_1$-$C_4$ alkyl).

In another embodiment, the invention relates to a compound according to formula (I) above, wherein $R^4$ is selected from methyl, ethyl, propyl, —$CH_2$-cycloalkyl, cycloalkyl, —$CH_2$—$CF_3$, or —$CH_2$—$CHF_2$.

In another embodiment, the invention relates to a compound according to formula (I) above, wherein each $R^5$ and each $R^6$ is independently selected from hydrogen, an optionally substituted $C_1$-$C_4$ alkyl or an optionally substituted heterocycloalkyl, wherein said $C_1$-$C_4$ alkyl is optionally substituted with one or more groups independently selected from halogen or —$CF_3$, and further wherein said heterocycloalkyl is optionally substituted with one or more groups independently selected from $C_1$-$C_4$ alkyl, halogen, or —$CF_3$.

In another embodiment, the invention relates to a compound according to formula (I) above, wherein each $R^5$ and each $R^6$ is independently selected from hydrogen or $C_1$-$C_4$ alkyl.

In a preferred embodiment, the invention relates to a compound according to formula (I) above, wherein said compound is selected from:
8-(6-Amino-pyridin-3-yl)-4-methyl-2-phenyl-4H-pyrazolo[1,5-a]quinazolin-5-one;
8-(4-Amino-phenyl)-4-methyl-2-phenyl-4H-pyrazolo[1,5-a]quinazolin-5-one;
4-Methyl-8-(6-morpholin-4-yl-pyridin-3-yl)-2-phenyl-4H-pyrazolo[1,5-a]quinazolin-5-one;
4-Methyl-2-phenyl-8-(3,4,5,6-tetrahydro-2H-[1,2]bipyridinyl-5'-yl)-4H-pyrazolo[1,5-a]quinazolin-5-one;
4-Methyl-2-phenyl-8-(1H-pyrazol-4-yl)-4H-pyrazolo[1,5-a]quinazolin-5-one;
8-(4-Methoxy-phenyl)-4-methyl-2-phenyl-4H-pyrazolo[1,5-a]quinazolin-5-one;
8-Imidazo[1,2-a]pyridin-6-yl-4-methyl-2-phenyl-4H-pyrazolo[1,5-a]quinazolin-5-one;
8-(3-Methoxymethyl-phenyl)-4-methyl-2-phenyl-4H-pyrazolo[1,5-a]quinazolin-5-one;
4-(4-Methyl-5-oxo-2-phenyl-4,5-dihydro-pyrazolo[1,5-a]quinazolin-8-yl)-benzenesulfonamide;
8-(3-Methoxy-phenyl)-4-methyl-2-phenyl-4H-pyrazolo[1,5-a]quinazolin-5-one;
8-(4-Fluoro-phenyl)-4-methyl-2-phenyl-4H-pyrazolo[1,5-a]quinazolin-5-one;
8-(4-Chloro-phenyl)-4-methyl-2-phenyl-4H-pyrazolo[1,5-a]quinazolin-5-one;
8-(3-Acetyl-phenyl)-4-methyl-2-phenyl-4H-pyrazolo[1,5-a]quinazolin-5-one;
8-(3,5-Dimethyl-1H-pyrazol-4-yl)-4-methyl-2-phenyl-4H-pyrazolo[1,5-a]quinazolin-5-one;
4-Methyl-8-(1-methyl-1H-pyrazol-4-yl)-2-phenyl-4H-pyrazolo[1,5-a]quinazolin-5-one;
4-Methyl-2-phenyl-8-(1H-pyrazol-3-yl)-4H-pyrazolo[1,5-a]quinazolin-5-one;
4-Methyl-8-(3-methyl-1H-pyrazol-4-yl)-2-phenyl-4H-pyrazolo[1,5-a]quinazolin-5-one;
4-Methyl-2-phenyl-8-(3-trifluoromethyl-1H-pyrazol-4-yl)-4H-pyrazolo[1,5-a]quinazolin-5-one;
4-Methyl-8-oxazol-2-yl-2-phenyl-4H-pyrazolo[1,5-a]quinazolin-5-one;
4-Methyl-8-oxazol-5-yl-2-phenyl-4H-pyrazolo[1,5-a]quinazolin-5-one;
4-Methyl-2-phenyl-8-(2H-tetrazol-5-yl)-4H-pyrazolo[1,5-a]quinazolin-5-one;
8-(3-Bromo-phenyl)-4-methyl-2-phenyl-4H-pyrazolo[1,5-a]quinazolin-5-one;
8-(6-Amino-4-methyl-pyridin-3-yl)-4-methyl-2-phenyl-4H-pyrazolo[1,5-a]quinazolin-5-one;
8-(6-Amino-2-methyl-pyridin-3-yl)-4-methyl-2-phenyl-4H-pyrazolo[1,5-a]quinazolin-5-one;
8-(6-Amino-5-methyl-pyridin-3-yl)-4-methyl-2-phenyl-4H-pyrazolo[1,5-a]quinazolin-5-one;
8-(6-Amino-2-ethyl-pyridin-3-yl)-4-methyl-2-phenyl-4H-pyrazolo[1,5-a]quinazolin-5-one;
8-(6-Amino-2,4-dimethyl-pyridin-3-yl)-4-methyl-2-phenyl-4H-pyrazolo[1,5-a]quinazolin-5-one;
8-(6-Amino-pyridazin-3-yl)-4-methyl-2-phenyl-4H-pyrazolo[1,5-a]quinazolin-5-one;
8-(5-Amino-pyrazin-2-yl)-4-methyl-2-phenyl-4H-pyrazolo[1,5-a]quinazolin-5-one;
8-(2-Amino-pyrimidin-5-yl)-4-methyl-2-phenyl-4H-pyrazolo[1,5-a]quinazolin-5-one;
8-(5-Amino-3-methyl-pyrazin-2-yl)-4-methyl-2-phenyl-4H-pyrazolo[1,5-a]quinazolin-5-one;
8-(6-Amino-2-trifluoromethyl-pyridin-3-yl)-4-methyl-2-phenyl-4H-pyrazolo[1,5-a]quinazolin-5-one;
3-(4-Methyl-5-oxo-2-phenyl-4,5-dihydro-pyrazolo[1,5-a]quinazolin-8-yl)-benzoic acid;
3-(4-Methyl-5-oxo-2-phenyl-4,5-dihydro-pyrazolo[1,5-a]quinazolin-8-yl)-benzonitrile;

4-Methyl-2-phenyl-8-[3-(2H-tetrazol-5-yl)-phenyl]-4H-pyrazolo[1,5-a]quinazolin-5-one;
8-(2,6-Dimethyl-pyridin-4-yl)-4-methyl-2-phenyl-4H-pyrazolo[1,5-a]quinazolin-5-one;
N,N-Dimethyl-3-(4-methyl-5-oxo-2-phenyl-4,5-dihydro-pyrazolo[1,5-a]quinazolin-8-yl)-benzenesulfonamide;
N,N-Dimethyl-3-(4-Ethyl-5-oxo-2-phenyl-4,5-dihydro-pyrazolo[1,5-a]quinazolin-8-yl)-benzenesulfonamide;
N,N-Dimethyl-3-(4-propyl-5-oxo-2-phenyl-4,5-dihydro-pyrazolo[1,5-a]quinazolin-8-yl)-benzenesulfonamide;
3-(4-Isobutyl-5-oxo-2-phenyl-4,5-dihydro-pyrazolo[1,5-a]quinazolin-8-yl)-N,N-dimethyl-benzenesulfonamide;
3-(4-Cyclopropylmethyl-5-oxo-2-phenyl-4,5-dihydro-pyrazolo[1,5-a]quinazolin-8-yl)-N,N-dimethyl-benzenesulfonamide;
8-(6-Amino-pyridin-3-yl)-4-ethyl-2-phenyl-4H-pyrazolo[1,5-a]quinazolin-5-one;
8-(6-Amino-pyridin-3-yl)-2-phenyl-4-propyl-4H-pyrazolo[1,5-a]quinazolin-5-one;
8-(6-Amino-pyridin-3-yl)-2-phenyl-4-(2,2,2-trifluoro-ethyl)-4H-pyrazolo[1,5-a]quinazolin-5-one;
8-(6-Amino-pyridin-3-yl)-4-(2,2-difluoro-ethyl)-2-phenyl-4H-pyrazolo[1,5-a]quinazolin-5-one;
8-(6-Amino-pyridin-3-yl)-4-isopropyl-2-phenyl-4H-pyrazolo[1,5-a]quinazolin-5-one;
8-(6-Amino-pyridin-3-yl)-4-cyclobutyl-2-phenyl-4H-pyrazolo[1,5-a]quinazolin-5-one;
8-(6-Amino-pyridin-3-yl)-2-ethyl-4-methyl-4H-pyrazolo[1,5-a]quinazolin-5-one;
8-(6-Amino-pyridin-3-yl)-4-methyl-2-propyl-4H-pyrazolo[1,5-a]quinazolin-5-one;
8-(6-Amino-pyridin-3-yl)-2-isopropyl-4-methyl-4H-pyrazolo[1,5-a]quinazolin-5-one;
8-(6-Amino-pyridin-3-yl)-2-tert-butyl-4-methyl-4H-pyrazolo[1,5-a]quinazolin-5-one;
8-(6-Amino-pyridin-3-yl)-2-(2-methoxy-ethyl)-4-methyl-4H-pyrazolo[1,5-a]quinazolin-5-one;
8-(2,6-Dimethyl-pyridin-4-yl)-2-(2-methoxy-ethyl)-4-methyl-4H-pyrazolo[1,5-a]quinazolin-5-one;
8-(6-Amino-pyridin-3-yl)-2-(2-methoxy-ethyl)-4-methyl($D_3$)-4H-pyrazolo[1,5-a]quinazolin-5-one;
8-(2,6-Dimethyl-pyridin-4-yl)-2-(2-methoxy-ethyl)-4-methyl($D_3$)-4H-pyrazolo[1,5-a]quinazolin-5-one;
8-(6-Amino-pyridin-3-yl)-4-ethyl-2-(2-methoxy-ethyl)-4H-pyrazolo[1,5-a]quinazolin-5-one;
8-(2,6-Dimethyl-pyridin-4-yl)-4-ethyl-2-(2-methoxy-ethyl)-4H-pyrazolo[1,5-a]quinazolin-5-one;
8-(6-Amino-pyridin-3-yl)-2-(2-methoxy-ethyl)-4-propyl-4H-pyrazolo[1,5-a]quinazolin-5-one;
8-(2,6-Dimethyl-pyridin-4-yl)-2-(2-methoxy-ethyl)-4-propyl-4H-pyrazolo[1,5-a]quinazolin-5-one;
8-(6-Amino-pyridin-3-yl)-2-methoxymethyl-4-methyl-4H-pyrazolo[1,5-a]quinazolin-5-one;
8-(2,6-Dimethyl-pyridin-4-yl)-2-methoxymethyl-4-methyl-4H-pyrazolo[1,5-a]quinazolin-5-one;
8-(6-Amino-pyridin-3-yl)-2-cyclopropyl-4-methyl-4H-pyrazolo[1,5-a]quinazolin-5-one;
8-(6-Amino-pyridin-3-yl)-2-cyclobutyl-4-methyl-4H-pyrazolo[1,5-a]quinazolin-5-one;
8-(6-Amino-pyridin-3-yl)-2-cyclopentyl-4-methyl-4H-pyrazolo[1,5-a]quinazolin-5-one;
2-Cyclopentyl-8-(2,6-dimethyl-pyridin-4-yl)-4-methyl-4H-pyrazolo[1,5-a]quinazolin-5-one;
8-(6-Amino-pyridin-3-yl)-2-cyclopentyl-4-methyl($D_3$)-4H-pyrazolo[1,5-a]quinazolin-5-one;
2-Cyclopentyl-8-(2,6-dimethyl-pyridin-4-yl)-4-methyl($D_3$)-4H-pyrazolo[1,5-a]quinazolin-5-one;
8-(6-Amino-pyridin-3-yl)-2-cyclopentyl-4-ethyl-4H-pyrazolo[1,5-a]quinazolin-5-one;
2-Cyclopentyl-8-(2,6-dimethyl-pyridin-4-yl)-4-ethyl-4H-pyrazolo[1,5-a]quinazolin-5-one;
8-(6-Amino-pyridin-3-yl)-2-cyclopentyl-4-propyl-4H-pyrazolo[1,5-a]quinazolin-5-one;
2-Cyclopentyl-8-(2,6-dimethyl-pyridin-4-yl)-4-propyl-4H-pyrazolo[1,5-a]quinazolin-5-one;
2-Cyclopentyl-8-(2,6-dimethyl-pyridin-4-yl)-4-(2,2,2-trifluoro-ethyl)-4H-pyrazolo[1,5-a]quinazolin-5-one;
8-(6-Amino-pyridin-3-yl)-2-cyclohexyl-4-methyl-4H-pyrazolo[1,5-a]quinazolin-5-one;
2-Cyclohexyl-4-methyl-8-(3-methyl-1H-pyrazol-4-yl)-4H-pyrazolo[1,5-a]quinazolin-5-one;
8-(6-Amino-pyridin-3-yl)-2-cycloheptyl-4-methyl-4H-pyrazolo[1,5-a]quinazolin-5-one;
2-Cycloheptyl-8-(2,6-dimethyl-pyridin-4-yl)-4-methyl-4H-pyrazolo[1,5-a]quinazolin-5-one;
2-Cycloheptyl-8-(2,6-dimethyl-pyridin-4-yl)-4-ethyl-4H-pyrazolo[1,5-a]quinazolin-5-one;
8-(6-Amino-pyridin-3-yl)-2-benzyl-4-methyl-4H-pyrazolo[1,5-a]quinazolin-5-one;
8-(6-Amino-pyridin-3-yl)-2-(4-fluoro-phenyl)-4-methyl-4H-pyrazolo[1,5-a]quinazolin-5-one;
2-(4-Fluoro-phenyl)-4-methyl-8-(3-methyl-1H-pyrazol-4-yl)-4H-pyrazolo[1,5-a]quinazolin-5-one;
8-(6-Amino-pyridin-3-yl)-2-furan-2-yl-4-methyl-4H-pyrazolo[1,5-a]quinazolin-5-one;
8-(6-Amino-pyridin-3-yl)-4-methyl-2-(tetrahydro-thiopyran-4-yl)-4H-pyrazolo[1,5-a]quinazolin-5-one;
8-(6-Amino-pyridin-3-yl)-2-(1,1-dioxo-tetrahydro-2H-thiopyran-4-yl)-4-methyl-4H-pyrazolo[1,5-a]quinazolin-5-one;
4-Methyl-8-(1-methyl-1H-pyrazol-4-yl)-2-pyridin-3-yl-4H-pyrazolo[1,5-a]quinazolin-5-one;
8-(6-Amino-pyridin-3-yl)-4-methyl-2-(tetrahydro-pyran-4-yl)-4H-pyrazolo[1,5-a]quinazolin-5-one;
4-Methyl-8-(1H-pyrazol-4-yl)-2-(tetrahydro-pyran-4-yl)-4H-pyrazolo[1,5-a]quinazolin-5-one;
3-[4-Methyl-5-oxo-2-(tetrahydro-pyran-4-yl)-4,5-dihydro-pyrazolo[1,5-a]quinazolin-8-yl]-benzonitrile;
4-Methyl-8-pyridin-3-yl-2-(tetrahydro-pyran-4-yl)-4H-pyrazolo[1,5-a]quinazolin-5-one;
4-Methyl-8-pyridin-4-yl-2-(tetrahydro-pyran-4-yl)-4H-pyrazolo[1,5-a]quinazolin-5-one;
4-Methyl-8-oxazol-2-yl-2-(tetrahydro-pyran-4-yl)-4H-pyrazolo[1,5-a]quinazolin-5-one;
4-Methyl-8-(5-methyl-1H-pyrazol-4-yl)-2-(tetrahydro-pyran-4-yl)-4H-pyrazolo[1,5-a]quinazolin-5-one;
4-Methyl-8-(2-methyl-pyridin-4-yl)-2-(tetrahydro-pyran-4-yl)-4H-pyrazolo[1,5-a]quinazolin-5-one;
4-Methyl-8-(2-methyl-pyridin-3-yl)-2-(tetrahydro-pyran-4-yl)-4H-pyrazolo[1,5-a]quinazolin-5-one;
4-Methyl-8-(6-methyl-pyridin-3-yl)-2-(tetrahydro-pyran-4-yl)-4H-pyrazolo[1,5-a]quinazolin-5-one;
4-Methyl-2-(tetrahydro-pyran-4-yl)-8-[3-(2H-tetrazol-5-yl)-phenyl]-4H-pyrazolo[1,5-a]quinazolin-5-one;
8-(2,6-Dimethyl-pyridin-4-yl)-4-methyl-2-(tetrahydro-pyran-4-yl)-4H-pyrazolo[1,5-a]quinazolin-5-one;
8-(6-Amino-pyridazin-3-yl)-4-methyl-2-(tetrahydro-pyran-4-yl)-4H-pyrazolo[1,5-a]quinazolin-5-one;
8-(2,6-Dimethyl-pyridin-3-yl)-4-methyl-2-(tetrahydro-pyran-4-yl)-4H-pyrazolo[1,5-a]quinazolin-5-one;
3-[4-Methyl-5-oxo-2-(tetrahydro-pyran-4-yl)-4,5-dihydro-pyrazolo[1,5-a]quinazolin-8-yl]-benzenesulfonamide;

N-(2-Hydroxy-1,1-dimethyl-ethyl)-3-[4-methyl-5-oxo-2-(tetrahydro-pyran-4-yl)-4,5-dihydro-pyrazolo[1,5-a]quinazolin-8-yl]-benzenesulfonamide;

4-(2,2-Difluoro-ethyl)-8-(2,6-dimethyl-pyridin-4-yl)-2-(tetrahydro-pyran-4-yl)-4H-pyrazolo[1,5-a]quinazolin-5-one;

8-(6-Amino-pyridin-3-yl)-4-(2,2-difluoro-ethyl)-2-(tetrahydro-pyran-4-yl)-4H-pyrazolo[1,5-a]quinazolin-5-one;

8-(6-Amino-pyridin-3-yl)-2-(tetrahydro-pyran-4-yl)-4-(2,2,2-trifluoro-ethyl)-4H-pyrazolo[1,5-a]quinazolin-5-one;

8-(2,6-Dimethyl-pyridin-4-yl)-2-(tetrahydro-pyran-4-yl)-4-(2,2,2-trifluoro-ethyl)-4H-pyrazolo[1,5-a]quinazolin-5-one;

8-(2,6-Dimethyl-pyridin-4-yl)-4-methyl-2-(tetrahydro-furan-3-yl)-4H-pyrazolo[1,5-a]quinazolin-5-one;

8-(2,6-Dimethyl-pyridin-4-yl)-4-methyl-2-(tetrahydro-furan-2-yl)-4H-pyrazolo[1,5-a]quinazolin-5-one;

8-(2,6-Dimethyl-pyridin-4-yl)-4-methyl-2-(tetrahydro-pyran-3-yl)-4H-pyrazolo[1,5-a]quinazolin-5-one;

8-(2,6-Dimethyl-pyridin-4-yl)-4-methyl-2-(tetrahydro-pyran-2-yl)-4H-pyrazolo[1,5-a]quinazolin-5-one;

8-(6-Amino-pyridin-3-yl)-4-methyl-2-phenyl-4H-pyrrolo[1,2-a]quinazolin-5-one;

8-(2,6-Dimethyl-pyridin-4-yl)-4-methyl-2-phenyl-4H-pyrrolo[1,2-a]quinazolin-5-one;

8-(6-Amino-pyridin-3-yl)-2-(2,6-dimethyl-pyridin-4-yl)-4-methyl-4H-pyrazolo[1,5-a]quinazolin-5-one;

2-(2,6-Dimethyl-pyridin-4-yl)-4-methyl-8-(2-methyl-pyridin-3-yl)-4H-pyrazolo[1,5-a]quinazolin-5-one;

2,8-Bis-(2,6-dimethyl-pyridin-4-yl)-4-methyl-4H-pyrazolo[1,5-a]quinazolin-5-one;

2-(2,6-Dimethyl-pyridin-4-yl)-4-methyl-8-phenyl-4H-pyrazolo[1,5-a]quinazolin-5-one;

2-(2,6-Dimethyl-pyridin-4-yl)-4-methyl-8-pyridin-3-yl-4H-pyrazolo[1,5-a]quinazolin-5-one;

2-(2,6-Dimethyl-pyridin-4-yl)-4-methyl-8-(6-methyl-pyridin-3-yl)-4H-pyrazolo[1,5-a]quinazolin-5-one;

2-(2,6-Dimethyl-pyridin-4-yl)-4-methyl-8-(5-methyl-pyridin-3-yl)-4H-pyrazolo[1,5-a]quinazolin-5-one;

2-(2,6-Dimethyl-pyridin-4-yl)-4-methyl-8-(4-methyl-pyridin-3-yl)-4H-pyrazolo[1,5-a]quinazolin-5-one;

2-(2,6-Dimethyl-pyridin-4-yl)-8-(2-ethyl-pyridin-3-yl)-4-methyl-4H-pyrazolo[1,5-a]quinazolin-5-one;

2-(2,6-Dimethyl-pyridin-4-yl)-4-methyl-8-(3-methyl-1H-pyrazol-4-yl)-4H-pyrazolo[1,5-a]quinazolin-5-one;

2-(2,6-Dimethyl-pyridin-4-yl)-4-methyl-8-(1-methyl-1H-pyrazol-4-yl)-4H-pyrazolo[1,5-a]quinazolin-5-one;

2-(2,6-Dimethyl-pyridin-4-yl)-4-methyl-8-(2H-pyrazol-3-yl)-4H-pyrazolo[1,5-a]quinazolin-5-one;

4-Methyl-2-(1-methyl-1H-pyrazol-4-yl)-8-phenyl-4H-pyrazolo[1,5-a]quinazolin-5-one;

8-(4-Methoxy-phenyl)-4-methyl-2-(1-methyl-1H-pyrazol-4-yl)-4H-pyrazolo[1,5-a]quinazolin-5-one;

4-Methyl-2-(1-methyl-1H-pyrazol-4-yl)-8-pyridin-3-yl-4H-pyrazolo[1,5-a]quinazolin-5-one;

4-Methyl-2-(1-methyl-1H-pyrazol-4-yl)-8-(2-methyl-pyridin-3-yl)-4H-pyrazolo[1,5-a]quinazolin-5-one;

8-(6-Amino-pyridin-3-yl)-4-methyl-2-(1-methyl-1H-pyrazol-4-yl)-4H-pyrazolo[1,5-a]quinazolin-5-one;

4-Methyl-2-(1-methyl-1H-pyrazol-4-yl)-8-pyridin-4-yl-4H-pyrazolo[1,5-a]quinazolin-5-one;

8-(2,6-Dimethyl-pyridin-4-yl)-4-methyl-2-(1-methyl-1H-pyrazol-4-yl)-4H-pyrazolo[1,5-a]quinazolin-5-one;

8-(6-Amino-pyridin-3-yl)-2-(1-ethyl-1H-pyrazol-4-yl)-4-methyl-4H-pyrazolo[1,5-a]quinazolin-5-one;

2-(2-methyl-pyridin-4-yl)-4-methyl-8-(2-methyl-pyridin-3-yl)-4H-pyrazolo[1,5-a]quinazolin-5-one;

8-(2,6-Dimethyl-pyridin-4-yl)-4-methyl-2-(2-methyl-pyridin-4-yl)-4H-pyrazolo[1,5-a]quinazolin-5-one;

4-Methyl-8-(2-methyl-pyridin-3-yl)-2-pyridin-3-yl-4H-pyrazolo[1,5-a]quinazolin-5-one;

4-Methyl-8-(2-methyl-pyridin-3-yl)-2-(2-trifluoromethyl-pyridin-4-yl)-4H-pyrazolo[1,5-a]quinazolin-5-one;

8-(6-Amino-pyridin-3-yl)-4-methyl-2-(2-trifluoromethyl-pyridin-4-yl)-4H-pyrazolo[1,5-a]quinazolin-5-one;

8-(2-Ethyl-pyridin-3-yl)-4-methyl-2-(2-trifluoromethyl-pyridin-4-yl)-4H-pyrazolo[1,5-a]quinazolin-5-one;

4-Methyl-8-(2-methyl-pyridin-4-yl)-2-(2-trifluoromethyl-pyridin-4-yl)-4H-pyrazolo[1,5-a]quinazolin-5-one;

4-Methyl-2,8-bis-(2-trifluoromethyl-pyridin-4-yl)-4H-pyrazolo[1,5-a]quinazolin-5-one.

8-(2-Fluoro-pyridin-4-yl)-4-methyl-2-(2-trifluoromethyl-pyridin-4-yl)-4H-pyrazolo[1,5-a]quinazolin-5-one;

8-(6-Fluoro-pyridin-3-yl)-4-methyl-2-(2-trifluoromethyl-pyridin-4-yl)-4H-pyrazolo[1,5-a]quinazolin-5-one;

4-Methyl-2-(2-trifluoromethyl-pyridin-4-yl)-8-(2-trifluoromethyl-pyridin-3-yl)-4H-pyrazolo[1,5-a]quinazolin-5-one;

8-(2,6-Dimethyl-pyridin-3-yl)-4-methyl-2-(2-trifluoromethyl-pyridin-4-yl)-4H-pyrazolo[1,5-a]quinazolin-5-one;

4-Methyl-8-(4-methyl-pyrimidin-5-yl)-2-(2-trifluoromethyl-pyridin-4-yl)-4H-pyrazolo[1,5-a]quinazolin-5-one;

8-(3,5-Dimethyl-1H-pyrazol-4-yl)-4-methyl-2-(2-trifluoromethyl-pyridin-4-yl)-4H-pyrazolo[1,5-a]quinazolin-5-one;

8-(3,5-Dimethyl-1H-pyrazol-4-yl)-2-(2,6-dimethyl-pyridin-4-yl)-4-methyl-4H-pyrazolo[1,5-a]quinazolin-5-one;

2-(2,6-Dimethyl-pyridin-4-yl)-4-methyl-8-(3-trifluoromethyl-1H-pyrazol-4-yl)-4H-pyrazolo[1,5-a]quinazolin-5-one;

or a pharmaceutically acceptable salt, solvate or prodrug thereof.

The present invention relates to a compound according to formula (I) above for use as a medicament.

The present invention relates also to a pharmaceutical composition comprising a compound according to formula (I) above and a pharmaceutically acceptable excipient.

The present invention relates also to a method of treating or preventing a disease or disorder, the method comprising the administration of the compound according to formula (I) above or the pharmaceutical composition described above, to a subject in need of such treatment or prevention. In a preferred embodiment, the invention relates to the method according to the present invention, wherein said subject is a human.

The invention relates also to the use of a compound according to general formula (I) as detailed above or the pharmaceutical composition also detailed above, for treating or preventing a condition associated with altered glutamatergic signalling and/or functions, or a condition which can be affected by alteration of glutamate level or signalling.

The invention relates also to a method of treating or preventing a condition associated with altered glutamatergic signalling and/or functions, or a condition which can be affected by alteration of glutamate level or signalling, the method comprising the administration of a compound according to general formula (I) as detailed above or the pharmaceutical composition also detailed above to a subject in need of such treatment or prevention. The invention pertains to the use of a compound, a pharmaceutical composition or a method according to the present invention wherein the condition to be treated or prevented is selected from: epilepsy; dementias; parkinsonism and movement disorders; motor neuron disease or amyotrophic lateral sclerosis; neurodegenerative and/or hereditary disorders of the nervous system; disorders of the peripheral nervous system; multiple sclerosis and other demyelinating diseases of the nervous system; infantile cerebral palsy; paralytic syndromes including hemiplegia and hemiparesis; cerebrovascular disorders; migraine; headache; myoneural disorders; disorders of the eye and visual pathways; intracranial trauma/injury and their sequels; trauma/injury to nerves and spinal cord and their sequels; poisoning and toxic effects of nonmedicinal substances; accidental poisoning by drugs, medicinal substances and biologicals acting on the central, peripheral and autonomic system; neurological and psychiatric adverse effects of drugs, medicinal and biological substances; disturbance of sphincter control and sexual function; mental disorders; delirium and cognitive disorders; substance related disorders; schizophrenia and psychotic disorders; mood disorders; anxiety disorders; eating disorders; sleep disorders; medication-induced movement disorders; endocrine and metabolic diseases; acute and chronic pain; nausea and vomiting; irritable bowel syndrome; or cancers.

In a particular embodiment, the invention relates to the use of a compound, a pharmaceutical composition or a method according to the present invention, wherein the condition to be treated or prevented is selected from: dementias; parkinsonism and movement disorders; acute or chronic pain; anxiety disorders; schizophrenia; mood disorders; endocrine or metabolic diseases; or cancers.

In a preferred embodiment, the invention relates to the use of a compound, a pharmaceutical composition or a method according to the present invention, wherein said dementias are selected from: dementias of the Alzheimer's type (DAT); Alzheimer's disease; Pick's disease; vascular dementias; Lewy-body disease; dementias due to metabolic, toxic and deficiency diseases, including alcoholism, hypothyroidism, and vitamin B12 deficiency; AIDS-dementia complex; Creutzfeld-Jacob disease; or atypical subacute spongiform encephalopathy.

In another preferred embodiment, the invention relates to the use of a compound, a pharmaceutical composition or a method according to the present invention, wherein said parkinsonism and movement disorders are selected from: Parkinson's disease; multiple system atrophy; progressive supranuclear palsy; corticobasal degeneration; hepatolenticular degeneration; chorea, including Huntington's disease and hemiballismus; athetosis; dystonias, including spasmodic torticollis, occupational movement disorder, and Gilles de la Tourette syndrome; tardive or drug induced dyskinesias; tremor; or myoclonus.

In another preferred embodiment, the invention relates to the use of a compound, a pharmaceutical composition or a method according to the present invention, wherein said anxiety disorders are selected from: panic disorders, phobias, obsessive-compulsive disorders, stress disorders, or generalized anxiety disorders.

In another preferred embodiment, the invention relates to the use of a compound, a pharmaceutical composition or a method according to the present invention, wherein said mood disorders are selected from depressive disorders or bipolar disorders.

In another preferred embodiment, the invention relates to the use of a compound, a pharmaceutical composition or a method according to the present invention, wherein said endocrine or metabolic diseases are selected from: diabetes; disorders of the endocrine glands; or hypoglycaemia.

In another preferred embodiment, the invention relates to the use of a compound, a pharmaceutical composition or a method according to the present invention, wherein said cancers are selected from: gliomas; colorectal cancer; melanoma; or prostate cancer.

The present invention describes also a method for identifying an agent that binds to metabotropic glutamate receptor 2 (mGluR2) or to metabotropic glutamate receptor 3 (mGluR3), comprising the following steps:
  (a) contacting mGluR2 or mGluR3 with the compound according to general formula (I), wherein said compound is radio-labeled or fluorescence-labeled, under conditions that permit binding of the compound to mGluR2 or mGluR3, thereby generating bound, labeled compound;
  (b) detecting a signal that corresponds to the amount of bound, labeled compound in the absence of test agent;
  (c) contacting the bound, labeled compound with a test agent;
  (d) detecting a signal that corresponds to the amount of bound labeled compound in the presence of test agent; and
  (e) comparing the signal detected in step (d) to the signal detected in step (b) to determine whether the test agent binds to mGluR2 or mGluR3.

The invention will now be described by reference to the following examples, which are merely illustrative and are not to be construed as a limitation of the scope of the present invention.

EXAMPLES

In this section, the term "compound" is used to refer to a synthesis intermediate while the term "example" refers to a compound of general formula (I) according to the present invention.

The compounds described in this section are defined by their chemical formulae and their corresponding chemical names. In case of conflict between any chemical formula and the corresponding chemical name indicated herein, the present invention relates to both the compound defined by the chemical formula and the compound defined by the chemical name.

Experimental:
Experimental Section.

All reagents were commercial grade and used without further purification. Commercially available anhydrous solvents were used for reactions conducted under inert atmosphere. Silica gel generally used for column chromatography was SDS silica gel (60AAC 40-63 µM). Thin layer chromatography was carried out using pre-coated silica gel F-254 plate. $^1$H NMR spectra were recorded on a Bruker AMX-400 spectrometer. Proton chemical shifts are listed relative to residual $CDCl_3$ (7.27 ppm), DMSO (2.51 ppm) or $D_2O$ (4.78 ppm). Splitting patterns are designated as s (singlet), d (doublet), dd (double-doublet), t (triplet), tt (triplet-trplet), td (triplet-doublet), q (quartet), quint (quintuplet), sex (sextuplet), sept (septuplet), m (multiplet), b (broad).

Electrospray MS spectra were obtained on a Waters micromass platform LCMS spectrometer.

All mass spectra were full-scan experiments (mass range 100-800 amu). Mass spectra were obtained using electro spray ionization. The HPLC system was a Waters platform with a 2767 sample manager, a 2525 pump, a photodiode array detector (190-400 nM). The column used was an XBridge $C_{18}$ 3.5 µM (4.6×50 mm) in analytical mode and an XBridge C18 OBD 5 µM (30×100 mm) in preparative mode. The mobile phase in both cases consisted in an appropriate gradient of A and B. A was water with 0.05% of TFA and B was MeOH with 0.05% of TFA. Flow rate was 1 mL per min in analytical mode and 25 mL min in preparative mode. All LCMS were performed at room temperature.

Microwave experiments were performed on a Biotage initiator. The microwave modulates the power in order to reach the selected temperature as fast as possible. The time of each experiment is the time at the selected temperature.

Melting Points are measured on a Barnstead Electrothermal 9100 and are not corrected.

General Procedure I: Formation of Hydrazine B from the Corresponding Amino Derivative a (Cf. Scheme 1).

To a suspension of amino acid A (1.0 equiv.) in concentrated aqueous HCl solution (40 equiv.) cooled by an ice bath, a cold solution of $NaNO_2$ (1.2 equiv.) in water (c=2.8 mol·$L^{-1}$) was added dropwise. The reaction mixture turned yellow with a beige suspension. After 1 hour, under vigorous stirring, a cold solution of $SnCl_2$ (3.1 equiv.) in concentrated aqueous HCl solution (c=2.8 mol·$L^{-1}$) was added dropwise. A white suspension was obtained. The reaction mixture was filtered off 2 hours later. The solid was washed with a minimum of cold water before being dried under reduced pressure at 80° C. with $P_2O_5$ for 18 hours.

Compound 1

4-Bromo-2-hydrazino-Benzoic Acid, HCl Salt

Compound 1 was obtained according to general procedure I, starting from 2-Amino-4-bromobenzoic acid, as a white solid in a quantitative yield.

$^1$H-NMR (400 MHz, DMSO): 7.14 (dd, J 8.5 Hz, 1.9 Hz, 1H, Ar); 7.37 (d, J 1.9 Hz, 1H, Ar); 7.81 (d, J 8.5 Hz, 1H, Ar); 9.15 (bs, 1H, NH); 10.63 (bs, 3H, $NH_3$). M/Z $(M[^{79}Br]-18+H)^+=213$.

General Procedure II: Formation of 4H-Pyrazolo[1,5-a]quinazolin-5-one D from Hydrazine B and Keto-Nitrile C (Cf. Scheme 1).

Method (i): Under Oil Bath Heating:

A suspension of hydrazine B (1.0 equiv.) and Keto-nitrile C (1.0 equiv.) in AcOH (c=0.2 mol·$L^{-1}$) was warmed at reflux for 2 hours. The reaction mixture turned homogeneous, and then a yellow suspension was obtained. After cooling, the reaction mixture was hydrolysed with water. The precipitate was collected, washed with water and was dried under reduced pressure at 80° C. with $P_2O_5$ for 18 hours.

Method (ii): Under Microwave Irradiation:

A suspension of hydrazine B (1.0 equiv.) and Keto-nitrile C (1.0 equiv.) in AcOH (c=0.2 mol·$L^{-1}$) was submitted to microwave irradiation (150° C.—5 min.). After cooling, the reaction mixture was hydrolysed with water. The precipitate was collected, washed with water and was dried under reduced pressure at 80° C. with $P_2O_5$ for 18 hours.

Method (iii): Under Oil Bath Heating:

A suspension of hydrazine B (1.0 equiv.) and Keto-nitrile C (1.0 equiv.) in AcOH (c=mol·$L^{-2}$) was warmed at reflux for 2 hours. After cooling, the reaction mixture was concentrated and hydrolysed with a saturated aqueous $NaHCO_3$ solution. The resulting precipitate was collected, washed with water and dried under reduced pressure at 80° C. with $P_2O_5$ for 18 hours.

Compound 2

8-Bromo-2-phenyl-4H-pyrazolo[1,5-a]quinazolin-5-one

Compound 2 was obtained according to general procedure II(i), starting from compound 1 in presence of 3-Oxo-3-phenyl-propionitrile, as a beige solid in 77% yield.

$^1$H-NMR (400 MHz, DMSO): 6.39 (s, 1H, Ar); 7.39-7.50 (m, 3H, Ar); 6.67 (dd, J 8.5 Hz, 1.9 Hz, 1H, Ar); 7.97-8.00 (m, 2H, Ar); 8.05 (d, J 8.5 Hz, 1H, Ar); 8.27 (d, J 1.9 Hz, 1H, Ar); 12.39 (s, 1H, NH). M/Z $(M[^{79}Br]+H)^+=340$.

General Procedure III: Formation of N-substituted 4H-Pyrazolo[1,5-a]quinazolin-5-one F or I or N-substituted 4H-Pyrolo[1,5-a]quinazolin-5-one P, from 4H-Pyrazolo[1,5-a]quinazolin-5-one D or L or 4H-Pyrolo[1,5-a]quinazolin-5-one O and electrophile E (cf. Scheme 1 and 2) and Formation of N-substituted 4H-Pyrolo[1,5-a]quinazolin-5-one P, 4H-Pyrolo[1,5-a]quinazolin-5-one O and Electrophile E (Cf. Scheme 3).

Under anhydrous condition, to a solution of quinazolin-5-one D, L or O (1.0 equiv.) in DMF (c=0.2 mol$L^{-1}$) cooled by an ice bath, NaH (in mineral oil 60%, 1.7 equiv.) was added in 3 portions. The mixture was stirred for 15 minutes, then the electrophile $R_4$—$X_2$ (2.0 equiv.) was added. The ice bath was removed, and the reaction was stirred at room temperature. When the reaction is completed, the mixture was hydrolysed with aqueous HCl 1N. The precipitate was collected, washed with water and was dried under reduced pressure at 80° C. with $P_2O_5$ for 18 hours.

Compound 3

8-Bromo-4-methyl-2-phenyl-4H-pyrazolo[1,5-a]quinazolin-5-one

Compound 3 was obtained according to general procedure III, starting from compound 2 in presence of iodomethane. The reaction mixture was stirred at room temperature for 90 min. Compound 3 was obtained as a beige solid in 97% yield.

$^1$H-NMR (400 MHz, DMSO): 3.56 (s, 3H, N—$CH_3$); 6.86 (s, 1H, Ar); 7.42-7.52 (m, 3H, Ar); 7.69 (dd, J 8.5 Hz, 1.9 Hz, 1H, Ar); 8.01 (m, 2H, Ar); 8.10 (d, J 8.5 Hz, 1H, Ar); 8.29 (d, J 1.9 Hz, 1H, Ar). M/Z $(M[^{79}Br]+H)^+=354$.

General Procedure IV: Formation of Example 1 from 4H-Pyrazolo[1,5-a]quinazolin-5-one F or D and Boronic Acid Derivatives G or from 4H-Pyrazolo[1,5-a]quinazolin-5-one J and Bromide K (cf. Scheme 1 and 2) or from 4H-Pyrolo[1,5-a]quinazolin-5-one P and Boronic Acid Derivatives G (Cf. Scheme 3)

Method (i): Under Microwave Irradiation:

Under inert atmosphere, a mixture of halide F, D, K or P (1.0 equiv.), boronic acid derivative $R_1$-M G or J (1.5 equiv.), $PdCl_2(dppf)_2$ (0.1 equiv.) and aqueous $NaHCO_3$ (1.2 M-3.0 equiv.) in DMF (C=0.1 mol$L^{-1}$) was submitted to microwave irradiation (120° C., 10 min, P<70 W). The reaction mixture was hydrolysed, and then extracted with EtOAc twice. The organic layers were combined, washed with brine, dried over $MgSO_4$, concentrated and purified to afford the product.

Method (ii): Under Oil Bath Heating:

Under inert atmosphere, a mixture of halide F, D, K or P (1.0 equiv.), boronic acid derivative G or J (1.5 equiv.), $PdCl_2(dppf)_2$ (0.1 equiv.) and aqueous $NaHCO_3$ (1.2 M-3.0 equiv.) in DMF (C=0.1 mol$L^{-1}$) was heated at 100° C. for 16 Hrs. After cooling, the reaction mixture was hydrolysed and then extracted with EtOAc. The organic layers were combined, washed with brine, dried over MgSO$_4$, concentrated and purified to afford the product.

Method (iii): Under Microwave Irradiation:

Under inert atmosphere, a mixture of halide F, D, K or P (1.0 equiv.), boronic acid derivative R$_1$-M G or J (1.5 equiv.), PdCl$_2$(dppf)$_2$ (0.1 equiv.) and aqueous Na$_2$CO$_3$ (1.2 M-3.0 equiv.) in DMF (C=0.1 molL$^{-1}$) was submitted to microwave irradiation (150° C., 15 min, P<70 W). The reaction mixture was hydrolysed, and then extracted with EtOAc twice. The organic layers were combined, washed with brine, dried over MgSO$_4$, concentrated and purified to afford the product.

Method (iv): Under Microwave Irradiation:

Under inert atmosphere, a mixture of halide F, D, K or P (1.0 equiv.), boronic acid derivative R$_1$-M G or J (1.5 equiv.), PdCl$_2$(dppf)$_2$ (0.1 equiv.) and aqueous Na$_2$CO$_3$ (1.2 M-3.0 equiv.) in DMF (C=0.1 molL$^{-1}$) was submitted to microwave irradiation (150° C., 15 min, P<70 W). After cooling, the reaction mixture was filtered through a pad of celite. The pad was rinsed twice with DMSO (5 volume of DMF each time) and water was added to the filtrate (25 volume of DMF). The resulting precipitate was collected and purified by flash-chromatography.

Method (v): Under Microwave Irradiation:

Under inert atmosphere, a mixture of halide F, D, K or P (1.0 equiv.), boronic acid derivative R$_1$-M G or J (1.5 equiv.), PdCl$_2$(dppf)$_2$ (0.1 equiv.) and aqueous Na$_2$CO$_3$ (1.2 M-3.0 equiv.) in DMF (C=0.1 molL$^{-1}$) was submitted to microwave irradiation (150° C., 15 min, P<70 W). After cooling, the reaction mixture was filtered through a pad of celite. The pad was rinsed twice with Et$_2$O (1 volume of DMF each time), then with MeOH and CH$_2$Cl$_2$. MeOH and CH$_2$Cl$_2$ filtrates were combined, concentrated and purified by flash-chromatography.

Method (vi): Under Microwave Irradiation:

Under inert atmosphere, a mixture of halide F, D, K or P (1.0 equiv.), boronic acid derivative R$_1$-M G or J (1.5 equiv.), PdCl$_2$(dppf)$_2$ (0.1 equiv.) and aqueous Na$_2$CO$_3$ (1.2 M-3.0 equiv.) in DMF (C=0.1 molL$^{-1}$) was submitted to microwave irradiation (150° C., 15 min, P<70 W). After cooling, the reaction mixture was filtered through a pad of celite. Water was added to the filtrate (25 volume of DMF). The resulting solid was collected, washed with water, dried under reduced pressure at 50° C. with P$_2$O$_5$ (solid 1). The pad was rinsed twice with Et$_2$O (1 volume of DMF each time), then with MeOH and CH$_2$Cl$_2$. MeOH and CH$_2$Cl$_2$ filtrates were combined and concentrated (solid 2). Solid 1 and solid 2 were combined and purified by flash-chromatography.

Method (vii): Under Microwave Irradiation:

Under inert atmosphere, a mixture of halide F, D, K or P (1.0 equiv.), boronic acid derivative R$_1$-M G or J (1.5 equiv.), PdCl$_2$(dppf)$_2$ (0.1 equiv.) and aqueous Na$_2$CO$_3$ (1.2 M-3.0 equiv.) in DMF (C=0.15 molL$^{-1}$) was submitted to microwave irradiation (150° C., 15 min, P<70 W). After cooling, the reaction mixture was centrifuged, the surnatant was removed and the remaining deposit was washed three times with DMSO (3 mL of DMSO each time). Upon addition of 50 mL of water, an unfilterable precipitate was obtained. The precipitate was extracted in AcOEt three times. The organic layers were combined, washed with brine, dried over MgSO$_4$, concentrated and purified by flash chromatography to afford the product.

Method (viii): Under Microwave Irradiation:

Under inert atmosphere, a mixture of halide F, D, K or P (1.0 equiv.), boronic acid derivative R$_1$-M G or J (1.5 equiv.), PdCl$_2$(dppf)$_2$ (0.1 equiv.) and aqueous Na$_2$CO$_3$ (1.2 M-3.0 equiv.) in DMF (C=0.15 molL$^{-1}$) was submitted to microwave irradiation (150° C., 15 min, P<70 W). After cooling, the reaction mixture was centrifuged, the surnatant was removed and the remaining deposit was washed three times with DMSO (3 mL of DMSO each time). Upon addition of 50 mL of water, a precipitate was obtained. The precipitate was filtered and purified by flash chromatography to afford the product.

Method (ix): Under Microwave Irradiation:

Under inert atmosphere, a mixture of halide F, D, K or P (1.0 equiv.), boronic acid derivative R$_1$-M G or J (1.5 equiv.), PdCl$_2$(dppf)$_2$ (0.1 equiv.) and aqueous Na$_2$CO$_3$ (1.2 M-3.0 equiv.) in DMF (C=0.1 molL$^{-1}$) was submitted to microwave irradiation (150° C., 15 min, P<70 W). After cooling, the reaction mixture was centrifuged, the surnatant was removed and the remaining deposit was washed twice with Et$_2$O. The precipitate was filtered and purified by flash chromatography to afford the product.

In some cases, the HCl salt was prepared.

General Procedure V: Formation of HCl Salt

Method (I): in DCM:

To a solution of the free base in DCM, HCl in Et$_2$O (2N, 5 equiv.) was added. The resulting precipitate was collected, washed with Et$_2$O and dried at 50° C. under reduce pressure with P$_2$O$_5$.

Method (ii): Concentration from MeOH:

To a solution or suspension of the free base in MeOH, HCl in MeOH (1.25N, 5 equiv.) was added. The mixture was vigorously stirred, then concentrated. The residue was taken in Et$_2$O. The resulting solid was collected, washed with Et$_2$O and dried at 50° C. under reduced pressure with P$_2$O$_5$.

Method (iii): Filtration from MeOH:

The free base was suspended in MeOH and HCl in MeOH (1.25N, 5 equiv.) was added. The suspension was vigorously stirred, and then the solid was collected, washed with Et$_2$O and dried at 50° C. under reduced pressure with P$_2$O$_5$.

Example 1

3-(4-Methyl-5-oxo-2-phenyl-4,5-dihydro-pyrazolo[1,5-a]quinazolin-8-yl)-benzenesulfonamide

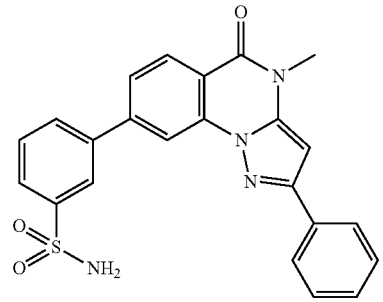

Example 1 was obtained according to general procedure IV(i) starting from compound 3 in presence of 3-Boronobenzensulfonamide pinacol ester. Purification by flash-chromatography (AcOEt in cyclohexane, 50 to 80%) afforded the product as a yellow solid in 44% yield.

$^1$H-NMR (400 MHz, DMSO): 3.61 (s, 3H, N—CH$_3$); 6.82 (s, 1H, Ar); 7.44 (t, J 7.3 Hz, 1H, Ar); 7.52 (m, 4H, Ar+NH$_2$); 7.79 (t, J 7.8 Hz, 1H, Ar); 7.86 (dd, J 8.3 Hz, 1.4 Hz, 1H, Ar); 7.95 (d, J 7.8 Hz, 1H, Ar); 8.04 (m, 1H, Ar);

8.12 (d, J 7.8 Hz, 2H, Ar); 8.30 (m, 1H, Ar); 8.33 (d, J 8.3 Hz, 1H, Ar); 8.42 (d, J 1.4 Hz, 1H, Ar). M/Z (M+H)$^+$=431.0. MP: 220-230° C.

Example 2

8-(6-Amino-pyridin-3-yl)-4-methyl-2-phenyl-4H-pyrazolo[1,5-a]quinazolin-5-one, HCl salt

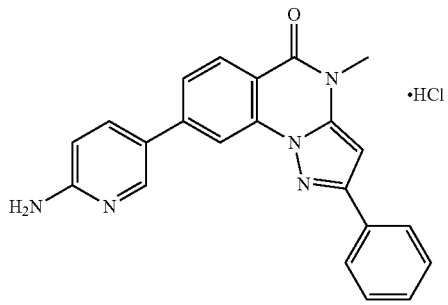 [SMILES: Cn1c(=O)c2ccc(-c3ccc(N)nc3)cc2n2nc(-c3ccccc3)cc12 ; Cl]

Example 2 was obtained according to general procedure IV(i) starting from compound 3 in presence of 2-aminopyridine-5-boronic acid pinacol ester. Purification by flash-chromatography (MeOH in EtOAc, 0 to 20%) and salt formation according to procedure V(ii), afforded example 2 as a yellow solid in 53% yield.

$^1$H-NMR (400 MHz, DMSO): 3.57 (s, 3H, N—CH$_3$); 6.87 (s, 1H, Ar); 7.14 (d, J 9.3 Hz, 1H, Ar); 7.40-7.54 (m, 3H, Ar); 7.79 (dd, J 8.3 Hz, 1.5 Hz, 1H, Ar); 8.02-8.05 (m, 2H, Ar); 8.20 (bs, 2H, NH$_2$); 8.25 (d, J 8.3 Hz, 1H, Ar); 8.34 (d, J 1.7 Hz, 1H, Ar); 8.46 (dd, J 9.3 Hz, J 2.2 Hz 1H, Ar); 8.57 (d, J 2.2 Hz, 1H, Ar). M/Z (M+H)$^+$=368.1. MP: 241-244° C.

Example 3

8-(4-Amino-phenyl)-4-methyl-2-phenyl-4H-pyrazolo[1,5-a]quinazolin-5-one

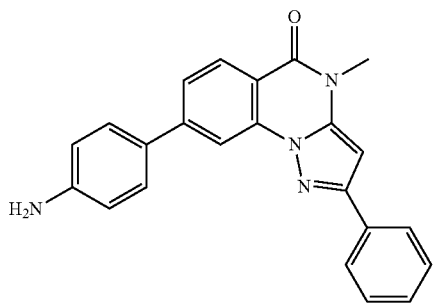 [SMILES: Cn1c(=O)c2ccc(-c3ccc(N)cc3)cc2n2nc(-c3ccccc3)cc12]

Example 3 was obtained according to general procedure IV(i) starting from compound 3 in presence of 4-aminophenyl boronic acid pinacol ester. Purification by flash-chromatography (AcOEt in cyclohexane, 50 to 100%) afforded the product as a yellow solid in 43% yield.

$^1$H-NMR (400 MHz, DMSO): 3.58 (s, 3H, N—CH$_3$); 6.73 (d, J 8.3 Hz, 1H, Ar); 6.81 (s, 1H, Ar); 7.43-7.88 (m, 8H, Ar); 8.03-8.36 (m, 5H, Ar). NH$_2$ signal is under one of the aromatic massif. M/Z (M+H)$^+$=367.1. MP: 173-175° C.

Example 4

4-Methyl-8-(6-morpholin-4-yl-pyridin-3-yl)-2-phenyl-4H-pyrazolo[1,5-a]quinazolin-5-one, HCl Salt

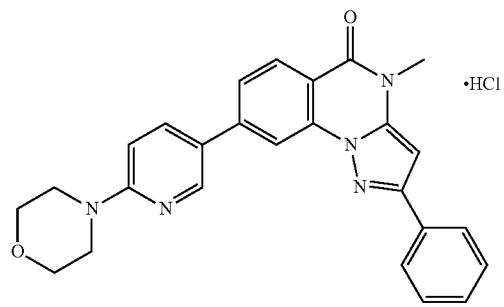 [SMILES: Cn1c(=O)c2ccc(-c3ccc(N4CCOCC4)nc3)cc2n2nc(-c3ccccc3)cc12 ; Cl]

Example 4 was obtained according to general procedure IV(i) starting compound 3 in presence of 6-(morpholin-4-yl) pyridine-3-boronic acid pinacol ester. Purification by flash-chromatography (AcOEt in cyclohexane, 50%) and salt formation according to procedure V(i) afforded example 4 as a yellow solid in 46% yield.

$^1$H-NMR (400 MHz, DMSO): 3.58 (s, 3H, (N—CH$_3$); 3.71 (s, 4H, 2(N—CH$_2$)); 3.78 (s, 4H, 2(O—CH$_2$)); 6.83 (s, 1H, Ar); 7.27 (d, J 9.0 Hz, 1H, Ar); 7.41-7.52 (m, 3H, Ar); 7.81 (d, J 8.0 Hz, 1H, Ar); 8.02 (d, J 7.6 Hz, 2H, Ar); 8.21 (d, J 8.2 Hz, 1H, Ar); 8.32 (bs, 2H, Ar); 8.56 (d, J 1.3 Hz, 1H, Ar). M/Z (M+H)$^+$=438.1. MP: 194-196° C.

Example 5

4-Methyl-2-phenyl-8-(3,4,5,6-tetrahydro-2H-[1,2']bipyridinyl-5'-yl)-4H-pyrazolo[1,5-a]quinazolin-5-one, HCl Salt

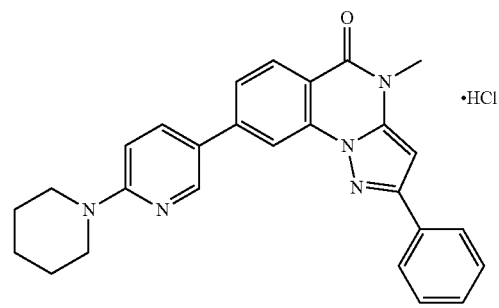 [SMILES: Cn1c(=O)c2ccc(-c3ccc(N4CCCCC4)nc3)cc2n2nc(-c3ccccc3)cc12 ; Cl]

Example 5 was obtained according to general procedure IV(i), starting from compound 3 in presence of 6-(piperidin-1-yl) pyridine-3-boronic acid pinacol ester. Purification by flash-chromatography (AcOEt in cyclohexane, 40%) and salt formation according to procedure V(i) afforded example 5 as a yellow solid in 34% yield.

$^1$H-NMR (400 MHz, DMSO): 1.66 (s, 6H, 3(CH$_2$)); 3.56 (s, 3H, N—CH$_3$); 3.74 (s, 4H, 2(N—CH$_2$)); 6.82 (s, 1H, Ar); 7.34-7.50 (m, 4H, Ar); 7.79 (dd, J 8.3 Hz, J 1.3 Hz, 1H, Ar); 8.00 (m, 2H, Ar); 8.20 (d, J 8.3 Hz, 1H, Ar); 8.30 (m, 2H, Ar); 8.45 (d, J 1.8 Hz, 1H, Ar). M/Z (M+H)$^+$=436.1. MP: 200-203° C.

Example 6

4-Methyl-2-phenyl-8-(1H-pyrazol-4-yl)-4H-pyrazolo[1,5-a]quinazolin-5-one

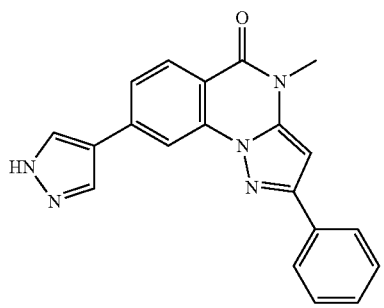 [SMILES: Cn1c(=O)c2ccc(-c3cn[nH]c3)cc2n2nc(-c3ccccc3)cc12]

Example 6 was obtained according to general procedure IV(ii) starting from Compound 3 in presence of 1-H-pyrazole-4-boronic acid. Purification by flash-chromatography (AcOEt in cyclohexane, 0 to 100%) afforded example 6 as a white solid in 25% yield.

$^1$H-NMR (400 MHz, DMSO): 3.57 (s, 3H, N—CH$_3$); 6.81 (s, 1H, Ar); 7.41-7.53 (m, 3H, Ar); 7.77 (dd, J 8.3 Hz, J 1.6 Hz, 1H, Ar); 8.05-8.07 (m, 2H, Ar); 8.14 (d, J 8.3 Hz, 1H, Ar); 8.18 (bs, 1H, Ar); 8.31 (d, J 1.6 Hz, 1H, Ar); 8.55 (bs, 1H, Ar); 13.24 (s, 1H, NH). M/Z (M+H)$^+$=342.2. MP: >250° C.

Example 7

8-(4-Methoxy-phenyl)-4-methyl-2-phenyl-4H-pyrazolo[1,5-a]quinazolin-5-one

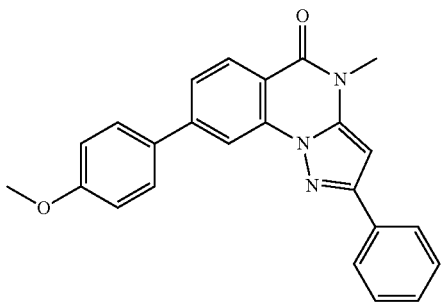 [SMILES: COc1ccc(-c2ccc3c(=O)n(C)c4cc(-c5ccccc5)nn4c3c2)cc1]

Example 7 was obtained according to general procedure IV(i) starting from compound 3 in presence of 4-methoxyphenyl boronic acid. Purification by flash-chromatography (AcOEt in cyclohexane, 40 to 60%) afforded example 7 as a yellow solid in 55% yield.

$^1$H-NMR (400 MHz, DMSO): 3.60 (s, 3H, N—CH$_3$); 3.86 (s, 3H, O—CH$_3$); 6.86 (s, 1H, Ar); 7.14 (d, J 8.9 Hz, 2H, Ar); 7.41-7.53 (m, 3H, Ar); 7.80 (dd, J 8.4 Hz, J 1.7 Hz, 1H, Ar); 7.83-7.86 (m, 2H, Ar); 8.04-8.06 (m, 2H, Ar); 8.22 (d, J 8.4 Hz, 1H, Ar); 8.33 (d, J 1.7 Hz, 1H, Ar). M/Z (M+H)$^+$=382.1. MP: >250° C.

Example 8

8-Imidazo[1,2-a]pyridin-6-yl-4-methyl-2-phenyl-4H-pyrazolo[1,5-a]quinazolin-5-one

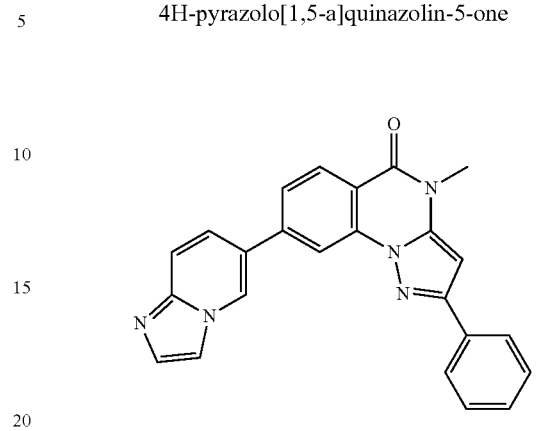

Example 8 was obtained according to general procedure IV(i) starting from compound 3 in presence of imidazo[1,2-a]pyridine-6-boronic acid. Purification by flash-chromatography (MeOH in EtOAc, 0 to 10%) afforded example 8 as a beige solid in 51% yield.

$^1$H-NMR (400 MHz, DMSO): 3.58 (s, 3H, N—CH$_3$); 6.83 (s, 1H, Ar); 7.41-7.52 (m, 3H, Ar); 7.68-7.75 (m, 3H, Ar); 7.84 (dd, J 8.3 Hz, J 1.6 Hz, 1H, Ar); 8.03-8.07 (m, 3H, Ar); 8.25 (d, J 8.3 Hz, 1H, Ar); 8.40 (d, J 1.6 Hz, 1H, Ar); 9.23 (s, 1H, Ar). M/Z (M+H)$^+$=392.0. MP: >250° C.

Example 9

8-(3-Methoxymethyl-phenyl)-4-methyl-2-phenyl-4H-pyrazolo[1,5-a]quinazolin-5-one

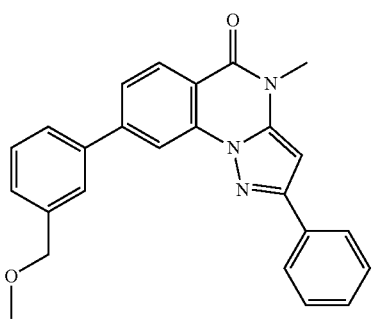 [SMILES: COCc1cccc(-c2ccc3c(=O)n(C)c4cc(-c5ccccc5)nn4c3c2)c1]

Example 9 was obtained according to general procedure IV(i) starting from compound 3 in presence of 3-methoxymethylbenzene boronic acid. Purification by flash-chromatography (AcOEt in cyclohexane, 20 to 40%) afforded example 9 as a white solid in 60% yield.

$^1$H-NMR (400 MHz, DMSO): 3.37 (s, 3H, O—CH$_3$); 3.57 (s, 3H, N—CH$_3$); 4.55 (s, 2H, O—CH$_2$); 6.82 (s, 1H, Ar); 7.41-7.57 (m, 5H, Ar); 7.76-7.80 (m, 3H, Ar); 8.01-8.04 (m, 2H, Ar); 8.24 (d, J 8.2 Hz, 1H, Ar); 8.33 (d, J 1.5 Hz, 1H, Ar). M/Z (M+H)$^+$=396.1. MP: 132-134° C.

Example 10

4-(4-Methyl-5-oxo-2-phenyl-4,5-dihydro-pyrazolo[1,5-a]quinazolin-8-yl)-benzenesulfonamide

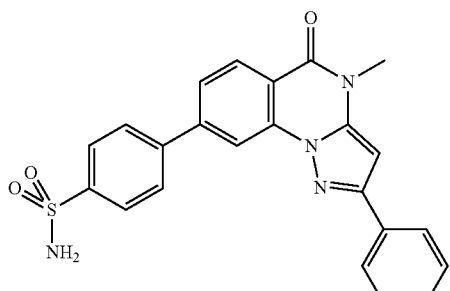

Example 10 was obtained according to general procedure IV(i) starting from compound 3 in presence of 4-sulfamoyl-benzeneboronic acid. The reaction mixture was submitted to microwave irradiation for 1 Hr at 150° C. Purification by flash-chromatography (AcOEt in cyclohexane, 30 to 100%) afforded example 10 as a white solid in 44% yield.

$^1$H-NMR (400 MHz, DMSO): 3.58 (s, 3H, N—CH$_3$); 6.83 (s, 1H, Ar); 7.38-7.51 (m, 5H, Ar+NH$_2$); 7.85 (dd, J 8.3 Hz, 1.6 Hz, 1H, Ar); 7.96-8.07 (m, 6H, Ar); 8.27 (d, J 8.3 Hz, 1H, Ar); 8.42 (d, J 1.6 Hz, 1H, Ar). M/Z (M+H)$^+$=431.0. MP: >250° C.

Example 11

8-(3-Methoxy-phenyl)-4-methyl-2-phenyl-4H-pyrazolo[1,5-a]quinazolin-5-one

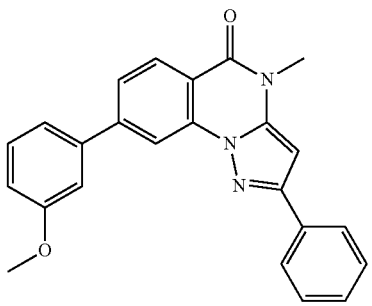 [SMILES: COc1cccc(-c2ccc3c(=O)n(C)c4cc(-c5ccccc5)nn4c3c2)c1]

Example 11 was obtained according to general procedure IV(i) starting from compound 3 in presence of 3-methoxy-phenyl boronic acid. Purification by flash-chromatography (AcOEt in cyclohexane, 0 to 40%) afforded example 11 as a yellow solid in 64% yield.

$^1$H-NMR (400 MHz, DMSO): 3.59 (s, 3H, N—CH$_3$); 3.88 (s, 3H, O—CH$_3$); 6.84 (s, 1H, Ar); 7.08 (dd, J 8.1 Hz, J 1.6 Hz, 1H, Ar); 7.35-7.52 (m, 6H, Ar); 7.81 (dd, J 8.3 Hz, J 1.6 Hz, 1H, Ar); 8.02-8.05 (m, 2H, Ar); 8.24 (d, J 8.3 Hz, 1H, Ar); 8.35 (d, J 1.6 Hz, 1H, Ar). M/Z (M+H)$^+$=382.1. MP: 182-185° C.

Example 12

8-(4-Fluoro-phenyl)-4-methyl-2-phenyl-4H-pyrazolo[1,5-a]quinazolin-5-one

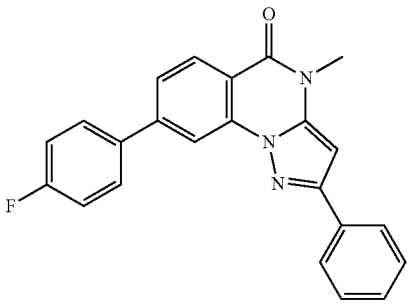 [SMILES: Cn1c(=O)c2ccc(-c3ccc(F)cc3)cc2n2nc(-c3ccccc3)cc12]

Example 12 was obtained according to general procedure IV(i) starting from compound 3 in presence of 4-fluorophenyl boronic acid. Purification by flash-chromatography (AcOEt in cyclohexane, 20%) afforded example 12 as a white solid in 67% yield.

$^1$H-NMR (400 MHz, DMSO): 3.57 (s, 3H, N—CH$_3$); 6.83 (s, 1H, Ar); 7.37-7.53 (m, 5H, Ar); 7.78 (dd, J 8.3 Hz, J 1.6 Hz, 1H, Ar); 7.90-7.93 (m, 2H, Ar); 8.02-8.04 (m, 2H, Ar); 8.22 (d, J 8.3 Hz, 1H, Ar); 8.32 (d, J 1.6 Hz, 1H, Ar). M/Z (M+H)$^+$=370.1. MP: 178-180° C.

Example 13

8-(4-Chloro-phenyl)-4-methyl-2-phenyl-4H-pyrazolo[1,5-a]quinazolin-5-one

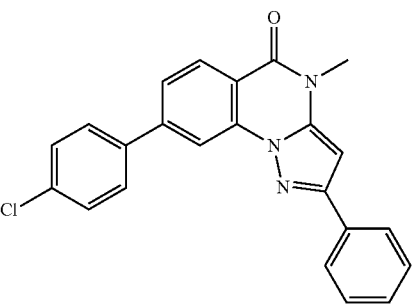 [SMILES: Cn1c(=O)c2ccc(-c3ccc(Cl)cc3)cc2n2nc(-c3ccccc3)cc12]

Example 13 was obtained according to general procedure IV(i) starting from compound 3 in presence of potassium-4-Chlorophenyl trifluoroborate. The reaction mixture was submitted to microwave irradiation for 30 min at 130° C. Purification by flash-chromatography (AcOEt in cyclohexane, 20%) and then by preparative HPLC afforded example 13 as a light yellow solid in 4% yield.

$^1$H-NMR (400 MHz, DMSO): 3.60 (s, 3H, N—CH$_3$); 6.86 (s, 1H, Ar); 7.42-7.54 (m, 3H, Ar); 7.62-7.66 (m, 2H, Ar); 7.83 (dd, J 8.3 Hz, J 1.7 Hz, 1H, Ar); 7.90-7.93 (m, 2H, Ar); 8.02-8.05 (m, 2H, Ar); 8.27 (d, J 8.3 Hz, 1H, Ar); 8.38 (d, J 1.7 Hz 1H, Ar). M/Z (M[$^{35}$Cl]+H)$^+$=386.0. MP: 184-186° C.

Example 14

8-(3-Acetyl-phenyl)-4-methyl-2-phenyl-4H-pyrazolo[1,5-a]quinazolin-5-one

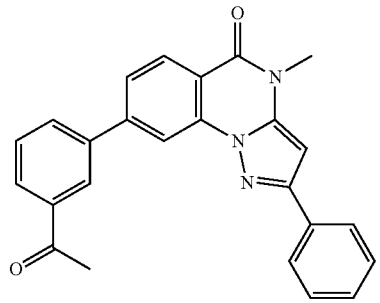 [SMILES: CC(=O)c1cccc(-c2ccc3c(=O)n(C)c4cc(-c5ccccc5)nn4c3c2)c1]

Example 14 was obtained according to general procedure IV(i) starting from compound 3 in presence of 3-acetylphenylboronic acid. The reaction mixture was submitted to microwave irradiation for 30 min at 130° C. Purification by flash-chromatography (AcOEt in cyclohexane, 40 to 50%) afforded example 14 as a white solid in 87% yield.

$^1$H-NMR (400 MHz, DMSO): 2.71 (s, 3H, C(O)CH$_3$); 3.60 (s, 3H, N—CH$_3$); 6.86 (s, 1H, Ar); 7.41-7.53 (m, 3H, Ar); 7.74 (t, J 7.6 Hz, 1H, Ar); 7.89 (dd, J 8.3 Hz, J 1.3 Hz, 1H, Ar); 8.03-8.05 (m, 2H, Ar); 8.09 (d, J 7.6 Hz, 1H, Ar); 8.13 (d, J 7.6 Hz, 1H, Ar); 8.29 (d, J 8.3 Hz, 1H, Ar); 8.34 (bs, 1H, Ar); 8.41 (bs, 1H, Ar). M/Z (M+H)$^+$=394.1. MP: 207-209° C.

Example 15

8-(3,5-Dimethyl-1H-pyrazol-4-yl)-4-methyl-2-phenyl-4H-pyrazolo[1,5-a]quinazolin-5-one

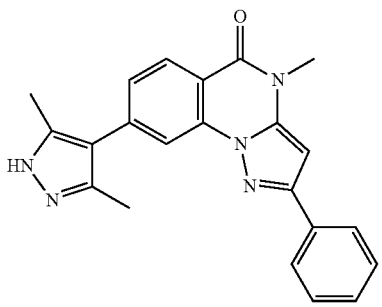 [SMILES: Cc1n[nH]c(C)c1-c1ccc2c(=O)n(C)c3cc(-c4ccccc4)nn3c2c1]

Example 15 was obtained according to general procedure IV(i) starting from compound 3 in presence of 3,5-dimethylpyrazole-4-boronic acid pinacol ester. The reaction mixture was submitted twice to microwave irradiation for 30 min at 130° C. Purification by flash-chromatography (AcOEt in cyclohexane, 70 to 80%) afforded example 15 as a light yellow solid in 53% yield.

$^1$H-NMR (400 MHz, DMSO): 2.33 (m, 6H, 2(CCH$_3$)); 3.59 (s, 3H, N—CH$_3$); 6.83 (s, 1H, Ar); 7.40-7.52 (m, 4H, Ar); 8.00-8.02 (m, 2H, Ar); 8.05 (d, J 1.5 Hz, 1H, Ar); 8.19 (d, J 8.3 Hz, 1H, Ar); 12.56 (bs, 1H, NH). M/Z (M+H)$^+$= 370.0. MP: >250° C.

Example 16

4-Methyl-8-(1-methyl-1H-pyrazol-4-yl)-2-phenyl-4H-pyrazolo[1,5-a]quinazolin-5-one

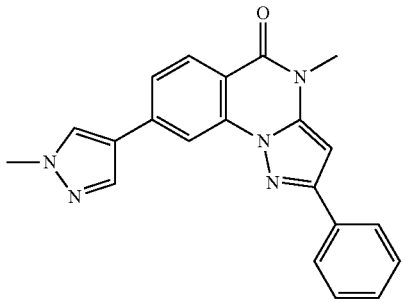 [SMILES: Cn1cc(-c2ccc3c(=O)n(C)c4cc(-c5ccccc5)nn4c3c2)cn1]

Under anhydrous condition, to a solution of example 7 (25 mg, 1.0 equiv.) in DMF (1.5 mL) cooled by an ice bath, NaH (in mineral oil 60%, 5.0 mg, 1.7 equiv.) was added. The mixture was stirred for 15 minutes, then methyl iodide (9.5 µL, 2.1 equiv.) was added. The ice bath was removed, and the reaction mixture was stirred at room temperature for 90 min. The reaction mixture was hydrolysed with aqueous HCl 1N (15 mL) and extracted with Ethyl acetate (30 mL). The organic layer was washed with brine (15 mL), dried over MgSO$_4$ and concentrated. Purification by flash-chromatography (AcOEt in cyclohexane, 50 to 100%) afforded example 16 as a light yellow solid in 51% yield.

$^1$H-NMR (400 MHz, DMSO): 3.56 (s, 3H, N—CH$_3$); 3.92 (s, 3H, N—CH$_3$); 6.81 (s, 1H, Ar); 7.41-7.53 (m, 3H, Ar); 7.71 (dd, J 8.4 Hz, J 1.6 Hz, 1H, Ar); 8.03-8.05 (m, 2H, Ar); 8.12 (bs, 1H, Ar); 8.14 (d, J 8.4 Hz, 1H, Ar); 8.25 (d, J 1.6 Hz 1H, Ar); 8.49 (s, 1H, Ar). M/Z (M+H)$^+$=356.1. MP: >250° C.

Example 17

4-Methyl-2-phenyl-8-(1H-pyrazol-3-yl)-4H-pyrazolo[1,5-a]quinazolin-5-one

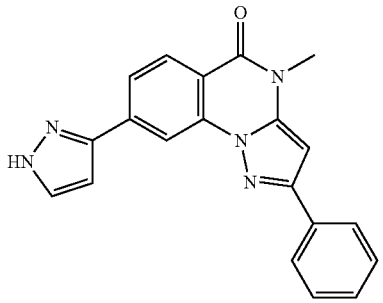 [SMILES: Cn1c(=O)c2ccc(-c3cc[nH]n3)cc2n2nc(-c3ccccc3)cc12]

Example 17 was obtained according to general procedure IV(i) starting from compound 3 in presence potassium 1H-pyrazole-3-trifluoroborate. The reaction mixture was submitted twice to microwave irradiation for 1 Hr at 130° C., then for 1 Hr at 150° C. after addition of potassium 1H-pyrazole-3-trifluoroborate (0.5 equiv.). Purification by flash-chromatography (AcOEt in cyclohexane, 50 to 60%) afforded example 17 as a white solid in 34% yield.

¹H-NMR (400 MHz, DMSO): 3.58 (s, 3H, N—CH₃); 6.83 (s, 1H, Ar); 7.00 (d, J 2.0 Hz, 1H, Ar); 7.43-7.54 (m, 3H, Ar); 7.92 (m, 1H, Ar); 7.96 (dd, J 8.3 Hz, J 1.3 Hz, 1H, Ar); 8.03-8.06 (m, 2H, Ar); 8.21 (d, J 8.3 Hz, 1H, Ar); 8.60 (d, J 1.3 Hz, 1H, Ar); 13.24 (bs, 1H, NH). Presence of the pyrazole tautomeric form (around 10%). M/Z (M+H)⁺= 342.1. MP: 245-249° C.

Example 18

4-Methyl-8-(3-methyl-1H-pyrazol-4-yl)-2-phenyl-4H-pyrazolo[1,5-a]quinazolin-5-one

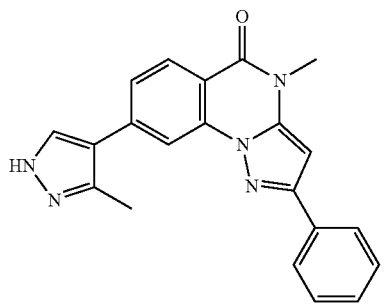 [SMILES: Cc1n[nH]cc1-c1ccc2c(=O)n(C)c3cc(-c4ccccc4)nn3c2c1]

Example 18 was obtained according to general procedure IV(i) starting from compound 3 in presence 3-methyl-1H-pyrazole-4-boronic acid pinacol ester. The reaction mixture was submitted to microwave irradiation for 1 Hr at 130° C., then for 1 Hr at 150° C. after addition of 3-methyl-1H-pyrazole-4-boronic acid pinacol ester (0.5 equiv.). Purification by flash-chromatography (AcOEt in cyclohexane, 70%) afforded example 18 as a light yellow solid in 46% yield.

¹H-NMR (400 MHz, DMSO): 2.54 (bs, 3H, CH₃); 3.57 (s, 3H, N—CH₃); 6.81 (s, 1H, Ar); 7.40-7.53 (m, 3H, Ar); 7.64 (d, J 8.3 Hz, 1H, Ar); 7.96 (m, 1H, Ar); 8.01-8.03 (m, 2H, Ar); 8.16 (d, 1H, J 8.3 Hz, 1H, Ar); 8.19 (m, 1H, Ar); 12.88-12.94 (m, 1H, NH). Presence of the pyrazole tautomeric form (around 5%). M/Z (M+H)⁺=356.1. MP: 174-176° C.

Example 19

4-Methyl-2-phenyl-8-(3-trifluoromethyl-1H-pyrazol-4-yl)-4H-pyrazolo[1,5-a]quinazolin-5-one

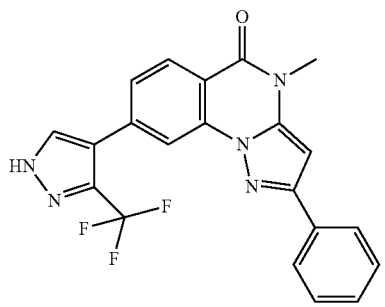 [SMILES: Cn1c(=O)c2ccc(-c3c[nH]nc3C(F)(F)F)cc2n2nc(-c3ccccc3)cc12]

Example 19 was obtained according to general procedure IV(i) starting from compound 3 in presence 3-trifluoromethyl-1H-pyrazole-4-boronic acid pinacol ester. The reaction mixture was submitted to microwave irradiation for 1 Hr at 150° C. Purification by flash-chromatography (AcOEt in cyclohexane, 60%) afforded example 19 as a white solid in 82% yield.

¹H-NMR (400 MHz, DMSO): 3.59 (s, 3H, N—CH₃); 6.84 (s, 1H, Ar); 7.41-7.53 (m, 3H, Ar); 7.59 (dd, J 8.3 Hz, J 1.6 Hz, 1H, Ar); 7.99-8.01 (m, 2H, Ar); 8.23 (d, J 8.3 Hz, 1H, Ar); 8.25 (d, J 1.6 Hz, 1H, Ar); 8.54 (bs, 1H, Ar); 14.01 (bs, 1H, NH). M/Z (M+H)⁺=410.1. MP: >250° C.

Example 20

4-Methyl-8-oxazol-2-yl-2-phenyl-4H-pyrazolo[1,5-a]quinazolin-5-one

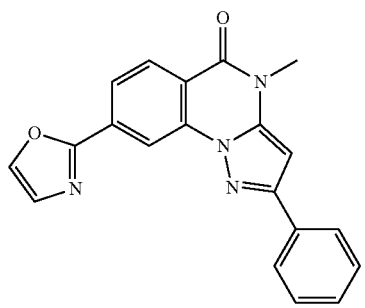 [SMILES: Cn1c(=O)c2ccc(-c3ncco3)cc2n2nc(-c3ccccc3)cc12]

Under inert atmosphere, a mixture of compound 3 (50 mg, 1.0 equiv.), isoxazole (19 μL, 2.0 equiv.), pivalic acid (6 mg, 0.4 equiv.), palladium acetate (1.6 mg, 0.05 equiv.), Ruphos® (6.6 mg, 0.1 equiv.), and K₂CO₃ (58 mg, 3.0 equiv.) in toluene (1 mL) was heated at 110° C. for 16 Hrs. After cooling, the reaction mixture was hydrolysed with aqueous HCl 1N (10 mL) and was extracted twice with EtOAc (20 mL). The organic layers were combined, washed with brine (30 mL), dried over MgSO₄, and concentrated. Purification by preparative HPLC afforded example 20 as a white solid in 24% yield.

¹H-NMR (400 MHz, DMSO): 3.57 (s, 3H, N—CH₃); 6.85 (s, 1H, Ar); 7.42-7.54 (m, 3H, Ar); 7.55 (d, J 0.7 Hz, 1H, Ar); 8.01-8.06 (m, 3H, Ar); 8.31 (d, J 8.3 Hz, 1H, Ar); 8.39 (d, J 0.7 Hz, 1H, Ar); 8.64 (d, J 1.4 Hz, 1H, Ar). M/Z (M+H)⁺=343.1. MP: 228-231° C.

Example 21

4-Methyl-8-oxazol-5-yl-2-phenyl-4H-pyrazolo[1,5-a]quinazolin-5-one

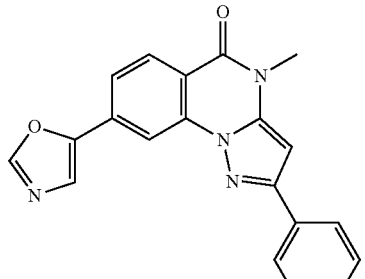

Under inert atmosphere, a mixture of compound 3 (50 mg, 1.0 equiv.), isoxazole (19 µL, 2.0 equiv.), pivalic acid (6 mg, 0.4 equiv.), palladium acetate (1.6 mg, 0.05 equiv.), CataCxium® AHI (7.0 mg, 0.1 equiv.), and $K_2CO_3$ (60 mg, 3.1 equiv.) in DMA (1 mL) was heated at 110° C. for 16 Hrs. After cooling, the reaction mixture was hydrolysed with aqueous HCl 1N (10 mL) and was extracted twice with EtOAc (20 mL). The organic layers were combined, washed with brine (30 mL), dried over $MgSO_4$, and concentrated. Purification by preparative HPLC afforded example 21 as a white solid in 24% yield.

$^1$H-NMR (400 MHz, DMSO): 3.56 (s, 3H, N—$CH_3$); 6.83 (s, 1H, Ar); 7.41-7.53 (m, 3H, Ar); 7.84 (dd, J 8.3 Hz, J 1.6 Hz, 1H, Ar); 8.01-8.04 (m, 2H, Ar); 8.08 (bs, 1H, Ar); 8.24 (d, J 8.3 Hz, 1H, Ar); 8.36 (d, J 1.6 Hz, 1H, Ar); 8.62 (bs, 1H, Ar). M/Z (M+H)$^+$=343.1. MP: 222-225° C.

Compound 4

4-Methyl-5-oxo-2-phenyl-4,5-dihydro-pyrazolo[1,5-a]quinazoline-8-carbonitrile

Under inert atmosphere, a mixture of compound 3 (250 mg, 1.0 equiv.), zinc cyanide (166 mg, 2.0 equiv.) and Pd(PPh$_3$)$_4$ (82 mg, 0.10 equiv.) in DMF (5 mL) was submitted to microwave irradiation for 30 min. at 130° C. After cooling, the reaction mixture was hydrolysed with NaHCO$_3$ aqueous saturated solution (50 mL) and Et$_2$O (70 mL) was added. A solid was collected. The solid was washed with aqueous HCl 1N, water and was dried under reduced pressure with P$_2$O$_5$ at 50° C. Compound 4 was isolated without further purification as a yellow solid in 77% yield.

$^1$H-NMR (400 MHz, DMSO): 3.58 (s, 3H, N—CH$_3$); 6.90 (s, 1H, Ar); 7.43-7.54 (m, 3H, Ar); 7.90 (dd, J 8.2 Hz, J 1.3 Hz, 1H, Ar); 8.02-8.04 (m, 2H, Ar); 8.32 (d, J 8.2 Hz, 1H, Ar); 8.55 (d, J 1.6 Hz, 1H, Ar). M/Z (M+H)$^+$=301.0. MP: >250° C.

Example 22

4-Methyl-2-phenyl-8-(2H-tetrazol-5-yl)-4H-pyrazolo[1,5-a]quinazolin-5-one

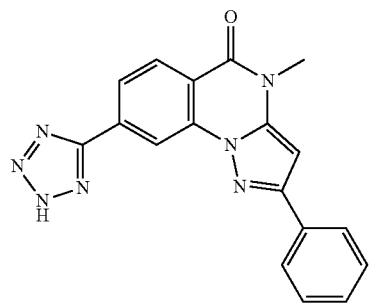 [SMILES: Cn1c(=O)c2ccc(-c3nn[nH]n3)cc2n2nc(-c3ccccc3)cc12]

Under inert atmosphere, a mixture of compound 4 (50 mg, 1.0 equiv.) sodium azide (275 mg, 25 equiv.) and ammonium chloride (223 mg, 25 equiv.) in DMF (2.4 mL) was heated at 80° C. for 26 Hrs. After cooling, the reaction mixture was hydrolysed (20 mL) and was extracted twice with EtOAc (25 mL). The organic layers were combined, washed with brine (40 mL), dried over MgSO$_4$, and concentrated. The crude material was triturated in methanol followed by pentane to afford example 22 as a beige solid in 9% yield.

$^1$H-NMR (400 MHz, DMSO): 3.59 (s, 3H, N—CH$_3$); 6.88 (s, 1H, Ar); 7.42-7.53 (m, 3H, Ar); 8.01-8.04 (m, 2H, Ar); 8.14 (dd, J 8.2 Hz, J 1.5 Hz, 1H, Ar); 8.38 (d, J 8.2 Hz, 1H, Ar); 8.82 (d, J 1.5 Hz, 1H, Ar). Signal for the proton of the tetrazole is not observed. M/Z (M+H)$^+$=344.1. MP: >250° C.

Compound 5

4-Iodo-2-hydrazino-benzoic acid, HCl Salt

Compound 5 was obtained according to general procedure I, starting from 2-Amino-4-iodo-benzoic acid, as a white solid in 80% yield.

$^1$H-NMR (400 MHz, DMSO): 7.35 (dd, J 8.2 Hz, 1.3 Hz, 1H, Ar); 7.53 (d, J 1.3 Hz, 1H, Ar); 7.61 (d, J 8.2 Hz, 1H, Ar); 9.09 (bs, 1H, NH); 10.46 (bs, 3H, NH$_3$). M/Z (M–18+H)$^+$=261.

Compound 6

8-Iodo-2-phenyl-4H-pyrazolo[1,5-a]quinazolin-5-one

Compound 6 was obtained according to general procedure II(i), starting from compound 5 in presence of 3-Oxo-3-phenyl-propionitrile, as a beige solid in 45% yield.

$^1$H-NMR (400 MHz, DMSO): 6.38 (s, 1H, Ar); 7.39-7.50 (m, 3H, Ar); 7.83-7.88 (m, 2H, Ar); 7.97-7.99 (m, 2H, Ar); 8.48 (bs, 1H, Ar); 12.36 (s, 1H, NH). M/Z (M+H)$^+$=387.9. MP: >250° C.

Compound 7

8-Iodo-4-methyl-2-phenyl-4H-pyrazolo[1,5-a]quinazolin-5-one

Compound 7 was obtained according to general procedure III starting from compound 6 in presence of iodomethane. The reaction mixture was stirred at room temperature for 15 Hrs. Compound 7 was obtained as a beige solid in 71% yield.

$^1$H-NMR (400 MHz, DMSO): 3.54 (s, 3H, N—CH$_3$); 6.84 (s, 1H, Ar); 7.41-7.52 (m, 3H, Ar); 7.84-7.92 (m, 2H, Ar); 8.00-8.02 (m, 2H, Ar); 8.49 (bs, 1H, Ar). M/Z (M+H)$^+$= 402. MP: >250° C.

Example 23

8-(3-Bromo-phenyl)-4-methyl-2-phenyl-4H-pyrazolo[1,5-a]quinazolin-5-one

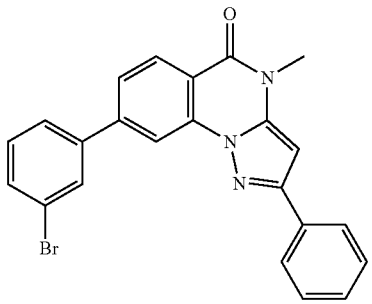 [SMILES: Cn1c(=O)c2ccc(-c3cccc(Br)c3)cc2n2nc(-c3ccccc3)cc12]

Example 23 was obtained according to general procedure IV(ii) starting from compound 7 in presence of 3-bromophenylboronic acid. The reaction mixture was heated for 1 Hr at 90° C. Purification by flash-chromatography (AcOEt in cyclohexane, 20 to 30%) afforded example 23 as a white solid in 89% yield.

$^1$H-NMR (400 MHz, DMSO): 3.59 (s, 3H, N—CH$_3$); 6.85 (s, 1H, Ar); 7.41-7.55 (m, 4H, Ar); 7.70-7.73 (m, 1H, Ar); 7.82 (dd, J 8.2 Hz, J 1.7 Hz, 1H, Ar); 7.86-7.88 (m, 1H, Ar); 8.03-8.05 (m, 3H, Ar); 8.25 (d, J 8.2 Hz, 1H, Ar); 8.34 (d, J 1.7 Hz, 1H, Ar). M/Z (M[$^{79}$Br]+H)$^+$=430.

General Procedure VI: Formation of the Compound J from N-substituted 4H-Pyrazolo[1,5-a]quinazolin-5-one F and bis(pinacolato)diboron (Cf. Scheme 1)

Under inert atmosphere, a mixture of the N-substituted 4H-Pyrazolo[1,5-a]quinazolin-5-one F (1.0 equiv.), bis(pinacolato)diboron (1.3 equiv.), Sodium acetate (1.5 equiv.) and PdCl$_2$(dppf)$_2$ (0.1 equiv.) in DMF (C=0.1 mol·L$^{-1}$) was warmed at 80° C. for 16 Hrs. After cooling, the reaction mixture was hydrolysed and then extracted twice with EtOAc. The organic layers were combined, washed with brine, dried over MgSO$_4$ and concentrated.

Compound 8

4-Methyl-2-phenyl-8-(4,4,5,5-tetramethyl-[1,3,2]dioxaborolan-2-yl)-4H-pyrazolo[1,5-a]quinazolin-5-one Compound 8 was obtained according to general procedure VI starting from compound 3. Trituration of the crude product in Et$_2$O afforded the pure product as a beige solid in 80% yield.

$^1$H-NMR (400 MHz, DMSO): 1.36 (s, 12H, 4(C—CH$_3$)); 3.56 (s, 3H, N—CH$_3$); 6.84 (s, 1H, Ar); 7.39-7.52 (m, 3H, Ar); 7.74 (dd, J 7.9 Hz, J 0.9 Hz, 1H, Ar); 7.98-8.02 (m, 2H, Ar); 8.19 (d, J 7.9 Hz, 1H, Ar); 8.41 (bs, 1H, Ar). M/Z (M−82+H)$^+$=320.2.

Example 24

8-(6-Amino-4-methyl-pyridin-3-yl)-4-methyl-2-phenyl-4H-pyrazolo[1,5-a]quinazolin-5-one, HCl Salt

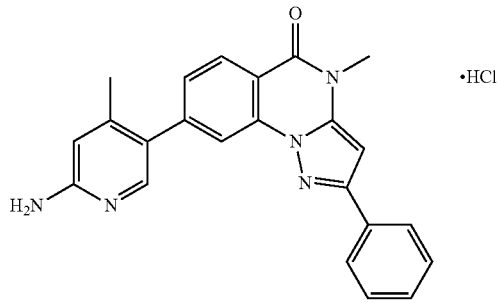 [SMILES: Cc1cc(N)ncc1-c1ccc2c(=O)n(C)c3cc(-c4ccccc4)nn3c2c1 ; Cl]

Example 24 was obtained according to general procedure IV(iii) starting from Compound 8 in presence of 2-amino-5-bromo-4-methyl pyridine. Purification by flash-chromatography (EtOAc) and salt formation according to procedure V(ii) afforded example 24 as a brown solid in 63% yield.

$^1$H-NMR (400 MHz, DMSO): 2.30 (s, 3H, C—CH$_3$); 3.60 (s, 3H, N—CH$_3$); 6.89 (s, 1H, Ar); 6.95 (s, 1H, Ar); 7.39-7.55 (m, 4H, Ar); 7.98-8.04 (m, 2H, Ar); 8.04 (s, 1H, Ar); 8.09 (bs, 2H, NH$_2$); 8.14 (d, J 1.5 Hz, 1H, Ar); 8.25 (d, J 8.2 Hz, 1H, Ar); 13.86 (bs, 1H, NH). M/Z (M+H)$^+$=382.2. MP: 235-240° C.

Example 25

8-(6-Amino-2-methyl-pyridin-3-yl)-4-methyl-2-phenyl-4H-pyrazolo[1,5-a]quinazolin-5-one, HCl Salt

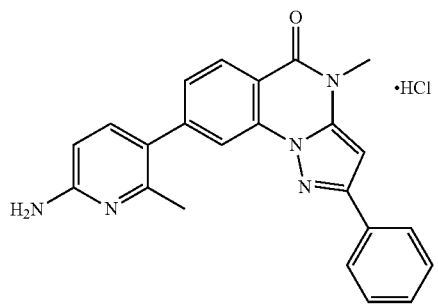 [SMILES: Cc1nc(N)ccc1-c1ccc2c(=O)n(C)c3cc(-c4ccccc4)nn3c2c1 ; Cl]

Example 25 was obtained according to general procedure IV(iii) starting from compound 8 in presence of 6-amino-3-bromo-2-methyl pyridine. Purification by flash-chromatography (EtOAc) and salt formation according to procedure V(ii) afforded example 25 as a brown solid in 49% yield.

$^1$H-NMR (400 MHz, DMSO): 2.45 (s, 3H, C—CH$_3$); 3.58 (s, 3H, N—CH$_3$); 6.86 (s, 1H, Ar); 6.95 (d, J 9.0 Hz, 1H, Ar); 7.37-7.51 (m, 4H, Ar); 7.91 (bs, 2H, NH$_2$); 7.96-7.99 (m, 3H, Ar); 8.11 (d, J 1.5 Hz, 1H, Ar); 8.25 (d, J 8.2 Hz, 1H, Ar); 14.10 (bs, 1H, NH). M/Z (M+H)$^+$=382.1. MP: 218-220° C.

Example 26

8-(6-Amino-5-methyl-pyridin-3-yl)-4-methyl-2-phenyl-4H-pyrazolo[1,5-a]quinazolin-5-one, HCl Salt

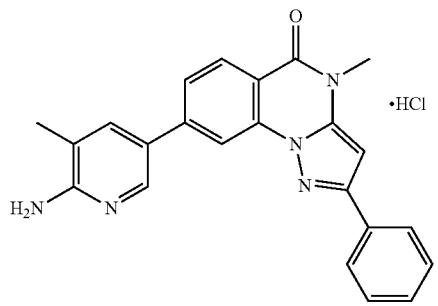 [SMILES: Cc1cc(-c2ccc3c(=O)n(C)c4cc(-c5ccccc5)nn4c3c2)cnc1N ; Cl]

Example 26 was obtained according to general procedure IV(iii) starting from Compound 8 in presence of 2-amino-5-bromo-3-methyl pyridine. Purification by flash-chromatography (EtOAc in Hexane, 90%) and salt formation according to procedure V(ii) afforded example 26 as a beige solid in 19% yield.

$^1$H-NMR (400 MHz, DMSO): 2.32 (s, 3H, C—CH$_3$); 3.58 (s, 3H, N—CH$_3$); 6.86 (s, 1H, Ar); 7.41-7.53 (m, 3H, Ar); 7.81 (dd, J 8.4 Hz, J 1.7 Hz, 1H, Ar); 8.02-8.05 (m, 2H, Ar); 8.13 (bs, 2H, NH$_2$); 8.25 (d, J 8.4 Hz, 1H, Ar); 8.36 (d, J 1.7 Hz, 1H, Ar); 8.43 (bs, 1H, Ar); 8.48 (bs, 1H, Ar); 14.16 (bs, 1H, NH). M/Z (M+H)$^+$=382.1. MP: 226-227° C.

Compound 9

5-Bromo-6-ethyl-pyridin-2-ylamine

Under inert condition, to a solution 6-amino-2-ethylpyridine (110 mg, 1.0 equiv.) in Chloroform (4.1 mL) cooled by an ice bath, NBS (147 mg, 1.0 equiv.) was added in 3 portions. The light yellow mixture was stirred for 30 minutes, and then concentrated. Purification by flash-chromatography (AcOEt in cyclohexane, 40%) afforded compound 9 as a yellow solid in 83% yield.

$^1$H-NMR (400 MHz, DMSO): 1.13 (t, J 7.5 Hz, 3H, CH$_2$—CH$_3$); 2.63 (q, J 7.5 Hz, 2H, CH$_2$—CH$_3$); 6.03 (bs, 2H, NH$_2$); 6.23 (d, J 8.7 Hz, 1H, Ar); 7.44 (d, J 8.7 Hz, 1H, Ar). M/Z (M[$^{79}$Br]+H)$^+$=201.0.

Example 27

8-(6-Amino-2-ethyl-pyridin-3-yl)-4-methyl-2-phenyl-4H-pyrazolo[1,5-a]quinazolin-5-one, HCl Salt

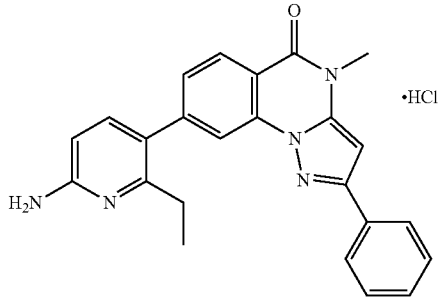 [SMILES: CCc1nc(N)ccc1-c1ccc2c(=O)n(C)c3cc(-c4ccccc4)nn3c2c1 ; Cl]

Example 27 was obtained according to general procedure IV(iii) starting from compound 8 in presence of compound 9. Purification by flash-chromatography (EtOAc in Hexane, 70%) and salt formation according to procedure V(ii) afforded example 27 as a white solid in 17% yield.

$^1$H-NMR (400 MHz, DMSO): 1.24 (t, J 7.5 Hz, 3H, CH$_2$—CH$_3$); 2.74 (q, J 7.5 Hz, 2H, CH$_2$—CH$_3$); 3.59 (s, 3H, N—CH$_3$); 6.87 (s, 1H, Ar); 6.97 (d, J 9.1 Hz, 1H, Ar); 7.40-7.51 (m, 4H, Ar); 7.95 (d, J 9.1 Hz, 1H, Ar); 7.98-8.00 (m, 2H, Ar); 8.05 (bs, 2H, NH$_2$); 8.11 (d, J 1.6 Hz, 1H, Ar); 8.27 (d, J 8.2 Hz, 1H, Ar); 14.28 (bs, 1H, NH). M/Z (M+H)$^+$=396.2. MP: 239-240° C.

Example 28

8-(6-Amino-2,4-dimethyl-pyridin-3-yl)-4-methyl-2-phenyl-4H-pyrazolo[1,5-a]quinazolin-5-one, HCl Salt

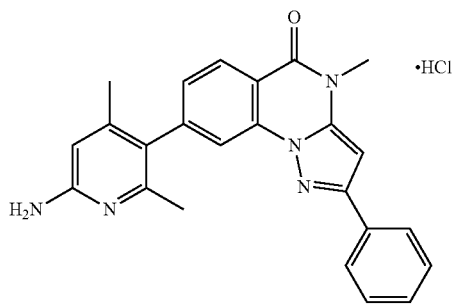 [SMILES: Cc1cc(N)nc(C)c1-c1ccc2c(=O)n(C)c3cc(-c4ccccc4)nn3c2c1 ; Cl]

Example 28 was obtained according to general procedure IV(iii) starting from compound 8 in presence of 2-amino-5-bromo-4,6-dimethyl pyridine. Purification by flash-chromatography (EtOAc) and salt formation according to procedure V(ii) afforded example 28 as a white solid in 21% yield.

$^1$H-NMR (400 MHz, DMSO): 2.06 (s, 3H, C—CH$_3$); 2.19 (s, 3H, C—CH$_3$); 3.60 (s, 3H, N—CH$_3$); 6.79 (bs, 1H, Ar); 6.87 (s, 1H, Ar); 7.37 (dd, J 8.1 Hz, J 1.6 Hz, 1H, Ar); 7.39-7.51 (m, 3H, Ar); 7.68 (bs, 2H, NH$_2$); 7.97-8.00 (m, 2H, Ar); 8.04 (d, J 1.6 Hz, 1H, Ar); 8.30 (d, J 8.1 Hz, 1H, Ar); 13.71 (bs, 1H, NH). M/Z (M+H)$^+$=396.2. MP: >250° C.

Example 29

8-(6-Amino-pyridazin-3-yl)-4-methyl-2-phenyl-4H-pyrazolo[1,5-a]quinazolin-5-one, HCl Salt

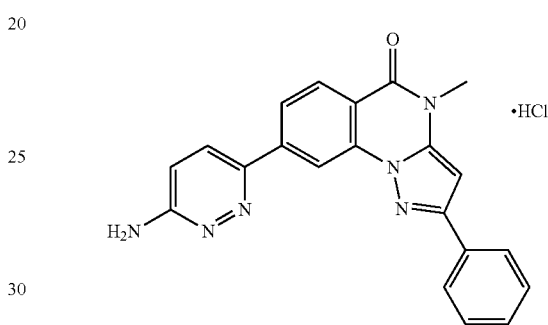

Example 29 was obtained according to general procedure IV(iii) starting from compound 8 in presence of 3-amino-6-chloropyridazine. Purification by flash-chromatography (EtOAc) and salt formation according to procedure V(ii) afforded example 29 as a yellow solid in 41% yield.

$^1$H-NMR (400 MHz, DMSO): 3.59 (s, 3H, N—CH$_3$); 6.88 (s, 1H, Ar); 7.41-7.57 (m, 3H, Ar); 8.02-8.04 (m, 2H, Ar); 8.06 (dd, J 8.3 Hz, J 1.7 Hz, 1H, Ar); 8.32 (d, J 8.3 Hz, 1H, Ar); 8.53 (bm, 3H, Ar+NH$_2$); 8.32 (d, J 8.3 Hz, 1H, Ar); 8.62 (d, J 1.7 Hz, 1H, Ar). Signal for HCl salt is not observed. M/Z (M+H)$^+$=369.1. MP: >250° C.

Example 30

8-(5-Amino-pyrazin-2-yl)-4-methyl-2-phenyl-4H-pyrazolo[1,5-a]quinazolin-5-one, HCl Salt

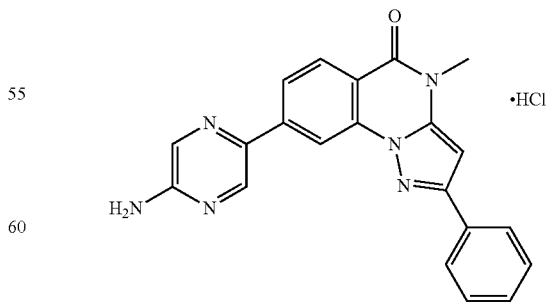

Example 30 was obtained according to general procedure IV(iii) starting from compound 8 in presence of 2-amino-5-bromopyrazine. Purification by flash-chromatography (EtOAc) and salt formation according to procedure V(ii) afforded example 30 as a white solid in 19% yield.

$^1$H-NMR (400 MHz, DMSO): 3.57 (s, 3H, N—CH$_3$); 6.82 (s, 1H, Ar); 7.38-7.52 (m, 3H, Ar); 7.99-8.07 (m, 3H, Ar); 8.09 (d, J 1.4 Hz, 1H, Ar); 8.18 (d, J 8.5 Hz, 1H, Ar); 8.69 (d, J 1.6 Hz, 1H, Ar); 8.75 (d, J 1.4 Hz, 1H, Ar). Signals for NH$_2$ and HCl salt are not observed. M/Z (M+H)$^+$=369.1. MP: 192-193° C.

Example 31

8-(2-Amino-pyrimidin-5-yl)-4-methyl-2-phenyl-4H-pyrazolo[1,5-a]quinazolin-5-one, HCl Salt

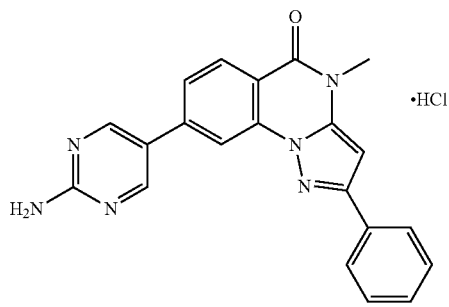 [SMILES: Cn1c(=O)c2ccc(-c3cnc(N)nc3)cc2n2nc(-c3ccccc3)cc12 ; Cl]

Example 31 was obtained according to general procedure IV(iii) starting from compound 3 in presence of 2-aminopyridine-5-boronic acid. Purification by flash-chromatography (EtOAc) and salt formation according to procedure V(ii) afforded example 31 as a white solid in 6% yield.

$^1$H-NMR (400 MHz, DMSO): 3.60 (s, 3H, N—CH$_3$); 6.86 (s, 1H, Ar); 7.05-7.53 (m, 5H, NH2+3Ar); 7.81 (dd, J 8.3 Hz, J 1.6 Hz, 1H, Ar); 804-8.07 (m, 2H, Ar); 8.22 (d, J 8.3 Hz, 1H, Ar); 8.36 (d, J 1.6 Hz, 1H, Ar); 8.88 (s, 2H, Ar). Signal for HCl salt is not observed. M/Z (M+H)$^+$=369.1. MP: >250° C.

Compound 10

5-Bromo-6-methyl-pyrazin-2-ylamine

Under inert condition, to a solution 6-amino-2-methylpyrazine (100 mg, 1.0 equiv.) in a mixture of DMSO (4.6 mL) and water (0.2 mL) cooled by an ice bath, NBS (179 mg, 1.1 equiv.) was added in 3 portions. The light yellow mixture was stirred for 15 minutes, and then for 5 hrs at room temperature. The reaction mixture was hydrolysed with NaHCO3 saturated solution (25 mL) and extracted with EtOAc (30 mL). The organic layer was washed with brine, dried over Na$_2$SO$_4$ and concentrated. Purification by flash-chromatography afforded compound 10 as a light yellow solid in 36% yield.

$^1$H-NMR (400 MHz, DMSO): 2.34 (bs, 3H, C—CH$_3$); 6.52 (bs, 2H, NH$_2$); 7.49 (s, 1H, Ar). M/Z (M[$^{79}$Br]+H)$^+$=188.2.

Example 32

8-(5-Amino-3-methyl-pyrazin-2-yl)-4-methyl-2-phenyl-4H-pyrazolo[1,5-a]quinazolin-5-one, HCl Salt

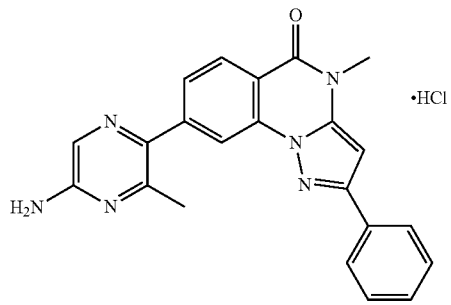 [SMILES: Cc1nc(N)cnc1-c1ccc2c(=O)n(C)c3cc(-c4ccccc4)nn3c2c1 ; Cl]

Example 32 was obtained according to general procedure IV(iii) starting from compound 8 in presence of compound 10. Purification by flash-chromatography (EtOAc) and salt formation according to procedure V(ii) afforded example 32 as a white solid in 7% yield.

$^1$H-NMR (400 MHz, DMSO): 3.59 (s, 3H, N—CH$_3$); 6.84 (s, 1H, Ar); 7.40-7.52 (m, 3H, Ar); 7.69 (dd, J 8.4 Hz, J 1.6 Hz, 1H, Ar); 7.99-8.02 (m, 3H, Ar); 8.22 (d, J 8.4 Hz, 1H, Ar); 8.33 (d, J 1.6 Hz, 1H, Ar). Signals for CH$_3$, NH$_2$ and HCl salt are not observed. M/Z (M+H)$^+$=383.0. MP: 188-189° C.

Example 33

8-(6-Amino-2-trifluoromethyl-pyridin-3-yl)-4-methyl-2-phenyl-4H-pyrazolo[1,5-a]quinazolin-5-one, HCl Salt

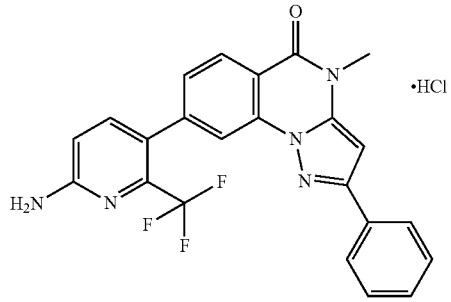 [SMILES: Cn1c(=O)c2ccc(-c3ccc(N)nc3C(F)(F)F)cc2n2nc(-c3ccccc3)cc12 ; Cl]

Example 33 was obtained according to general procedure IV(iii) starting from compound 8 in presence of 6-amino-3-bromo-2-trifluoromethyl. Purification by flash-chromatography (EtOAc in cyclohexane, 70%) and salt formation according to procedure V(ii) afforded example 33 as a white solid in 43% yield.

$^1$H-NMR (400 MHz, DMSO): 3.59 (s, 3H, N—CH$_3$); 6.79 (d, J 8.5 Hz, 1H, Ar); 6.85 (s, 1H, Ar); 7.39-7.50 (m, 4H, Ar); 7.58 (d, J 8.5 Hz, 1H, Ar); 7.97-7.99 (m, 2H, Ar); 8.03 (d, J 1.6 Hz, 1H, Ar); 8.21 (d, J 8.1 Hz, 1H, Ar). Signals for NH$_2$ and HCl salt are not observed. M/Z (M+H)$^+$=436.1. MP: >250° C.

Example 34

3-(4-Methyl-5-oxo-2-phenyl-4,5-dihydro-pyrazolo[1,5-a]quinazolin-8-yl)-benzoic Acid

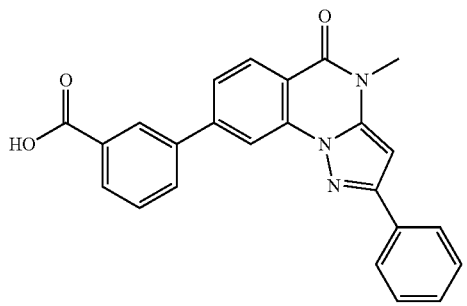 [SMILES: Cn1c(=O)c2ccc(-c3cccc(C(=O)O)c3)cc2n2nc(-c3ccccc3)cc12]

Example 34 was obtained according to general procedure IV(iii) starting from compound 3 in presence of 3-carboxyphenylboronic acid. To a solution of the crude material in DMA, Smopex-234© was added. The mixture was stirred for 2 Hrs at room temperature and then was filtrated. The solid was washed with DMA. Water was added to the filtrate. Solid precipitated which was collected, washed with water and dried under reduced pressure at 50° C. with $P_2O_5$. Example 34 was obtained as a grey solid in 72% yield.

$^1$H-NMR (400 MHz, DMSO): 3.59 (s, 3H, N—CH$_3$); 6.86 (s, 1H, Ar); 7.40-7.52 (m, 3H, Ar); 7.71 (t, J 7.7 Hz, 1H, Ar); 7.85 (dd, J 8.4 Hz, 1.5 Hz, 1H, Ar); 8.02-8.04 (m, 2H, Ar); 8.07 (d, J 7.7 Hz, 1H, Ar); 8.12 (d, J 7.7 Hz, 1H, Ar); 8.28 (d, J 8.4 Hz, 1H, Ar); 8.32 (bs, 1H, Ar); 8.37 (d, J 1.5 Hz, 1H, Ar); 8.28 (bs, 1H, COOH). M/Z (M+H)$^+$=396.1. MP: >250° C.

Example 35

3-(4-Methyl-5-oxo-2-phenyl-4,5-dihydro-pyrazolo[1,5-a]quinazolin-8-yl)-benzonitrile

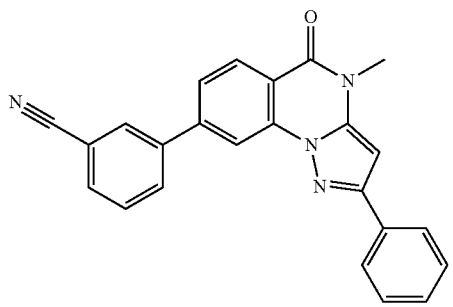 [SMILES: Cn1c(=O)c2ccc(-c3cccc(C#N)c3)cc2n2nc(-c3ccccc3)cc12]

Example 35 was obtained according to general procedure IV(iii) starting from compound 3 in presence of 3-cyanophenylboronic acid. Purification by flash-chromatography (MeOH in CH$_2$Cl$_2$, 0 to 20%) afforded example 35 as a white solid in 76% yield.

$^1$H-NMR (400 MHz, DMSO): 3.59 (s, 3H, N—CH$_3$); 6.86 (s, 1H, Ar); 7.40-7.53 (m, 3H, Ar); 7.71 (t, J 7.7 Hz, 1H, Ar); 7.88 (dd, J 8.2 Hz, 1.2 Hz, 1H, Ar); 7.97 (d, J 7.7 Hz, 1H, Ar); 8.03-8.06 (m, 2H, Ar); 8.22 (d, J 7.7 Hz, 1H, Ar); 8.27 (d, J 8.2 Hz, 1H, Ar); 8.39 (bs, 1H, Ar); 8.43 (bs, J 1.5 Hz, 1H, Ar). M/Z (M+H)$^+$=377.1. MP: >250° C.

Example 36

4-Methyl-2-phenyl-8-[3-(2H-tetrazol-5-yl)-phenyl]-4H-pyrazolo[1,5-a]quinazolin-5-one, Sodium Salt

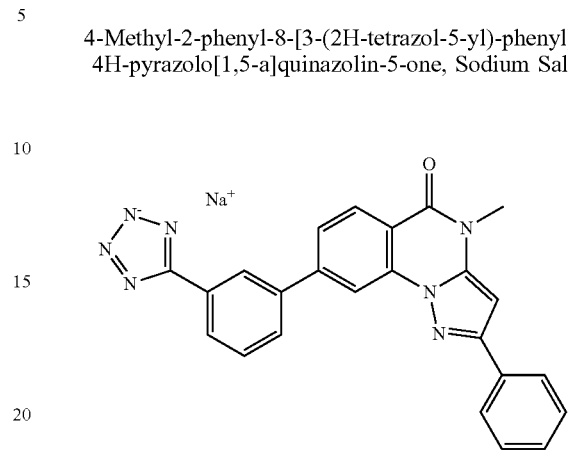

Under inert atmosphere, a mixture of example 35 (80 mg, 1.0 equiv.), sodium azide (142 mg, 10 equiv.) and ammonium chloride (117 mg, 10 equiv.) in DMF (6.0 mL) was heated at 80° C. for 4 days. After cooling, the reaction mixture was filtered. The solid was washed with DMF (1.0 mL) and the filtrate was purified by preparative HPLC. The tetrazole was obtained as a white solid.

Under anhydrous condition, to a suspension of the above tetrazole, sodium methoxide (1.0 equiv.) was added. The mixture slowly turned homogeneous. After 2 Hrs at room temperature the reaction mixture was concentrated. The resulting yellow solid was washed with a minimum of cold MeOH, then Et$_2$O and was filtrated. The solid was dried under reduced pressure at 50° C. with $P_2O_5$. Example 36 was obtained as a white solid in 49% yield.

$^1$H-NMR (400 MHz, DMSO): 3.64 (s, 3H, N—CH$_3$); 6.73 (s, 1H, Ar); 7.41-7.51 (m, 3H, Ar); 7.57 (t, J 7.7 Hz, 1H, Ar); 7.71 (d, J 7.7 Hz, 1H, Ar); 7.85 (dd, J 8.2 Hz, 1.6 Hz, 1H, Ar); 8.03-8.05 (m, 2H, Ar); 8.13 (d, J 7.7 Hz, 1H, Ar); 8.32 (d, J 8.2 Hz, 1H, Ar); 8.43-8.46 (bs, 3H, Ar). M/Z (M+H)$^+$=420.1. MP: >250° C.

Example 37

8-(2,6-Dimethyl-pyridin-4-yl)-4-methyl-2-phenyl-4H-pyrazolo[1,5-a]quinazolin-5-one, HCl Salt

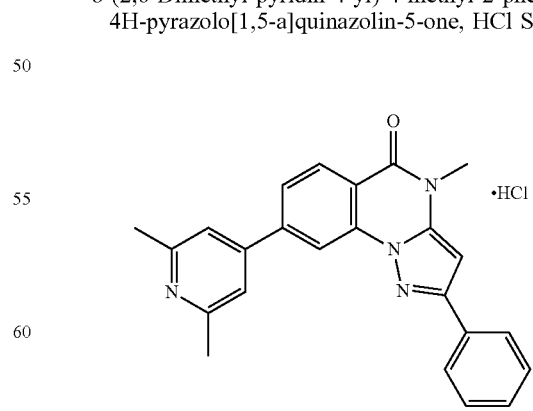

Example 37 was obtained according to general procedure IV(iv) starting from compound 3 in presence of 2,6-dimethylpyridine-4-boronic acid pinacol ester. The filtrate was hydrolysed with water (25 DMF volumes) and extracted twice with EtOAc (2*25 DMF volumes). The organic layers were combined, washed with brine, dried over MgSO₄, and concentrated. Purification by flash-chromatography (EtOAc in Cyclohexane, 0 to 60%) and salt formation according to procedure V(ii) afforded example 37 as a yellow solid in 18% yield.

¹H-NMR (400 MHz, DMSO): 2.86 (s, 6H, 2CH₃); 3.61 (s, 3H, N—CH₃); 6.92 (s, 1H, Ar); 7.43-7.55 (m, 3H, Ar); 8.02-8.07 (m, 3H, Ar); 8.30 (s, 2H, Ar); 8.39 (d, J 8.2 Hz, 1H, Ar); 8.61 (d, J 1.5 Hz, 1H, Ar). Signal for HCl salt is not observed. M/Z (M+H)⁺=381.2. MP: >250° C.

Compound 11

N,N-Dimethyl-3-(5-oxo-2-phenyl-4,5-dihydro-pyrazolo[1,5-a]quinazolin-8-yl)-benzenesulfonamide Compound 11 was obtained according to general procedure IV(i) starting from compound 2 in presence of N,N-dimethyl-3-borobenzenesulfonamide and PdCl₂(PPh₃)₂ instead of PdCl₂(dppf)₂. Trituration in Et₂O afforded the product as a beige solid in 84% yield.

¹H-NMR (400 MHz, DMSO): 2.73 (s, 6H, 2*N—CH₃); 6.41 (s, 1H, Ar); 7.39-7.50 (m, 3H, Ar); 7.84-7.90 (m, 3H, Ar); 7.99-8.01 (m, 2H, Ar); 8.07 (m, 1H, Ar); 8.20-8.23 (m, 1H, Ar); 8.26 (d, J 8.2 Hz, 1H, Ar); 8.38 (d, J 1.6 Hz, 1H, Ar); 12.37 (bs, 1H, NH). M/Z (M+H)⁺=445.1. MP: >250° C.

Example 38

N,N-Dimethyl-3-(4-methyl-5-oxo-2-phenyl-4,5-dihydro-pyrazolo[1,5-a]quinazolin-8-yl)-benzenesulfonamide

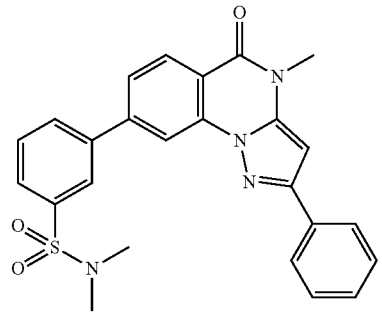 [SMILES: CN(C)S(=O)(=O)c1cccc(-c2ccc3c(=O)n(C)c4cc(-c5ccccc5)nn4c3c2)c1]

Example 38 was obtained according to general procedure III starting from compound 11 in presence of iodomethane. The reaction mixture was stirred for 15 Hrs at room temperature. Purification by preparative HPLC afforded example 38 as a white solid in 55% yield.

¹H-NMR (400 MHz, DMSO): 2.69 (s, 6H, 2*N—CH₃); 3.60 (s, 3H, N—CH₃); 6.88 (s, 1H, Ar); 7.41-7.53 (m, 3H, Ar); 7.84-7.90 (m, 3H, Ar); 8.02-8.04 (m, 2H, Ar); 8.09 (m, 1H, Ar); 8.22-8.24 (m, 1H, Ar); 8.31 (d, J 8.2 Hz, 1H, Ar); 8.40 (d, J 1.5 Hz, 1H, Ar). M/Z (M+H)⁺=459.2. MP: 202-204° C.

Example 39

N,N-Dimethyl-3-(4-Ethyl-5-oxo-2-phenyl-4,5-dihydro-pyrazolo[1,5-a]quinazolin-8-yl)-benzenesulfonamide

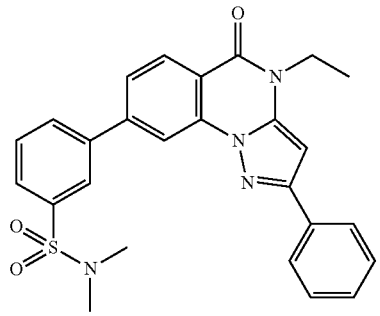 [SMILES: CCn1c(=O)c2ccc(-c3cccc(S(=O)(=O)N(C)C)c3)cc2n2nc(-c3ccccc3)cc12]

Example 39 was obtained according to general procedure III starting from compound 11 in presence of iodoethane. The reaction mixture was stirred for 21 Hrs at room temperature. Purification by preparative HPLC afforded example 39 as a white solid in 45% yield.

¹H-NMR (400 MHz, DMSO): 1.35 (t, J 7.0 Hz, 3H, N—CH₂—CH₃); 2.69 (s, 6H, 2*N—CH₃); 4.17 (q, J 7.0 Hz, 2H, N—CH₂—CH₃); 6.94 (s, 1H, Ar); 7.41-7.53 (m, 3H, Ar); 7.84-7.91 (m, 3H, Ar); 8.02-8.05 (m, 2H, Ar); 8.08 (m, 1H, Ar); 8.22-8.24 (m, 1H, Ar); 8.30 (d, J 8.3 Hz, 1H, Ar); 8.40 (d, J 1.6 Hz, 1H, Ar). M/Z (M+H)⁺=473.1. MP: 197-198° C.

Example 40

N,N-Dimethyl-3-(4-propyl-5-oxo-2-phenyl-4,5-dihydro-pyrazolo[1,5-a]quinazolin-8-yl)-benzenesulfonamide

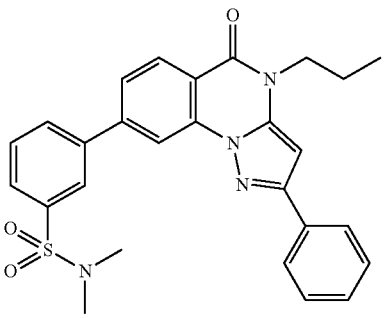 [SMILES: CCCn1c(=O)c2ccc(-c3cccc(S(=O)(=O)N(C)C)c3)cc2n2nc(-c3ccccc3)cc12]

Example 40 was obtained according to general procedure III starting from compound 11 in presence of 1-bromopropane. The reaction mixture was stirred for 17 Hrs at room temperature. Purification by preparative HPLC afforded example 40 as a white solid in 35% yield.

¹H-NMR (400 MHz, DMSO): 1.00 (t, J 7.4 Hz, 3H, N—CH₂—CH₂—CH₃); 1.82 (sex, J 7.4 Hz, 2H, N—CH₂—CH₂—CH₃); 2.70 (s, 6H, 2*N—CH₃); 4.10 (q, J 7.4 Hz, 2H, N—CH₂—CH₂—CH₃); 6.95 (s, 1H, Ar); 7.41-7.53 (m, 3H, Ar); 7.85-7.91 (m, 3H, Ar); 8.04-8.06 (m, 2H, Ar); 8.08 (m, 1H, Ar); 8.22-8.24 (m, 1H, Ar); 8.31 (d, J 8.3 Hz, 1H, Ar); 8.40 (d, J 1.6 Hz, 1H, Ar). M/Z (M+H)⁺=487.2. MP: 112-116° C.

Example 41

3-(4-isobutyl-5-oxo-2-phenyl-4,5-dihydro-pyrazolo[1,5-a]quinazolin-8-yl)-N,N-dimethyl-benzenesulfonamide

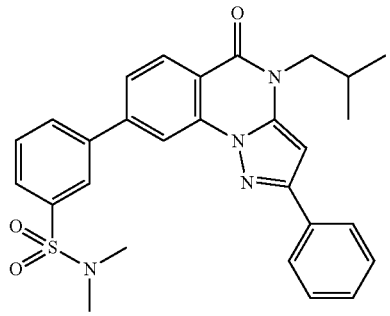 [SMILES: CC(C)Cn1c(=O)c2ccc(-c3cccc(S(=O)(=O)N(C)C)c3)cc2n2nc(-c3ccccc3)cc12]

Example 41 was obtained according to general procedure III starting from compound 11 in presence of 1-chloro-2-methylpropane. The reaction mixture was submitted to microwave irradiation (160° C.—1 Hrs). Purification by preparative HPLC afforded example 41 as a light yellow solid in 10% yield.

¹H-NMR (400 MHz, DMSO): 0.99 (d, J 6.6 Hz, 6H, N—CH₂—(CH₃)₂); 1.82 (m, 1H, N—CH₂—CH—(CH₃)₂); 2.70 (s, 6H, 2*N—CH₃); 3.98 (d, J 7.6 Hz, 2H, N—CH₂—CH—(CH₃)₂); 6.95 (s, 1H, Ar); 7.41-7.53 (m, 3H, Ar); 7.85-7.91 (m, 3H, Ar); 8.04-8.07 (m, 3H, Ar); 8.22-8.24 (m, 1H, Ar); 8.31 (d, J 8.3 Hz, 1H, Ar); 8.41 (bs, 1H, Ar). M/Z (M+H)⁺=501.1. MP: 159-163° C.

Example 42

3-(4-Cyclopropylmethyl-5-oxo-2-phenyl-4,5-dihydro-pyrazolo[1,5-a]quinazolin-8-yl)-N,N-dimethyl-benzenesulfonamide

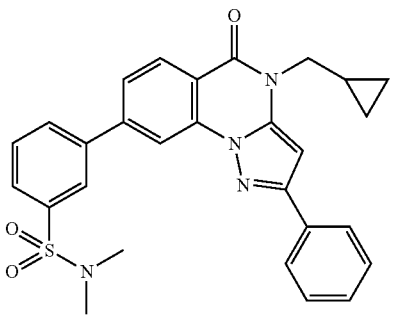 [SMILES: CN(C)S(=O)(=O)c1cccc(-c2ccc3c(=O)n(CC4CC4)c4cc(-c5ccccc5)nn4c3c2)c1]

Example 42 was obtained according to general procedure III starting from compound 11 in presence of chloromethylcyclopropane. The reaction mixture was submitted to microwave irradiation (150° C.—15 min.). Purification by preparative HPLC afforded example 42 as a beige solid in 19% yield.

¹H-NMR (400 MHz, DMSO): 0.53 (m, 4H, N—CH₂—CH—(CH₂)₂); 1.39-1.45 (m, 1H, N—CH₂—CH—(CH₂)₂); 2.70 (s, 6H, 2*N—CH₃); 4.05 (d, J 7.1 Hz, 2H, N—CH₂—CH—(CH₂)₂); 7.00 (s, 1H, Ar); 7.41-7.53 (m, 3H, Ar); 7.84-7.88 (m, 3H, Ar); 8.04-8.09 (m, 3H, Ar); 8.22-8.24 (m, 1H, Ar); 8.31 (d, J 8.2 Hz, 1H, Ar); 8.41 (bs, 1H, Ar). M/Z (M+H)⁺=499.1. MP: 115-119° C.

Compound 12

8-Bromo-4-ethyl-2-phenyl-4H-pyrazolo[1,5-a]quinazolin-5-one

Compound 12 was obtained according to general procedure III starting from compound 2 in presence of iodoethane. The reaction mixture was stirred for 2 Hrs at room temperature. Compound 12 was obtained as a beige solid in 95% yield.

¹H-NMR (400 MHz, DMSO): 1.27 (t, J 7.1 Hz, 3H, N—CH₂—CH₃); 4.12 (q, J 7.1 Hz, 2H, N—CH₂—CH₃); 6.92 (s, 1H, Ar); 7.41-7.53 (m, 3H, Ar); 7.69 (dd, J 8.5 Hz, 1.9 Hz, 1H, Ar); 8.01-8.04 (m, 2H, Ar); 8.10 (d, J 8.5 Hz, 1H, Ar); 8.29 (d, J 1.9 Hz, 1H, Ar). M/Z (M[⁷⁹Br]+H)⁺=368.0. MP: 186-188° C.

Example 43

8-(6-Amino-pyridin-3-yl)-4-ethyl-2-phenyl-4H-pyrazolo[1,5-a]quinazolin-5-one, HCl Salt

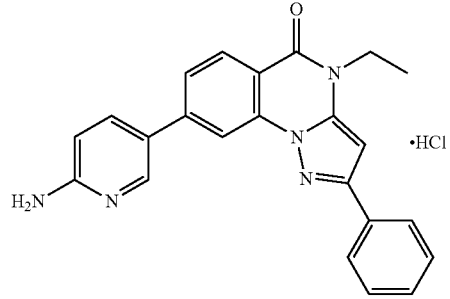 [SMILES: CCn1c(=O)c2ccc(-c3ccc(N)nc3)cc2n2nc(-c3ccccc3)cc12 ; Cl]

Example 43 was obtained according to general procedure IV(iii) starting from compound 12 in presence of 2-aminopyridine-5-boronic acid pinacol ester. The free base of example 43 was purified by flash-chromatography (EtOAc) then by preparative HPLC. Coevaporation with a solution of 1.25N HCl in MeOH afforded example 43 as a white solid in 5% yield.

¹H-NMR (400 MHz, DMSO): 1.34 (t, J 7.1 Hz, 3H, N—CH₂—CH₃); 4.16 (q, J 7.1 Hz, 2H, N—CH₂—CH₃); 6.93 (s, 1H, Ar); 7.13 (d, J 9.2 Hz, 1H, Ar); 7.41-7.53 (m, 3H, Ar); 7.81 (dd, J 8.3 Hz, 1.5 Hz, 1H, Ar); 8.04-8.06 (m, 2H, Ar); 8.17 (bs, 2H, NH₂); 8.26 (d, J 8.3 Hz, 1H, Ar); 8.36 (d, J 1.5 Hz, 1H, Ar); 8.44 (dd, J 9.2 Hz, J 1.4, Hz 1H, Ar); 8.57 (d, J 1.4 Hz, 1H, Ar). Signal for HCl salt is not observed. M/Z (M+H)⁺=382.2. MP: 207-208° C.

Compound 13

8-Bromo-2-phenyl-4-propyl-4H-pyrazolo[1,5-a]quinazolin-5-one

Compound 13 was obtained according to general procedure III starting from compound 2 in presence of bromopropane. The reaction mixture was stirred for 4 Hrs at room temperature. Compound 13 was obtained as a beige solid in 95% yield.

¹H-NMR (400 MHz, DMSO): 0.98 (t, J 7.4 Hz, 3H, N—CH$_2$—CH$_2$—CH$_3$); 1.74-1.83 (m, 2H, N—CH$_2$—CH$_2$—CH$_3$); 4.02-4.06 (m, 2H, N—CH$_2$—CH$_2$—CH$_3$); 6.93 (s, 1H, Ar); 7.43-7.51 (m, 3H, Ar); 7.68 (dd, J 8.5 Hz, 1.9 Hz, 1H, Ar); 8.01-8.04 (m, 2H, Ar); 8.09 (d, J 8.5 Hz, 1H, Ar); 8.29 (d, J 1.9 Hz, 1H, Ar). M/Z (M[$^{79}$Br]+H)$^+$=382.0. MP: 173-176° C.

Example 44

8-(6-Amino-pyridin-3-yl)-2-phenyl-4-propyl-4H-pyrazolo[1,5-a]quinazolin-5-one, HCl Salt

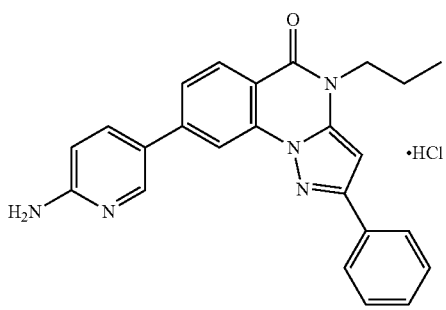 [SMILES: CCCn1c(=O)c2ccc(-c3ccc(N)nc3)cc2n2nc(-c3ccccc3)cc12 ; Cl]

Example 44 was obtained according to general procedure IV(iii) starting from compound 13 in presence of 2-aminopyridine-5-boronic acid pinacol ester and The free base of example 44 was purified by flash-chromatography (EtOAc) then by preparative HPLC. Coevaporation with a solution of 1.25N HCl in MeOH afforded example 44 as a white solid in 25% yield.

¹H-NMR (400 MHz, DMSO): 1.00 (t, J 7.4 Hz, 3H, N—CH$_2$—CH$_2$—CH$_3$); 1.76-1.86 (m, 2H, N—CH$_2$—CH$_2$—CH$_3$); 4.02-4.10 (m, 2H, N—CH$_2$—CH$_2$—CH$_3$); 6.95 (s, 1H, Ar); 7.14 (d, J 9.2 Hz, 1H, Ar); 7.42-7.54 (m, 3H, Ar); 7.81 (dd, J 8.3 Hz, 1.8 Hz, 1H, Ar); 8.04-8.06 (m, 2H, Ar); 8.16 (bs, 2H, NH$_2$); 8.26 (d, J 8.3 Hz, 1H, Ar); 8.37 (d, J 1.8 Hz, 1H, Ar); 8.46 (dd, J 9.2 Hz, J 2.1, Hz 1H, Ar); 8.57 (d, J 2.1 Hz, 1H, Ar); 14.10 (bs, 1H, NH). M/Z (M+H)$^+$=396.1. MP: >250° C.

Compound 14

8-bromo-2-phenyl-4-(2,2,2-trifluoro-ethyl)-4H-pyrazolo[1,5-a]quinazolin-5-one

Compound 14 was obtained according to general procedure III starting from compound 2 in presence of 1,1,1-trifluoro-2-iodoethane. The reaction mixture was submitted twice to microwave irradiation (150° C., 5 min), then NaH (1.7 equiv.) and 1,1,1-trifluoro-2-iodoethane (2.1 equiv.) were added and the reaction mixture was submitted again to microwave irradiation (150° C., 5 min). Compound 14 was obtained as a brown solid in 97% yield.

¹H-NMR (400 MHz, DMSO): 5.0 (q, J 9.1, 2H, N—CH$_2$—CF$_3$); 7.03 (s, 1H, Ar); 7.42-7.54 (m, 3H, Ar); 7.71 (dd, J 8.4 Hz, 1.9 Hz, 1H, Ar); 7.97-7.99 (m, 2H, Ar); 8.12 (d, J 8.4 Hz, 1H, Ar); 8.32 (d, J 1.9 Hz, 1H, Ar). M/Z (M[$^{79}$Br]+H)$^+$=422.0.

Example 45

8-(6-Amino-pyridin-3-yl)-2-phenyl-4-(2,2,2-trifluoro-ethyl)-4H-pyrazolo[1,5-a]quinazolin-5-one, HCl Salt

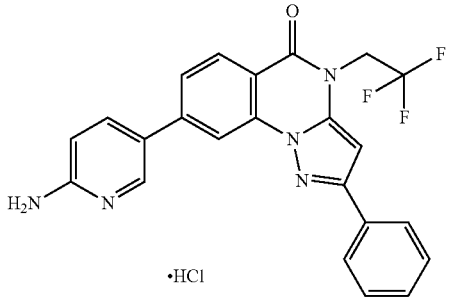 [SMILES: Nc1ccc(-c2ccc3c(=O)n(CC(F)(F)F)c4cc(-c5ccccc5)nn4c3c2)cn1 ; Cl]

Example 45 was obtained according to general procedure IV(iii) starting from compound 14 in presence of 2-aminopyridine-5-boronic acid pinacol ester Purification by flash-chromatography (EtOAc) and salt formation according to procedure V(iii) afforded example 45 as a white solid in 19% yield.

¹H-NMR (400 MHz, DMSO): 5.05 (q, J 9.1 Hz, 2H, N—CH$_2$—CF$_3$); 7.06 (s, 1H, Ar); 7.13 (d, J 9.3 Hz, 1H, Ar); 7.42-7.55 (m, 3H, Ar); 7.84 (dd, J 8.2 Hz, 1.8 Hz, 1H, Ar); 8.00-8.02 (m, 2H, Ar); 8.14 (bs, 2H, NH$_2$); 8.29 (d, J 8.2 Hz, 1H, Ar); 8.39 (d, J 1.8 Hz, 1H, Ar); 8.47 (dd, J 9.3 Hz, J 2.1, Hz 1H, Ar); 8.59 (d, J 2.1 Hz, 1H, Ar). Signal for HCl salt is not observed. M/Z (M+H)$^+$=436.1. MP: 227-230° C.

Compound 15

8-bromo-4-(2,2-difluoro-ethyl)-2-phenyl-4H-pyrazolo[1,5-a]quinazolin-5-one

Compound 15 was obtained according to general procedure III starting from compound 2 in presence of 1,1-difluoro-2-iodoethane. The reaction mixture was stirred for 18 Hrs at 80° C. The solid was purified by flash-chromatography (AcOEt in cyclohexane, 0 to 80%). Compound 15 was obtained as a beige solid in 66% yield.

¹H-NMR (400 MHz, DMSO): 4.56 (td, J 14.6 Hz, 3.8 Hz, 2H, N—CH$_2$—CHF$_2$); 6.44 (tt, J 55.2 Hz, 3.8 Hz, 1H, N—CH$_2$—CHF$_2$); 7.00 (s, 1H, Ar); 7.42-7.53 (m, 3H, Ar); 7.71 (dd, J 8.4 Hz, 1.9 Hz, 1H, Ar); 7.98-8.01 (m, 2H, Ar); 8.11 (d, J 8.4 Hz, 1H, Ar); 8.31 (d, J 1.9 Hz, 1H, Ar). M/Z (M[$^{79}$Br]+H)$^+$=404.0.

Example 46

8-(6-Amino-pyridin-3-yl)-4-(2,2-difluoro-ethyl)-2-phenyl-4H-pyrazolo[1,5-a]quinazolin-5-one, HCl Salt

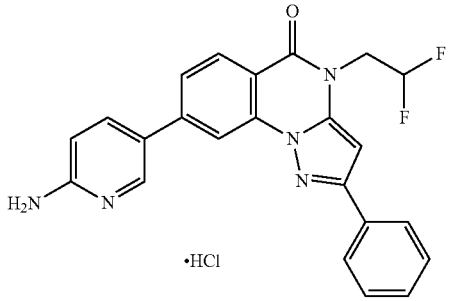 [SMILES: Nc1ccc(-c2ccc3c(=O)n(CC(F)F)c4cc(-c5ccccc5)nn4c3c2)cn1 ; Cl]

Example 46 was obtained according to general procedure IV(iv) starting from compound 15 in presence of 2-aminopyridine-5-boronic acid pinacol ester. Purification by flash-chromatography (AcOEt in cyclohexane, 70% to 100%) and salt formation according to procedure V(iii) afforded the product as a white solid in 84% yield.

$^1$H-NMR (400 MHz, DMSO): 4.59 (td, J 14.6 Hz, 3.9 Hz, 2H, N—CH$_2$—CHF$_2$); 6.48 (tt, J 55.1 Hz, 3.9 Hz, 1H, N—CH$_2$—CHF$_2$); 7.02 (s, 1H, Ar); 7.17 (d, J 9.3 Hz, 1H, Ar); 7.43-7.54 (m, 3H, Ar); 7.84 (dd, J 8.3 Hz, 1.8 Hz, 1H, Ar); 8.00-8.03 (m, 2H, Ar); 8.27 (d, J 8.3 Hz, 1H, Ar); 8.34 (bs, 2H, NH$_2$); 8.38 (d, J 1.8 Hz, 1H, Ar); 8.50 (dd, J 9.3 Hz, J 2.1, Hz 1H, Ar); 8.60 (d, J 2.1 Hz, 1H, Ar); 14.21 (bs, 1H, NH). M/Z (M+H)$^+$=418.2. MP: >250° C.

Compound 16

8-Bromo-4-isopropyl-2-phenyl-4H-pyrazolo[1,5-a]quinazolin-5-one

Compound 16 was obtained according to general procedure III starting from compound 2 in presence of 2-bromopropane. The reaction mixture was submitted twice to microwave irradiation (150° C., 10 min), then NaH (1.7 equiv.) and 2-bromopropane (2.1 equiv.) were added and the reaction mixture was submitted to microwave irradiation (150° C., 20 min). The crude material was purified by flash-chromatography (EtOAc in Cyclohexane, 0 to 80%). Compound 16 was obtained as a white solid (58 mg) contaminated with Compound 17 (8-Bromo-5-isopropoxy-2-phenyl-pyrazolo[1,5-a]quinazoline). M/Z (M[$^{79}$Br]+H)$^+$= 382.0.

Example 47

8-(6-Amino-pyridin-3-yl)-4-isopropyl-2-phenyl-4H-pyrazolo[1,5-a]quinazolin-5-one, HCl Salt

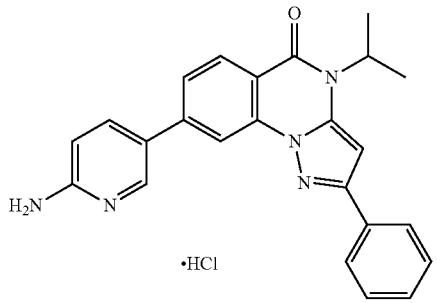 [SMILES: CC(C)n1c(=O)c2ccc(-c3ccc(N)nc3)cc2n2nc(-c3ccccc3)cc12 ; Cl]

Example 47 was obtained according to general procedure IV(iii) starting from compound 16 in presence of 2-aminopyridine-5-boronic acid pinacol ester. The free base of example 47 was purified by flash-chromatography (EtOAc) then by preparative HPLC. Coevaporation with a solution of 1.25N HCl in MeOH afforded example 47 as a white solid in 40% yield.

$^1$H-NMR (400 MHz, DMSO): 1.60 (d, J 6.9 Hz, 6H, CH(CH$_3$)$_2$); 5.18 (m, 1H, CH(CH$_3$)$_2$); 7.02 (s, 1H, Ar); 7.12 (d, J 9.1 Hz, 1H, Ar); 7.41-7.53 (m, 3H, Ar); 7.81 (dd, J 8.3 Hz, 1.7 Hz, 1H, Ar); 8.08-8.10 (m, 4H, 2Ar+NH$_2$); 8.25 (d, J 8.3 Hz, 1H, Ar); 8.37 (d, J 1.7 Hz, 1H, Ar); 8.44 (dd, J 9.1 Hz, J 1.5, Hz 1H, Ar); 8.57 (d, J 1.5 Hz, 1H, Ar). Signal for HCl salt is not observed. M/Z (M+H)$^+$=396.1. MP: 214-216° C.

Compound 18

8-Bromo-4-cyclobutyl-2-phenyl-4H-pyrazolo[1,5-a]quinazolin-5-one

Under inert atmosphere, to a solution of compound 2 (100 mg, 1.0 equiv.) in DMF (2.0 mL), bromocyclobutane (117 mg, 3.0 equiv.) and K$_2$CO$_3$ (120 mg, 3.0 equiv.) were added. The reaction mixture was submitted to microwave irradiation (200° C., 3 Hrs). After cooling, the reaction mixture was hydrolysed with aqueous 1N HCl (20 mL), and then extracted with EtOAc (2*20 mL). The organic layers were combined, washed with brine (20 mL), dried over Na$_2$SO$_4$, concentrated and purified by flash-chromatography (EtOAc in cyclohexane, 0 to 90%). Compound 18 was obtained as a white solid (70 mg) contaminated with compound 19 (8-Bromo-5-cyclobutoxy-2-phenyl-pyrazolo[1,5-a]quinazoline). M/Z (M[$^{79}$Br]+H)$^+$=394.0.

Example 48

8-(6-Amino-pyridin-3-yl)-4-cyclobutyl-2-phenyl-4H-pyrazolo[1,5-a]quinazolin-5-one, HCl Salt

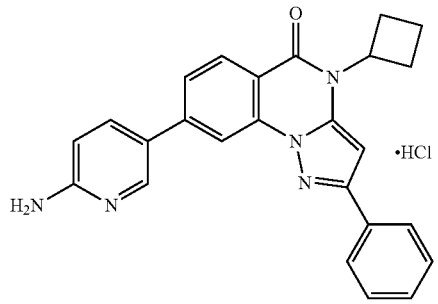 [SMILES: Nc1ccc(-c2ccc3c(=O)n(C4CCC4)c4cc(-c5ccccc5)nn4c3c2)cn1 ; Cl]

Example 48 was obtained according to general procedure IV(iii) starting from Compound 18 in presence of 2-aminopyridine-5-boronic acid pinacol ester. After cooling, the reaction mixture was filtered through a pad of celite and the filtrate was purified by preparative HPLC. Coevaporation with a solution of 1.25N HCl in MeOH afforded example 48 as a white solid in 10% yield.

$^1$H-NMR (400 MHz, DMSO): 1.81-2.02 (m, 2H, CH$_2$); 2.44 (m, 2H, CH$_2$); 2.90-2.99 (m, 2H, CH$_2$); 5.16-5.23 (m, 1H, CH); 6.96 (s, 1H, Ar); 7.13 (d, J 9.3 Hz, 1H, Ar); 7.42-7.54 (m, 3H, Ar); 7.79 (dd, J 8.2 Hz, 1.5 Hz, 1H, Ar); 8.08-8.10 (m, 2H, 2Ar); 8.15 (bs, 2H, NH$_2$); 8.23 (d, J 8.2 Hz, 1H, Ar); 8.35 (d, J 1.5 Hz, 1H, Ar); 8.45 (dd, J 9.3 Hz, J 1.8, Hz 1H, Ar); 8.57 (d, J 1.8 Hz, 1H, Ar); 14.06 (bs, 1H, NH). M/Z (M+H)$^+$=408.1. MP: 203-205° C.

General Procedure VII: Formation of keto-nitrile C from Activated Acid (Cf. Scheme 1).

Method (i):

Under anhydrous condition, to a solution of acetonitrile (2.0 equiv.) in THF (c=0.4 cooled at −78° C., BuLi (1.6N in hexane—2 equiv.) was added dropwise. The reaction mixture turned light beige. The mixture was stirred for 1 hour at −78° C., then the acid derivative (acid chloride or ester—1.0 equiv.) was added dropwise. The reaction mixture was stirred at −78° C. for 1 hour, after which time it was allowed to warm to room temperature and hydrolysed with aqueous 1N HCl solution and extracted with EtOAc or DCM. The organic layer was washed with brine, dried over MgSO$_4$ or Na$_2$SO$_4$, concentrated and purified by flash-chromatography to afford the product.

Method (ii):

Under anhydrous condition, to a solution of acetonitrile (2.0 equiv.) in THF (c=0.4 mol·L$^{-1}$) cooled at −78° C., BuLi (1.6N in hexane—2 equiv.) was added dropwise. The reaction mixture turned light beige. The mixture was stirred for 1 hour at −78° C., then the acid derivative (acid chloride or ester—1.0 equiv.) was added dropwise. The reaction mixture was stirred at −78° C. for 1 hour, after which time it was allowed to warm to 0° C. and hydrolysed with AcOH. The reaction mixture was concentrated, dried under reduced pressure at 50° C. with $P_2O_5$ for 18 hours.

Compound 20

3-Oxo-pentanenitrile

Compound 20 was obtained according to general procedure VII(i) starting from propionyl chloride. Purification by flash-chromatography (AcOEt in cyclohexane, 0 to 30%) afforded the product as a yellow oil in 53% yield.

$^1$H-NMR (400 MHz, DMSO): 0.93 (bs, 3H, $CH_3$); 3.37 (bs, 2H, $CH_2$); 4.00 (bs, 2H, $CH_2$).

Compound 21

8-Bromo-2-ethyl-4H-pyrazolo[1,5-a]quinazolin-5-one

Compound 21 was obtained according to general procedure II (i), starting from compound 1 in presence of compound 20, as a white solid in 64% yield.

$^1$H-NMR (400 MHz, DMSO): 1.24 (t, J 7.6 Hz, 3H, $CH_2$—$CH_3$); 2.65 (q, J 7.6 Hz, 2H, $CH_2$—$CH_3$); 5.79 (s, 1H, Ar); 7.61 (dd, J 8.4 Hz, 1.9 Hz, 1H, Ar); 8.01 (d, J 8.4 Hz, 1H, Ar); 8.11 (d, J 1.9 Hz, 1H, Ar); 12.19 (bs, 1H, NH). M/Z (M[$^{79}$Br]+H)$^+$=292.0. MP: >250° C.

Compound 22

8-Bromo-2-ethyl-4-methyl-4H-pyrazolo[1,5-a]quinazolin-5-one

Compound 22 was obtained according to general procedure III starting from compound 22 in presence of iodomethane. The reaction mixture was stirred at room temperature for 90 min. Compound 22 was obtained as a white solid in 86% yield.

$^1$H-NMR (400 MHz, DMSO): 1.27 (t, J 7.6 Hz, 3H, $CH_2$—$CH_3$); 2.66 (q, J 7.6 Hz, 2H, $CH_2$—$CH_3$); 3.47 (s, 3H, N—$CH_3$); 6.16 (s, 1H, Ar); 7.62 (dd, J 8.5 Hz, 1.9 Hz, 1H, Ar); 8.04 (d, J 8.5 Hz, 1H, Ar); 8.11 (d, J 1.9 Hz, 1H, Ar). M/Z (M+H)$^+$=306.1. MP: 126-127° C.

Example 49

8-(6-Amino-pyridin-3-yl)-2-ethyl-4-methyl-4H-pyrazolo[1,5-a]quinazolin-5-one, HCl Salt

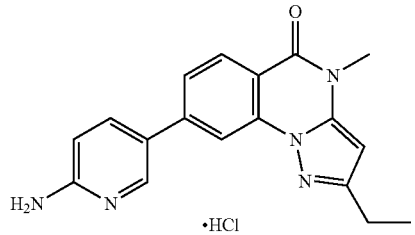 [SMILES: CCc1cc2n(C)c(=O)c3ccc(-c4ccc(N)nc4)cc3n2n1 ; Cl]

Example 49 was obtained according to general procedure IV(i) starting from compound 22 in presence of 2-aminopyridine-5-boronic acid pinacol ester. The reaction mixture was submitted to microwave irradiation for 60 min at 150° C. Purification by flash-chromatography (EtOAc) and salt formation according to procedure V(iii) afforded example 49 as a beige solid in 44% yield.

$^1$H-NMR (400 MHz, DMSO): 1.28 (t, J 7.6 Hz, 3H, $CH_2$—$CH_3$); 2.71 (q, J 7.6 Hz, 2H, $CH_2$—$CH_3$); 3.51 (s, 3H, N—$CH_3$); 6.18 (s, 1H, Ar); 7.12 (d, J 9.2 Hz, 1H, Ar); 7.74 (dd, J 8.3 Hz, 1.9 Hz, 1H, Ar); 8.20-8.23 (m, 4H, 2Ar+$NH_2$); 8.42 (dd, J 9.2 Hz, J 2.2, Hz 1H, Ar); 8.53 (d, J 2.2 Hz, 1H, Ar); 14.11 (bs, 1H, NH). M/Z (M+H)$^+$=320.1. MP: >250° C.

Compound 23

3-Oxo-hexanenitrile

Compound 23 was obtained according to general procedure VII(i) starting from butyryl chloride. Purification by flash-chromatography (AcOEt in cyclohexane, 0 to 30%) afforded the product as a yellow oil in 61% yield.

Compound 24

8-Bromo-2-propyl-4H-pyrazolo[1,5-a]quinazolin-5-one

Compound 24 was obtained according to general procedure II(i), starting from compound 1 in presence of compound 23, as a white solid in 39% yield.

$^1$H-NMR (400 MHz, DMSO): 0.94 (t, J 7.4 Hz, 3H, $CH_2$—$CH_2$—$CH_3$); 1.66 (sex, J 7.4 Hz, 2H, $CH_2$, $CH_2$—$CH_3$); 2.60 (t, J 7.4 Hz, 2H, $CH_2$—$CH_2$—$CH_3$); 5.77 (s, 1H, Ar); 7.61 (dd, J 8.5 Hz, 1.9 Hz, 1H, Ar); 8.01 (d, J 8.5 Hz, 1H, Ar); 8.10 (d, J 1.9 Hz, 1H, Ar); 12.20 (bs, 1H, NH). M/Z (M[$^{79}$Br]+H)$^+$=306.0. MP: 227-228° C.

Compound 25

8-Bromo-4-methyl-2-propyl-4H-pyrazolo[1,5-a]quinazolin-5-one

Compound 25 was obtained according to general procedure III starting from compound 24 in presence of iodomethane. The reaction mixture was stirred at room temperature for 60 min. Compound 25 was obtained as a white solid in quantitative yield.

$^1$H-NMR (400 MHz, DMSO): 0.96 (t, J 7.4 Hz, 3H, $CH_2$—$CH_2$—$CH_3$); 1.70 (sex, J 7.4 Hz, 2H, $CH_2$—$CH_2$—$CH_3$); 2.63 (t, J 7.4 Hz, 2H, $CH_2$—$CH_2$—$CH_3$); 3.46 (s, 3H, N—$CH_3$); 6.15 (s, 1H, Ar); 7.62 (dd, J 8.4 Hz, 1.6 Hz, 1H, Ar); 8.04 (d, J 8.4 Hz, 1H, Ar); 8.11 (d, J 1.6 Hz, 1H, Ar). M/Z (M[$^{79}$Br]d+H)$^+$=320.0. MP: 129-131° C.

Example 50

8-(6-Amino-pyridin-3-yl)-4-methyl-2-propyl-4H-pyrazolo[1,5-a]quinazolin-5-one, HCl Salt

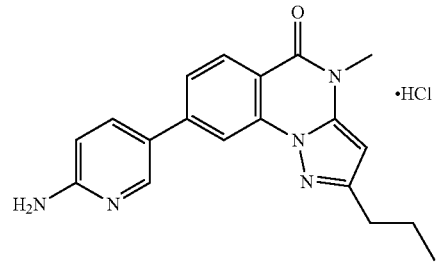 [SMILES: CCCc1cc2n(C)c(=O)c3ccc(-c4ccc(N)nc4)cc3n2n1 ; Cl]

Example 50 was obtained according to general procedure IV(iii) starting from compound 25 in presence of 2-aminopyridine-5-boronic acid pinacol ester. Purification by flash-chromatography (EtOAc) and salt formation according to procedure V(ii), afforded example 50 as a white solid in 30% yield.

$^1$H-NMR (400 MHz, DMSO): 0.98 (t, J 7.4 Hz, 3H, CH$_2$—CH$_2$—CH$_3$); 1.72 (sex, J 7.4 Hz, 2H, CH$_2$—CH$_2$—CH$_3$); 2.66 (t, J 7.4 Hz, 3H, CH$_2$—CH$_2$—CH$_3$); 3.50 (s, 3H, N—CH$_3$); 6.16 (s, 1H, Ar); 7.12 (d, J 9.2 Hz, 1H, Ar); 7.74 (dd, J 8.3 Hz, 1.9 Hz, 1H, Ar); 8.19-8.23 (m, 4H, 2Ar+NH$_2$); 8.42 (dd, J 9.2 Hz, J 2.2, Hz 1H, Ar); 8.53 (d, J 2.2 Hz, 1H, Ar); 14.14 (bs, 1H, NH). M/Z (M+H)$^+$=334.1. MP: >250° C.

Compound 26

4-Methyl-3-oxo-pentanenitrile

Compound 26 was obtained according to general procedure VII(i) starting from isobutyryl chloride. Purification by flash-chromatography (AcOEt in cyclohexane, 0 to 30%) afforded the product as a yellow oil in 10% yield.

$^1$H-NMR (400 MHz, DMSO): 1.04 (d, J 7.0 Hz, 6H, CH(CH$_3$)$_2$); 2.67 (sep, J 7.0 Hz, 1H, CH(CH$_3$)$_2$); 4.14 (s, 2H, CH$_2$).

Compound 27

8-Bromo-2-isopropyl-4H-pyrazolo[1,5-a]quinazolin-5-one

Compound 27 was obtained according to general procedure II(i), starting from compound 1 in presence of compound 27, as a beige solid in 36% yield.

$^1$H-NMR (400 MHz, DMSO): 1.24 (d, J 7.0 Hz, 6H, CH(CH$_3$)$_2$); 2.97 (sep, J 7.0 Hz, 1H, CH(CH$_3$)$_2$); 5.78 (s, 1H, Ar); 7.61 (dd, J 8.5 Hz, 1.9 Hz, 1H, Ar); 8.01 (d, J 8.5 Hz, 1H, Ar); 8.10 (d, J 1.9 Hz, 1H, Ar); 12.19 (bs, 1H, NH). M/Z (M[$^{79}$Br]+H)$^+$=306.0. MP: >250° C.

Compound 28

8-Bromo-2-isopropyl-4-methyl-4H-pyrazolo[1,5-a]quinazolin-5-one

Compound 28 was obtained according to general procedure III starting from compound 27 in presence of iodomethane. The reaction mixture was stirred at room temperature for 60 min. Compound 28 was obtained as a beige solid in 92% yield.

$^1$H-NMR (400 MHz, DMSO): 1.29 (d, J 6.9 Hz, 6H, CH(CH$_3$)$_2$); 3.01 (sep, J 6.9 Hz, 1H, CH(CH$_3$)$_2$);); 3.47 (s, 3H, N—CH$_3$); 6.19 (s, 1H, Ar); 7.62 (dd, J 8.5 Hz, 1.9 Hz, 1H, Ar); 8.04 (d, J 8.5 Hz, 1H, Ar); 8.11 (d, J 1.9 Hz, 1H, Ar). M/Z (M[$^{79}$Br]+H)$^+$=320.1. MP: 149-150° C.

Example 51

8-(6-Amino-pyridin-3-yl)-2-isopropyl-4-methyl-4H-pyrazolo[1,5-a]quinazolin-5-one, HCl Salt

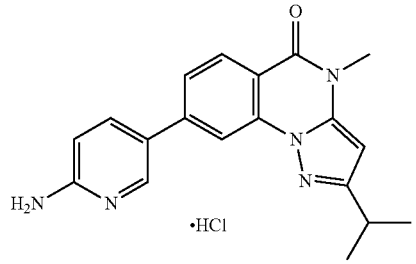 [SMILES: CC(C)c1cc2n(C)c(=O)c3ccc(-c4ccc(N)nc4)cc3n2n1 ; Cl]

Example 51 was obtained according to general procedure IV(iii) starting from compound 28 in presence of 2-aminopyridine-5-boronic acid pinacol ester. Purification by flash-chromatography (EtOAc) and salt formation according to procedure V(ii), afforded example 51 as a white solid in 64% yield.

$^1$H-NMR (400 MHz, DMSO): 1.30 (d, J 7.0 Hz, 6H, CH(CH$_3$)$_2$); 3.03 (sep, J 7.0 Hz, 1H, CH(CH$_3$)$_2$); 3.51 (s, 3H, N—CH$_3$); 6.22 (s, 1H, Ar); 7.16 (d, J 9.3 Hz, 1H, Ar); 7.74 (dd, J 8.3 Hz, 1.9 Hz, 1H, Ar); 8.19-8.22 (m, 2H, Ar); 8.36 (bs, 2H, NH$_2$); 8.44 (dd, J 9.3 Hz, J 2.2, Hz 1H, Ar); 8.54 (d, J 2.2 Hz, 1H, Ar); 14.26 (bs, 1H, NH). M/Z (M+H)$^+$=334.1. MP: 240-244° C.

Compound 29

4,4-Dimethyl-3-oxo-pentanenitrile

Compound 29 was obtained according to general procedure VII(i) starting from trimethylacethyl chloride. Purification by flash-chromatography (AcOEt in cyclohexane, 0 to 30%) afforded the product as a yellow oil in 49% yield.

$^1$H-NMR (400 MHz, DMSO): 1.10 (s, 9H, C(CH$_3$)$_3$); 4.24 (s, 2H, CH$_2$).

Compound 30

8-Bromo-2-tert-butyl-4H-pyrazolo[1,5-a]quinazolin-5-one

Compound 30 was obtained according to general procedure II(i), starting from compound 1 in presence of compound 29, as a white solid in 24% yield.

$^1$H-NMR (400 MHz, DMSO): 1.31 (s, 9H, c(CH$_3$)$_3$); 5.81 (s, 1H, Ar); 7.61 (dd, J 8.3 Hz, 1.4 Hz, 1H, Ar); 8.01 (d, J 8.3 Hz, 1H, Ar); 8.10 (d, J 1.4 Hz, 1H, Ar); 12.18 (bs, 1H, NH). M/Z (M[$^{79}$Br]+H)$^+$=320.0. MP: >250° C.

Compound 31

8-Bromo-2-tert-butyl-4-methyl-4H-pyrazolo[1,5-a]quinazolin-5-one

Compound 31 was obtained according to general procedure III starting from compound 30 in presence of iodomethane. The reaction mixture was stirred at room temperature for 60 min. Compound 31 was obtained as a white solid in 97% yield.

$^1$H-NMR (400 MHz, DMSO): 1.34 (s, 9H, c(CH$_3$)$_3$); 3.47 (s, 3H, N—CH$_3$); 6.26 (s, 1H, Ar); 7.62 (dd, J 8.4 Hz, 2.0

Hz, 1H, Ar); 8.04 (d, J 8.4 Hz, 1H, Ar); 8.10 (d, J 2.0 Hz, 1H, Ar). M/Z (M[$^{79}$Br]+H)$^+$=334.1. MP: 178-179° C.

Example 52

8-(6-Amino-pyridin-3-yl)-2-tert-butyl-4-methyl-4H-pyrazolo[1,5-a]quinazolin-5-one, HCl Salt

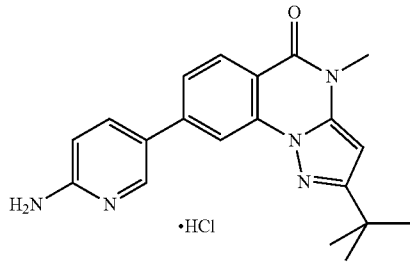 [SMILES: Cn1c(=O)c2ccc(-c3ccc(N)nc3)cc2n2nc(C(C)(C)C)cc12 ; Cl]

Example 52 was obtained according to general procedure IV(iii) starting from compound 31 in presence of 2-aminopyridine-5-boronic acid pinacol ester. Purification by flash-chromatography (EtOAc) and salt formation according to procedure V(ii) afforded example 52 as a white solid in quantitative yield.

$^1$H-NMR (400 MHz, DMSO): 1.36 (s, 9H, c(CH$_3$)$_3$); 3.51 (s, 3H, N—CH$_3$); 6.27 (s, 1H, Ar); 7.17 (d, J 9.3 Hz, 1H, Ar); 7.73 (dd, J 8.3 Hz, 1.7 Hz, 1H, Ar); 8.17 (d, J 1.7 Hz, 1H, Ar); 8.22 (d, J 8.3 Hz, 1H, Ar); 8.28 (bs, 2H, NH$_2$); 8.42 (dd, J 9.3 Hz, J 2.0 Hz, 1H, Ar); 8.53 (d, J 2.0 Hz, 1H, Ar); 14.17 (bs, 1H, NH). M/Z (M+H)$^+$=348.2.

Compound 32

5-Methoxy-3-oxo-pentanenitrile

Compound 32 was obtained according to general procedure VII(i) starting from Methyl-3-methoxypropionate. Purification by flash-chromatography (AcOEt in cyclohexane, 70 to 100%) afforded the product as an orange oil in 68% yield.

$^1$H-NMR (400 MHz, DMSO): 2.73 (t, J 6.2 Hz, 2H, O—CH$_2$—CH$_2$); 3.22 (s, 3H, OCH$_3$); 3.54 (t, J 6.2 Hz, 2H, O—CH$_2$—CH$_2$); 4.06 (s, 2H, CH$_2$).

Compound 33

8-Bromo-2-(2-methoxy-ethyl)-4H-pyrazolo[1,5-a]quinazolin-5-one

Compound 33 was obtained according to general procedure II(i), starting from compound 1 in presence of compound 32, as a beige solid in 85% yield.

$^1$H-NMR (400 MHz, DMSO): 2.86 (t, J 6.7 Hz, 2H, O—CH$_2$—CH$_2$); 3.26 (s, 3H, OCH$_3$); 3.63 (t, J 6.7 Hz, 2H, O—CH$_2$—CH$_2$); 5.82 (s, 1H, Ar); 7.62 (dd, J 8.5 Hz, 1.9 Hz, 1H, Ar); 8.01 (d, J 8.5 Hz, 1H, Ar); 8.10 (d, J 1.9 Hz, 1H, Ar); 12.21 (bs, 1H, NH). M/Z (M[$^{79}$Br]+H)$^+$=322.0.

Compound 34

8-Bromo-2-(2-methoxy-ethyl)-4-methyl-4H-pyrazolo[1,5-a]quinazolin-5-one

Compound 34 was obtained according to general procedure III starting from compound 33 in presence of iodomethane. The reaction mixture was stirred at room temperature for 2 Hrs. Compound 34 was obtained as a white solid in 72% yield.

Example 53

8-(6-Amino-pyridin-3-yl)-2-(2-methoxy-ethyl)-4-methyl-4H-pyrazolo[1,5-a]quinazolin-5-one, HCl Salt

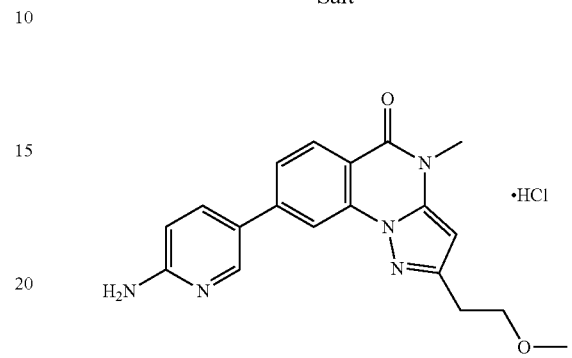

Example 53 was obtained according to general procedure IV(iv) starting from compound 34 in presence of 2-aminopyridine-5-boronic acid pinacol ester. The filtrate was hydrolysed with water (25 DMF volumes) and extracted twice with EtOAc (2*25 DMF volumes). The organic layers were combined, washed with brine, dried over MgSO$_4$ and concentrated. Purification by flash-chromatography (MeOH in DCM, 0 to 5%) and salt formation according to procedure V(ii) afforded the product as a white solid in 48% yield.

$^1$H-NMR (400 MHz, DMSO): 2.92 (t, J 6.8 Hz, 2H, O—CH$_2$—CH$_2$); 3.29 (s, 3H, OCH$_3$); 3.50 (s, 3H, N—CH$_3$); 3.68 (t, J 6.8 Hz, 2H, O—CH$_2$—CH$_2$); 6.19 (s, 1H, Ar); 7.15 (d, J 9.3 Hz, 1H, Ar); 7.75 (dd, J 8.2 Hz, 1.9 Hz, 1H, Ar); 8.21-8.23 (m, 2H, Ar); 8.34 (bs, 2H, NH$_2$); 8.45 (dd, J 9.3 Hz, J 2.3, Hz 1H, Ar); 8.54 (d, J 2.3 Hz, 1H, Ar); 14.27 (bs, 1H, NH). M/Z (M+H)$^+$=350.1. MP: 198-202° C.

Example 54

8-(2,6-Dimethyl-pyridin-4-yl)-2-(2-methoxy-ethyl)-4-methyl-4H-pyrazolo[1,5-a]quinazolin-5-one, HCl Salt

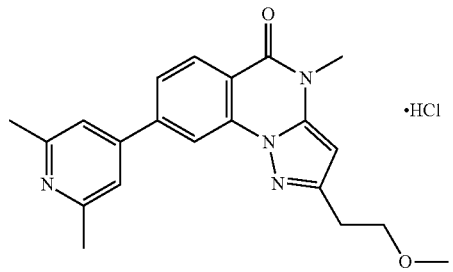

Example 54 was obtained according to general procedure IV(iv) starting from compound 34 in presence of 2,6-dimethylpyridine-4-boronic acid pinacol ester. Purification by flash-chromatography (MeOH in CH$_2$Cl$_2$, 0 to 3%) and salt formation according to procedure V(iii) afforded example 54 as a yellow solid in 52% yield.

¹H-NMR (400 MHz, DMSO): 2.81 (s, 6H, 2CH₃); 2.94 (t, J 6.8 Hz, 2H, O—CH₂—CH₂); 3.29 (s, 3H, OCH₃); 3.52 (s, 3H, N—CH₃); 3.70 (t, J 6.8 Hz, 2H, O—CH₂—CH₂); 6.24 (s, 1H, Ar); 7.98 (dd, J 8.3 Hz, J 1.7 Hz, 1H, Ar); 8.27 (bs, 2H, Ar); 8.34 (d, J 8.3 Hz, 1H, Ar); 8.46 (d, J 1.7 Hz, 1H, Ar). Signal of HCl salt is not observed. M/Z (M+H)⁺=363.1. MP: 241-245° C.

Compound 35

8-Bromo-2-(2-methoxy-ethyl)-4-methyl(D₃)-4H-pyrazolo[1,5-a]quinazolin-5-one

Compound 35 was obtained according to general procedure III starting from compound 33 in presence of iodomethane D₃. The reaction mixture was stirred at room temperature for 17 Hrs. Compound 35 was obtained as a white solid in 60% yield.

¹H-NMR (400 MHz, DMSO): 2.90 (t, J 6.7 Hz, 2H, O—CH₂—CH₂); 3.28 (s, 3H, OCH₃); 3.68 (t, J 6.7 Hz, 2H, O—CH₂—CH₂); 6.18 (s, 1H, Ar); 7.64 (dd, J 8.5 Hz, 1.9 Hz, 1H, Ar); 8.06 (d, J 8.5 Hz, 1H, Ar); 8.12 (d, J 1.9 Hz, 1H, Ar). M/Z (M[⁷⁹Br]+H)⁺=339.1.

Example 55

8-(6-Amino-pyridin-3-yl)-2-(2-methoxy-ethyl)-4-methyl(D₃)-4H-pyrazolo[1,5-a]quinazolin-5-one, HCl Salt

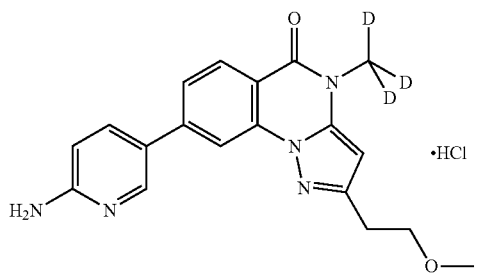 [SMILES: [2H]C([2H])([2H])n1c(=O)c2ccc(-c3ccc(N)nc3)cc2n2nc(CCOC)cc12 ; Cl]

Example 55 was obtained according to general procedure IV(iv) starting from compound 35 in presence of 2-aminopyridine-5-boronic acid pinacol ester. The filtrate was hydrolysed with water (50 DMF volumes) and extracted twice with EtOAc (2*25 DMF volumes). The organic layers were combined, washed with brine, dried over MgSO₄ and concentrated. Purification by flash-chromatography (MeOH in DCM, 0 to 5%) and salt formation according to procedure V(ii) afforded example 55 as a beige solid in 52% yield.

¹H-NMR (400 MHz, DMSO): 2.92 (t, J 6.8 Hz, 2H, O—CH₂—CH₂); 3.29 (s, 3H, OCH₃); 3.69 (t, J 6.8 Hz, 2H, O—CH₂—CH₂); 6.18 (s, 1H, Ar); 7.17 (d, J 9.3 Hz, 1H, Ar); 7.74 (dd, J 8.2 Hz, 1.9 Hz, 1H, Ar); 8.19-8.21 (m, 2H, Ar); 8.40 (bs, 2H, NH₂); 8.44 (dd, J 9.3 Hz, J 2.3, Hz 1H, Ar); 8.55 (d, J 2.3 Hz, 1H, Ar); 14.40 (bs, 1H, NH). M/Z (M+H)⁺=353.1. MP: 187-193° C.

Example 56

8-(2,6-Dimethyl-pyridin-4-yl)-2-(2-methoxy-ethyl)-4-methyl(D₃)-4H-pyrazolo[1,5-a]quinazolin-5-one, HCl Salt

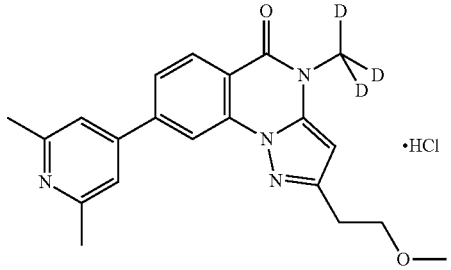

Example 56 was obtained according to general procedure IV(iv) starting from compound 35 in presence of 2,6-dimethylpyridine-4-boronic acid pinacol ester. Purification by flash-chromatography (MeOH in CH₂Cl₂ 0 to 5%) and salt formation according to procedure V(ii) afforded example 56 as a beige solid in 38% yield.

¹H-NMR (400 MHz, DMSO): 2.81 (s, 6H, 2CH₃); 2.94 (t, J 6.8 Hz, 2H, O—CH₂—CH₂); 3.30 (s, 3H, OCH₃); 3.70 (t, J 6.8 Hz, 2H, O—CH₂—CH₂); 6.24 (s, 1H, Ar); 7.99 (dd, J 8.3 Hz, J 1.8 Hz, 1H, Ar); 8.28 (bs, 2H, Ar); 8.36 (d, J 8.3 Hz, 1H, Ar); 8.48 (d, J 1.8 Hz, 1H, Ar). Signal for HCl salt is not observed. M/Z (M+H)⁺=366.1. MP: 232-237° C.

Compound 36

8-Bromo-4-ethyl-2-(2-methoxy-ethyl)-4H-pyrazolo[1,5-a]quinazolin-5-one

Compound 36 was obtained according to general procedure III starting from compound 33 in presence of iodoethane. The reaction mixture was stirred for 2 Hrs at room temperature, then hydrolysed with aqueous 1N HCl, and extracted twice with EtOAc. The organic layers were combined, washed with brine, dried over MgSO₄ and concentrated. Purification by flash-chromatography (AcOEt in cyclohexane, 0 to 50%) afforded compound 36 as a white solid in 47% yield.

¹H-NMR (400 MHz, DMSO): 1.25 (t, J 7.1 Hz, 3H, N—CH₂—CH₃); 2.91 (t, J 6.8 Hz, 2H, O—CH₂—CH₂); 3.29 (s, 3H, OCH₃); 3.68 (t, J 6.8 Hz, 2H, O—CH₂—CH₂); 4.04 (q, J 7.1 Hz, 2H, N—CH₂—CH₃); 6.24 (s, 1H, Ar); 7.64 (dd, J 8.4 Hz, 1.9 Hz, 1H, Ar); 8.06 (d, J 8.4 Hz 1H, Ar); 8.13 (d, J 1.9 Hz, 1H, Ar). M/Z (M[⁷⁹Br]+H)⁺=350.0.

Example 57

8-(6-Amino-pyridin-3-yl)-4-ethyl-2-(2-methoxy-ethyl)-4H-pyrazolo[1,5-a]quinazolin-5-one, HCl Salt

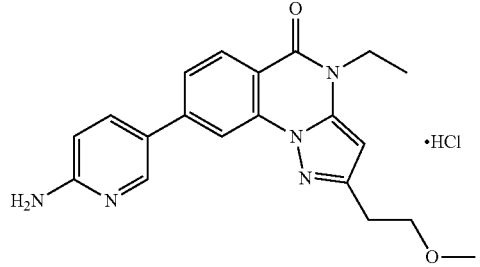 [SMILES: CCn1c(=O)c2ccc(-c3ccc(N)nc3)cc2n2nc(CCOC)cc12 ; Cl]

Example 57 was obtained according to general procedure IV(iv) starting from compound 36 in presence of 2-aminopyridine-5-boronic acid pinacol ester. The filtrate was hydrolysed with water (50 DMF volumes) and extracted twice with EtOAc (2*50 DMF volumes). The organic layers were combined, washed with brine, dried over MgSO$_4$ and concentrated. Purification by flash-chromatography (MeOH in DCM, 0 to 10%) and salt formation according to procedure V(ii) afforded the product as a blue solid in 78% yield.

$^1$H-NMR (400 MHz, DMSO): 1.28 (t, J 7.1 Hz, 3H, N—CH$_2$—CH$_3$); 2.93 (t, J 6.8 Hz, 2H, O—CH$_2$—CH$_2$); 3.30 (s, 3H, OCH$_3$); 3.70 (t, J 6.8 Hz, 2H, O—CH$_2$—CH$_2$); 4.08 (q, J 7.1 Hz, 2H, N—CH$_2$—CH$_3$); 6.26 (s, 1H, Ar); 7.15 (d, J 9.3 Hz, 1H, Ar); 7.77 (dd, J 8.2 Hz, 1.8 Hz, 1H, Ar); 8.23-8.25 (m, 2H, Ar); 8.27 (bs, 2H, NH$_2$); 8.46 (dd, J 9.3 Hz, J 2.0 Hz 1H, Ar); 8.55 (d, J 2.0 Hz, 1H, Ar); 14.40 (bs, 1H, NH). M/Z (M+H)$^+$=364.1. MP: 163-170° C.

Example 58

8-(2,6-Dimethyl-pyridin-4-yl)-4-ethyl-2-(2-methoxy-ethyl)-4H-pyrazolo[1,5-a]quinazolin-5-one, HCl Salt

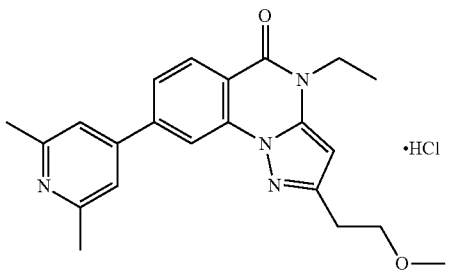

Example 58 was obtained according to general procedure IV(iv) starting from compound 36 in presence of 2,6-dimethylpyridine-4-boronic acid pinacol ester. To the celite pad suspension In DMSO-MeOH mixture (1-1 (v-v)) Smopex resin (2 equiv. referred to initial Pd amount) was added. The mixture was stirred for 2 Hrs, filtered off and the solid was washed with a mixture of DMSO-MeOH. MeOH was removed and water was added to the resulting DMSO solution. The resulting solid was collected, washed with water and dried under reduced pressure with P$_2$O$_5$ at 50° C. Salt formation according to procedure V(ii) afforded the example 58 as a beige solid in 56% yield.

$^1$H-NMR (400 MHz, DMSO): 1.30 (t, J 7.1 Hz, 3H, N—CH$_2$—CH$_3$); 2.79 (s, 6H, 2CH$_3$); 2.95 (t, J 6.8 Hz, 2H, O—CH$_2$—CH$_2$); 3.30 (s, 3H, OCH$_3$); 3.71 (t, J 6.8 Hz, 2H, O—CH$_2$—CH$_2$); 4.10 (q, J 7.1 Hz, 2H, N—CH$_2$—CH$_3$); 6.30 (s, 1H, Ar); 7.99 (dd, J 8.3 Hz, J 1.6 Hz, 1H, Ar); 8.26 (bs, 2H, Ar); 8.36 (d, J 8.3 Hz, 1H, Ar); 8.48 (d, J 1.6 Hz, 1H, Ar). Signal for HCl salt is not observed. M/Z (M+H)$^+$= 377.1. MP: 173-180° C.

Compound 37

8-Bromo-2-(2-methoxy-ethyl)-4-propyl-4H-pyrazolo[1,5-a]quinazolin-5-one

Compound 37 was obtained according to general procedure III starting from compound 33 in presence of bromopropane. The reaction mixture was stirred for 19 Hrs at room temperature, then hydrolysed with aqueous 1N HCl, and extracted twice with EtOAc. The organic layers were combined, washed with brine, dried over MgSO$_4$ and concentrated. Purification by flash-chromatography (AcOEt in cyclohexane, 0 to 50%) afforded compound 37 as white a solid in 49% yield.

$^1$H-NMR (400 MHz, DMSO): 0.94 (t, J 7.4 Hz, 3H, N—CH$_2$—CH$_2$—CH$_3$); 1.67-1.76 (m, 2H, N—CH$_2$—CH$_2$—CH$_3$); 2.90 (t, J 6.8 Hz, 2H, O—CH$_2$—CH$_2$); 3.29 (s, 3H, OCH$_3$); 3.68 (t, J 6.8 Hz, 2H, O—CH$_2$—CH$_2$); 3.94-3.98 (m, 2H, N—CH$_2$—CH$_2$—CH$_3$); 6.24 (s, 1H, Ar); 7.64 (dd, J 8.5 Hz, 1.9 Hz, 1H, Ar); 8.06 (d, J 8.5 Hz, 1H, Ar); 8.13 (d, J 1.9 Hz, 1H, Ar). M/Z (M[$^{79}$Br]+H)$^+$=364.1.

Example 59

8-(6-Amino-pyridin-3-yl)-2-(2-methoxy-ethyl)-4-propyl-4H-pyrazolo[1,5-a]quinazolin-5-one, HCl Salt

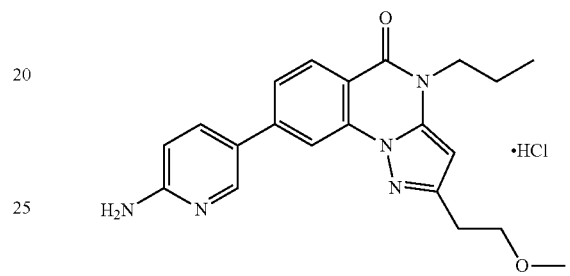

Example 59 was obtained according to general procedure IV(iv) starting from compound 37 in presence of 2-aminopyridine-5-boronic acid pinacol ester. Purification by flash-chromatography (MeOH in DCM, 0 to 5%) and salt formation according to procedure V(i) afforded example 59 as a white solid in 55% yield.

$^1$H-NMR (400 MHz, DMSO): 0.94 (t, J 7.4 Hz, 3H, N—CH$_2$—CH$_2$—CH$_3$); 1.68-1.77 (m, 2H, N—CH$_2$—CH$_2$—CH$_3$); 2.92 (t, J 6.8 Hz, 2H, O—CH$_2$—CH$_2$); 3.29 (s, 3H, OCH$_3$); 3.68 (t, J 6.8 Hz, 2H, O—CH$_2$—CH$_2$); 3.97-4.01 (m, 2H, N—CH$_2$—CH$_2$—CH$_3$); 6.26 (s, 1H, Ar); 7.15 (d, J 9.3 Hz, 1H, Ar); 7.76 (dd, J 8.5 Hz, 1.7 Hz, 1H, Ar); 8.21-8.23 (m, 2H, Ar); 8.31 (bs, 2H, NH$_2$); 8.45 (dd, J 9.3 Hz, J 2.3 Hz 1H, Ar); 8.54 (d, J 2.3 Hz, 1H, Ar); 14.22 (bs, 1H, NH). M/Z (M+H)$^+$=378.1. MP: 96-102° C.

Example 60

8-(2,6-Dimethyl-pyridin-4-yl)-2-(2-methoxy-ethyl)-4-propyl-4H-pyrazolo[1,5-a]quinazolin-5-one, HCl Salt

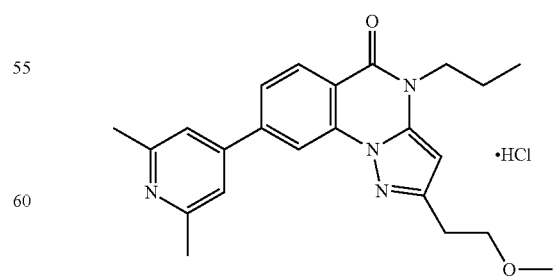

Example 60 was obtained according to general procedure IV(iv) starting from compound 37 in presence of 2,6-dimethylpyridine-4-boronic acid pinacol ester. The filtrate was hydrolysed with water (50 DMF volumes) and extracted twice with EtOAc (2*50 DMF volumes). The organic layers were combined, washed with brine, dried over MgSO₄ and concentrated. Purification by flash-chromatography (MeOH in DCM, 0 to 5%) and salt formation according to procedure V(ii) afforded the product as a beige solid in 37% yield.

$^1$H-NMR (400 MHz, DMSO): 0.96 (t, J 7.4 Hz, 3H, N—CH$_2$—CH$_2$—CH$_3$); 1.70-1.80 (m, 2H, N—CH$_2$—CH$_2$—CH$_3$); 2.82 (s, 6H, 2CH$_3$); 2.94 (t, J 6.8 Hz, 2H, O—CH$_2$—CH$_2$); 3.29 (s, 3H, OCH$_3$); 3.70 (t, J 6.8 Hz, 2H, O—CH$_2$—CH$_2$); 4.00-4.04 (m, 2H, N—CH$_2$—CH$_2$—CH$_3$); 6.31 (s, 1H, Ar); 7.99 (dd, J 8.3 Hz, J 1.6 Hz, 1H, Ar); 8.28 (bs, 2H, Ar); 8.35 (d, J 8.3 Hz, 1H, Ar); 8.48 (d, J 1.6 Hz, 1H, Ar). Signal for HCl salt is not observed. M/Z (M+H)$^+$=391.2. MP: 120-125° C.

Compound 38

4-Methoxy-3-oxo-butyronitrile

Compound 38 was obtained according to general procedure VII(i) starting from methoxyacethylene chloride. Purification by flash-chromatography (AcOEt in cyclohexane, 20 to 70%) afforded the product as a yellow oil in 17% yield.

$^1$H-NMR (400 MHz, DMSO): 3.30 (s, 3H, OCH$_3$); 4.09 (s, 2H, CH$_2$); 4.13 (s, 2H, CH$_2$).

Compound 39

8-Bromo-2-methoxymethyl-4H-pyrazolo[1,5-a]quinazolin-5-one

Compound 39 was obtained according to general procedure II(i) starting from compound 1 in presence of compound 38. Purification by flash-chromatography (AcOEt in cyclohexane, 30 to 60%) afforded compound 39 as a light yellow solid in 16% yield.

$^1$H-NMR (400 MHz, DMSO): 3.33 (s, 3H, OCH$_3$); 4.45 (s, 2H, OCH$_2$); 5.90 (s, 1H, Ar); 7.66 (dd, J 8.4 Hz, 1.9 Hz, 1H, Ar); 8.04 (d, J 8.4 Hz, 1H, Ar); 8.15 (d, J 1.9 Hz, 1H, Ar); 12.26 (bs, 1H, NH). M/Z (M[$^{79}$Br]+H)$^+$=308.0. MP: >250° C.

Compound 40

8-Bromo-2-methoxymethyl-4-methyl-4H-pyrazolo[1,5-a]quinazolin-5-one

Compound 40 was obtained according to general procedure III starting from compound 39 in presence of iodomethane. The reaction mixture was stirred at room temperature for 2 Hrs. Purification by flash-chromatography (AcOEt in cyclohexane, 0 to 80%) afforded Compound 40 as a light pink solid in 48% yield.

$^1$H-NMR (400 MHz, DMSO): 3.34 (s, 3H, OCH$_3$); 3.49 (s, 3H, N—CH$_3$); 4.48 (s, 2H, OCH$_2$); 6.29 (s, 1H, Ar); 7.67 (dd, J 8.4 Hz, 1.9 Hz, 1H, Ar); 8.08 (d, J 8.4 Hz, 1H, Ar); 8.16 (d, J 1.9 Hz, 1H, Ar). M/Z (M+H)$^+$=322.0.

Example 61

8-(6-Amino-pyridin-3-yl)-2-methoxymethyl-4-methyl-4H-pyrazolo[1,5-a]quinazolin-5-one, HCl Salt

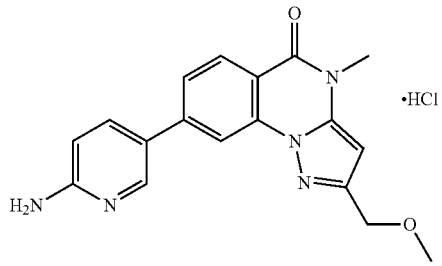 [SMILES: COCc1cc2n(C)c(=O)c3ccc(-c4ccc(N)nc4)cc3n2n1 ; Cl]

Example 61 was obtained according to general procedure IV(iv) starting from compound 40 in presence of 2-aminopyridine-5-boronic acid pinacol ester. Purification by flash-chromatography (MeOH in CH$_2$Cl$_2$ 0 to 5%) and salt formation according to procedure V(iii) afforded example 61 as a white solid in 15% yield.

$^1$H-NMR (400 MHz, DMSO): 3.37 (s, 3H, OCH$_3$); 3.54 (s, 3H, N—CH$_3$); 4.51 (s, 2H, OCH$_2$); 6.31 (s, 1H, Ar); 7.11 (d, J 9.3 Hz, 1H, Ar); 7.79 (dd, J 8.4 Hz, 1.7 Hz, 1H, Ar); 8.12 (bs, 2H, NH$_2$); 8.25-8.27 (m, 2H, Ar); 8.43 (dd, J 9.3 Hz, J 2.1, Hz 1H, Ar); 8.55 (d, J 2.1 Hz, 1H, Ar); 14.00 (bs, 1H, NH). M/Z (M+H)$^+$=336.1. MP: 235-242° C.

Example 62

8-(2,6-Dimethyl-pyridin-4-yl)-2-methoxymethyl-4-methyl-4H-pyrazolo[1,5-a]quinazolin-5-one, HCl Salt

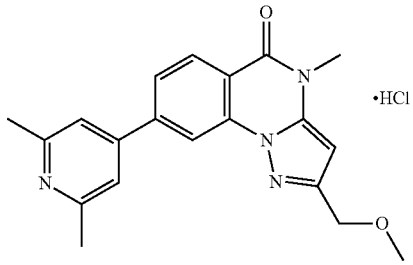

Example 62 was obtained according to general procedure IV(iv) starting from compound 40 in presence of 2,6-dimethylpyridine-4-boronic acid pinacol ester. Purification by flash-chromatography (MeOH in CH$_2$Cl$_2$ 0 to 5%) and salt formation according to procedure V(ii) afforded example 62 as a red solid in 48% yield.

$^1$H-NMR (400 MHz, DMSO): 2.81 (s, 6H, 2CH$_3$); 3.37 (s, 3H, OCH$_3$); 3.55 (s, 3H, N—CH$_3$); 4.52 (s, 2H, OCH$_2$); 6.35 (s, 1H, Ar); 8.01 (dd, J 8.3 Hz, J 1.9 Hz, 1H, Ar); 8.27 (bs, 2H, Ar); 8.37 (d, J 8.3 Hz, 1H, Ar); 8.50 (d, J 1.9 Hz, 1H, Ar). Signal for HCl salt is not observed. M/Z (M+H)$^1$=349.2. MP: >250° C.

Compound 41

3-Cyclopropyl-3-oxo-propionitrile

Compound 41 was obtained according to general procedure VII(i) starting from Cyclopropanecarbonyl chloride. Purification by flash-chromatography (AcOEt in cyclohexane, 0 to 30%) afforded the product as a yellow oil in 50% yield.

$^1$H-NMR (400 MHz, DMSO): 0.95-0.99 (m, 4H, 2CH$_2$); 2.04-2.06 (m, 1H, CH); 4.21 (bs, 2H, CH$_2$).

Compound 42

8-Bromo-2-cyclopropyl-4H-pyrazolo[1,5-a]quinazolin-5-one

Compound 42 was obtained according to general procedure II(i), starting from compound 1 in presence of compound 41, as a white solid in 61% yield.

$^1$H-NMR (400 MHz, DMSO): 0.79-0.82 (m, 2H, 2CH); 0.94-0.99 (m, 2H, 2CH); 1.95-2.02 (m, 1H, CH); 5.64 (s, 1H, Ar); 7.60 (dd, J 8.4 Hz, 1.9 Hz, 1H, Ar); 8.00 (d, J 8.4 Hz, 1H, Ar); 8.08 (d, J 1.9 Hz, 1H, Ar); 12.17 (bs, 1H, NH). M/Z (M[$^{79}$Br]+H)$^+$=303.9. MP: >250° C.

Compound 43

8-Bromo-2-cyclopropyl-4-methyl-4H-pyrazolo[1,5-a]quinazolin-5-one

Compound 43 was obtained according to general procedure III starting from compound 42 in presence of iodomethane. The reaction mixture was stirred at room temperature for 60 min. Compound 43 was obtained as a white solid in 92% yield.

$^1$H-NMR (400 MHz, DMSO): 0.81-0.85 (m, 2H, 2CH); 0.98-1.03 (m, 2H, 2CH); 1.98-2.05 (m, 1H, CH); 3.44 (s, 3H, N—CH$_3$); 6.03 (s, 1H, Ar); 7.60 (dd, J 8.5 Hz, 1.9 Hz, 1H, Ar); 8.03 (d, J 8.5 Hz, 1H, Ar); 8.08 (d, J 1.9 Hz, 1H, Ar). M/Z (M[$^{79}$Br]+H)$^+$=318.0. MP: >250° C.

Example 63

8-(6-Amino-pyridin-3-yl)-2-cyclopropyl-4-methyl-4H-pyrazolo[1,5-a]quinazolin-5-one, HCl Salt

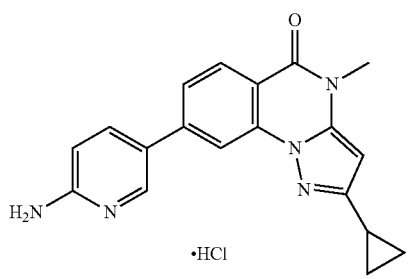 [SMILES: Cn1c(=O)c2ccc(-c3ccc(N)nc3)cc2n2nc(C3CC3)cc12 ; Cl]

Example 63 was obtained according to general procedure IV(iii) starting from compound 43 in presence of 2-aminopyridine-5-boronic acid pinacol ester. The reaction mixture was submitted to microwave irradiation for 60 min at 150° C. Purification by flash-chromatography (EtOAc) and salt formation according to procedure V(iii) afforded example 63 as a beige solid in 27% yield $^1$H-NMR (400 MHz, DMSO): 0.81-0.85 (m, 2H, 2CH); 0.98-1.03 (m, 2H, 2CH); 2.00-2.06 (m, 1H, CH); 3.47 (s, 3H, N—CH$_3$); 6.02 (s, 1H, Ar); 7.12 (d, J 9.3 Hz, 1H, Ar); 7.72 (dd, J 8.3 Hz, 1.8 Hz, 1H, Ar); 8.17 (d, J 1.8 Hz, 1H, Ar); 8.20 (bs, 2H, NH$_2$); 8.21 (d, J 8.3 Hz, 1H, Ar); 8.41 (dd, J 9.3 Hz, J 2.4 Hz, 1H, Ar); 8.52 (d, J 2.4 Hz, 1H, Ar); 14.31 (bs, 1H, NH). M/Z (M+H)$^+$=332.1. MP: >250° C.

Compound 44

3-Cyclobutyl-3-oxo-propionitrile

Compound 44 was obtained according to general procedure VII(i) starting from Cyclobutanecarbonyl chloride. Purification by flash-chromatography (AcOEt in cyclohexane, 0 to 30%) afforded the product as an orange oil in 56% yield.

$^1$H-NMR (400 MHz, DMSO): 1.85-1.98 (m, 2H, CH$_2$); 2.05-2.20 (m, 4H, 2CH$_2$); 3.33-3.41 (m, 1H, CH); 3.95 (s, 2H, CH$_2$).

Compound 45

8-Bromo-2-cyclobutyl-4H-pyrazolo[1,5-a]quinazolin-5-one

Compound 45 was obtained according to general procedure II(i), starting from compound 1 in presence of compound 44, as a white solid in 60% yield.

$^1$H-NMR (400 MHz, DMSO): 1.84-2.06 (m, 2H, CH$_2$); 2.17-2.34 (m, 4H, 2CH$_2$); 3.55 (qui, J 8.6 Hz, 1H, CH); 5.83 (s, 1H, Ar); 7.61 (dd, J 8.5 Hz, 1.9 Hz, 1H, Ar); 8.01 (d, J 8.5 Hz, 1H, Ar); 8.11 (d, J 1.9 Hz, 1H, Ar); 12.20 (bs, 1H, NH). M/Z (M[$^{79}$Br]+H)$^+$=318.0. MP: >250° C.

Compound 46

8-Bromo-2-cyclobutyl-4-methyl-4H-pyrazolo[1,5-a]quinazolin-5-one

Compound 46 was obtained according to general procedure III starting from compound 45 in presence of iodomethane. The reaction mixture was stirred at room temperature for 90 min. Compound 46 was obtained as a white solid in 89% yield.

$^1$H-NMR (400 MHz, DMSO): 1.87-2.06 (m, 2H, CH$_2$); 2.21-2.37 (m, 4H, 2CH$_2$); 3.48 (s, 3H, N—CH$_3$); 3.59 (qui, J 8.5 Hz, 1H, CH); 6.24 (s, 1H, Ar); 7.62 (dd, J 8.5 Hz, 1.9 Hz, 1H, Ar); 8.04 (d, J 8.5 Hz, 1H, Ar); 8.11 (d, J 1.9 Hz, 1H, Ar). M/Z (M[$^{79}$Br]+H)$^+$=332.0. MP: 157-159° C.

Example 64

8-(6-Amino-pyridin-3-yl)-2-cyclobutyl-4-methyl-4H-pyrazolo[1,5-a]quinazolin-5-one, HCl Salt

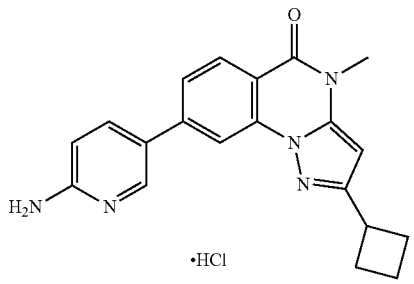 [SMILES: Cn1c(=O)c2ccc(-c3ccc(N)nc3)cc2n2nc(C3CCC3)cc12 ; Cl]

Example 64 was obtained according to general procedure IV(i) starting from compound 46 in presence of 2-aminopyridine-5-boronic acid pinacol ester. The reaction mixture was submitted to microwave irradiation for 30 min at 150° C. Purification by flash-chromatography (EtOAc) and salt formation according to procedure V(ii), afforded example 64 as a beige solid in 53% yield.

$^1$H-NMR (400 MHz, DMSO): 1.88-2.10 (m, 2H, CH$_2$); 2.23-2.38 (m, 4H, 2CH$_2$); 3.52 (s, 3H, N—CH$_3$); 3.62 (quint, J 8.5 Hz, 1H, CH); 6.28 (s, 1H, Ar); 7.14 (d, J 9.3 Hz, 1H, Ar); 7.74 (dd, J 8.3 Hz, 1.9 Hz, 1H, Ar); 8.20 (d, J 1.9 Hz, 1H, Ar); 8.22 (d, J 8.3 Hz, 1H, Ar); 8.26 (bs, 2H, NH$_2$); 8.44 (dd, J 9.3 Hz, J 2.3, Hz 1H, Ar); 8.54 (d, J 2.3 Hz, 1H, Ar); 14.15 (bs, 1H, NH). M/Z (M+H)$^+$=346.1. MP: >250° C.

Compound 47

3-Cyclopentyl-3-oxo-propionitrile

Compound 47 was obtained according to general procedure VII(i) starting from Cyclopentylcarbonyl chloride. Purification by flash-chromatography (AcOEt in cyclohexane, 0 to 50%) afforded the product as a light yellow oil in 86% yield.

$^1$H-NMR (400 MHz, DMSO): 1.52-1.90 (m, 8H, 3CH$_2$); 2.92-3.00 (m, 1H, CH); 4.10 (s, 2H, CH$_2$).

Compound 48

8-Bromo-2-cyclopentyl-4H-pyrazolo[1,5-a]quinazolin-5-one

Compound 48 was obtained according to general procedure II(i), starting from compound 1 in presence of compound 47, as a beige solid in 54% yield.

$^1$H-NMR (400 MHz, DMSO): 1.62-1.75 (m, 6H, 2CH$_2$+2CH); 1.97-2.03 (m, 2H, 2CH); 3.04-3.15 (m, 1H, CH); 5.76 (s, 1H, Ar); 7.60 (dd, J 8.5 Hz, 1.9 Hz, 1H, Ar); 8.00 (d, J 8.5 Hz, 1H, Ar); 8.09 (d, J 1.9 Hz, 1H, Ar); 12.19 (bs, 1H, NH). M/Z (M[$^{79}$Br]+H)$^+$=332.0. MP: >250° C.

Compound 49

8-Bromo-2-cyclopentyl-4-methyl-4H-pyrazolo[1,5-a]quinazolin-5-one

Compound 49 was obtained according to general procedure III starting from compound 48 in presence of iodomethane. The reaction mixture was stirred at room temperature for 90 min. Compound 49 was obtained as a white solid in 93% yield.

$^1$H-NMR (400 MHz, DMSO): 1.64-1.76 (m, 6H, 2CH$_2$+2CH); 2.00-2.06 (m, 2H, 2CH); 3.09-3.17 (m, 1H, CH); 3.47 (s, 3H, N—CH$_3$); 6.17 (s, 1H, Ar); 7.61 (dd, J 8.5 Hz, 1.9 Hz, 1H, Ar); 8.04 (d, J 8.5 Hz, 1H, Ar); 8.10 (d, J 1.9 Hz, 1H, Ar). M/Z (M[$^{79}$Br]+H)$^+$=346.0. MP: 131-133° C.

Example 65

8-(6-Amino-pyridin-3-yl)-2-cyclopentyl-4-methyl-4H-pyrazolo[1,5-a]quinazolin-5-one, HCl Salt

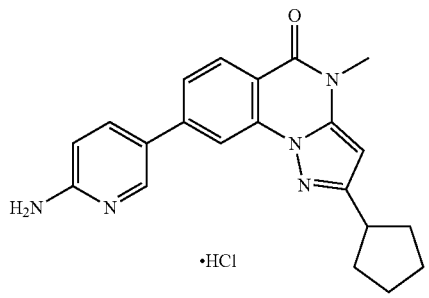 [SMILES: Cn1c(=O)c2ccc(-c3ccc(N)nc3)cc2n2nc(C3CCCC3)cc12 ; Cl]

Example 65 was obtained according to general procedure IV(iii) starting from compound 49 in presence of 2-aminopyridine-5-boronic acid pinacol ester. Purification by flash-chromatography (EtOAc) and salt formation according to procedure V(ii) afforded example 65 as a white solid in 63% yield.

$^1$H-NMR (400 MHz, DMSO): 1.65-1.79 (m, 6H, 2CH$_2$+2CH); 2.01-2.07 (m, 2H, 2CH); 3.11-3.20 (m, 1H, CH); 3.50 (s, 3H, N—CH$_3$); 6.19 (s, 1H, Ar); 7.12 (d, J 9.3 Hz, 1H, Ar); 7.73 (dd, J 8.3 Hz, 1.8 Hz, 1H, Ar); 8.18 (d, J 1.8 Hz, 1H, Ar); 8.21 (bs, 2H, NH$_2$); 8.21 (d, J 8.3 Hz, 1H, Ar); 8.41 (dd, J 9.3 Hz, J 2.2, Hz 1H, Ar); 8.53 (d, J 2.2 Hz, 1H, Ar); 14.18 (bs, 1H, NH). M/Z (M+H)$^+$=360.1. MP: >250° C.

Example 66

2-Cyclopentyl-8-(2,6-dimethyl-pyridin-4-yl)-4-methyl-4H-pyrazolo[1,5-a]quinazolin-5-one, HCl Salt

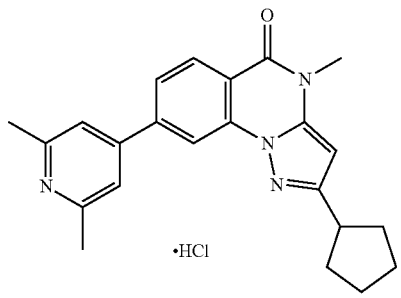 [SMILES: Cc1cc(-c2ccc3c(=O)n(C)c4cc(C5CCCC5)nn4c3c2)cc(C)n1 ; Cl]

Example 66 was obtained according to general procedure IV(iv) starting from compound 49 in presence of 2,6-dimethylpyridine-4-boronic acid pinacol ester. To a celite pad suspension in DMSO-MeOH mixture (1-1 (v-v)) Smopex resin (2 equiv. referred to initial Pd quantity) was added. The mixture was stirred for 2 Hrs, filtered off and the solid was washed with a mixture of DMSO-MeOH. The filtrate was concentrated and the residue was hydrolysed. The resulting solid was collected, washed with water and dried under reduced pressure with P$_2$O$_5$ at 50° C. Salt formation according to procedure V(ii) afforded the example 66 as a light yellow solid in 40% yield.

¹H-NMR (400 MHz, DMSO): 1.67-1.81 (m, 6H, 2CH₂+2CH); 2.03-2.09 (m, 2H, 2CH); 2.80 (s, 6H, 2CH₃); 3.14-3.23 (m, 1H, CH); 3.53 (s, 3H, N—CH₃); 6.25 (s, 1H, Ar); 7.96 (dd, J 8.2 Hz, J 1.6 Hz, 1H, Ar); 8.26 (bs, 2H, Ar); 8.35 (d, J 8.2 Hz, 1H, Ar); 8.45 (d, J 1.6 Hz, 1H, Ar). Signal of HCl salt is not observed. M/Z (M+H)⁺=373.1. MP: >250° C.

Compound 50

8-Bromo-2-cyclopentyl-4-methyl(D₃)-4H-pyrazolo[1,5-a]quinazolin-5-one

Compound 50 was obtained according to general procedure III starting from compound 48 in presence of iodomethane D₃. The reaction mixture was stirred at room temperature for 2 Hrs. Compound 50 was obtained as a white solid in quantitative yield.

¹H-NMR (400 MHz, DMSO): 1.65-1.78 (m, 6H, 2CH₂+2CH); 2.00-2.05 (m, 2H, 2CH); 3.09-3.17 (m, 1H, CH); 6.18 (s, 1H, Ar); 7.62 (dd, J 8.5 Hz, 1.9 Hz, 1H, Ar); 8.04 (d, J 8.5 Hz, 1H, Ar); 8.11 (d, J 1.9 Hz, 1H, Ar). M/Z (M[⁷⁹Br]+H)⁺=349.1.

Example 67

8-(6-Amino-pyridin-3-yl)-2-cyclopentyl-4-methyl(D₃)-4H-pyrazolo[1,5-a]quinazolin-5-one, HCl Salt

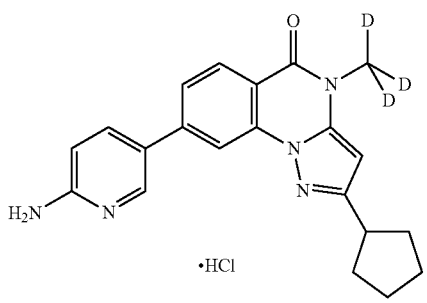 [SMILES: [2H]C([2H])([2H])n1c(=O)c2ccc(-c3ccc(N)nc3)cc2n2nc(C3CCCC3)cc12 ; Cl]

Example 67 was obtained according to general procedure IV(iv) starting from compound 50 in presence of 2-aminopyridine-5-boronic acid pinacol ester. Purification by flash-chromatography (EtOAc in Cyclohexane, 70 to 100%) and salt formation according to procedure V(ii) afforded example 67 as a white solid in 53% yield.

¹H-NMR (400 MHz, DMSO): 1.66-1.80 (m, 6H, 2CH₂+2CH); 2.01-2.08 (m, 2H, 2CH); 3.12-3.20 (m, 1H, CH); 6.20 (s, 1H, Ar); 7.12 (d, J 9.3 Hz, 1H, Ar); 7.74 (dd, J 8.4 Hz, 1.8 Hz, 1H, Ar); 8.19 (bs, 2H, NH₂); 8.19 (d, J 1.8 Hz, 1H, Ar); 8.22 (d, J 8.4 Hz, 1H, Ar); 8.42 (dd, J 9.3 Hz, J 2.2, Hz 1H, Ar); 8.54 (d, J 2.2 Hz, 1H, Ar); 14.10 (bs, 1H, NH). M/Z (M+H)⁺=363.2. MP: >250° C.

Example 68

2-Cyclopentyl-8-(2,6-dimethyl-pyridin-4-yl)-4-methyl(D₃)-4H-pyrazolo[1,5-a]quinazolin-5-one, HCl Salt

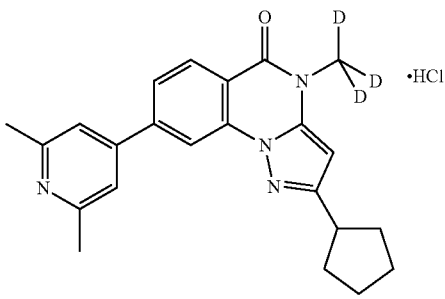 [SMILES: [2H]C([2H])([2H])n1c(=O)c2ccc(-c3cc(C)nc(C)c3)cc2n2nc(C3CCCC3)cc12 ; Cl]

Example 68 was obtained according to general procedure IV(iv) starting from compound 50 in presence of 2,6-dimethylpyridine-4-boronic acid pinacol ester. To a celite pad suspension in DMSO-MeOH mixture (1-1 (v-v)) Smopex resin (2 equiv. referred to initial Pd quantity) was added. The mixture was stirred for 2 Hrs, filtered off and the solid was washed with a mixture of DMSO-MeOH. MeOH was removed and water was added to the resulting DMSO solution. The resulting solid was collected, washed with water and dried under reduced pressure with P₂O₅ at 50° C. Salt formation according to procedure V(ii) afforded example 68 as a white solid in 31% yield.

¹H-NMR (400 MHz, DMSO): 1.67-1.81 (m, 6H, 2CH₂+2CH); 2.02-2.09 (m, 2H, 2CH); 2.81 (s, 6H, 2CH₃); 3.13-3.21 (m, 1H, CH); 6.25 (s, 1H, Ar); 7.97 (dd, J 8.3 Hz, J 1.8 Hz, 1H, Ar); 8.28 (bs, 2H, Ar); 8.35 (d, J 8.3 Hz, 1H, Ar); 8.45 (d, J 1.8 Hz, 1H, Ar). Signal for HCl salt is not observed. M/Z (M+H)⁺=376.2. MP: >250° C.

Compound 51

8-Bromo-2-cyclopentyl-4-ethyl-4H-pyrazolo[1,5-a]quinazolin-5-one

Compound 51 was obtained according to general procedure III starting from compound 48 in presence of iodoethane. The reaction mixture was stirred for 2 Hrs at room temperature. Purification by flash-chromatography (AcOEt in cyclohexane, 0 to 10%) afforded compound 51 as a white solid in 82% yield.

¹H-NMR (400 MHz, DMSO): 1.26 (t, J 7.1 Hz, 3H, N—CH₂—CH₃); 1.63-1.79 (m, 6H, 2CH₂+2CH); 2.00-2.07 (m, 2H, 2CH); 3.10-3.18 (m, 1H, CH); 4.04 (q, J 7.1 Hz, 2H, N—CH₂—CH₃); 6.23 (s, 1H, Ar); 7.62 (dd, J 8.5 Hz, 1.9 Hz, 1H, Ar); 8.05 (d, J 8.5 Hz, 1H, Ar); 8.11 (d, J 1.9 Hz, 1H, Ar). M/Z (M[⁷⁹Br]+H)⁺=360.0.

Example 69

8-(6-Amino-pyridin-3-yl)-2-cyclopentyl-4-ethyl-4H-pyrazolo[1,5-a]quinazolin-5-one, HCl Salt

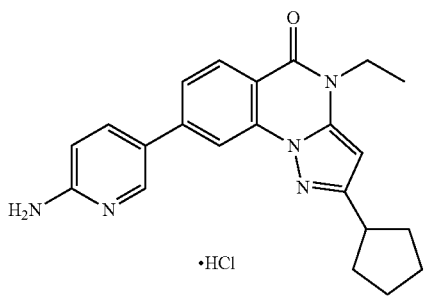 [SMILES: CCn1c(=O)c2ccc(-c3ccc(N)nc3)cc2n2nc(C3CCCC3)cc12 ; Cl]

Example 69 was obtained according to general procedure IV(iv) starting from compound 51 in presence of 2-aminopyridine-5-boronic acid pinacol ester. The filtrate was hydrolysed with water (50 DMF volumes) and extracted twice with EtOAc (2*50 DMF volumes). The organic layers were combined, washed with brine, dried over MgSO$_4$ and concentrated. Purification by flash-chromatography (EtOAc in Cyclohexane, 70 to 100%) and salt formation according to procedure V(ii) afforded example 69 as a beige solid in 76% yield.

$^1$H-NMR (400 MHz, DMSO): 1.30 (t, J 7.1 Hz, 3H, N—CH$_2$—CH$_3$); 1.66-1.82 (m, 6H, 2CH$_2$+2CH); 2.02-2.08 (m, 2H, 2CH); 3.12-3.20 (m, 1H, CH); 4.08 (q, J 7.1 Hz, 2H, N—CH$_2$—CH$_3$); 6.27 (s, 1H, Ar); 7.13 (d, J 9.3 Hz, 1H, Ar); 7.75 (dd, J 8.3 Hz, 1.9 Hz, 1H, Ar); 8.20 (d, J 1.9 Hz, 1H, Ar); 8.20 (bs, 2H, NH$_2$); 8.23 (d, J 8.3 Hz, 1H, Ar); 8.44 (dd, J 9.3 Hz, J 2.2, Hz 1H, Ar); 8.54 (d, J 2.2 Hz, 1H, Ar); 14.01 (bs, 1H, NH). M/Z (M+H)$^+$=374.1. MP: >250° C.

Example 70

2-Cyclopentyl-8-(2,6-dimethyl-pyridin-4-yl)-4-ethyl-4H-pyrazolo[1,5-a]quinazolin-5-one, HCl Salt

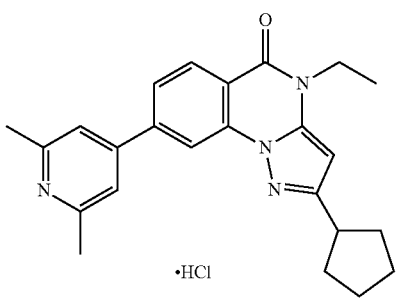 [SMILES: CCn1c(=O)c2ccc(-c3cc(C)nc(C)c3)cc2n2nc(C3CCCC3)cc12 ; Cl]

Example 70 was obtained according to general procedure IV(iv) starting from compound 51 in presence of 2,6-dimethylpyridine-4-boronic acid pinacol ester. The filtrate was hydrolysed with water (50 DMF volumes) and extracted twice with EtOAc (2*50 DMF volumes). The organic layers were combined, washed with brine, dried over MgSO$_4$ and concentrated. Purification by flash-chromatography (EtOAC in Cyclohexane, 60 to 100%) and salt formation according to procedure V(ii) afforded the product as a white solid in 66% yield.

$^1$H-NMR (400 MHz, DMSO): 1.29 (t, J 7.1 Hz, 3H, N—CH$_2$—CH$_3$); 1.66-1.81 (m, 6H, 2CH$_2$+2CH); 2.02-2.09 (m, 2H, 2CH); 2.81 (s, 6H, 2CH$_3$); 3.13-3.21 (m, 1H, CH); 4.09 (q, J 7.1 Hz, 2H, N—CH$_2$—CH$_3$); 6.31 (s, 1H, Ar); 7.95 (dd, J 8.3 Hz, J 1.9 Hz, 1H, Ar); 8.25 (bs, 2H, Ar); 8.33 (d, J 8.3 Hz, 1H, Ar); 8.43 (d, J 1.9 Hz, 1H, Ar). Signal for HCl salt is not observed. M/Z (M+H)$^+$=387.2. MP: >250° C.

Compound 52

8-Bromo-2-cyclopentyl-4-propyl-4H-pyrazolo[1,5-a]quinazolin-5-one

Compound 52 was obtained according to general procedure III starting from compound 48 in presence of bromopropane. The reaction mixture was stirred for 4 Hrs at room temperature, then hydrolysed with aqueous 1N HCl, and extracted twice with EtOAc. The organic layers were combined, washed with brine, dried over MgSO$_4$ and concentrated. Purification by flash-chromatography (AcOEt in cyclohexane, 0 to 10%) afforded compound 52 as a white solid in 76% yield.

$^1$H-NMR (400 MHz, DMSO): 0.94 (t, J 7.4 Hz, 3H, N—CH$_2$—CH$_2$—CH$_3$); 1.65-1.79 (m, 8H, 3CH$_2$+2CH); 2.00-2.07 (m, 2H, 2CH); 3.09-3.17 (m, 1H, CH); 3.95-3.98 (m, 2H, N—CH$_2$—CH$_2$—CH$_3$); 6.24 (s, 1H, Ar); 7.62 (dd, J 8.5 Hz, 1.9 Hz, 1H, Ar); 8.05 (d, J 8.5 Hz, 1H, Ar); 8.12 (d, J 1.9 Hz, 1H, Ar). M/Z (M[$^{79}$Br]+H)$^+$=374.0.

Example 71

8-(6-Amino-pyridin-3-yl)-2-cyclopentyl-4-propyl-4H-pyrazolo[1,5-a]quinazolin-5-one, HCl Salt

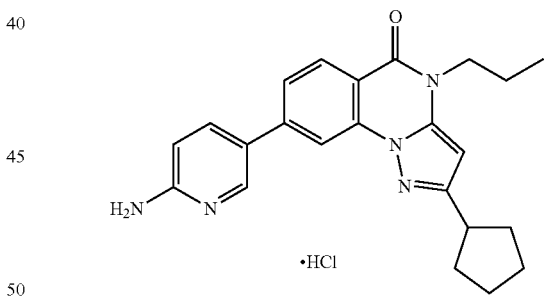

Example 71 was obtained according to general procedure IV(iv) starting from compound 52 in presence of 2-aminopyridine-5-boronic acid pinacol ester. Purification by flash-chromatography (EtOAc in Cyclohexane, 70 to 100%) and salt formation according to procedure V(ii) afforded example 71 as a beige solid in 71% yield.

$^1$H-NMR (400 MHz, DMSO): 0.94 (t, J 7.4 Hz, 3H, N—CH$_2$—CH$_2$—CH$_3$); 1.65-1.80 (m, 8H, 3CH$_2$+2CH); 2.01-2.07 (m, 2H, 2CH); 3.11-3.19 (m, 1H, CH); 3.97-4.01 (m, 2H, N—CH$_2$—CH$_2$—CH$_3$); 6.26 (s, 1H, Ar); 7.14 (d, J 9.3 Hz, 1H, Ar); 7.73 (dd, J 8.3 Hz, 1.8 Hz, 1H, Ar); 8.18 (d, J 1.8 Hz, 1H, Ar); 8.20 (d, J 8.3 Hz, 1H, Ar); 8.31 (bs, 2H, NH$_2$); 8.42 (dd, J 9.3 Hz, J 2.3, Hz 1H, Ar); 8.54 (d, J 2.3 Hz, 1H, Ar); 14.28 (bs, 1H, NH). M/Z (M+H)$^+$=388.2. MP: >250° C.

Example 72

2-Cyclopentyl-8-(2,6-dimethyl-pyridin-4-yl)-4-propyl-4H-pyrazolo[1,5-a]quinazolin-5-one, HCl Salt

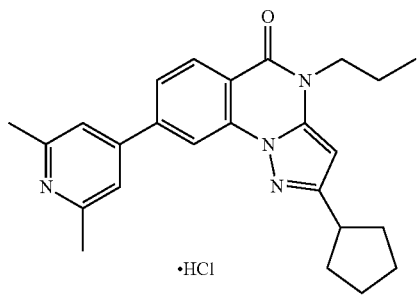 [SMILES: CCCn1c(=O)c2ccc(-c3cc(C)nc(C)c3)cc2n2nc(C3CCCC3)cc12 ; Cl]

Example 72 was obtained according to general procedure IV(iv) starting from compound 52 in presence of 2,6-dimethylpyridine-4-boronic acid pinacol ester. The filtrate was hydrolysed with water (50 DMF volumes) and extracted twice with EtOAc (2*50 DMF volumes). The Organic layers were combined, washed with brine, dried over $MgSO_4$, concentrated and purified by flash-chromatography (EtOAC in Cyclohexane, 60 to 100%). Salt formation according to procedure V(ii) afforded example 72 as a yellow solid in 44% yield.

$^1$H-NMR (400 MHz, DMSO): 0.94 (t, J 7.4 Hz, 3H, N—$CH_2$—$CH_2$—$CH_3$); 1.66-1.81 (m, 8H, $3CH_2+2CH$); 2.02-2.08 (m, 2H, 2CH); 2.82 (s, 6H, $2CH_3$); 3.12-3.20 (m, 1H, CH); 4.00-4.03 (m, 2H, N—$CH_2$—$CH_2$—$CH_3$); 6.32 (s, 1H, Ar); 7.96 (dd, J 8.4 Hz, J 1.8 Hz, 1H, Ar); 8.27 (bs, 2H, Ar); 8.34 (d, J 8.4 Hz, 1H, Ar); 8.44 (d, J 1.8 Hz, 1H, Ar). Signal for HCl salt is not observed. M/Z $(M+H)^+$=401.2. MP: >250° C.

Compound 53

8-Bromo-2-cyclopentyl-4-(2,2,2-trifluoro-ethyl)-4H-pyrazolo[1,5-a]quinazolin-5-one Compound 53 was obtained according to general procedure III starting from compound 48 in presence of 1,1,1-trifluoro-2-iodoethane. The reaction mixture was stirred at room temperature for 4 days. Each time after the $1^{st}$, $2^{nd}$ and $3^{rd}$ days, NaH (1.7 equiv.) and 1,1,1-trifluoro-2-iodoethane (2.1 equiv.) were added. Purification by flash-chromatography (AcOEt in cyclohexane, 0 to 30%) afforded compound 53 as a light yellow solid in 47% yield.

$^1$H-NMR (400 MHz, DMSO): 1.65-1.78 (m, 6H, $2CH_2+$ 2CH); 1.99-2.07 (m, 2H, 2CH); 3.11-3.18 (m, 1H, CH); 4.94 (q, J 9.2 Hz, 2H, N—$CH_2$—$CF_3$); 6.37 (s, 1H, Ar); 7.66 (dd, J 8.5 Hz, J 1.9 Hz, 1H, Ar); 8.07 (d, J 8.5 Hz, 1H, Ar); 8.14 (d, J 1.9 Hz, 1H, Ar). M/Z $(M[^{79}Br]+H)^+$=414.0.

Example 73

2-Cyclopentyl-8-(2,6-dimethyl-pyridin-4-yl)-4-(2,2,2-trifluoro-ethyl)-4H-pyrazolo[1,5-a]quinazolin-5-one, HCl Salt

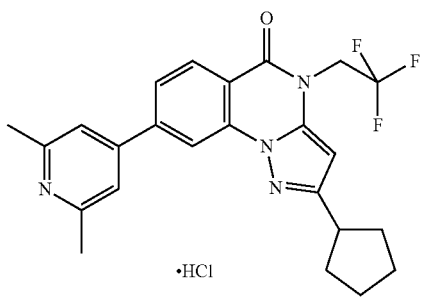 [SMILES: Cc1cc(-c2ccc3c(=O)n(CC(F)(F)F)c4cc(C5CCCC5)nn4c3c2)cc(C)n1 ; Cl]

Example 73 was obtained according to general procedure IV(iv) starting from compound 53 in presence of 2,6-dimethylpyridine-4-boronic acid pinacol ester. The filtrate was hydrolysed with water (50 DMF volumes) and extracted twice with EtOAc (2*50 DMF volumes). The organic layers were combined, washed with brine, dried over $MgSO_4$ and concentrated. Purification by flash-chromatography (EtOAC in Cyclohexane, 0 to 50%) and salt formation according to procedure V(iii) afforded the product as a yellow solid in 17% yield.

$^1$H-NMR (400 MHz, DMSO): 1.64-1.81 (m, 6H, $2CH_2+$ 2CH); 2.03-2.08 (m, 2H, 2CH); 2.76 (s, 6H, $2CH_3$); 3.14-3.21 (m, 1H, CH); 4.99 (q, J 9.1 Hz, 2H, N—$CH_2$—$CF_3$); 6.42 (s, 1H, Ar); 7.96 (dd, J 8.2 Hz, J 1.5 Hz, 1H, Ar); 8.16 (bs, 2H, Ar); 8.35 (d, J 8.2 Hz, 1H, Ar); 8.43 (d, J 1.5 Hz, 1H, Ar). Signal for HCl salt is not observed. M/Z $(M+H)^+$= 441.2. MP: >250° C.

Compound 54

3-Cyclohexyl-3-oxo-propionitrile

Compound 54 was obtained according to general procedure VII(i) starting from Cyclohexanecarbonyl chloride. Purification by flash-chromatography (AcOEt in cyclohexane, 0 to 30%) afforded the product as a light yellow oil in 87% yield.

$^1$H-NMR (400 MHz, DMSO): 1.21-1.25 (m, 5H, $2CH_2+$ CH); 1.59-1.71 (m, 3H, $CH_2+CH$); 1.81-1.83 (m, 2H, $CH_2$); 2.42-2.44 (m, 1H, CH); 4.12 (s, 2H, $CH_2$). M/Z $(M+H)^+$= 152.2.

Compound 55

8-Bromo-2-cyclohexyl-4H-pyrazolo[1,5-a]quinazolin-5-one

Compound 55 was obtained according to general procedure II (i), starting from compound 1 in presence of compound 54, as a light beige solid in 81% yield.

$^1$H-NMR (400 MHz, DMSO): 1.20-1.50 (m, 5H, $2CH_2+$ CH); 1.67-1.79 (m, 3H, $CH_2+CH$); 1.92-1.95 (m, 2H, $CH_2$); 2.62-2.68 (m, 1H, CH); 5.76 (s, 1H, Ar); 7.61 (dd, J 8.5 Hz, 1.4 Hz, 1H, Ar); 8.00 (d, J 8.5 Hz, 1H, Ar); 8.09 (d, J 1.4 Hz, 1H, Ar); 12.17 (bs, 1H, NH). M/Z $(M[^{79}Br]+H)^+$=346.0. MP: >250° C.

Compound 56

8-Bromo-2-cyclohexyl-4-methyl-4H-pyrazolo[1,5-a]quinazolin-5-one

Compound 56 was obtained according to general procedure III starting from compound 55 in presence of iodomethane. The reaction mixture was stirred at room temperature for 2 Hrs. Compound 56 was obtained as a beige solid in 91% yield.

$^1$H-NMR (400 MHz, DMSO): 1.26-1.55 (m, 5H, 2CH$_2$+CH); 1.69-1.81 (m, 3H, CH$_2$+CH); 1.96-1.99 (m, 2H, CH$_2$); 2.67-2.72 (m, 1H, CH); 3.47 (s, 3H, N—CH$_3$); 6.17 (s, 1H, Ar); 7.62 (dd, J 8.4 Hz, 1.2 Hz, 1H, Ar); 8.05 (d, J 8.4 Hz, 1H, Ar); 8.12 (d, J 1.2 Hz, 1H, Ar). M/Z (M[$^{79}$Br]+H)$^+$= 360.0. MP: 153-155° C.

Example 74

8-(6-Amino-pyridin-3-yl)-2-cyclohexyl-4-methyl-4H-pyrazolo[1,5-a]quinazolin-5-one, HCl Salt

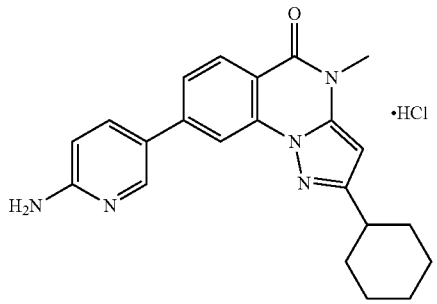 [SMILES: Cn1c(=O)c2ccc(-c3ccc(N)nc3)cc2n2nc(C3CCCCC3)cc12 ; Cl]

Example 74 was obtained according to general procedure IV(i) starting from compound 56 in presence of 2-aminopyridine-5-boronic acid pinacol ester. The reaction mixture was submitted to microwave irradiation for 30 min at 150° C. Purification by flash-chromatography (EtOAc) and salt formation according to procedure V(ii) afforded example 74 as a white solid in 64% yield.

$^1$H-NMR (400 MHz, DMSO): 1.21-1.56 (m, 5H, 2CH$_2$+CH); 1.65-1.83 (m, 3H, CH$_2$+CH); 1.95-1.99 (m, 2H, CH$_2$); 2.66-2.75 (m, 1H, CH); 3.50 (s, 3H, N—CH$_3$); 6.18 (s, 1H, Ar); 7.12 (d, J 9.3 Hz, 1H, Ar); 7.73 (dd, J 8.3 Hz, 1.8 Hz, 1H, Ar); 8.10 (d, J 1.8 Hz, 1H, Ar); 8.21 (bs, 2H, NH$_2$); 8.21 (d, J 8.3 Hz, 1H, Ar); 8.41 (dd, J 9.3 Hz, J 2.2, Hz 1H, Ar); 8.52 (d, J 2.2 Hz, 1H, Ar); 14.12 (bs, 1H, NH). M/Z (M+H)$^+$=374.2. MP: 194-197° C.

Example 75

2-Cyclohexyl-4-methyl-8-(3-methyl-1H-pyrazol-4-yl)-4H-pyrazolo[1,5-a]quinazolin-5-one

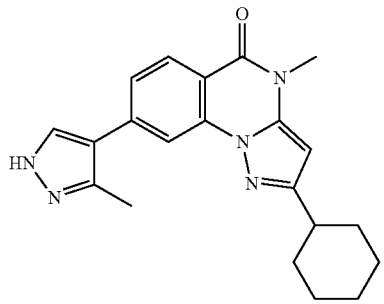 [SMILES: Cc1n[nH]cc1-c1ccc2c(=O)n(C)c3cc(C4CCCCC4)nn3c2c1]

Example 75 was obtained according to general procedure IV(i) starting from compound 56 in presence of 3-methyl-1H-pyrazol-4-boronic acid. The reaction mixture was submitted to microwave irradiation for 60 min at 150° C. Purification by flash-chromatography (MeOH in DCM, 10%) afforded the product as a white solid in 34% yield.

$^1$H-NMR (400 MHz, DMSO): 1.24-1.60 (m, 5H, 2CH$_2$+CH); 1.68-1.84 (m, 3H, CH$_2$+CH); 2.00-2.04 (m, 2H, CH$_2$); 2.71-2.78 (m, 1H, CH); 3.51 (s, 3H, N—CH$_3$); 6.07 (s, 1H, Ar); 7.57 (dd, J 8.2 Hz, 1.6 Hz, 1H, Ar); 7.94 (bs, 1H, Ar); 8.07 (d, J 1.6 Hz, 1H, Ar); 8.15 (d, J 8.2 Hz, 1H, Ar); 12.66 (bs, 1H, NH). Signal for protons of the pyrazole methyl is not observed (supposed under DMSO signal). M/Z (M+H)$^+$= 362.1. MP: >250° C.

Compound 57

3-Cycloheptyl-3-oxo-propionitrile

Compound 57 was obtained according to general procedure VII(i) starting from methyl cycloheptanecarboxylate. Purification by flash-chromatography (AcOEt in cyclohexane, 5 to 55%) afforded the product as a yellow oil in 86% yield.

$^1$H-NMR (400 MHz, DMSO): 1.41-1.68 (m, 10H, 4CH$_2$+2CH); 1.80-1.86 (m, 2H, 2CH); 2.60-2.68 (m, 1H, CH); 4.12 (s, 2H, CH$_2$).

Compound 58

8-Bromo-2-cycloheptyl-4H-pyrazolo[1,5-a]quinazolin-5-one

Compound 58 was obtained according to general procedure II (i), starting from compound 1 in presence of compound 57, as a white solid in 38% yield.

$^1$H-NMR (400 MHz, DMSO): 1.79-1.77 (m, 10H, 4CH$_2$+2CH); 1.94-2.00 (m, 2H, 2CH); 2.83-2.89 (m, 1H, CH); 5.76 (s, 1H, Ar); 7.61 (dd, J 8.5 Hz, 1.9 Hz, 1H, Ar); 8.01 (d, J 8.5 Hz, 1H, Ar); 8.10 (d, J 1.9 Hz, 1H, Ar); 12.19 (bs, 1H, NH). M/Z (M[$^{79}$Br]+H)$^+$=360.0.

Compound 59

8-Bromo-2-cycloheptyl-4-methyl-4H-pyrazolo[1,5-a]quinazolin-5-one

Compound 59 was obtained according to general procedure III starting from compound 58 in presence of iodomethane. The reaction mixture was stirred at room temperature for 2 Hrs. Compound 59 was obtained as a white solid in 96% yield.

$^1$H-NMR (400 MHz, DMSO): 1.54-1.80 (m, 10H, 4CH$_2$+2CH); 1.98-2.05 (m, 2H, 2CH); 2.86-2.93 (m, 1H, CH); 3.47 (s, 3H, N—CH$_3$); 6.17 (s, 1H, Ar); 7.62 (dd, J 8.5 Hz, 1.9 Hz, 1H, Ar); 8.05 (d, J 8.5 Hz, 1H, Ar); 8.12 (d, J 1.9 Hz, 1H, Ar). M/Z (M[$^{79}$Br]+H)$^+$=374.1.

Example 76

8-(6-Amino-pyridin-3-yl)-2-cycloheptyl-4-methyl-4H-pyrazolo[1,5-a]quinazolin-5-one, HCl Salt

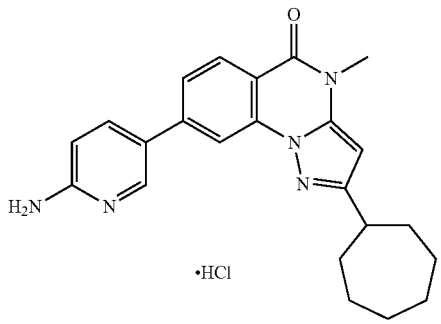 [SMILES: Cn1c(=O)c2ccc(-c3ccc(N)nc3)cc2n2nc(C3CCCCCC3)cc12 ; Cl]

Example 76 was obtained according to general procedure IV(iv) starting from compound 59 in presence of 2-aminopyridine-5-boronic acid pinacol ester. Purification by flash-chromatography (MeOH in DCM, 5%) and salt formation according to procedure V(ii) afforded example 76 as a yellow solid in 60% yield.

$^1$H-NMR (400 MHz, DMSO): 1.51-1.81 (m, 10H, 4CH$_2$+2CH); 1.99-2.06 (m, 2H, 2CH); 2.88-2.95 (m, 1H, CH); 3.51 (s, 3H, N—CH$_3$); 6.19 (s, 1H, Ar); 7.16 (d, J 9.3 Hz, 1H, Ar); 7.74 (dd, J 8.4 Hz, 1.8 Hz, 1H, Ar); 8.20 (d, J 1.8 Hz, 1H, Ar); 8.22 (d, J 8.4 Hz, 1H, Ar); 8.33 (bs, 2H, NH$_2$); 8.45 (dd, J 9.3 Hz, J 2.1 Hz, 1H, Ar); 8.55 (d, J 2.1 Hz, 1H, Ar); 14.22 (bs, 1H, NH). M/Z (M+H)$^+$=415.1. MP: 155-166° C.

Example 77

2-Cycloheptyl-8-(2,6-dimethyl-pyridin-4-yl)-4-methyl-4H-pyrazolo[1,5-a]quinazolin-5-one, HCl Salt

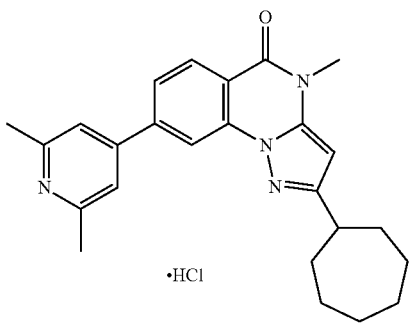 [SMILES: Cc1cc(-c2ccc3c(=O)n(C)c4cc(C5CCCCCC5)nn4c3c2)cc(C)n1 ; Cl]

Example 77 was obtained according to general procedure IV(iv) starting from compound 59 in presence of 2,6-dimethylpyridine-4-boronic acid pinacol ester. To a celite pad suspension in DMSO-MeOH mixture (1-1 (v-v)) Smopex resin (2 equiv. to Pd) was added. The mixture was stirred for 2 Hrs, filtered off and the solid was washed with a mixture of DMSO-MeOH. MeOH was removed and water was added to the resulting DMSO solution. The resulting solid was collected, washed with water and dried under reduced pressure with P$_2$O$_5$ at 50° C. Salt formation according to procedure V(ii) afforded the example 77 as a yellow solid in 41% yield.

$^1$H-NMR (400 MHz, DMSO): 1.53-1.80 (m, 10H, 4CH$_2$+2CH); 1.98-2.05 (m, 2H, 2CH); 2.81 (s, 6H, 2CH$_3$); 2.88-2.95 (m, 1H, CH); 3.52 (s, 3H, N—CH$_3$); 6.23 (s, 1H, Ar); 7.95 (dd, J 8.3 Hz, J 1.6 Hz, 1H, Ar); 8.26 (bs, 2H, Ar); 8.33 (d, J 8.3 Hz, 1H, Ar); 8.44 (d, J 1.6 Hz, 1H, Ar). Signal for HCl salt is not observed. M/Z (M+H)$^+$=401.2. MP: >250° C.

Compound 60

8-Bromo-2-cycloheptyl-4-ethyl-4H-pyrazolo[1,5-a]quinazolin-5-one

Compound 60 was obtained according to general procedure III starting from compound 58 in presence of iodoethane. The reaction mixture was stirred for 2 Hrs at room temperature, then hydrolysed with aqueous 1N HCl, and extracted twice with EtOAc. The organic layers were combined, washed with brine, dried over MgSO$_4$ and concentrated. Compound 60 was obtained as an orange solid in 99% yield.

$^1$H-NMR (400 MHz, DMSO): 1.26 (t, J 7.1 Hz, 3H, N—CH$_2$—CH$_3$); 1.53-1.80 (m, 10H, 4CH$_2$+2CH); 1.99-2.06 (m, 2H, 2CH); 2.90 (tt, J 9.09 Hz, J 4.1 Hz, 1H, CH); 4.04 (q, J 7.1 Hz, 2H, N—CH$_2$—CH$_3$); 6.23 (s, 1H, Ar); 7.62 (dd, J 8.5 Hz, J 1.9 Hz, 1H, Ar); 8.05 (d, J 8.5 Hz, 1H, Ar); 8.12 (d, J 1.9 Hz, 1H, Ar). M/Z (M[$^{79}$Br]+H)$^+$=388.0.

Example 78

2-Cycloheptyl-8-(2,6-dimethyl-pyridin-4-yl)-4-ethyl-4H-pyrazolo[1,5-a]quinazolin-5-one, HCl Salt

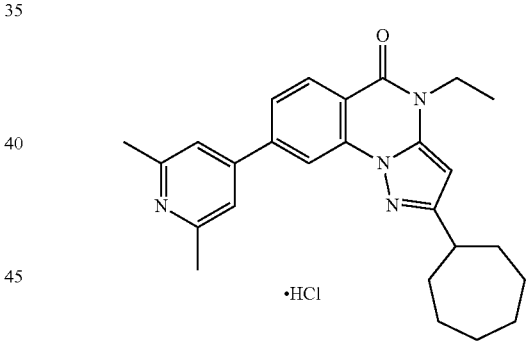

Example 78 was obtained according to general procedure IV(iv) starting from compound 60 in presence of 2,6-dimethylpyridine-4-boronic acid pinacol ester. The filtrate was hydrolysed with water (50 DMF volumes) and extracted twice with EtOAc (2*50 DMF volumes). The organic layers were combined, washed with brine, dried over MgSO$_4$ and concentrated. Purification by flash-chromatography (EtOAc in Cyclohexane, 0 to 100%) and salt formation according to procedure V(ii) afforded the example 78 as a yellow solid in 44% yield.

$^1$H-NMR (400 MHz, DMSO): 1.29 (t, J 7.1 Hz, 3H, N—CH$_2$—CH$_3$); 1.51-1.83 (m, 10H, 4CH$_2$+2CH); 2.00-2.07 (m, 2H, 2CH); 2.79 (s, 6H, 2CH$_3$); 2.92 (tt, J 10.0 Hz, J 4.0 Hz, 1H, CH); 4.10 (q, J 7.1 Hz, 2H, N—CH$_2$—CH$_3$); 6.29 (s, 1H, Ar); 7.95 (dd, J 8.3 Hz, J 1.5 Hz, 1H, Ar); 8.20 (bs, 2H, Ar); 8.34 (d, J 8.3 Hz, 1H, Ar); 8.43 (d, J 1.5 Hz, 1H, Ar). Signal for HCl salt is not observed. M/Z (M+H)$^+$=401.2. MP: >250° C.

Compound 61

3-Oxo-4-phenyl-butyronitrile

Compound 61 was obtained according to general procedure VII(i) starting from phenylacethyl chloride. Purification by flash-chromatography (AcOEt in cyclohexane, 0 to 30%) afforded the product as an orange oil in 76% yield.

$^1$H-NMR (400 MHz, DMSO): 3.87 (s, 2H, $CH_2$); 4.12 (s, 2H, $CH_2$); 7.18-7.27 (m, 5H, Ar).

Compound 62

2-Benzyl-8-bromo-4H-pyrazolo[1,5-a]quinazolin-5-one

Compound 62 was obtained according to general procedure II(i), starting from compound 1 in presence of compound 61, as a light yellow solid in 67% yield.

$^1$H-NMR (400 MHz, DMSO): 3.99 (s, 2H, $CH_2$); 5.69 (s, 1H, Ar); 7.22-7.24 (m, 1H, Ar); 7.30-7.33 (m, 4H, Ar); 7.63 (dd, J 8.5 Hz, 1.6 Hz, 1H, Ar); 8.01 (d, J 8.5 Hz, 1H, Ar); 8.13 (d, J 1.6 Hz, 1H, Ar); 12.17 (bs, 1H, NH). M/Z $(M[^{79}Br]+H)^+$=354.0. MP: >250° C.

Compound 63

2-Benzyl-8-bromo-4-methyl-4H-pyrazolo[1,5-a]quinazolin-5-one

Compound 63 was obtained according to general procedure III starting from compound 62 in presence of iodomethane. The reaction mixture was stirred at room temperature for 90 min. Compound 63 was obtained as a beige solid in 77% yield.

$^1$H-NMR (400 MHz, DMSO): 3.43 (s, 3H, N—$CH_3$) 4.02 (s, 2H, $CH_2$); 6.08 (s, 1H, Ar); 7.22-7.24 (m, 1H, Ar); 7.30-7.33 (m, 4H, Ar); 7.63 (dd, J 8.4 Hz, 1.5 Hz, 1H, Ar); 8.04 (d, J 8.4 Hz, 1H, Ar); 8.14 (d, J 1.5 Hz, 1H, Ar). M/Z $(M[^{79}Br]+H)^+$=368.0. MP: 134-135° C.

Example 79

8-(6-Amino-pyridin-3-yl)-2-benzyl-4-methyl-4H-pyrazolo[1,5-a]quinazolin-5-one, HCl Salt

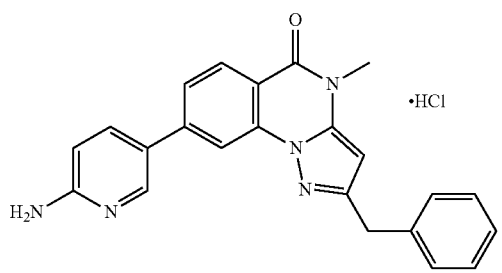 [SMILES: Cn1c(=O)c2ccc(-c3ccc(N)nc3)cc2n2nc(Cc3ccccc3)cc12 ; Cl]

Example 79 was obtained according to general procedure IV(i) starting from compound 63 in presence of 2-aminopyridine-5-boronic acid pinacol ester. The reaction mixture was submitted to microwave irradiation for 60 min at 150° C. Purification by flash-chromatography (EtOAc), and salt formation according to procedure V(ii) afforded example 79 as a white solid in 27% yield.

$^1$H-NMR (400 MHz, DMSO): 3.47 (s, 3H, N—$CH_3$); 4.05 (s, 2H, $CH_2$); 6.10 (s, 1H, Ar); 7.13 (d, J 9.3 Hz, 1H, Ar); 7.21-7.25 (m, 1H, Ar); 7.31-7.37 (m, 4H, Ar); 7.76 (dd, J 8.3 Hz, 1.8 Hz, 1H, Ar); 8.22 (d, J 8.3 Hz, 1H, Ar); 8.22 (bs, 2H, $NH_2$); 8.24 (d, J 1.8 Hz, 1H, Ar); 8.43 (dd, J 9.3 Hz, J 2.3 Hz, 1H, Ar); 8.55 (d, J 2.3 Hz, 1H, Ar); 14.06 (bs, 1H, NH). M/Z $(M+H)^+$=382.2. MP: >250° C.

Compound 64

3-(4-Fluoro-phenyl)-3-oxo-propionitrile

Compound 64 was obtained according to general procedure VII(i) starting from 4-Fluorobenzyl chloride. Purification by flash-chromatography (AcOEt in cyclohexane, 0 to 30%) afforded the product as a yellow solid in 84% yield.

$^1$H-NMR (400 MHz, DMSO): 4.75 (s, 2H, $CH_2$); 7.41 (t, J 8.6 Hz, 2H, Ar); 8.01-8.05 (m, 2H, Ar). M/Z $(M+H)^+$=164.1.

Compound 65

8-Bromo-2-(4-fluoro-phenyl)-4H-pyrazolo[1,5-a]quinazolin-5-one

Compound 65 was obtained according to general procedure II(i), starting from compound 1 in presence of compound 64, as a white solid in 77% yield.

$^1$H-NMR (400 MHz, DMSO): 6.39 (s, 1H, Ar); 7.30 (t, J 8.9 Hz, 2H, Ar); 7.67 (dd, J 8.5 Hz, J 1.9 Hz, 1H, Ar); 8.02-8.06 (m, 3H, Ar); 8.27 (d, J 1.9 Hz, 1H, Ar); 12.39 (bs, 1H, NH). M/Z $(M[^{79}Br]+H)^+$=358.0. MP: >250° C.

Compound 66

8-Bromo-2-(4-fluoro-phenyl)-4-methyl-4H-pyrazolo[1,5-a]quinazolin-5-one

Compound 66 was obtained according to general procedure III starting from compound 65 in presence of iodomethane. The reaction mixture was stirred at room temperature for 2 Hrs. Compound 66 was obtained as a white solid in 89% yield.

$^1$H-NMR (400 MHz, DMSO): 3.55 (s, 3H, N—$CH_3$); 6.85 (s, 1H, Ar); 7.34 (t, J 8.5 Hz, 2H, Ar); 7.69 (d, J 8.5 Hz, 1H, Ar); 8.04-8.11 (m, 3H, Ar); 8.28 (s, 1H, Ar). M/Z $(M[^{79}Br]+H)^+$=372.0. MP: >250° C.

Example 80

8-(6-Amino-pyridin-3-yl)-2-(4-fluoro-phenyl)-4-methyl-4H-pyrazolo[1,5-a]quinazolin-5-one, HCl Salt

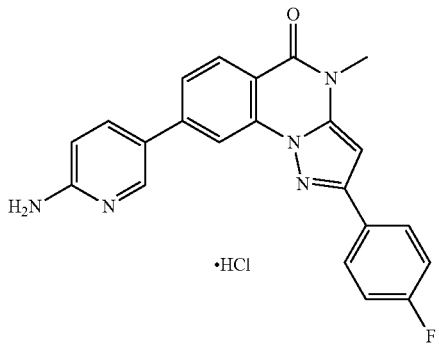 [SMILES: Cn1c(=O)c2ccc(-c3ccc(N)nc3)cc2n2nc(-c3ccc(F)cc3)cc12 ; Cl]

Example 80 was obtained according to general procedure IV(iii) starting from compound 66 in presence of 2-aminopyridine-5-boronic acid pinacol ester. The reaction mixture was submitted to microwave irradiation for 30 min at 150° C. Purification by flash-chromatography (MeOH in EtOAC, 0 to 10%) and salt formation according to procedure V(ii) afforded example 80 as a beige solid in 67% yield.

$^1$H-NMR (400 MHz, DMSO): 3.57 (s, 3H, N—CH$_3$); 6.85 (s, 1H, Ar); 7.15 (d, J 9.2 Hz, 1H, Ar); 7.31-7.37 (m, 2H, Ar); 7.89 (dd, J 8.3 Hz, 1.7 Hz, 1H, Ar); 8.04-8.09 (m, 2H, Ar); 8.24 (d, J 8.3 Hz, 1H, Ar); 8.26 (bs, 2H, NH$_2$); 8.32 (d, J 1.7 Hz, 1H, Ar); 8.46 (dd, J 9.2 Hz, J 2.1, Hz 1H, Ar); 8.56 (d, J 2.1 Hz, 1H, Ar); 14.10 (bs, 1H, NH). M/Z (M+H)$^+$=386.2. MP: >250° C.

Example 81

2-(4-Fluoro-phenyl)-4-methyl-8-(3-methyl-1H-pyrazol-4-yl)-4H-pyrazolo[1,5-a]quinazolin-5-one

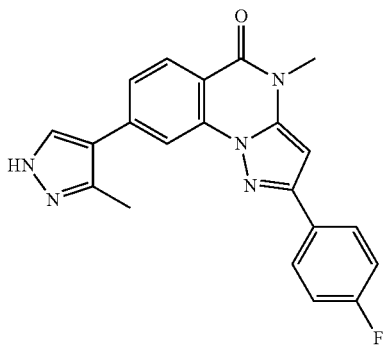 [SMILES: Cc1n[nH]cc1-c1ccc2c(=O)n(C)c3cc(-c4ccc(F)cc4)nn3c2c1]

Example 81 was obtained according to general procedure IV(i) starting from compound 66 in presence of 3-methyl-1H-pyrazol-4-boronic acid. The reaction mixture was submitted to microwave irradiation for 60 min at 150° C. Purification by flash-chromatography (AcOEt in cyclohexane, 80%) afforded the product as a white solid in 66% yield.

$^1$H-NMR (400 MHz, DMSO): 3.55 (s, 3H, N—CH$_3$); 6.79 (s, 1H, Ar); 7.31-7.36 (m, 2H, Ar); 7.61-7.64 (m, 1H, Ar); 8.03-8.09 (m, 3H, Ar); 8.13-8.18 (m, 2H, Ar). Signals for protons of the pyrazole methyl and NH are not observed (supposed under DMSO signal). M/Z (M+H)$^+$=374.1. MP: >250° C.

Compound 67

3-Furan-2-yl-3-oxo-propionitrile

Compound 67 was obtained according to general procedure VII(i) starting from 2-furyl chloride. Tituration in iPr$_2$O afforded the product as a brown solid in 44% yield.

$^1$H-NMR (400 MHz, DMSO): 4.52 (s, 2H, CH$_2$); 6.78 (dd, J 3.7 Hz, 1.5 Hz, 1H, Ar); 7.56 (d, J 3.7 Hz, 1H, Ar); 8.09 (d, J 1.5 Hz, 1H, Ar).

Compound 68

8-Bromo-2-furan-2-yl-4H-pyrazolo[1,5-a]quinazolin-5-one

Compound 68 was obtained according to general procedure II (1), starting from compound 1 in presence of compound 67, as a beige solid in 41% yield.

$^1$H-NMR (400 MHz, DMSO): 6.20 (s, 1H, Ar); 6.65 (dd, J 3.3 Hz, 1.8 Hz, 1H, Ar); 7.04 (d, J 3.3 Hz, 1H, Ar); 7.67 (dd, J 8.4 Hz, 1.9 Hz, 1H, Ar); 7.81 (d, J 1.8 Hz, 1H, Ar); 8.04 (d, J 8.4 Hz, 1H, Ar); 8.18 (d, J 1.9 Hz, 1H, Ar); 12.38 (bs, 1H, NH). M/Z (M[$^{79}$Br]+H)$^+$=330.0. MP: >250° C.

Compound 69

8-Bromo-2-furan-2-yl-4-methyl-4H-pyrazolo[1,5-a]quinazolin-5-one

Compound 69 was obtained according to general procedure III starting from compound 68 in presence of iodomethane. The reaction mixture was stirred at room temperature for 60 min. Compound 69 was obtained as a green solid in 60% yield.

$^1$H-NMR (400 MHz, DMSO): 3.52 (s, 3H, N—CH$_3$); 6.63 (s, 1H, Ar); 6.68 (dd, J 3.4 Hz, 1.7 Hz, 1H, Ar); 7.02 (d, J 3.4 Hz, 1H, Ar); 7.68 (dd, J 8.5 Hz, 1.9 Hz, 1H, Ar); 7.85 (d, J 1.7 Hz, 1H, Ar); 8.08 (d, J 8.5 Hz, 1H, Ar); 8.19 (d, J 1.9 Hz, 1H, Ar). M/Z (M[$^{79}$Br]+H)$^+$=344.0. MP: 192-194° C.

Example 82

8-(6-Amino-pyridin-3-yl)-2-furan-2-yl-4-methyl-4H-pyrazolo[1,5-a]quinazolin-5-one, HCl Salt

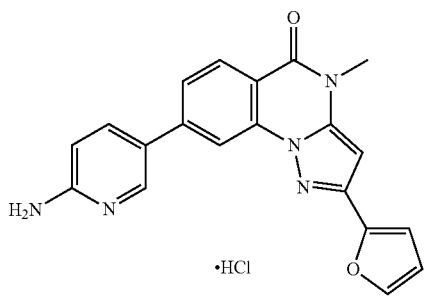 [SMILES: Cn1c(=O)c2ccc(-c3ccc(N)nc3)cc2n2nc(-c3ccco3)cc12 ; Cl]

Example 82 was obtained according to general procedure IV(iii) starting from Compound 69 in presence of 2-aminopyridine-5-boronic acid pinacol ester. Purification by flash-chromatography (EtOAc) and salt formation according to procedure V(ii) afforded example 82 as a brown solid in 51% yield.

$^1$H-NMR (400 MHz, DMSO): 3.56 (s, 3H, N—CH$_3$); 6.66 (s, 1H, Ar); 6.68 (dd, J 3.3 Hz, 1.7 Hz, 1H, Ar); 7.00 (d, J 3.3 Hz, 1H, Ar); 7.14 (d, J 9.2 Hz, 1H, Ar); 7.80 (dd, J 8.4 Hz, 1.7 Hz, 1H, Ar); 7.85 (d, J 1.7 Hz, 1H, Ar); 8.24-8.27 (m, 4H, 2Ar+NH2); 8.46 (dd, J 9.2 Hz, J 2.0, Hz 1H, Ar); 8.57 (d, J 2.0 Hz, 1H, Ar); 14.03 (bs, 1H, NH). M/Z (M+H)$^+$=358.1. MP: 218-229° C.

Compound 70

3-Oxo-3-(tetrahydro-thiopyran-4-yl)-propionitrile

Compound 70 was obtained according to general procedure VII(i) starting from methyl tetrahydrothiopyran-4-carboxylate. Purification by flash-chromatography (AcOEt in cyclohexane, 0 to 70%) afforded the product as a yellow oil in 61% yield.

¹H-NMR (400 MHz, DMSO): 1.44-1.57 (m, 2H, 2CH); 2.08-2.15 (m, 2H, 2CH); 2.53-2.63 (m, 5H, CH+S(CH₂)₂); 4.14 (s, 2H, CH₂).

Compound 71

8-Bromo-2-(tetrahydro-thiopyran-4-yl)-4H-pyrazolo[1,5-a]quinazolin-5-one

Compound 71 was obtained according to general procedure II (11), starting from compound 1 in presence of compound 70, as a white solid in 44% yield.

¹H-NMR (400 MHz, DMSO): 1.71-1.84 (m, 2H, 2CH); 2.20-2.28 (m, 2H, 2CH); 2.63-2.82 (m, 5H, CH+S(CH₂)₂); 5.80 (s, 1H, Ar); 7.62 (dd, J 8.4 Hz, 1.8 Hz, 1H, Ar); 8.01 (d, J 8.4 Hz, 1H, Ar); 8.10 (d, J 1.8 Hz, 1H, Ar); 12.21 (bs, 1H, NH). M/Z (M[$^{79}$B]+H)$^+$=364.0. MP: >250° C.

Compound 72

8-Bromo-4-methyl-2-(tetrahydro-thiopyran-4-yl)-4H-pyrazolo[1,5-a]quinazolin-5-one Compound 72 was obtained according to general procedure III starting from compound 71 in presence of iodomethane. The reaction mixture was stirred at room temperature for 3 Hrs. Compound 72 was obtained as a beige solid in 91% yield.

¹H-NMR (400 MHz, DMSO): 1.76-1.86 (m, 2H, 2CH); 2.23-2.27 (m, 2H, 2CH); 2.67-2.71 (m, 2H, 2S—CH); 2.76-2.84 (m, 3H, CH+2S—CH); 3.47 (s, 3H, N—CH₃); 6.22 (s, 1H, Ar); 7.62 (dd, J 8.5 Hz, 1.9 Hz, 1H, Ar); 8.04 (d, J 8.5 Hz, 1H, Ar); 8.11 (d, J 1.9 Hz, 1H, Ar). M/Z (M[$^{79}$Br]+H)$^+$=378.0.

Example 83

8-(6-Amino-pyridin-3-yl)-4-methyl-2-(tetrahydro-thiopyran-4-yl)-4H-pyrazolo[1,5-a]quinazolin-5-one, HCl Salt

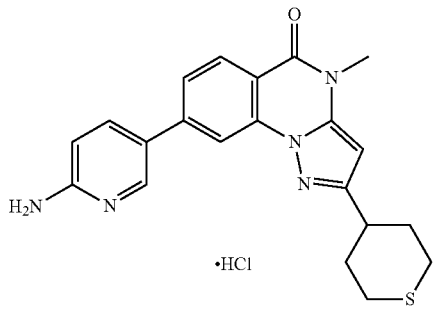 [SMILES: Cn1c(=O)c2ccc(-c3ccc(N)nc3)cc2n2nc(C3CCSCC3)cc12 ; Cl]

Example 83 was obtained according to general procedure IV(iv) starting from compound 72 in presence of 2-aminopyridine-5-boronic acid pinacol ester. The filtrate was hydrolysed with water (25 DMF volumes) and extracted twice with EtOAc (2*25 DMF volumes). The organic layers were combined, washed with brine, dried over MgSO₄, concentrated. Salt formation according to procedure V(ii) afforded example 83 as a white solid in 83% yield.

¹H-NMR (400 MHz, DMSO): 1.79-1.89 (m, 2H, 2CH); 2.24-2.28 (m, 2H, 2CH); 2.67-2.71 (m, 2H, 2S—CH); 2.77-2.85 (m, 3H, CH+2S—CH); 3.50 (s, 3H, N—CH₃); 6.23 (s, 1H, Ar); 7.11 (d, J 9.3 Hz, 1H, Ar); 7.74 (dd, J 8.4 Hz, 1.9 Hz, 1H, Ar); 8.19 (d, J 1.9 Hz, 1H, Ar); 8.20 (bs, 2H, NH₂); 8.21 (d, J 8.4 Hz, 1H, Ar); 8.40 (dd, J 9.3 Hz, J 2.2, Hz 1H, Ar); 8.53 (d, J 2.2 Hz, 1H, Ar); 14.20 (bs, 1H, NH). M/Z (M+H)$^+$=392.1. MP: >250° C.

Compound 73

8-Bromo-2-(1,1-dioxo-tetrahydro-2H-thiopyran-4-yl)-4-methyl-4H-pyrazolo[1,5-a]quinazolin-5-one Under inert atmosphere, to a suspension of compound 72 (85 mg) in CH₂Cl₂ (1.5 mL) cooled by an ice bath, mCPBA (90 mg, 2.3 equiv.) was added. The reaction mixture was stirred at room temperature for 6 days, then was hydrolysed by NaHCO₃ aqueous saturated solution (30 mL) and was extracted twice with EtOAc (2*25 mL). The organic layer were combined, dried over MgSO₄ and concentrated. Compound 73 was obtained with a purity of 57%, and was not fully characterized. M/Z (M[$^{79}$Br]+H)$^+$=410.0.

Example 84

8-(6-Amino-pyridin-3-yl)-2-(1,1-dioxo-tetrahydro-2H-thiopyran-4-yl)-4-methyl-4H-pyrazolo[1,5-a]quinazolin-5-one, HCl Salt

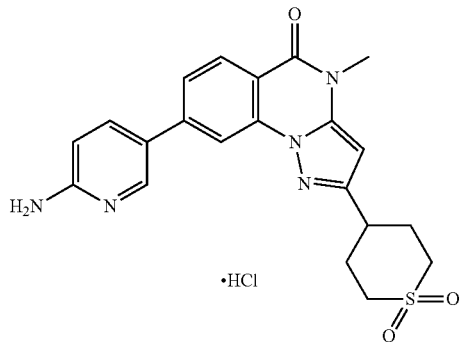 [SMILES: Cn1c(=O)c2ccc(-c3ccc(N)nc3)cc2n2nc(C3CCS(=O)(=O)CC3)cc12 ; Cl]

Example 84 was obtained according to general procedure IV(iii) starting from compound 73 in presence of 2-aminopyridine-5-boronic acid pinacol ester. Purification by flash-chromatography (MeOH in CH₂Cl₂, 0 to 10%) and salt formation according to procedure V(iii) afforded example 84 as a white solid in 16% yield.

¹H-NMR (400 MHz, DMSO): 2.16-2.25 (m, 2H, 2CH); 2.32-2.36 (m, 2H, 2CH); 3.11-3.16 (m, 3H, CH+2SO₂CH); 3.30-3.37 (m, 2H, 2SO₂CH); 3.49 (s, 3H, N—CH₃); 6.26 (s, 1H, Ar); 7.11 (d, J 9.3 Hz, 1H, Ar); 7.74 (dd, J 8.4 Hz, 1.8 Hz, 1H, Ar); 8.18 (bs, 2H, NH₂); 8.18 (d, J 1.8 Hz, 1H, Ar); 8.22 (d, J 8.4 Hz, 1H, Ar); 8.38 (dd, J 9.3 Hz, J 2.2, Hz 1H, Ar); 8.45 (d, J 2.2 Hz, 1H, Ar); 14.17 (bs, 1H, NH). M/Z (M+H)$^+$=424.2. MP: >250° C.

Compound 74

8-Bromo-2-pyridin-3-yl-4H-pyrazolo[1,5-a]quinazolin-5-one

Compound 74 was obtained according to general procedure II(i), starting from compound 1 in presence of 3-oxo-3-pyridine-3-ylpropane nitrile, as a greenish solid in 68% yield.

¹H-NMR (400 MHz, DMSO): 6.56 (s, 1H, Ar); 7.58 (dd, J 7.5 Hz, J 4.9 Hz, 1H, Ar); 7.71 (dd, J 8.5 Hz, J 1.8 Hz, 1H, Ar); 8.07 (d, J 8.5 Hz, 1H, Ar); 8.32 (d, J 1.8 Hz, 1H, Ar); 8.44-8.47 (m, 1H, Ar); 8.65 (d, 1H, J 4.8 Hz, J 1.5 Hz, 1H, Ar); 9.23 (d, 1H, J 2.0 Hz, 1H, Ar); 12.49 (bs, 1H, NH). M/Z (M[$^{79}$Br]+H)$^+$=341.0.

Compound 75

8-(1H-Pyrazol-4-yl)-2-pyridin-3-yl-4H-pyrazolo[1,5-a]quinazolin-5-one

Compound 75 was obtained according to general procedure IV(i) starting from compound 74 in presence of 3-methyl-1H-pyrazol-4-boronic acid. The reaction mixture was submitted to microwave irradiation for 30 min at 120° C. Water was added to the reaction mixture which precipitated. The resulting solid was collected, washed with water, EtOAc, and dried under reduced pressure at 50° C. with P$_2$O$_5$. Compound 75 was obtained as a brown solid in quantitative yield.

M/Z (M+H)$^+$=329.1. MP: >250° C.

Example 85

4-Methyl-8-(1-methyl-1H-pyrazol-4-yl)-2-pyridin-3-yl-4H-pyrazolo[1,5-a]quinazolin-5-one

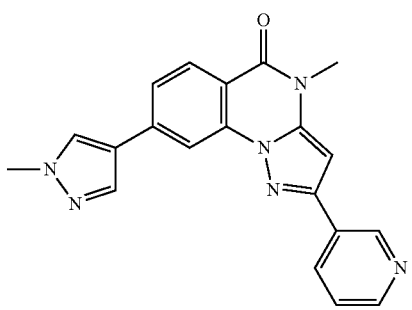 [SMILES: Cn1cc(-c2ccc3c(=O)n(C)c4cc(-c5cccnc5)nn4c3c2)cn1]

Under anhydrous condition, to a solution of compound 75 (1.0 equiv.) in DMF (c=0.2 molL$^{-1}$) cooled by an ice bath, NaH (in mineral oil 60%, 3.4 equiv.) was added in 3 portions. The mixture was stirred for 15 minutes, and then iodomethane (4.2 equiv.) was added. The ice bath was removed, and the reaction was stirred for 4 Hrs at room temperature. The reaction mixture was hydrolysed with water, then extracted twice with EtOAc. The organic layers were combined, washed with brine, dried over MgSO$_4$ and concentrated. The residue was taken in Et$_2$O. The resulting solid was collected, washed with Et$_2$O and dried under reduced pressure with P$_2$O$_5$ at 50° C. Example 85 was obtained as a brown solid in 18% yield.

¹H-NMR (400 MHz, DMSO): 3.57 (s, 3H, N—CH$_3$); 3.92 (s, 3H, N—CH$_3$); 6.93 (s, 1H, Ar); 7.55 (dd, J 7.9 Hz, J 4.8 Hz, 1H, Ar); 7.74 (dd, J 8.3 Hz, J 1.3 Hz, 1H, Ar); 8.13-8.18 (m, 2H, Ar); 8.29 (d, J 1.3 Hz, 1H, Ar); 8.37-8.39 (m, 1H, Ar); 8.50 (s, 1H, Ar); 8.63 (d, 1H, J 4.8 Hz, J 1.2 Hz, 1H, Ar); 9.25 (d, 1H, J 1.2 Hz, 1H, Ar). M/Z (M+H)$^+$=357.1. MP: >250° C.

Compound 76

3-Oxo-3-(tetrahydro-pyran-4-yl)-propionitrile

Compound 76 was obtained according to general procedure VII(i) starting from methyl tetrahydro-2H-pyran-4-carboxylate. Purification by flash-chromatography (AcOEt in cyclohexane, 0 to 70%) afforded the product as a yellow oil in 83% yield.

¹H-NMR (400 MHz, DMSO): 1.40-1.50 (m, 2H, 2CH); 1.72-1.75 (m, 2H, 2CH); 2.69 (tt, J 11.4 Hz, J 4.0 Hz, 1H, CH); 3.30 (td, J 11.6 Hz, J 1.9 Hz, 2H, 2OCH); 3.82-3.87 (m, 2H, 2OCH); 4.15 (s, 2H, CH$_2$).

Compound 77

8-Bromo-2-(tetrahydro-pyran-4-yl)-4H-pyrazolo[1,5-a]quinazolin-5-one

Compound 77 was obtained according to general procedure II(i), starting from compound 1 in presence of compound 76, as a beige solid in 57% yield.

¹H-NMR (400 MHz, DMSO): 1.66-1.76 (m, 2H, 2CH); 1.84-1.88 (m, 2H, 2CH); 2.93 (tt, J 11.6 Hz, J 3.9 Hz, 1H, CH); 3.45 (td, J 11.6 Hz, J 2.1 Hz, 2H, 2O—CH); 3.90-3.94 (m, 2H, 2O—CH); 5.81 (s, 1H, Ar); 7.62 (dd, J 8.5 Hz, 1.9 Hz, 1H, Ar); 8.01 (d, J 8.5 Hz, 1H, Ar); 8.10 (d, J 1.9 Hz, 1H, Ar); 12.21 (bs, 1H, NH). M/Z (M[$^{79}$Br]+H)$^1$=348.0. MP: >250° C.

Compound 78

8-Bromo-4-methyl-2-(tetrahydro-pyran-4-yl)-4H-pyrazolo[1,5-a]quinazolin-5-one

Compound 78 was obtained according to general procedure III starting from compound 77 in presence of iodomethane. The reaction mixture was stirred at room temperature for 2 Hrs. Compound 78 was obtained as a white solid in quantitative yield.

¹H-NMR (400 MHz, DMSO): 1.69-1.80 (m, 2H, 2CH); 1.87-1.91 (m, 2H, 2CH); 2.97 (tt, J 11.5 Hz, J 3.9 Hz, 1H, CH); 3.48 (td, J 11.5 Hz, J 2.2 Hz, 2H, 2O—CH); 3.48 (s, 3H, NCH$_3$); 3.93-3.96 (m, 2H, 2O—CH); 6.24 (s, 1H, Ar); 7.64 (dd, J 8.5 Hz, 1.9 Hz, 1H, Ar); 8.06 (d, J 8.5 Hz, 1H, Ar); 8.12 (d, J 1.9 Hz, 1H, Ar). M/Z (M[$^{79}$Br]+H)$^+$=362.2. MP: >250° C.

Example 86

8-(6-Amino-pyridin-3-yl)-4-methyl-2-(tetrahydro-pyran-4-yl)-4H-pyrazolo[1,5-a]quinazolin-5-one, HCl Salt

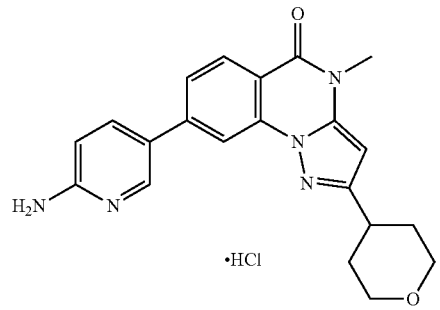 [SMILES: Cn1c(=O)c2ccc(-c3ccc(N)nc3)cc2n2nc(C3CCOCC3)cc12 ; Cl]

Example 86 was obtained according to general procedure IV(iii) starting from compound 78 in presence of 2-aminopyridine-5-boronic acid pinacol ester. Purification by flash-chromatography (MeOH in CH$_2$Cl$_2$, 10%) and salt formation according to procedure V(ii) afforded example 86 as a white solid in 67% yield.

$^1$H-NMR (400 MHz, DMSO): 1.70-1.91 (m, 4H, 2CH$_2$); 2.98 (tt, J 11.4 Hz, J 4.2 Hz, 1H, CH); 3.44-3.51 (m, 5H, 2O—CH+NCH$_3$); 3.93-3.98 (m, 2H, 2O—CH); 6.24 (s, 1H, Ar); 7.10 (d, J 9.2 Hz, 1H, Ar); 7.74 (dd, J 8.3 Hz, 1.7 Hz, 1H, Ar); 8.12 (bs, 2H, NH$_2$); 8.19 (d, J 1.7 Hz, 1H, Ar); 8.21 (d, J 8.3 Hz, 1H, Ar); 8.39 (dd, J 9.2 Hz, J 2.2, Hz 1H, Ar); 8.52 (d, J 2.2 Hz, 1H, Ar); 14.17 (bs, 1H, NH). M/Z (M+H)$^+$=376.2. MP: >250° C.

Example 87

4-Methyl-8-(1H-pyrazol-4-yl)-2-(tetrahydro-pyran-4-yl)-4H-pyrazolo[1,5-a]quinazolin-5-one

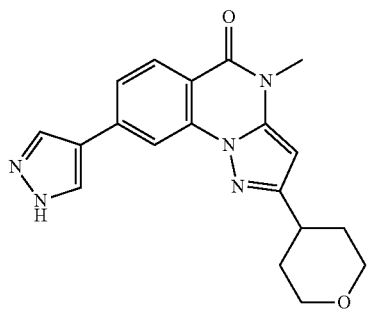 [SMILES: Cn1c(=O)c2ccc(-c3cn[nH]c3)cc2n2nc(C3CCOCC3)cc12]

Example 87 was obtained according to general procedure IV(iv) starting from compound 78 in presence of 1-H-pyrazol-4-boronic acid. The filtrate was purified by preparative HPLC. The residue was taken in Et$_2$O The resulting solid collected, washed with Et$_2$O and dried under reduced pressure with P$_2$O$_5$ at 50° C. Example 87 was obtained as a white solid in 44% yield.

$^1$H-NMR (400 MHz, DMSO): 1.70-1.91 (m, 4H, 2CH$_2$); 2.99 (tt, J 11.5 Hz, J 4.1 Hz, 1H, CH); 3.44-3.52 (m, 5H, 2O—CH+NCH$_3$); 3.93-3.98 (m, 2H, 2O—CH); 6.20 (s, 1H, Ar); 7.72 (dd, J 8.3 Hz, J 1.4 Hz, 1H, Ar); 8.10 (d, 1H, J 8.3 Hz, 1H, Ar); 8.14 (d, 1H, J 1.4 Hz, 1H, Ar); 8.32 (bs, 2H, Ar). The NH of the pyrazole ring was not observed. M/Z (M+H)$^+$=350.1. MP: >250° C.

Example 88

3-[4-Methyl-5-oxo-2-(tetrahydro-pyran-4-yl)-4,5-dihydro-pyrazolo[1,5-a]quinazolin-8-yl]-benzonitrile

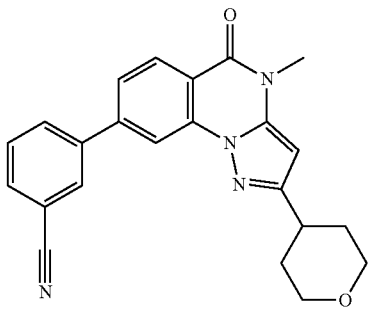 [SMILES: Cn1c(=O)c2ccc(-c3cccc(C#N)c3)cc2n2nc(C3CCOCC3)cc12]

Example 88 was obtained according to general procedure IV(iii) starting from compound 78 in presence of 3-cyanophenylboronic acid. Purification by flash-chromatography (EtOAc in Cyclohexane, 30 to 60%) afforded example 88 as a white solid in 97% yield.

$^1$H-NMR (400 MHz, DMSO): 1.70-1.92 (m, 4H, 2CH$_2$); 2.98 (tt, J 11.4 Hz, J 4.0 Hz, 1H, CH); 3.43-3.51 (m, 5H, 2O—CH+NCH$_3$); 3.93-3.97 (m, 2H, 2O—CH); 6.24 (s, 1H, Ar); 7.74 (t, J 7.8 Hz, 1H, Ar); 7.81 (dd, J 8.3 Hz, J 1.4 Hz, 1H, Ar); 7.93-7.95 (m, 1H, Ar); 7.93-7.94 (m, 1H, Ar); 8.14-8.16 (m, 2H, Ar); 8.32 (bs, 1H, Ar). M/Z (M+H)$^+$=385.2. MP: 210-216° C.

Example 89

4-Methyl-8-pyridin-3-yl-2-(tetrahydro-pyran-4-yl)-4H-pyrazolo[1,5-a]quinazolin-5-one, HCl Salt

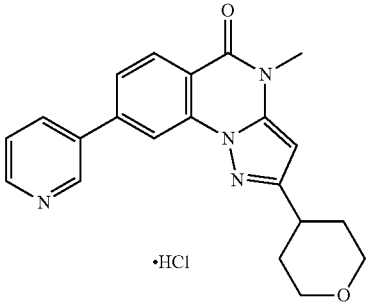 [SMILES: Cn1c(=O)c2ccc(-c3cccnc3)cc2n2nc(C3CCOCC3)cc12 ; Cl]

Example 89 was obtained according to general procedure IV(iv) starting from compound 78 in presence of 3-pyridinboronic acid. The filtrate was purified by preparative HPLC. After Co-evaporation with aqueous 1N HCl, the residue was taken in Et$_2$O, the solid collected, washed with Et$_2$O and dried under reduced pressure with P$_2$O$_5$ at 50° C. Example 89 was obtained as a yellow solid in 67% yield.

$^1$H-NMR (400 MHz, DMSO): 1.72-1.82 (m, 2H, 2CH); 1.88-1.91 (m, 2H, 2CH); 2.99 (tt, J 11.5 Hz, J 3.9 Hz, 1H, CH); 3.48 (td, J 11.6 Hz, J 2.1 Hz, 2H, 2O—CH); 3.52 (s, 3H, NCH$_3$); 3.93-3.97 (m, 2H, 2O—CH); 6.26 (s, 1H, Ar); 7.88 (dd, J 8.3 Hz, J 1.8 Hz, 1H, Ar); 7.92 (dd, J 7.9 Hz, J 5.0 Hz, 1H, Ar); 8.28 (d, J 8.3 Hz, 1H, Ar); 8.34 (d, J 1.8 Hz, 1H, Ar); 8.67-8.69 (m, 1H, Ar); 8.86 (d, J 5.0 Hz, 1H, Ar); 9.25 (bs, 1H, Ar). Signal for HCl salt is not observed. M/Z (M+H)$^+$=361.2. MP: 202-224° C.

Example 90

4-Methyl-8-pyridin-4-yl-2-(tetrahydro-pyran-4-yl)-4H-pyrazolo[1,5-a]quinazolin-5-one, HCl Salt

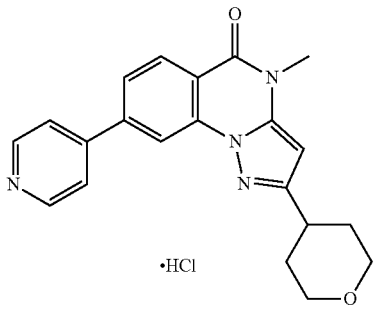 [SMILES: Cn1c(=O)c2ccc(-c3ccncc3)cc2n2nc(C3CCOCC3)cc12 ; Cl]

Example 90 was obtained according to general procedure IV(iv) starting from compound 78 in presence of 4-pyridineboronic acid. The filtrate was purified by preparative HPLC. After Co-evaporation with aqueous 1N HCl, the residue was taken in Et₂O, the solid collected, washed with Et₂O and dried under reduced pressure with P₂O₅ at 50° C. Example 90 was obtained as a light yellow solid in 30% yield.

¹H-NMR (400 MHz, DMSO): 1.72-1.82 (m, 2H, 2CH); 1.88-1.92 (m, 2H, 2CH); 2.99 (tt, J 11.5 Hz, J 4.0 Hz, 1H, CH); 3.48 (td, J 11.5 Hz, J 2.1 Hz, 2H, 2 O—CH); 3.53 (s, 3H, N—CH₃); 3.94-3.97 (m, 2H, 2 O—CH); 6.28 (s, 1H, Ar); 7.98 (dd, J 8.3 Hz, J 1.8 Hz, 1H, Ar); 8.32 (d, J 8.3 Hz, 1H, Ar); 8.38-8.40 (m, 2H, Ar); 8.43 (d, J 1.8 Hz, 1H, Ar); 8.97-8.99 (m, 2H, Ar). Signal for HCl salt is not observed. M/Z (M+H)⁺=361.2. MP: 218-223° C.

Example 91

4-Methyl-8-oxazol-2-yl-2-(tetrahydro-pyran-4-yl)-4H-pyrazolo[1,5-a]quinazolin-5-one

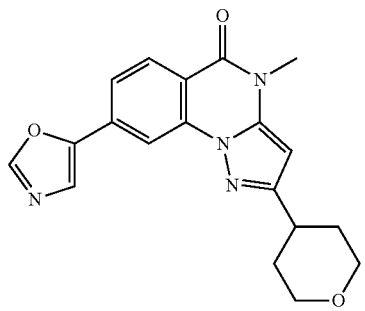 [SMILES: Cn1c(=O)c2ccc(-c3cnco3)cc2n2nc(C3CCOCC3)cc12]

Under inert atmosphere, a mixture of compound 78 (75 mg, 1.0 equiv.), isoxazole (27 μL, 2.0 equiv.), pivalic acid (9 mg, 0.4 equiv.), palladium acetate (2.4 mg, 0.05 equiv.), CataCxium® AHI (10 mg, 0.1 equiv.), and K₂CO₃ (90 mg, 3.1 equiv.) in DMA (1.4 mL) was heated at 110° C. for 16 Hrs. After cooling, the reaction mixture was hydrolysed with aqueous 1N HCl (20 mL) and extracted twice with EtOAc (30 mL). The organic layers were combined, washed with brine (40 mL), dried over MgSO₄, and concentrated. The crude material was purified by preparative HPLC. The residue was taken in Et₂O. The resulting solid was collected, washed with Et₂O and dried under reduced pressure with P₂O₅ at 50° C. Example 91 was obtained as a white solid in 8% yield.

¹H-NMR (400 MHz, DMSO): 1.72-1.82 (m, 2H, 2CH); 1.89-1.93 (m, 2H, 2CH); 3.00 (tt, J 11.4 Hz, J 4.0 Hz, 1H, CH); 3.49 (td, J 11.6 Hz, J 1.8 Hz, 2H, 2 O—CH); 3.50 (s, 3H, N—CH₃); 3.94-3.98 (m, 2H, 2 O—CH); 6.24 (s, 1H, Ar); 7.82 (dd, J 8.3 Hz, J 1.5 Hz, 1H, Ar); 8.04 (s, 1H, Ar); 8.21 (d, J 8.3 Hz, 1H, Ar); 8.24 (d, J 1.5 Hz, 1H, Ar); 8.61 (s, 1H, Ar). M/Z (M+H)⁺=351.2. MP: 209-216° C.

Example 92

4-Methyl-8-(5-methyl-1H-pyrazol-4-yl)-2-(tetrahydro-pyran-4-yl)-4H-pyrazolo[1,5-a]quinazolin-5-one

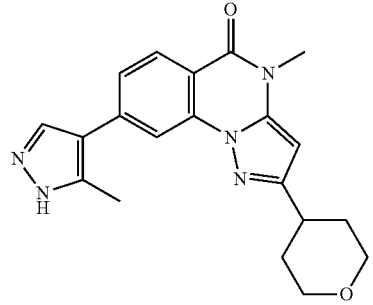 [SMILES: Cc1[nH]ncc1-c1ccc2c(=O)n(C)c3cc(C4CCOCC4)nn3c2c1]

Example 92 was obtained according to general procedure IV(iv) starting from compound 78 in presence of 3-methyl-1-H-pyrazol-4-boronic acid. The filtrate was purified by preparative HPLC. The residue was taken in Et₂O and the resulting solid collected, washed with Et₂O and dried under reduced pressure with P₂O₅ at 50° C. Example 92 was obtained as a white solid in 42% yield.

¹H-NMR (400 MHz, DMSO): 1.68-1.81 (m, 2H, 2CH); 1.85-1.90 (m, 2H, 2CH); 2.48 (s, 3H, CH₃); 2.98 (tt, J 11.3 Hz, J 4.0 Hz, 1H, CH); 3.47 (td, J 11.4 Hz, J 2.0 Hz, 2H, 2 O—CH); 3.49 (s, 3H, N—CH₃); 3.92-3.97 (m, 2H, 2 O—CH); 6.21 (s, 1H, Ar); 7.59 (dd, J 8.3 Hz, J 1.7 Hz, 1H, Ar); 8.04 (d, 1H, J 1.7 Hz, 1H, Ar); 8.06 (s, 1H, Ar); 8.12 (d, 1H, J 8.3 Hz, 1H, Ar). The NH of the pyrazole ring was not observed. M/Z (M+H)⁺=364.1. MP: 223-229° C.

Example 93

4-Methyl-8-(2-methyl-pyridin-4-yl)-2-(tetrahydro-pyran-4-yl)-4H-pyrazolo[1,5-a]quinazolin-5-one, HCl Salt

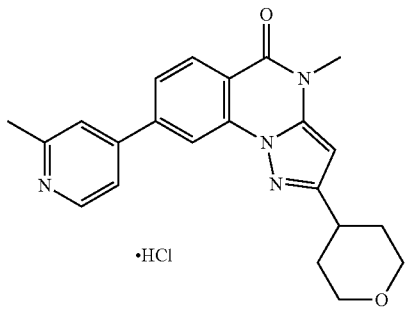 [SMILES: Cc1cc(-c2ccc3c(=O)n(C)c4cc(C5CCOCC5)nn4c3c2)ccn1 ; Cl]

Example 93 was obtained according to general procedure IV(iv) starting from compound 78 in presence of 2-methyl-methylpyridine-4-boronic acid. To a celite pad suspension in a DMSO-MeOH mixture (1-1 (v-v)) Smopex resin (2 equiv. to Pd) was added. The mixture was stirred for 2 Hrs, filtered off and the solid was washed with a mixture of DMSO-MeOH. MeOH was removed and water was added to the resulting DMSO solution. The resulting solid was collected, washed with water and dried under reduce pressure with P₂O₅ at 50° C. Salt formation according to procedure V(iii), afforded example 93 as a beige solid in 46% yield.

¹H-NMR (400 MHz, DMSO): 1.73-1.83 (m, 2H, 2CH); 1.88-1.92 (m, 2H, 2CH); 2.84 (s, 3H, CH₃); 3.00 (tt, J 11.5 Hz, J 4.0 Hz, 1H, CH); 3.49 (td, J 11.5 Hz, J 2.1 Hz, 2H, 2

O—CH); 3.53 (s, 3H, N—CH₃); 3.95-3.98 (m, 2H, 2 O—CH); 6.30 (s, 1H, Ar); 8.00 (dd, J 8.3 Hz, J 1.8 Hz, 1H, Ar); 8.31 (dd, J 6.2 Hz, J 1.4 Hz, 1H, Ar); 8.34 (d, J 8.3 Hz, 1H, Ar); 8.44 (d, J 1.4 Hz, 1H, Ar); 8.46 (d, J 1.8 Hz, 1H, Ar); 8.88 (d, J 6.2 Hz, 1H, Ar). Signal of HCl salt is not observed. M/Z (M+H)⁺=375.2. MP: 159-161° C.

Example 94

4-Methyl-8-(2-methyl-pyridin-3-yl)-2-(tetrahydro-pyran-4-yl)-4H-pyrazolo[1,5-a]quinazolin-5-one, HCl Salt

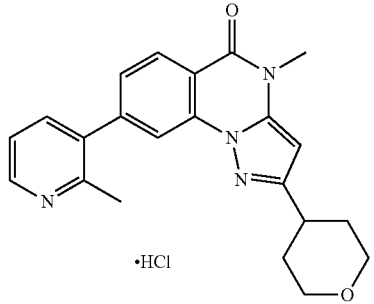 [SMILES: Cc1ncccc1-c1ccc2c(=O)n(C)c3cc(C4CCOCC4)nn3c2c1 ; Cl]

Example 94 was obtained according to general procedure IV(iv) starting from compound 78 in presence of 2-methyl-pyridine-3-boronic acid pinacol ester. To a celite pad suspension in a DMSO-MeOH mixture (1-1 (v-v)) Smopex resin (2 equiv. to Pd) was added. The mixture was stirred for 2 Hrs, filtered off and the solid was washed with a mixture of DMSO-MeOH. MeOH was removed and water was added to the resulting DMSO solution. The resulting solid was collected, washed with water and dried under reduce pressure with P₂O₅ at 50° C. Salt formation according to procedure V(iii), afforded example 94 as a white solid in 56% yield.

¹H-NMR (400 MHz, DMSO): 1.69-1.79 (m, 2H, 2CH); 1.86-1.89 (m, 2H, 2CH); 2.67 (s, 3H, CH₃); 2.96 (tt, J 11.5 Hz, J 4.0 Hz, 1H, CH); 3.46 (td, J 11.6 Hz, J 2.1 Hz, 2H, 2 O—CH); 3.54 (s, 3H, N—CH₃); 3.91-3.95 (m, 2H, 2 O—CH); 6.27 (s, 1H, Ar); 7.58 (dd, J 8.1 Hz, J 1.7 Hz, 1H, Ar); 7.93 (dd, J 7.6 Hz, J 5.8 Hz, 1H, Ar); 8.10 (d, J 1.7 Hz, 1H, Ar); 8.29 (d, J 8.1 Hz, 1H, Ar); 8.45 (d, J 7.6 Hz, 1H, Ar); 8.83 (dd, J 5.7 Hz, J 1.3 Hz, 1H, Ar). Signal for HCl salt is not observed. M/Z (M+H)⁺=375.2. MP: 167-169° C.

Example 95

4-Methyl-8-(6-methyl-pyridin-3-yl)-2-(tetrahydro-pyran-4-yl)-4H-pyrazolo[1,5-a]quinazolin-5-one, HCl Salt

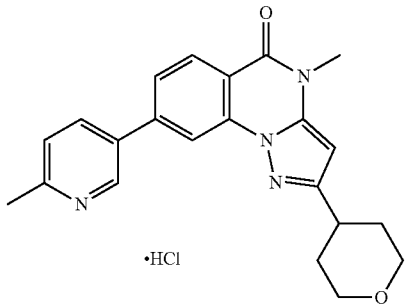 [SMILES: Cc1ccc(-c2ccc3c(=O)n(C)c4cc(C5CCOCC5)nn4c3c2)cn1 ; Cl]

Example 95 was obtained according to general procedure IV(iv) starting from compound 78 in presence of 2-methyl-pyridine-5-boronic acid. The filtrate was hydrolysed with water (25 DMF volumes) and extracted twice with EtOAc (2*25 DMF volumes). The organic layers were combined, washed with brine, dried over MgSO₄, and concentrated. Salt formation from the crude without purification according to procedure V(ii) afforded example 95 as a brown solid in 63% yield.

¹H-NMR (400 MHz, DMSO): 1.72-1.82 (m, 2H, 2CH); 1.85-1.91 (m, 2H, 2CH); 2.75 (s, 3H, CH₃); 2.99 (tt, J 11.5 Hz, J 3.9 Hz, 1H, CH); 3.48 (td, J 11.5 Hz, J 1.9 Hz, 2H, 2 O—CH); 3.52 (s, 3H, N—CH₃); 3.93-3.97 (m, 2H, 2 O—CH); 6.27 (s, 1H, Ar); 7.54 (m, 1H, NH); 7.86-7.90 (m, 2H, Ar); 8.27 (d, J 8.36 Hz, 1H, Ar); 8.34 (d, J 1.4 Hz, 1H, Ar); 8.70 (d, J 7.6 Hz, 1H, Ar); 9.15 (s, 1H, Ar). M/Z (M+H)⁺=375.1. MP: Decomposed at 167° C.

Example 96

4-Methyl-2-(tetrahydro-pyran-4-yl)-8-[3-(2H-tetrazol-5-yl)-phenyl]-4H-pyrazolo[1,5-a]quinazolin-5-one, Sodium salt

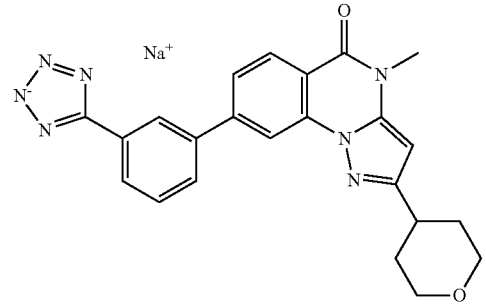 [SMILES: Cn1c(=O)c2ccc(-c3cccc(-c4nn[n-]n4)c3)cc2n2nc(C3CCOCC3)cc12 ; [Na+]]

Under inert atmosphere, a mixture of example 88 (142 mg, 1.0 equiv.), sodium azide (122 mg, 5 equiv.) and ammonium chloride (99 mg, 5 equiv.) in DMF (3.7 mL) was heated at 80° C. for 5 days. After cooling, the reaction mixture was filtered. The solid was washed with DMF (1.0 mL) and the filtrate was purified by preparative HPLC. The tetrazole was obtained as a white solid.

Under anhydrous condition, to a suspension of the above tetrazole in MeOH, sodium methoxide (1.0 equiv.) was added. The mixture slowly turned less heterogeneous. After 2 Hrs at room temperature, the reaction mixture was filtrated. The filtrate was concentrated and dried under reduced pressure at 50° C. with P₂O₅. Example 96 was obtained as a white solid in 31% yield.

¹H-NMR (400 MHz, DMSO): 1.72-1.82 (m, 2H, 2CH); 1.91-1.95 (m, 2H, 2CH); 3.05 (tt, J 11.5 Hz, J 4.0 Hz, 1H, CH); 3.49 (td, J 11.5 Hz, J 1.9 Hz, 2H, 2 O—CH); 3.53 (s, 3H, N—CH₃); 3.94-3.97 (m, 2H, 2 O—CH₂); 6.27 (s, 1H, Ar); 7.57 (t, J 7.7 Hz, 1H, Ar); 7.72-7.74 (m, 1H, Ar); 7.84 (dd, J 8.3 Hz, 1.8 Hz, 1H, Ar); 8.08-8.09 (m, 1H, Ar); 8.26 (d, J 8.3 Hz, 1H, Ar); 8.29 (d, J 1.8 Hz, 1H, Ar); 8.40 (m, 1H, Ar); 8.50 (bs, 1H, Ar). M/Z (M+H)⁺=428.2. MP: 219-227° C.

Example 97

8-(2,6-Dimethyl-pyridin-4-yl)-4-methyl-2-(tetrahydro-pyran-4-yl)-4H-pyrazolo[1,5-a]quinazolin-5-one, HCl Salt

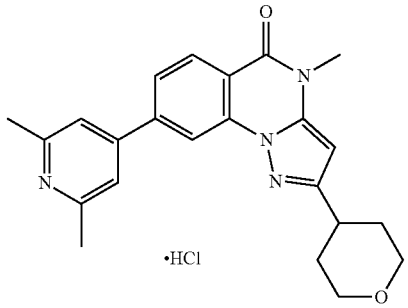 [SMILES: Cc1cc(-c2ccc3c(=O)n(C)c4cc(C5CCOCC5)nn4c3c2)cc(C)n1 ; Cl]

Example 97 was obtained according to general procedure IV(iv) starting from compound 78 in presence of 2,6-dimethylpyridine-4-boronic acid pinacol ester. Purification by flash-chromatography of the solid from filtrate precipitation and the initial solid (EtOAc in Cyclohexane, 80 to 100%) and salt formation according to procedure V(ii) afforded example 97 as a light beige solid in 95% yield.

$^1$H-NMR (400 MHz, DMSO): 1.73-1.83 (m, 2H, 2CH); 1.87-1.90 (m, 2H, 2CH); 2.82 (s, 6H, 2CH$_3$); 2.99 (tt, J 11.5 Hz, J 4.1 Hz, 1H, CH); 3.48 (td, J 11.6 Hz, J 2.1 Hz, 2H, 2 O—CH); 3.53 (s, 3H, N—CH$_3$); 3.94-3.98 (m, 2H, 2 O—CH); 6.29 (s, 1H, Ar); 7.96 (dd, J 8.3 Hz, J 1.8 Hz, 1H, Ar); 8.25 (bs, 2H, Ar); 8.34 (d, J 8.3 Hz, 1H, Ar); 8.44 (d, J 1.8 Hz, 1H, Ar). Signal of HCl salt is not observed. M/Z (M+H)$^+$=389.1. MP: >250° C.

Compound 79

4-Methyl-2-(tetrahydro-pyran-4-yl)-8-(4,4,5,5-tetramethyl-[4,3,2]dioxaborolan-2-yl)-4H-pyrazolo[1,5-a]quinazolin-5-one Compound 79 was obtained according to general procedure VI starting from compound 78.
Trituration of the crude product in Et$_2$O afforded the pure product as a light beige solid in 99% yield.

$^1$H-NMR (400 MHz, DMSO): 1.36 (s, 12H, 4*CH$_3$); 1.70-1.80 (m, 2H, 2CH); 1.89-1.93 (m, 2H, 2CH); 2.98 (tt, J 11.5 Hz, J 3.9 Hz, 1H, CH); 3.48 (dt, J 11.6 Hz, J 2.1 Hz, 5H, 2 O—CH); 3.50 (s, 3H, N—CH$_3$); 3.94-3.97 (m, 2H, 2 O—CH); 6.22 (s, 1H, Ar); 7.69 (dd, J 7.8 Hz, 1.0 Hz, 1H, Ar); 8.16 (d, J 7.8 Hz, 1H, Ar); 8.30 (d, J 1.0 Hz, 1H, Ar). M/Z (M+H)$^+$=328.2.

Example 98

8-(6-Amino-pyridazin-3-yl)-4-methyl-2-(tetrahydro-pyran-4-yl)-4H-pyrazolo[1,5-a]quinazolin-5-one, HCl Salt

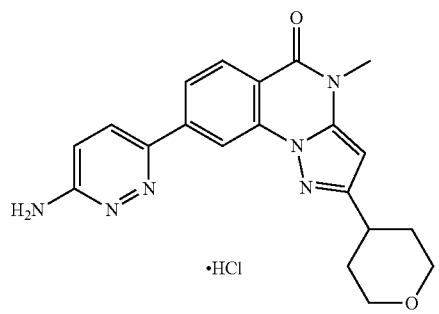 [SMILES: Cn1c(=O)c2ccc(-c3ccc(N)nn3)cc2n2nc(C3CCOCC3)cc12 ; Cl]

Example 98 was obtained according to general procedure IV(iv) starting from compound 79 in presence of 3-amino-6-chloropyridazine.

The filtrate was hydrolysed with water (25 DMF volumes) and extracted twice with EtOAc (2*25 DMF volumes). The organic layers were combined, washed with brine, dried over MgSO$_4$, and concentrated. Purification by flash-chromatography (MeOH in CH$_2$Cl$_2$, 0 to 10%) and salt formation according to procedure V(iii) afforded example 98 as a brown solid in 26% yield.

$^1$H-NMR (400 MHz, DMSO): 1.72-1.82 (m, 2H, 2CH); 1.89-1.93 (m, 2H, 2CH); 3.00 (tt, J 11.5 Hz, J 4.0 Hz, 1H, CH); 3.46-3.54 (m, 5H, 2 O—CH+N—CH$_3$); 3.93-3.98 (m, 2H, 2 O—CH); 6.28 (s, 1H, Ar); 7.55 (bs, 2H, NH$_2$); 7.62 (d, J 9.6 Hz, 1H, Ar); 8.02 (dd, J 8.3 Hz, 1.6 Hz, 1H, Ar); 8.31 (d, J 8.3 Hz, 1H, Ar); 8.56 (d, J 1.6 Hz, 1H, Ar); 8.55 (d, J 9.6 Hz, 1H, Ar); 8.70 (bs, 1H, NH). M/Z (M+H)$^+$=377.2. MP: 140-146° C.

Example 99

8-(2,6-Dimethyl-pyridin-3-yl)-4-methyl-2-(tetrahydro-pyran-4-yl)-4H-pyrazolo[1,5-a]quinazolin-5-one, HCl Salt

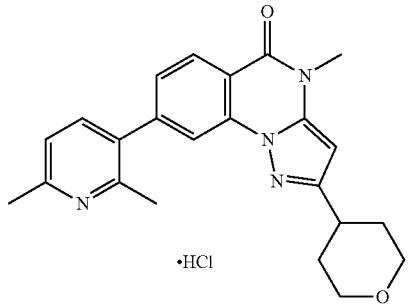 [SMILES: Cc1ccc(-c2ccc3c(=O)n(C)c4cc(C5CCOCC5)nn4c3c2)c(C)n1 ; Cl]

Example 99 was obtained according to general procedure IV(iv) starting from compound 79 in presence of 3-Bromo-2,6-dimethylpyridine. To a celite pad suspension in a DMSO-MeOH mixture (1-1 (v-v)), Smopex resin (2 equiv. to Pd) was added. The mixture was stirred for 2 Hrs, filtered off and the solid was washed with a mixture of DMSO-MeOH. MeOH was removed and water was added to the resulting DMSO solution. The resulting solid was collected, washed with water and dried under reduced pressure with P$_2$O$_5$ at 50° C. Salt formation according to procedure V(iii) afforded example 99 as a purple solid in 84% yield.

$^1$H-NMR (400 MHz, DMSO): 1.69-1.80 (m, 2H, 2CH); 1.86-1.90 (m, 2H, 2CH); 2.67 (s, 3H, CH$_3$); 2.81 (s, 3H, CH$_3$); 2.96 (tt, J 11.4 Hz, J 4.0 Hz, 1H, CH); 3.47 (td, J 11.5 Hz, J 2.2 Hz, 2H, 2 O—CH); 3.54 (s, 3H, N—CH$_3$); 3.92-3.96 (m, 2H, 2 O—CH); 6.28 (s, 1H, Ar); 7.55 (dd, J 8.2 Hz, 1.6 Hz, 1H, Ar); 7.83 (d, J 8.1 Hz, 1H, Ar); 8.07 (d, J 1.6 Hz, 1H, Ar); 8.29 (d, J 8.6 Hz, 1H, Ar); 8.40 (d, J 8.1 Hz, 1H, Ar). Signal of HCl salt is not observed. M/Z (M+H)$^+$=388.2. MP: 231-235° C.

Example 100

3-[4-Methyl-5-oxo-2-(tetrahydro-pyran-4-yl)-4,5-dihydro-pyrazolo[1,5-a]quinazolin-8-yl]-benzenesulfonamide

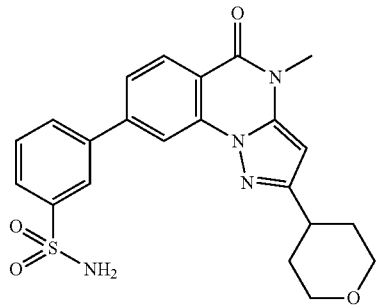 [SMILES: Cn1c(=O)c2ccc(-c3cccc(S(N)(=O)=O)c3)cc2n2nc(C3CCOCC3)cc12]

Example 100 was obtained according to general procedure IV(iv) starting from compound 78 in presence of 3-Boronobenzensulfonamide pinacol ester. Purification by flash-chromatography (MeOH in $CH_2Cl_2$, 0 to 2%) afforded example 100 as a beige solid in 34% yield.

$^1$H-NMR (400 MHz, DMSO): 1.71-1.82 (m, 2H, 2CH); 1.87-1.91 (m, 2H, 2CH); 3.00 (tt, J 11.7 Hz, J 4.0 Hz, 1H, CH); 3.48 (td, J 11.6 Hz, J 2.1 Hz, 2H, 2 O—CH); 3.52 (s, 3H, N—$CH_3$); 3.93-3.97 (m, 2H, 2 O—CH); 6.25 (s, 1H, Ar); 7.50 (s, 2H, $NH_2$); 7.76 (t, J 7.8 Hz, 1H, Ar); 7.81 (dd, J 8.3 Hz, 1.7 Hz, 1H, Ar); 7.91-7.94 (m, 1H, Ar); 8.06-8.08 (m, 1H, Ar); 8.25 (m, 1H, Ar); 8.26 (d, J 1.7 Hz, 1H, Ar); 8.28 (d, J 8.3 Hz, 1H, Ar). M/Z $(M+H)^+$=439.1. MP: decomposed at 178° C.

Example 101

N-(2-Hydroxy-1,1-dimethyl-ethyl)-3-[4-methyl-5-oxo-2-(tetrahydro-pyran-4-yl)-4,5-dihydro-pyrazolo[1,5-a]quinazolin-8-yl]-benzenesulfonamide

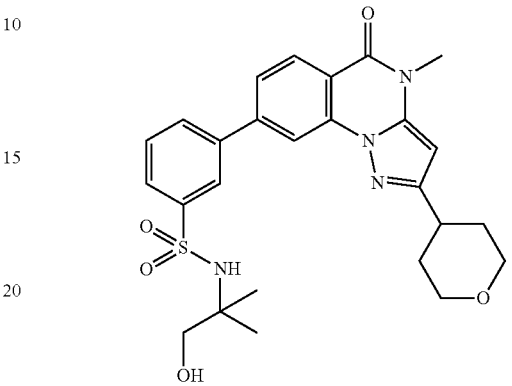

Example 101 was obtained according to general procedure IV(iii) starting from compound 79 in presence of compound 80. Purification by flash-chromatography (MeOH in $CH_2Cl_2$, 0 to 10%) afforded example 101 as a light pink solid in 28% yield.

$^1$H-NMR (400 MHz, DMSO): 1.05 (s, 6H, 2$CH_3$); 1.71-1.82 (m, 2H, 2CH); 1.87-1.91 (m, 2H, 2CH); 3.00 (tt, J 11.5 Hz, J 4.0 Hz, 1H, CH); 3.22 (d, J 5.9 Hz, 2H, $CH_2OH$); 3.48 (td, J 11.7 Hz, J 2.2 Hz, 2H, 2 O—CH); 3.52 (s, 3H, N—$CH_3$); 3.93-3.97 (m, 2H, 2 O—CH); 4.77 (t, 5.9 Hz, 1H, $CH_2OH$); 6.25 (s, 1H, Ar); 7.51 (s, 1H, NH); 7.74 (t, J 7.8 Hz, 1H, Ar); 7.81 (dd, J 8.3 Hz, 1.8 Hz, 1H, Ar); 7.92-7.95 (m, 1H, Ar); 8.05-8.08 (m, 1H, Ar); 8.25 (d, J 1.8 Hz, 1H, Ar); 8.27 (m, 1H, Ar); 8.27 (d, J 8.3 Hz, 1H, Ar). M/Z $(M+H)^+$=511.2. MP: 223-226° C.

Compound 80

3-Bromo-N-(2-hydroxy-1,1-dimethyl-ethyl)-benzenesulfonamide

Under anhydrous conditions, to a solution of 3-bromobenzenesulfonylchloride (140 µL, 1 equiv.) in $CH_2Cl_2$ (5 mL) cooled by an ice bath, diisopropylethylamine (260 µL, 1.5 equiv.) and 2-amino-2-methyl-1-propanol (110 µL, 1.2 equiv.) were added successively. The ice bath was removed and the reaction mixture was stirred for 2 Hrs at room temperature, hydrolysed with aqueous 0.5 N HCl (25 mL) and extracted with $CH_2Cl_2$ twice (2*30 mL). The organic layers were combined, washed with brine, dried over $MgSO_4$ and concentrated. Compound 80 was obtained without further purification as a white solid in 80% yield.

$^1$H-NMR (400 MHz, DMSO): 1.02 (s, 6H, 2$CH_3$); 3.20 (d, J 5.8 Hz, 2H, $CH_2OH$); 4.78 (t, 5.8 Hz, 1H, $CH_2OH$); 7.48 (s, 1H, NH); 7.53 (t, J 7.9 Hz, 1H, Ar); 7.79-7.84 (m, 2H, Ar); 7.99 (t, J 1.8 Hz, 1H, Ar). M/Z $(M[^{79}Br]+Na^+)^+$=330.0.

Compound 81

8-Bromo-4-(2,2-difluoro-ethyl)-2-(tetrahydro-pyran-4-yl)-4H-pyrazolo[1,5-a]quinazolin-5-one Compound 81 was obtained according to general procedure III starting from compound 77 in presence of 1,1-difluoro-2-iodoethane. The reaction mixture was stirred for 17 Hrs at 80° C. Compound 81 was obtained as a white solid in 99% yield contaminated with compound 82 (8-Bromo-5-difluoromethoxy-2-(tetrahydro-pyran-4-yl)-pyrazolo[1,5-a]quinazoline-26%).

$^1$H-NMR (400 MHz, DMSO): 1.69-1.80 (m, 2H, 2CH); 1.87-1.91 (m, 2H, 2CH); 2.97 (tt, J 11.5 Hz, J 3.9 Hz, 1H, CH); 3.48 (td, J 11.5 Hz, J 2.0 Hz, 2H, 2 O—CH); 3.92-3.96 (m, 2H, 2 O—CH); 4.49 (td, J 14.6 Hz, 3.8 Hz, 2H, N—$CH_2$—$CHF_2$); 6.37 (s, 1H, Ar); 6.39 (tt, J 55.0 Hz, 3.8 Hz, 1H, N—$CH_2$—$CHF_2$); 7.66 (dd, J 8.5 Hz, J 1.9 Hz, 1H, Ar); 8.07 (d, J 8.5 Hz, 1H, Ar); 8.15 (d, J 1.9 Hz, 1H, Ar). M/Z $(M[^{79}Br]+H)'$=412.0. MP: 126-130° C.

Example 102

4-(2,2-Difluoro-ethyl)-8-(2,6-dimethyl-pyridin-4-yl)-2-(tetrahydro-pyran-4-yl)-4H-pyrazolo[1,5-a]quinazolin-5-one, HCl Salt

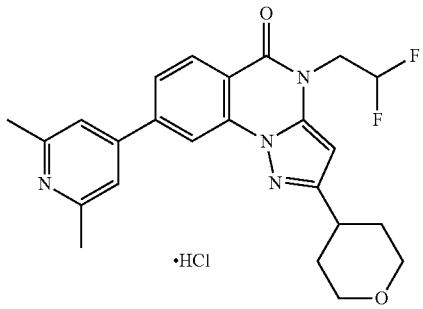 [SMILES: Cc1cc(-c2ccc3c(=O)n(CC(F)F)c4cc(C5CCOCC5)nn4c3c2)cc(C)n1 ; Cl]

Example 102 was obtained according to general procedure IV(iv) starting from compound 81 in presence of 2,6-dimethylpyridine-4-boronic acid pinacol ester. The filtrate was hydrolysed with water (25 DMF volumes) and extracted twice with EtOAc (2*25 DMF volumes). The organic layers were combined, washed with brine, dried over MgSO$_4$ and concentrated. Purification by 2 flash-chromatographies (first: MeOH in CH$_2$Cl$_2$, 0 to 10%, second: EtOAc) and salt formation according to procedure V(ii) afforded example 102 as a white solid in 32% yield.

$^1$H-NMR (400 MHz, DMSO): 1.71-1.81 (m, 2H, 2CH); 1.87-1.91 (m, 2H, 2CH); 2.81 (s, 6H, 2CH$_3$); 2.99 (tt, J 11.6 Hz, J 3.9 Hz, 1H, CH); 3.48 (td, J 11.5 Hz, J 2.0 Hz, 2H, 2 O—CH); 3.94-3.97 (m, 2H, 2 O—CH); 4.54 (td, J 14.7 Hz, 3.9 Hz, 2H, N—CH$_2$—CHF$_2$); 6.42 (tt, J 55.0 Hz, 3.9 Hz, 1H, N—CH$_2$—CHF$_2$); 6.43 (s, 1H, Ar); 7.99 (dd, J 8.3 Hz, J 1.7 Hz, 1H, Ar); 8.27 (bs, 2H, Ar); 8.36 (d, J 8.3 Hz, 1H, Ar); 8.47 (d, J 1.7 Hz, 1H, Ar). Signal for HCl salt is not observed. M/Z (M+H)$^+$=439.2. MP: >250° C.

Example 103

8-(6-Amino-pyridin-3-yl)-4-(2,2-difluoro-ethyl)-2-(tetrahydro-pyran-4-yl)-4H-pyrazolo[1,5-a]quinazolin-5-one, HCl Salt

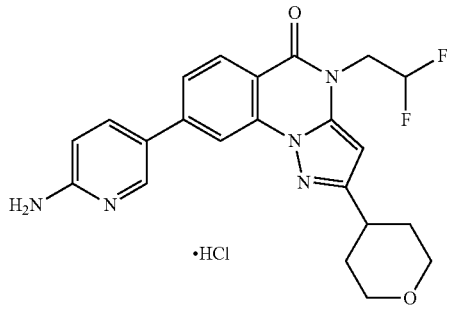 [SMILES: Nc1ccc(-c2ccc3c(=O)n(CC(F)F)c4cc(C5CCOCC5)nn4c3c2)cn1 ; Cl]

Example 103 was obtained according to general procedure IV(iv) starting from compound 81 in presence of 2-aminopyridine-5-boronic acid pinacol ester. The solid was purified by preparative HPLC. The residue was taken in HCl in MeOH (1.25 N), the resulting solid was collected, washed with Et$_2$O and dried under reduced pressure with P$_2$O$_5$ at 50° C. Example 103 was obtained as a yellow solid in 40% yield.

$^1$H-NMR (400 MHz, DMSO): 1.71-1.81 (m, 2H, 2CH); 1.87-1.91 (m, 2H, 2CH); 2.99 (tt, J 11.5 Hz, J 4.0 Hz, 1H, CH); 3.48 (td, J 11.4 Hz, J 2.0 Hz, 2H, 2 O—CH); 3.94-3.97 (m, 2H, 2 O—CH); 4.52 (td, J 14.6 Hz, 3.8 Hz, 2H, N—CH$_2$—CHF$_2$); 6.39 (s, 1H, Ar); 6.46 (tt, J 55.1 Hz, 3.8 Hz, 1H, N—CH$_2$—CHF$_2$); 7.08 (d, J 9.2 Hz, 1H, Ar); 7.78 (dd, J 8.4 Hz, 1.8 Hz, 1H, Ar); 8.06 (bs, 2H, NH$_2$); 8.21 (d, J 1.8 Hz, 1H, Ar); 8.23 (d, J 8.4 Hz, 1H, Ar); 8.38 (dd, J 9.2 Hz, J 2.1, Hz 1H, Ar); 8.53 (d, J 2.1 Hz, 1H, Ar). Signal for HCl salt is not observed. M/Z (M+H)$^+$=426.1. MP: >250° C.

Compound 83

8-Bromo-2-(tetrahydro-pyran-4-yl)-4-(2,2,2-trifluoro-ethyl)-4H-pyrazolo[1,5-a]quinazolin-5-one Compound 83 was obtained according to general procedure III starting from compound 77 in presence of 1,1,1-trifluoro-2-iodoethane. The reaction mixture was stirred at 80° C. for 4 days. After one day, NaH (1.7 equiv.) and 1,1,1-trifluoro-2-iodoethane (2.1 equiv.) were added. The reaction mixture was hydrolysed with aqueous HCl 1N and extracted twice with EtOAc. The organic layers were combined, washed with brine, dried over MgSO$_4$ and concentrated Purification by flash-chromatography (AcOEt in cyclohexane, 0 to 20%) afforded compound 83 as a white solid in 47% yield.

$^1$H-NMR (400 MHz, DMSO): 1.67-1.77 (m, 2H, 2CH); 1.87-1.91 (m, 2H, 2CH); 2.98 (tt, J 11.5 Hz, J 4.0 Hz, 1H, CH); 3.48 (td, J 11.6 Hz, J 2.1 Hz, 2H, 2 O—CH); 3.92-3.96 (m, 2H, 2 O—CH); 4.95 (q, J 9.1 Hz, 2H, N—CH$_2$—CF$_3$); 6.42 (s, 1H, Ar); 7.67 (dd, J 8.5 Hz, 1.9 Hz, 1H, Ar); 8.08 (d, J 8.5 Hz, 1H, Ar); 8.15 (d, J 1.8 Hz, 1H, Ar). M/Z (M[$^{79}$Br]+H)$^+$=430.0.

Example 104

8-(6-Amino-pyridin-3-yl)-2-(tetrahydro-pyran-4-yl)-4-(2,2,2-trifluoro-ethyl)-4H-pyrazolo[1,5-a]quinazolin-5-one, HCl Salt

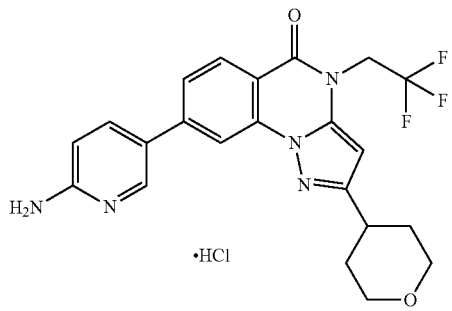 [SMILES: Nc1ccc(-c2ccc3c(=O)n(CC(F)(F)F)c4cc(C5CCOCC5)nn4c3c2)cn1 ; Cl]

Example 104 was obtained according to general procedure IV(iv) starting from compound 83 in presence of 2-aminopyridine-5-boronic acid pinacol ester. Purification by flash-chromatography (EtOAc in Cyclohexane, 70 to 100%) and salt formation according to procedure V(iii) afforded example 104 as a white solid in 53% yield.

$^1$H-NMR (400 MHz, DMSO): 1.70-1.80 (m, 2H, 2CH); 1.88-1.91 (m, 2H, 2CH); 3.00 (tt, J 11.4 Hz, J 4.0 Hz, 1H, CH); 3.49 (td, J 11.6 Hz, J 2.2 Hz, 2H, 2 O—CH); 3.95-3.98 (m, 2H, 2 O—CH); 4.98 (q, J 9.1 Hz, 2H, N—CH$_2$—CF$_3$); 6.44 (s, 1H, Ar); 7.12 (d, J 9.2 Hz, 1H, Ar); 7.79 (dd, J 8.3 Hz, 1.8 Hz, 1H, Ar); 8.18 (bs, 2H, NH$_2$); 8.23 (d, J 1.8 Hz, 1H, Ar); 8.25 (d, J 8.3 Hz, 1H, Ar); 8.42 (dd, J 9.2 Hz, J 2.2 Hz, 1H, Ar); 8.55 (d, J 2.3 Hz, 1H, Ar); 14.08 (bs, 1H, NH). M/Z (M+H)$^+$=444.1. MP: >250° C.

Example 105

8-(2,6-Dimethyl-pyridin-4-yl)-2-(tetrahydro-pyran-4-yl)-4-(2,2,2-trifluoro-ethyl)-4H-pyrazolo[1,5-a]quinazolin-5-one, HCl Salt

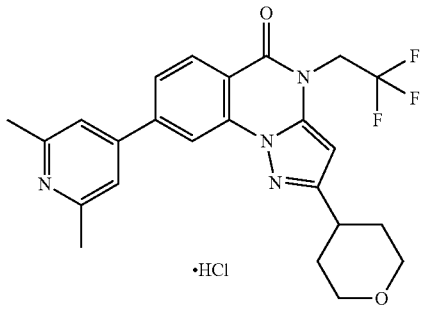 [SMILES: Cc1cc(-c2ccc3c(=O)n(CC(F)(F)F)c4cc(C5CCOCC5)nn4c3c2)cc(C)n1 ; Cl]

Example 105 was obtained according to general procedure IV(iv) starting from compound 83 in presence of 2,6-dimethylpyridine-4-boronic acid pinacol ester. The filtrate was hydrolysed with water (25 DMF volumes) and extracted twice with EtOAc (2*25 DMF volumes). The organic layers were combined, washed with brine, dried over $MgSO_4$ and concentrated. Purification by flash-chromatography (EtOAc in Cyclohexane, 9% to 100%) and salt formation according to procedure V(iii) afforded example 105 as a yellow solid in 29% yield.

$^1$H-NMR (400 MHz, DMSO): 1.71-1.81 (m, 2H, 2CH); 1.88-1.92 (m, 2H, 2CH); 2.79 (s, 6H, 2CH$_3$); 3.01 (tt, J 11.5 Hz, J 3.8 Hz, 1H, CH); 3.49 (td, J 11.4 Hz, J 1.9 Hz, 2H, 2 O—CH); 3.95-3.98 (m, 2H, 2 O—CH); 5.0 (q, J 9.0 Hz, 2H, N—CH$_2$—CF$_3$); 6.48 (s, 1H, Ar); 7.99 (dd, J 8.2 Hz, J 1.2 Hz, 1H, Ar); 8.18 (bs, 2H, Ar); 8.37 (d, J 8.2 Hz, 1H, Ar); 8.45 (d, J 1.2 Hz, 1H, Ar). Signal for HCl salt is not observed. M/Z (M+H)$^+$=457.1. MP: >250° C.

Compound 84

3-Oxo-3-(tetrahydro-furan-3-yl)-propionitrile

Compound 84 was obtained according to general procedure VII(i) starting from Tetrahydrofurane-3-carboxyl chloride. Purification by flash-chromatography (AcOEt in cyclohexane, 0% to 70%) afforded the product as a yellow oil in 72% yield.

$^1$H-NMR (400 MHz, DMSO): 1.97-2.07 (m, 2H, CH$_2$); 3.60-3.77 (m, 4H, OCH$_2$+O—CH+CH); 3.82 (dd, J 8.8 Hz, 5.3 Hz, 1H, O—CH); 4.16 (s, 2H, CH$_2$). M/Z (M+H)$^+$=140.1.

Compound 85

8-Bromo-2-(tetrahydro-furan-3-yl)-4H-pyrazolo[1,5-a]quinazolin-5-one

Compound 85 was obtained according to general procedure II(i), starting from compound 1 in presence of compound 84, as a beige solid in 45% yield.

$^1$H-NMR (400 MHz, DMSO): 2.08-2.14 (m, 1H, CH); 2.25-2.34 (m, 1H, CH); 3.45-3.53 (m, 1H, CH); 3.70-3.84 (m, 2H, CH$_2$); 3.87-3.92 (m, 1H, CH); 4.01-4.05 (m, 1H, CH); 5.84 (s, 1H, Ar); 7.63 (dd, J 8.5 Hz, 1.9 Hz, 1H, Ar); 8.02 (d, J 8.5 Hz, 1H, Ar); 8.12 (d, J 1.9 Hz, 1H, Ar); 12.25 (bs, 1H, NH). M/Z (M[$^{79}$Br]+H)$^+$=334.0.

Compound 86

8-Bromo-4-methyl-2-(tetrahydro-furan-3-yl)-4H-pyrazolo[1,5-a]quinazolin-5-one

Compound 86 was obtained according to general procedure III starting from compound 85 in presence of iodomethane. The reaction mixture was stirred at room temperature for 4 Hrs. Compound 86 was obtained as a white solid in 55% yield.

$^1$H-NMR (400 MHz, DMSO): 2.08-2.17 (m, 1H, CH); 2.28-2.36 (m, 1H, CH); 3.48 (s, 3H, N—CH$_3$); 3.51-3.56 (m, 1H, CH); 3.75-3.85 (m, 2H, CH$_2$); 3.90-3.95 (m, 1H, CH); 4.04-4.08 (m, 1H, CH); 6.25 (s, 1H, Ar); 7.64 (dd, J 8.5 Hz, 1.9 Hz, 1H, Ar); 8.05 (d, J 8.5 Hz, 1H, Ar); 8.13 (d, J 1.9 Hz, 1H, Ar). M/Z (M[$^{79}$Br]+H)$^+$=348.0.

Example 106

8-(2,6-Dimethyl-pyridin-4-yl)-4-methyl-2-(tetrahydro-furan-3-yl)-4H-pyrazolo[1,5-a]quinazolin-5-one, HCl Salt

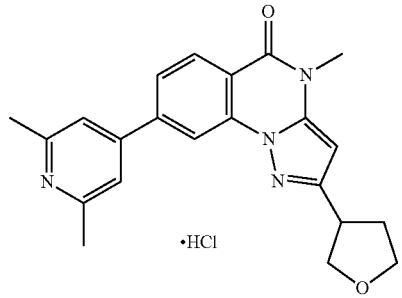 [SMILES: Cc1cc(-c2ccc3c(=O)n(C)c4cc(C5CCOC5)nn4c3c2)cc(C)n1 ; Cl]

Example 106 was obtained according to general procedure IV(iv) starting from compound 86 in presence of 2,6-dimethylpyridine-4-boronic acid pinacol ester. Purification by flash-chromatography (MeOH in CH$_2$Cl$_2$, 0 to 5%) and salt formation according to procedure V(ii) afforded example 106 as a yellow solid in 62% yield.

$^1$H-NMR (400 MHz, DMSO): 2.11-2.19 (m, 1H, CH); 2.31-2.39 (m, 1H, CH); 2.80 (s, 6H, 2CH$_3$); 3.54 (s, 3H, N—CH$_3$); 3.54-3.61 (m, 1H, CH); 3.79-3.87 (m, 2H, CH$_2$); 3.93-3.98 (m, 1H, CH); 4.06-4.10 (m, 1H, CH); 6.32 (s, 1H, Ar); 7.99 (dd, J 8.2 Hz, J 1.6 Hz, 1H, Ar); 8.27 (bs, 2H, Ar); 8.37 (d, J 8.2 Hz, 1H, Ar); 8.47 (d, J 1.6 Hz, 1H, Ar). Signal for HCl salt is not observed. M/Z (M+H)$^+$=375.1. MP: >250° C.

Compound 87

3-Oxo-3-(tetrahydro-furan-2-yl)-propionitrile

Compound 87 was obtained according to general procedure VII(i) starting from methyl tetrahydrofuran-2-carboxylate. Purification by flash-chromatography (AcOEt in cyclohexane, 15 to 60%) afforded the product as a yellow oil in 90% yield.

$^1$H-NMR (400 MHz, DMSO): 1.78-1.96 (m, 3H, CH$_2$+CH); 2.06-2.16 (m, 1H, CH); 3.76-3.86 (m, 2H, O—CH$_2$); 4.37 (s, 2H, CH$_2$); 4.37 (dd, J 8.1 Hz, 6.5 Hz, 1H, O—CH). M/Z (M+H)$^+$=140.1.

Compound 88

8-Bromo-2-(tetrahydro-furan-2-yl)-4H-pyrazolo[1,5-a]quinazolin-5-one

Compound 88 was obtained according to general procedure II (i) starting from compound 1 in presence of compound 87. The reaction mixture was hydrolyzed and extracted twice with EtOAc. The organic layer were combined, washed with brine, saturated aqueous NaHCO₃ solution, with brine, dried over MgSO₄ and concentrated. Purification by flash-chromatography (AcOEt in cyclohexane, 0 to 80%) afforded the product as a yellow solid in 15% yield.

$^1$H-NMR (400 MHz, DMSO): 1.90-2.04 (m, 3H, CH+CH₂); 2.20-2.29 (m, 1H, CH); 3.75-3.81 (m, 1H, CH); 3.87-3.93 (m, 1H, CH); 4.87-4.90 (m, 1H, CH); 5.83 (s, 1H, Ar); 7.64 (dd, J 8.5 Hz, 1.9 Hz, 1H, Ar); 8.02 (d, J 8.5 Hz, 1H, Ar); 8.11 (d, J 1.9 Hz, 1H, Ar); 12.26 (bs, 1H, NH). M/Z (M[$^{79}$Br]+H)$^+$=334.0.

Compound 89

8-Bromo-4-methyl-2-(tetrahydro-furan-2-yl)-4H-pyrazolo[1,5-a]quinazolin-5-one Compound 89 was obtained according to general procedure III starting from compound 88 in presence of iodomethane. The reaction mixture was stirred at room temperature for 2 Hrs. Compound 89 was obtained as a white solid in 88% yield.

$^1$H-NMR (400 MHz, DMSO): 1.94-2.09 (m, 3H, CH+CH₂); 2.26-2.34 (m, 1H, CH); 3.50 (s, 3H, N—CH₃); 3.79-3.84 (m, 1H, CH); 3.92-3.98 (m, 1H, CH); 4.91-4.95 (m, 1H, CH); 6.26 (s, 1H, Ar); 7.66 (dd, J 8.5 Hz, 1.9 Hz, 1H, Ar); 8.07 (d, J 8.5 Hz, 1H, Ar); 8.14 (d, J 1.9 Hz, 1H, Ar). M/Z (M[$^{79}$Br]+H)$^+$=350.1.

Example 107

8-(2,6-Dimethyl-pyridin-4-yl)-4-methyl-2-(tetrahydro-furan-2-yl)-4H-pyrazolo[1,5-a]quinazolin-5-one, HCl Salt

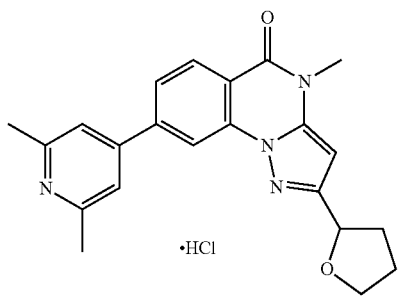 [SMILES: Cc1cc(-c2ccc3c(=O)n(C)c4cc(C5CCCO5)nn4c3c2)cc(C)n1 ; Cl]

Example 107 was obtained according to general procedure IV(iv) starting from compound 89 in presence of 2,6-dimethylpyridine-4-boronic acid pinacol ester. Salt formation from the solid without purification according to procedure V(ii), afforded example 107 as a brown solid in 51% yield.

$^1$H-NMR (400 MHz, DMSO): 1.96-2.07 (m, 3H, CH+CH₂); 2.28-2.35 (m, 1H, CH); 2.80 (s, 6H, 2CH₃); 3.54 (s, 3H, N—CH₃); 3.79-3.84 (m, 1H, CH); 3.94-4.00 (m, 1H, CH); 4.93-4.96 (m, 1H, CH); 6.31 (s, 1H, Ar); 7.99 (dd, J 8.3 Hz, J 1.7 Hz, 1H, Ar); 8.28 (bs, 2H, Ar); 8.35 (d, J 8.3 Hz, 1H, Ar); 8.47 (d, J 1.7 Hz, 1H, Ar). Signal for HCl salt is not observed. M/Z (M+H)$^+$=375.1. MP: 93.101° C.

Compound 90

3-Oxo-3-(tetrahydro-pyran-3-yl)-propionitrile

Compound 90 was obtained according to general procedure VII(i) starting from methyltetrahydro-2-H-pyran-3-carboxylate. Purification by flash-chromatography (AcOEt in cyclohexane, 0 to 70%) afforded the product as a yellow oil in 70% yield.

$^1$H-NMR (400 MHz, DMSO): 1.46-1.62 (m, 3H, CH₂+CH); 1.92-1.94 (m, 1H, CH); 2.71 (m, 1H, CH); 3.28-3.42 (m, 2H, 2O—CH); 3.70-3.73 (m, 1H, O—CH); 3.89-3.92 (m, 1H, O—CH); 4.16 (s, 2H, CH₂).

Compound 91

8-Bromo-2-(tetrahydro-pyran-3-yl)-4H-pyrazolo[1,5-a]quinazolin-5-one

Compound 91 was obtained according to general procedure II(i) starting from compound 1 in presence of compound 90. Purification by flash-chromatography (AcOEt in cyclohexane, 0 to 80%) afforded the product as a white solid in 16% yield.

$^1$H-NMR (400 MHz, DMSO): 1.61-1.69 (m, 2H, CH₂); 1.71-1.82 (m, 1H, CH); 2.05-2.09 (m, 1H, CH); 2.92 (tt, J 10.5 Hz, J 4.0 Hz, 1H, CH); 3.38-3.48 (m, 2H, CH₂); 3.84-3.87 (m, 1H, CH); 3.96-4.01 (m, 1H, CH); 5.84 (s, 1H, Ar); 7.63 (dd, J 8.5 Hz, J 1.8 Hz, 1H, Ar); 8.02 (d, J 8.5 Hz, 1H, Ar); 8.11 (d, J 1.8 Hz, 1H, Ar); 12.24 (bs, 1H, NH). M/Z (M[$^{79}$Br]+H)$^+$=348.0.

Compound 92

8-Bromo-2-(tetrahydro-pyran-3-yl)-4H-pyrazolo[1,5-a]quinazolin-5-one

Compound 92 was obtained according to general procedure III starting from compound 91 in presence of iodomethane. The reaction mixture was stirred at room temperature for 2 Hrs. Purification by flash-chromatography (AcOEt in cyclohexane, 0 to 70%) afforded the product as a white oil in 61% yield.

$^1$H-NMR (400 MHz, DMSO): 1.63-1.71 (m, 2H, CH₂); 1.75-1.85 (m, 1H, CH); 2.08-2.12 (m, 1H, CH); 2.94 (tt, J 10.6 Hz, J 4.1 Hz, 1H, CH); 3.38-3.50 (m, 5H, CH₂+N—CH₃); 3.86-3.90 (m, 1H, CH); 4.00-4.04 (m, 1H, CH); 6.25 (s, 1H, Ar); 7.64 (dd, J 8.5 Hz, J 1.9 Hz, 1H, Ar); 8.05 (d, J 8.5 Hz, 1H, Ar); 8.12 (d, J 1.9 Hz, 1H, Ar). M/Z (M[$^{79}$Br]+H)$^+$=362.0.

Example 108

8-(2,6-Dimethyl-pyridin-4-yl)-4-methyl-2-(tetrahydro-pyran-3-yl)-4H-pyrazolo[1,5-a]quinazolin-5-one, HCl Salt

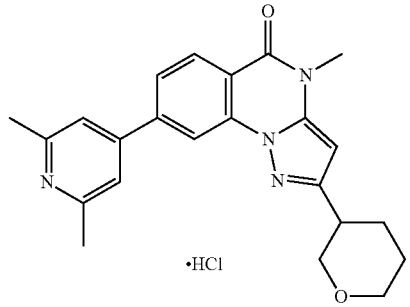 [SMILES: Cc1cc(-c2ccc3c(=O)n(C)c4cc(C5CCCOC5)nn4c3c2)cc(C)n1 ; Cl]

Example 108 was obtained according to general procedure IV(iv) starting from compound 92 in presence of 2,6-dimethylpyridine-4-boronic acid pinacol ester. To a celite pad suspension in a DMSO-MeOH mixture (1-1 (v-v)), Smopex resin (2 equiv. to Pd) was added. The mixture was stirred for 2 Hrs, filtered off and the solid was washed with a mixture of DMSO-MeOH. MeOH was removed and water was added to the resulting DMSO solution which precipitated. The resulting solid was collected, washed with water and dried under reduced pressure with $P_2O_5$ at 50° C. Salt formation according to procedure V(iii) afforded the example 108 as a white solid in 16% yield.

$^1$H-NMR (400 MHz, DMSO): 1.64-1.74 (m, 2H, $CH_2$); 1.77-1.88 (m, 1H, CH); 2.09-2.13 (m, 1H, CH); 2.79 (s, 6H, $2CH_3$); 2.98 (tt, J 10.5 Hz, J 4.0 Hz, 1H, CH); 3.39-3.45 (m, 1H, CH); 3.48-3.52 (m, 4H, CH+N—$CH_3$); 3.86-3.90 (m, 1H, CH); 4.00-4.04 (m, 1H, CH); 6.30 (s, 1H, Ar); 7.97 (dd, J 8.3 Hz, J 1.5 Hz, 1H, Ar); 8.24 (bs, 2H, Ar); 8.35 (d, J 8.3 Hz, 1H, Ar); 8.45 (d, J 1.5 Hz, 1H, Ar); 15.80 (bs, 1H, NH). M/Z (M+H)$^+$=389.1. MP: 182-193° C.

Compound 93

3-Oxo-3-(tetrahydro-pyran-2-yl)-propionitrile

Compound 93 was obtained according to general procedure VII(i) starting from methyltetrahydropyran-2-carboxylate. Purification by flash-chromatography (AcOEt in cyclohexane, 0 to 50%) afforded the product as a yellow oil in 83% yield.

$^1$H-NMR (400 MHz, DMSO): 1.33-1.58 (m, 4H, $2CH_2$); 1.74-1.82 (m, 2H, $CH_2$); 3.41-3.47 (m, 1H, OCH); 3.93-3.96 (m, 2H, $OCH_2$); 4.13 (d, J 2.6 Hz, 2H, $CH_2$).

Compound 94

8-Bromo-2-(tetrahydro-pyran-2-yl)-4H-pyrazolo[1,5-a]quinazolin-5-one

Compound 94 was obtained according to general procedure II(i), starting from compound 1 in presence of compound 93, as a beige solid in 66% yield.

$^1$H-NMR (400 MHz, DMSO): 1.56-1.68 (m, 4H, $2CH_2$); 1.87-1.92 (m, 2H, $CH_2$); 3.52-3.58 (m, 1H, CH); 3.96-3.99 (m, 1H, CH); 4.43-4.58 (m, 1H, CH); 5.48 (s, 1H, Ar); 7.65 (dd, J 8.5 Hz, J 1.9 Hz, 1H, Ar); 8.03 (d, J 8.5 Hz, 1H, Ar); 8.12 (d, J 1.9 Hz, 1H, Ar); 12.24 (bs, 1H, NH). M/Z (M[$^{79}$Br]+H)$^+$=348.0.

Compound 95

8-Bromo-4-methyl-2-(tetrahydro-pyran-2-yl)-4H-pyrazolo[1,5-a]quinazolin-5-one

Compound 95 was obtained according to general procedure III starting from compound 94 in presence of iodomethane. The reaction mixture was stirred at room temperature for 2 Hrs. Compound 94 was obtained as a beige solid in 98% yield.

$^1$H-NMR (400 MHz, DMSO): 1.55-1.73 (m, 4H, $2CH_2$); 1.88-1.94 (m, 2H, $CH_2$); 3.49 (s, 3H, N—$CH_3$); 3.54-3.61 (m, 1H, CH); 3.98-4.01 (m, 1H, CH); 4.47-4.50 (m, 1H, CH); 6.25 (s, 1H, Ar); 7.66 (dd, J 8.5 Hz, J 1.9 Hz, 1H, Ar); 8.07 (d, J 8.5 Hz, 1H, Ar); 8.13 (d, J 1.9 Hz, 1H, Ar). M/Z (M[$^{79}$Br]+H)$^+$, =362.0.

Example 109

8-(2,6-Dimethyl-pyridin-4-yl)-4-methyl-2-(tetrahydro-pyran-2-yl)-4H-pyrazolo[1,5-a]quinazolin-5-one, HCl Salt

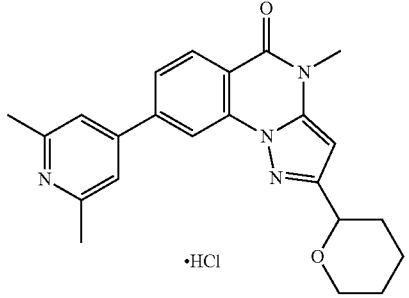 [SMILES: Cc1cc(-c2ccc3c(=O)n(C)c4cc(C5CCCCO5)nn4c3c2)cc(C)n1 ; Cl]

Example 109 was obtained according to general procedure IV(iv) starting from Compound 95 in presence of 2,6-dimethylpyridino-4-boronic acid pinacol ester. Purification by flash-chromatography (MeOH in $CH_2Cl_2$, 0 to 5%) and salt formation according to procedure V(ii) afforded example 109 as a yellow solid in 51% yield.

$^1$H-NMR (400 MHz, DMSO): 1.59-1.78 (m, 4H, $2CH_2$); 1.91-1.93 (m, 2H, $CH_2$); 2.81 (s, 6H, $2CH_3$); 3.54-3.61 (m, 4H, CH+N—$CH_3$); 4.00-4.03 (m, 1H, CH); 4.49-4.52 (m, 1H, CH); 6.32 (s, 1H, Ar); 8.00 (dd, J 8.3 Hz, J 1.8 Hz, 1H, Ar); 8.26 (bs, 2H, Ar); 8.36 (d, J 8.3 Hz, 1H, Ar); 8.47 (d, J 1.8 Hz, 1H, Ar); 16.01 (bs, 1H, NH). M/Z (M+H)$^+$=389.1. MP: 186-194° C.

Compound 96

8-Bromo-5-oxo-2-phenyl-4,5-dihydro-pyrrolo[1,2-a]quinazoline-3-carbonitrile

Under inert atmosphere, a solution of 2-amino-4-bromobenzoic acid (663 mg, 1.0 equiv.) and 2-(2-Bromo-1-phenyl-ethylidene)-malononitrile (758 mg, 1.0 equiv.) in EtOH (absolute 30 mL) was refluxed for 21 Hrs. The reaction mixture turned heterogeneous. After cooling, the solid was collected, washed twice with EtOH (2*10 mL) and dried under reduced pressure at 50° C. with $P_2O_5$. Compound 96 was obtained as a light yellow solid in 38% yield.

¹H-NMR (400 MHz, DMSO): 7.35-7.40 (m, 1H, Ar); 7.47-7.51 (m, 2H, Ar); 7.70 (dd, J 8.5 Hz, J 1.6 Hz, 1H, Ar); 7.73-7.75 (m, 2H, Ar); 8.05 (d, J 8.5 Hz, 1H, Ar); 8.26 (s, 1H, Ar); 8.52 (d, J 1.6 Hz, 1H, Ar); 12.93 (bs, 1H, NH). M/Z (M[⁷⁹Br]+H)⁺=364.0. MP: >250° C.

Compound 97

8-Bromo-2-phenyl-4H-pyrrolo[1,2-a]quinazolin-5-one

A suspension of compound 96 (67 mg) in aqueous H₂SO₄ solution (7N, 5.5 mL) was submitted to microwave irradiation (200° C., 90 min.). After cooling the suspension was filtered, washed twice with water (2*5 mL) and dried under reduced pressure at 50° C. with P₂O₅. Compound 97 was obtained as a yellow solid in quantitative yield.

¹H-NMR (400 MHz, DMSO): 6.38 (d, J 1.8 Hz, 1H, Ar); 7.23-7.26 (m, 1H, Ar); 7.39-7.42 (m, 2H, Ar); 7.58 (dd, J 8.5 Hz, J 1.4 Hz, 1H, Ar); 7.71-7.73 (m, 2H, Ar); 8.05 (d, J 8.5 Hz, 1H, Ar); 8.32 (d, J 1.8 Hz, 1H, Ar); 8.42 (d, J 1.4 Hz, 1H, Ar); 11.89 (bs, 1H, NH). M/Z (M[⁷⁹Br]+H)⁺=353.0.

Compound 98

8-bromo-4-methyl-2-phenyl-4H-pyrrolo[1,2-a]quinazolin-5-one

Compound 98 was obtained according to general procedure III starting from compound 97 in presence of iodomethane. The reaction mixture was stirred at room temperature for 2 Hrs. Compound 97 was obtained as a yellow solid in 78% yield.

¹H-NMR (400 MHz, DMSO): 3.50 (s, 3H, N—CH₃); 6.38 (d, J 1.8 Hz, 1H, Ar); 7.23-7.26 (m, 1H, Ar); 7.39-7.42 (m, 2H, Ar); 7.58 (dd, J 8.5 Hz, J 1.4 Hz, 1H, Ar); 7.71-7.73 (m, 2H, Ar); 8.05 (d, J 8.5 Hz, 1H, Ar); 8.32 (d, J 1.8 Hz, 1H, Ar); 8.42 (d, J 1.4 Hz, 1H, Ar). M/Z (M[⁷⁹Br]+H)⁺=353.0.

Example 110

8-(6-Amino-pyridin-3-yl)-4-methyl-2-phenyl-4H-pyrrolo[1,2-a]quinazolin-5-one, HCl Salt

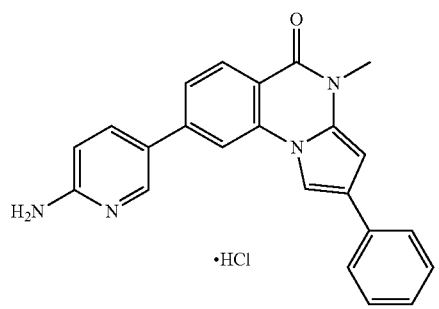 [SMILES: Cn1c(=O)c2ccc(-c3ccc(N)nc3)cc2n2cc(-c3ccccc3)cc12 ; Cl]

Example 110 was obtained according to general procedure IV(iv) starting from Compound 98 in presence of 2-aminopyridine-5-boronic acid pinacol ester. Purification by flash-chromatography (EtOAc in Cyclohexane, 70 to 100%) and salt formation according to procedure V(iii) afforded example 110 as a brown solid in 42% yield.

¹H-NMR (400 MHz, DMSO): 3.53 (s, 3H, N—CH₃); 6.39 (d, J 1.9 Hz, 1H, Ar); 7.18 (d, J 9.3 Hz, 1H, Ar); 7.24-7.28 (m, 1H, Ar); 7.40-7.44 (m, 2H, Ar); 7.72-7.75 (m, 3H, Ar); 8.22 (d, J 8.3 Hz, 1H, Ar); 8.28 (s, 2H, NH₂); 8.40 (d, J 1.9 Hz, 1H, Ar); 8.40-8.41 (m, 2H, Ar); 8.54 (dd, J 9.3 Hz, J 2.2, Hz 1H, Ar); 8.61 (d, J 2.2 Hz, 1H, Ar). M/Z (M+H)⁺=367.2. MP: >250° C.

Example 111

8-(2,6-Dimethyl-pyridin-4-yl)-4-methyl-2-phenyl-4H-pyrrolo[1,2-a]quinazolin-5-one, HCl Salt

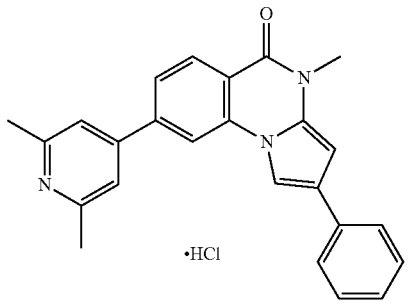 [SMILES: Cc1cc(-c2ccc3c(=O)n(C)c4cc(-c5ccccc5)cn4c3c2)cc(C)n1 ; Cl]

Example 111 was obtained according to general procedure IV(iv) starting from Compound 98 in presence of 2,6-dimethylpyridine-4-boronic acid pinacol ester. Purification by flash-chromatography (EtOAc in Cyclohexane, 0 to 100%) and salt formation according to procedure V(iii) afforded example 111 as a red solid in 47% yield.

¹H-NMR (400 MHz, DMSO): 2.79 (s, 6H, 2CH₃); 3.52 (s, 3H, N—CH₃); 6.35 (d, J 1.9 Hz, 1H, Ar); 7.24-7.28 (m, 1H, Ar); 7.40-7.44 (m, 2H, Ar); 7.70-7.73 (m, 2H, Ar); 7.92 (dd, J 8.3 Hz, J 1.6 Hz, 1H, Ar); 8.24 (d, J 8.3 Hz, 1H, Ar); 8.31 (s, 2H, Ar); 8.40 (d, J 1.9 Hz, 1H, Ar); 8.58 (d, J 1.6 Hz, 1H, Ar); 16.02 (bs, 1H, NH). M/Z (M+H)⁺=380.1. MP: >250° C.

Compound 99

2,6-Dimethyl-isonicotinic acid methyl ester

Under inert atmosphere, a mixture of methyl 2,6-dichloropyridine-4-carboxylate (2.00 g), dimethylzinc (2N in toluene, 14.6 mL, 3.0 equiv.) and PdCl₂(dppf)₂ (400 mg, 0.05 equiv.) in dioxane (50 mL), was heated at 80° C. for 4 Hrs. The reaction mixture was cooled by an ice bath, hydrolysed with water (100 mL) and filtered through a pad of celite. The pad was rinsed with water and EtAOc. The filtrate was extracted with EtOAc (250 mL). The organic layer was washed with brine (100 mL), dried over MgSO₄ and concentrated. Purification by flash-chromatography (MeOH in CH₂Cl₂, 0 to 2%) afforded compound 99 as an orange oil in 96% yield.

¹H-NMR (400 MHz, DMSO): 2.51 (s, 6H, 2CH₃); 3.88 (s, 3H, O—CH₃); 7.51 (s, 2H, Ar). M/Z (M+H)⁺=166.1.

Compound 100

3-(2,6-Dimethyl-pyridin-4-yl)-3-oxo-propionitrile

Compound 100 was obtained according to general procedure VII(ii) starting from compound 99. Compound 100 was used in the next step without further purification.
M/Z (M+H)⁺=175.2.

Compound 101

8-Bromo-2-(2,6-dimethyl-pyridin-4-yl)-4H-pyrazolo[1,5-a]quinazolin-5-one

Compound 101 was obtained according to general procedure II(iii), starting from compound 1 in presence of compound 100, as a beige solid in 72% yield.

¹H-NMR (400 MHz, DMSO): 6.50 (s, 1H, Ar); 7.63 (s, 2H, Ar); 7.70 (dd, J 8.5 Hz, J 1.9 Hz, 1H, Ar); 8.06 (d, J 8.5 Hz, 1H, Ar); 8.32 (d, J 1.9 Hz, 1H, Ar); 12.47 (bs, 1H, NH). Signal for 2CH₃ is not observed (supposed under DMSO signal). M/Z (M[⁷⁹Br]+H)⁺=369.0.

Compound 102

6-dimethyl-pyridin-4-yl)-4-methyl-4H-pyrazolo[1,5-a]quinazolin-5-one

Compound 102 was obtained according to general procedure III starting from compound 101 in presence of iodomethane. The reaction mixture was stirred at room temperature for 60 min. Compound 102 was obtained as a beige solid in 85% yield.

¹H-NMR (400 MHz, DMSO): 3.55 (s, 3H, N—CH₃); 6.97 (s, 1H, Ar); 7.64 (s, 2H, Ar); 7.73 (dd, J 8.5 Hz, J 1.9 Hz, 1H, Ar); 8.11 (d, J 8.5 Hz, 1H, Ar); 8.34 (d, J 1.9 Hz, 1H, Ar). Signal for 2CH₃ is not observed (supposed under DMSO signal). M/Z (M[⁷⁹Br]+H)⁺=383.1.

Example 112

8-(6-Amino-pyridin-3-yl)-2-(2,6-dimethyl-pyridin-4-yl)-4-methyl-4H-pyrazolo[1,5-a]quinazolin-5-one, diHCl Salt

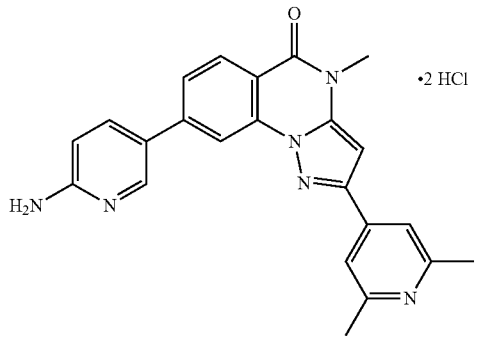 [SMILES: Cc1cc(-c2cc3n(C)c(=O)c4ccc(-c5ccc(N)nc5)cc4n3n2)cc(C)n1]

Example 112 was obtained according to general procedure IV(iv) starting from compound 102 in presence of 2-aminopyridine-5-boronic acid pinacol ester. The filtrate was hydrolysed with water (50 DMF volumes) and extracted twice with EtOAc (2*50 DMF volumes). The organic layers were combined, washed with brine, dried over MgSO₄ and concentrated. Purification by flash-chromatography (MeOH in CH₂Cl₂, 0 to 7%) and salt formation according to procedure V(i) afforded example 112 as a white solid in 11% yield.

¹H-NMR (400 MHz, DMSO): 2.78 (s, 6H, 2CH₃); 3.59 (s, 3H, N—CH₃); 7.15 (d, J 9.3 Hz, 1H, Ar); 7.19 (s, 1H, Ar); 7.89 (dd, J 8.3 Hz, J 1.6 Hz, 1H, Ar); 8.24 (bs, 4H, 2Ar+NH₂); 8.28 (d, J 8.3 Hz, 1H, Ar); 8.43-8.46 (m, 2H, Ar); 8.55 (d, J 1.9 Hz, 1H, Ar) Signals for HCl salt are not observed. M/Z (M+H)⁺=397.2. MP: >250° C.

Example 113

2-(2,6-Dimethyl-pyridin-4-yl)-4-methyl-8-(2-methyl-pyridin-3-yl)-4H-pyrazolo[1,5-a]quinazolin-5-one, diHCl Salt

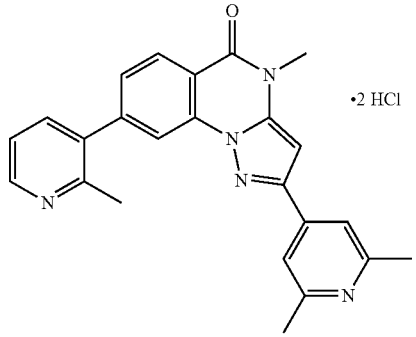 [SMILES: Cc1cc(-c2cc3n(C)c(=O)c4ccc(-c5cccnc5C)cc4n3n2)cc(C)n1]

Example 113 was obtained according to general procedure, from compound 102 in presence of 2-methylpyridine-3-boronic acid pinacol ester. Purification by flash-chromatography (MeOH in CH₂Cl₂, 0 to 6%) and salt formation according to procedure V(i) afforded example 113 as a white solid in 37% yield.

¹H-NMR (400 MHz, DMSO): 2.66 (s, 3H, CH₃); 2.78 (s, 6H, 2CH₃); 3.62 (s, 3H, N—CH₃); 7.24 (s, 1H, Ar); 7.72 (dd, J 8.2 Hz, J 1.6 Hz, 1H, Ar); 7.84 (dd, J 7.2 Hz, J 5.3 Hz, 1H, Ar); 8.25 (s, 2H, Ar); 8.29 (m, 1H, Ar); 8.32 (d, J 1.6 Hz, 1H, Ar); 8.36 (d, J 8.2 Hz, 1H, Ar); 8.80 (dd, J 5.3 Hz, J 1.7 Hz, 1H, Ar). Signals for HCl salt are not observed. M/Z (M+H)⁺= 396.2. MP: >250° C.

Example 114

2,8-Bis-(2,6-dimethyl-pyridin-4-yl)-4-methyl-4H-pyrazolo[1,5-a]quinazolin-5-one, diHCl Salt

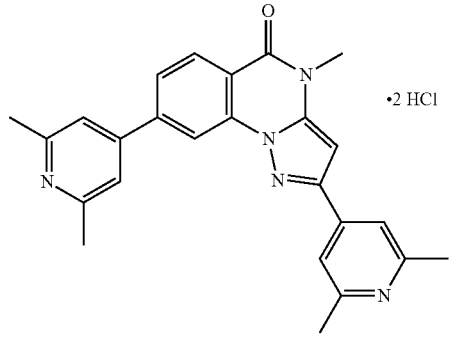

Example 114 was obtained according to general procedure IV(v) starting from compound 102 in presence of 2,6-dimethylpyridine-4-boronic acid pinacol ester. Purification by flash-chromatography (MeOH in CH₂Cl₂, 0 to 8%) and salt formation according to procedure V(i) afforded example 114 as a white solid in 40% yield.

¹H-NMR (400 MHz, DMSO)): 2.82 (s, 12H, 4CH₃); 3.67 (s, 3H, N—CH₃); 7.18 (s, 1H, Ar); 8.07-8.10 (m, 3H, Ar); 8.21 (s, 2H, Ar); 8.45 (d, J 8.3 Hz, 1H, Ar); 8.67 (d, J 1.7 Hz, 1H, Ar). Signals for HCl salt are not observed. M/Z (M+H)⁺= 410.3. MP: >250° C.

Example 115

2-(2,6-Dimethyl-pyridin-4-yl)-4-methyl-8-phenyl-4H-pyrazolo[1,5-a]quinazolin-5-one, HCl Salt

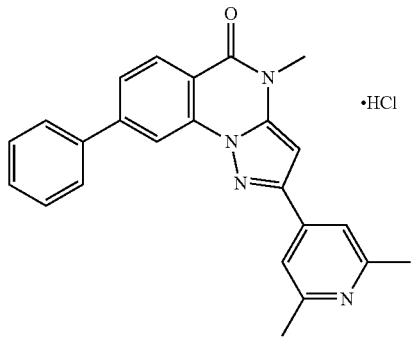 [SMILES: Cc1cc(-c2cc3n(C)c(=O)c4ccc(-c5ccccc5)cc4n3n2)cc(C)n1 ; Cl]

Example 115 was obtained according to general procedure IV(v) starting from compound 102 in presence of phenylboronic acid. Purification by flash-chromatography (AcOEt in cyclohexane, 50 to 100%) and salt formation according to procedure V(i) afforded example 115 as a white solid in 53% yield.

$^1$H-NMR (400 MHz, DMSO (80° C.): 2.80 (s, 6H, 2CH$_3$); 3.61 (s, 3H, N—CH$_3$); 7.12 (s, 1H, Ar); 7.51-7.61 (m, 3H, Ar); 7.84-7.88 (m, 2H, Ar); 7.89 (dd, J 8.3 Hz, J 1.6 Hz, 1H, Ar); 8.21 (s, 2H, Ar); 8.30 (d, J 8.3 Hz, 1H, Ar); 8.45 (d, J 1.6 Hz, 1H, Ar). Signal for HCl salt is not observed. M/Z (M+H)$^+$=381.2. MP: >250° C.

Example 116

2-(2,6-Dimethyl-pyridin-4-yl)-4-methyl-8-pyridin-3-yl-4H-pyrazolo[1,5-a]quinazolin-5-one, diHCl Salt

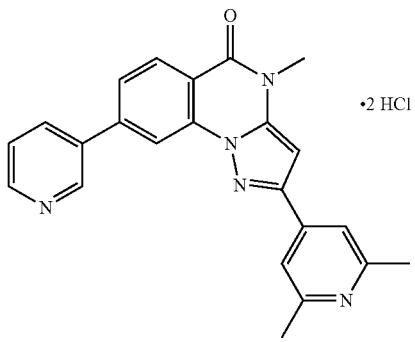 [SMILES: Cc1cc(-c2cc3n(C)c(=O)c4ccc(-c5cccnc5)cc4n3n2)cc(C)n1 ; "·2 HCl"]

Example 116 was obtained according to general procedure IV(v) starting from compound 102 in presence of 3-pyridineboronic acid. Purification by flash-chromatography (MeOH in CH$_2$Cl$_2$, 0 to 5%) and salt formation according to procedure V(i) afforded example 114 as a white solid in 55% yield.

$^1$H-NMR (400 MHz, DMSO): 2.78 (s, 6H, 2CH$_3$); 3.59 (s, 3H, N—CH$_3$); 7.20 (s, 1H, Ar); 7.83 (dd, J 8.0 Hz, J 5.1 Hz, 1H, Ar); 7.99 (dd, J 8.3 Hz, J 1.8 Hz, 1H, Ar); 8.27 (s, 2H, Ar); 8.31 (d, J 8.3 Hz, 1H, Ar); 8.53 (d, J 1.8 Hz, 1H, Ar); 8.55-8.57 (m, 1H, Ar); 8.83 (dd, J 5.1 Hz, J 1.5 Hz, 1H, Ar); 9.22 (d, J 2.1 Hz, 1H, Ar). Signals for HCl salt are not observed. M/Z (M+H)$^+$=382.3. MP: >250° C.

Example 117

2-(2,6-Dimethyl-pyridin-4-yl)-4-methyl-8-(6-methyl-pyridin-3-yl)-4H-pyrazolo[1,5-a]quinazolin-5-one, diHCl Salt

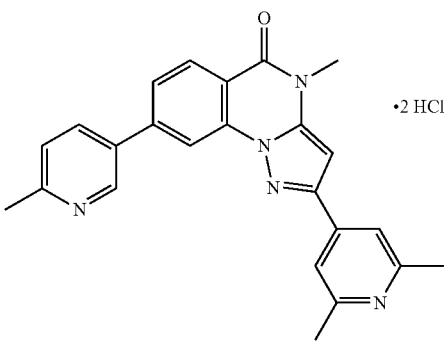

Example 117 was obtained according to general procedure IV(v) starting from compound 102 in presence of 6-methylpyridine-3-boronic acid. Purification by flash-chromatography (MeOH in CH$_2$Cl$_2$, 0 to 7%) and salt formation according to procedure V(i) afforded example 117 as a white solid in 80% yield.

$^1$H-NMR (400 MHz, DMSO): 2.75 (s, 3H, CH$_3$); 2.79 (s, 6H, 2CH$_3$); 3.58 (s, 3H, N—CH$_3$); 7.19 (s, 1H, Ar); 7.84 (d, J 7.8 Hz, 1H, Ar); 8.00 (dd, J 8.3 Hz, J 1.6 Hz, 1H, Ar); 8.25 (s, 2H, Ar); 8.30 (d, J 8.3 Hz, 1H, Ar); 8.53 (d, J 1.6 Hz, 1H, Ar); 8.64 (dd, J 7.8 Hz, J 1.4 Hz, 1H, Ar); 9.16 (d, J 1.4 Hz, 1H, Ar). Signals for HCl salt are not observed. M/Z (M+H)$^+$= 396.3. MP: >250° C.

Example 118

2-(2,6-Dimethyl-pyridin-4-yl)-4-methyl-8-(5-methyl-pyridin-3-yl)-4H-pyrazolo[1,5-a]quinazolin-5-one, diHCl Salt

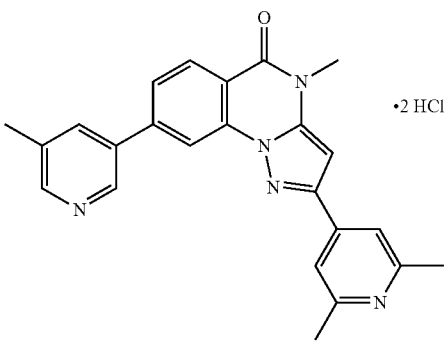

Example 118 was obtained according to general procedure IV(iii) starting from compound 102 in presence of 5-methylpyridine-3-boronic acid. Purification by flash-chromatography (MeOH in CH$_2$Cl$_2$, 0 to 5%) and salt formation according to procedure V(i) afforded example 118 as a beige solid in 43% yield.

$^1$H-NMR (400 MHz, D$_2$O): 2.52 (s, 3H, CH$_3$); 2.71 (s, 6H, 2CH$_3$); 3.46 (s, 3H, N—CH$_3$); 6.62 (s, 1H, Ar); 7.72 (d, J 8.3 Hz, 1H, Ar); 7.84 (s, 2H, Ar); 8.05 (d, J 8.3 Hz, 1H, Ar); 8.11 (s, 1H, Ar); 8.42 (s, 1H, Ar); 8.51 (s, 1H, Ar); 8.79 (s, 1H, Ar). M/Z (M+H)$^+$=396.3. MP: >250° C.

Example 119

2-(2,6-Dimethyl-pyridin-4-yl)-4-methyl-8-(4-methyl-pyridin-3-yl)-4H-pyrazolo[1,5-a]quinazolin-5-one, diHCl Salt

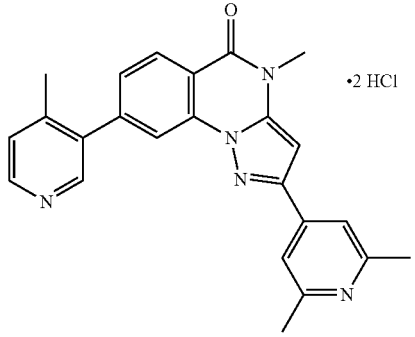 [SMILES: Cc1cc(-c2cc3n(C)c(=O)c4ccc(-c5cnccc5C)cc4n3n2)cc(C)n1 ; "·2 HCl"]

Example 119 was obtained according to general procedure IV(iii) starting from compound 102 in presence of 4-methylpyridine-3-boronic acid. Purification by flash-chromatography (MeOH in $CH_2Cl_2$, 0 to 5%) and salt formation according to procedure V(i) afforded example 119 as a white solid in 37% yield.

$^1$H-NMR (400 MHz, $D_2O$): 2.67 (s, 3H, $CH_3$); 2.79 (s, 6H, 2$CH_3$); 3.68 (s, 3H, N—$CH_3$); 6.88 (s, 1H, Ar); 7.68 (dd, J 8.2 Hz, J 1.4 Hz, 1H, Ar); 8.06 (s, 2H, Ar); 8.09 (d, J 6.2 Hz, 1H, Ar); 8.31 (d, J 1.4 Hz, 1H, Ar); 8.34 (d, J 8.2 Hz, 1H, Ar); 8.75 (d, J 6.2 Hz, 1H, Ar); 8.81 (s, 1H, Ar). M/Z (M+H)$^+$=396.3. MP: >250° C.

Example 120

2-(2,6-Dimethyl-pyridin-4-yl)-8-(2-ethyl-pyridin-3-yl)-4-methyl-4H-pyrazolo[1,5-a]quinazolin-5-one, diHCl Salt

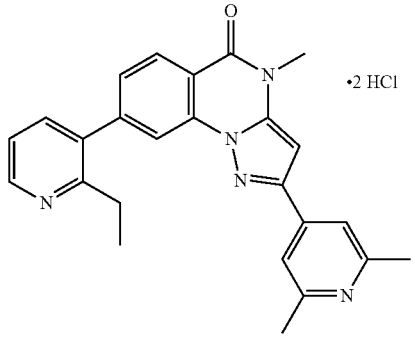 [SMILES: CCc1ncccc1-c1ccc2c(=O)n(C)c3cc(-c4cc(C)nc(C)c4)nn3c2c1 ; "·2 HCl"]

Example 120 was obtained according to general procedure IV(iii) starting from compound 102 in presence of 2-ethylpyridine-3-boronic acid. Purification by flash-chromatography (MeOH in $CH_2Cl_2$, 0 to 4%) and salt formation according to procedure V(i) afforded example 120 as a white solid in 53% yield.

$^1$H-NMR (400 MHz, $D_2O$): 1.30 (t, J 7.6 Hz, 3H, $CH_2$—$CH_3$); 2.78 (s, 6H, 2$CH_3$); 3.12 (q, J 7.6 Hz, 2H, $CH_2$—$CH_3$); 3.64 (s, 3H, N—$CH_3$); 6.84 (s, 1H, Ar); 7.68 (dd, J 8.2 Hz, J 1.4 Hz, 1H, Ar); 8.03 (s, 2H, Ar); 8.06 (dd, J 7.8 Hz, J 6.0 Hz, 1H, Ar); 8.27-8.29 (m, 2H, Ar); 8.59 (dd, J 7.8 Hz, J 1.1 Hz, 1H, Ar); 8.82 (dd, J 6.0 Hz, J 1.1 Hz, 1H, Ar). Signals for HCl salt are not observed. M/Z (M+H)$^+$=410.3. MP: >250° C.

Example 121

2-(2,6-Dimethyl-pyridin-4-yl)-4-methyl-8-(3-methyl-1H-pyrazol-4-yl)-4H-pyrazolo[1,5-a]quinazolin-5-one, HCl Salt

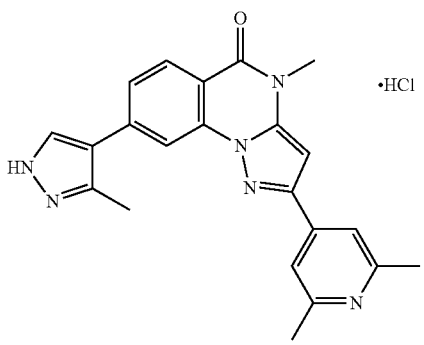 [SMILES: Cc1cc(-c2cc3n(C)c(=O)c4ccc(-c5c[nH]nc5C)cc4n3n2)cc(C)n1 ; Cl]

Example 121 was obtained according to general procedure IV(iv) starting from compound 102 in presence of 3-methyl-1H-pyrazole-4-boronic acid pinacol ester. Purification by flash-chromatography (MeOH in $CH_2Cl_2$, 0 to 5%) and salt formation according to procedure V(iii) afforded example 121 as a white solid in 44% yield.

$^1$H-NMR (400 MHz, DMSO): 2.54 (s, 3H, $CH_3$); 2.78 (s, 6H, 2$CH_3$); 3.57 (s, 3H, N—$CH_3$); 7.15 (s, 1H, Ar); 7.71 (dd, J 8.4 Hz, J 1.6 Hz, 1H, Ar); 8.10 (s, 1H, Ar); 8.18 (d, J 8.4 Hz, 1H, Ar); 8.24 (m, 3H, Ar). Signals for HCl salt and Pyrazol NH are not observed. M/Z (M+H)$^+$=385.3. MP: >250° C.

Example 122

2-(2,6-Dimethyl-pyridin-4-yl)-4-methyl-8-(1-methyl-1H-pyrazol-4-yl)-4H-pyrazolo[1,5-a]quinazolin-5-one, HCl Salt

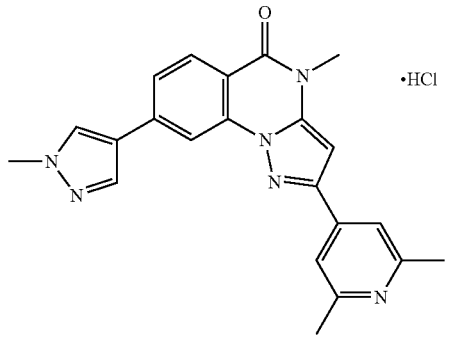

Example 122 was obtained according to general procedure IV(iii) starting from compound 102 in presence of 1-methyl-1H-pyrazole-4-boronic acid pinacol ester. Purification by flash-chromatography (MeOH in $CH_2Cl_2$, 0 to 5%) and salt formation according to procedure V(iii) afforded example 122 as a white solid in 27% yield.

$^1$H-NMR (400 MHz, DMSO): 2.78 (s, 6H, 2$CH_3$); 3.56 (s, 3H, N—$CH_3$); 3.93 (s, 3H, N—$CH_3$); 7.15 (s, 1H, Ar); 7.80 (dd, J 8.3 Hz, J 1.6 Hz, 1H, Ar); 8.14 (s, 1H, Ar); 8.17 (d, J 8.3 Hz, 1H, Ar); 8.27 (s, 2H, Ar); 8.33 (d, J 1.6 Hz, 1H, Ar); 8.48 (s, 1H, Ar). Signal for HCl salt is not observed. M/Z (M+H)$^+$=385.3. MP: >250° C.

Example 123

2-(2,6-Dimethyl-pyridin-4-yl)-4-methyl-8-(2H-pyrazol-3-yl)-4H-pyrazolo[1,5-a]quinazolin-5-one, HCl Salt

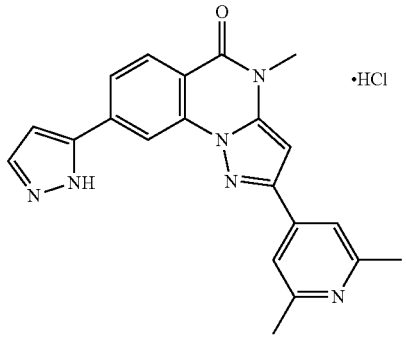 [SMILES: Cc1cc(-c2cc3n(C)c(=O)c4ccc(-c5ccn[nH]5)cc4n3n2)cc(C)n1 ; Cl]

Example 123 was obtained according to general procedure IV(iv) starting from compound 102 in presence of potassium 1H-pyrazole-3-trifluoroborate. Purification by flash-chromatography (MeOH in $CH_2Cl_2$, 0 to 5%) and salt formation according to procedure V(iii) afforded example 123 as a white solid in 25% yield.

$^1$H-NMR (400 MHz, DMSO): 2.78 (s, 6H, 2CH$_3$); 3.56 (s, 3H, N—CH$_3$); 6.98 (d, J 2.3 Hz, 1H, Ar); 7.14 (s, 1H, Ar); 7.90 (d, J 2.3 Hz, 1H, Ar); 8.01 (dd, J 8.3 Hz, J 1.5 Hz, 1H, Ar); 8.22 (d, J 8.3 Hz, 1H, Ar); 8.25 (s, 2H, Ar); 8.62 (d, J 1.5 Hz, 1H, Ar). Signals for HCl salt and Pyrazole NH are not observed. M/Z (M+H)$^+$=371.3. MP: >250° C.

Compound 103

1-Methyl-1H-pyrazole-4-carboxylic acid ethyl ester

Under anhydrous condition, to a solution of ethyl 4-pyrazolecarboxylate (3.00 g) in DMF (210 mL, c=0.1 molL$^{-1}$) cooled by an ice bath, NaH (in mineral oil 60%, 1.10 g, 1.3 equiv.) was added in 3 portions (over 5 minutes). The mixture was stirred for 15 minutes, then methyl iodide (1.6 mL, 1.2 equiv.) was added. The ice bath was removed, and the reaction was stirred at room temperature for 2 Hrs. The mixture was hydrolysed with a saturated aqueous solution of NaHCO$_3$ (1.0 L) and extracted twice with EtOAc (2*1.5 L). The organic layers were combined, washed with brine (0.5 L), dried over MgSO$_4$ and concentrated. Purification by flash-chromatography (AcOEt in cyclohexane, 0 to 90%) afforded compound 103 as a colourless oil in 79% yield (2.60 g).

$^1$H-NMR (400 MHz, DMSO): 1.26 (t, J 7.1 Hz, 3H, O—CH$_2$—CH$_3$); 3.87 (s, 3H, N—CH$_3$); 4.21 (q, J 7.1 Hz, 2H, O—CH$_2$—CH$_3$); 7.82 (s, 1H, Ar); 8.29 (s, 1H, Ar). M/Z (M+H)$^+$=155.1.

Compound 104

3-(1-Methyl-1H-pyrazol-4-yl)-3-oxo-propionitrile

Compound 104 was obtained according to general procedure VII(i) starting from compound 103. Purification by flash-chromatography (AcOEt in cyclohexane, 30 to 100%) afforded compound 104 as a white solid in 86% yield.

$^1$H-NMR (400 MHz, DMSO): 3.90 (s, 3H, N—CH$_3$); 4.43 (s, 2H, CH$_2$); 7.98 (s, 1H, Ar); 8.44 (s, 1H, Ar). M/Z (M+H)$^+$=150.0.

Compound 105

8-Bromo-2-(1-methyl-1H-pyrazol-4-yl)-4H-pyrazolo[1,5-a]quinazolin-5-one

Compound 105 was obtained according to general procedure II (i), starting from compound 1 in presence of compound 104, as a beige solid in 68% yield.

$^1$H-NMR (400 MHz, DMSO): 3.89 (s, 3H, N—CH$_3$); 6.14 (s, 1H, Ar); 7.63 (dd, J 8.5 Hz, J 1.8 Hz, 1H, Ar); 7.91 (s, 1H, Ar); 8.03 (d, J 8.5 Hz, 1H, Ar); 8.16 (d, J 1.8 Hz, 1H, Ar); 8.23 (s, 1H, Ar); 12.32 (bs, 1H, NH). M/Z (M[$^{79}$Br]+H)$^+$=344.0.

Compound 106

8-Bromo-4-methyl-2-(1-methyl-1H-pyrazol-4-yl)-4H-pyrazolo[1,5-a]quinazolin-5-one Compound 106 was obtained according to general procedure III starting from compound 105 in presence of iodomethane. The reaction mixture was stirred at room temperature for 30 min. Compound 106 was obtained as a white solid in 82% yield.

$^1$H-NMR (400 MHz, DMSO): 3.51 (s, 3H, N—CH$_3$); 3.91 (s, 3H, N—CH$_3$); 6.50 (s, 1H, Ar); 7.64 (dd, J 8.5 Hz, J 1.8 Hz, 1H, Ar); 7.91 (s, 1H, Ar); 8.07 (d, J 8.5 Hz, 1H, Ar); 8.16 (d, J 1.8 Hz, 1H, Ar); 8.21 (s, 1H, Ar). M/Z (M[$^{79}$Br]+H)$^+$=358.1.

Example 124

4-Methyl-2-(1-methyl-1H-pyrazol-4-yl)-8-phenyl-4H-pyrazolo[1,5-a]quinazolin-5-one

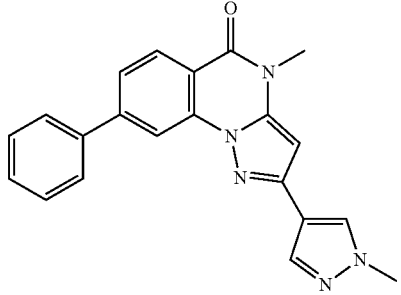 [SMILES: Cn1cc(-c2cc3n(C)c(=O)c4ccc(-c5ccccc5)cc4n3n2)cn1]

Example 124 was obtained according to general procedure IV(iv) starting from compound 106 in presence of phenylboronic acid. The filtrate was hydrolysed with water (50 DMF volumes) and extracted twice with EtOAc (2*50 DMF volumes). The organic layers were combined, washed with brine, dried over MgSO$_4$ and concentrated. Purification by flash-chromatography (EtOAc in Cyclohexane, 50 to 100%) afforded example 124 as a white solid in 82% yield.

$^1$H-NMR (400 MHz, DMSO): 3.55 (s, 3H, N—CH$_3$); 3.91 (s, 3H, N—CH$_3$); 6.51 (s, 1H, Ar); 7.49-7.60 (m, 3H, Ar); 7.77 (dd, J 8.3 Hz, J 1.8 Hz, 1H, Ar); 7.82-7.88 (m, 2H, Ar); 7.91 (s, 1H, Ar); 8.23 (s, 1H, Ar); 8.23 (d, J 8.3 Hz, 1H, Ar); 8.25 (d, J 1.8 Hz, 1H, Ar). M/Z (M+H)$^+$=356.1. MP: 228-231° C.

Example 125

8-(4-Methoxy-phenyl)-4-methyl-2-(1-methyl-1H-pyrazol-4-yl)-4H-pyrazolo[1,5-a]quinazolin-5-one

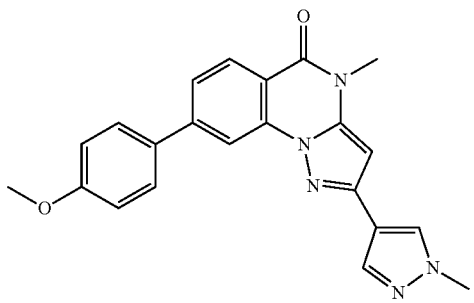

Example 125 was obtained according to general procedure IV(iii) starting from compound 106 in presence of 4-methoxyphenylboronic acid. Purification by flash-chromatography (EtOAc in Cyclohexane, 50 to 100%) afforded example 125 as a white solid in 59% yield.

$^1$H-NMR (400 MHz, DMSO): 3.54 (s, 3H, N—CH$_3$); 3.85 (s, 3H, O—CH$_3$); 3.90 (s, 3H, N—CH$_3$); 6.49 (s, 1H, Ar); 7.10-7.13 (m, 2H, Ar); 7.72 (dd, J 8.3 Hz, J 1.8 Hz, 1H, Ar); 7.77-7.79 (m, 2H, Ar); 7.91 (s, 1H, Ar); 8.18 (d, J 8.3 Hz, 1H, Ar); 8.19 (d, J 1.8 Hz, 1H, Ar); 8.22 (s, 1H, Ar). M/Z (M+H)$^+$=386.2. MP: 211-213° C.

Example 126

4-Methyl-2-(1-methyl-1H-pyrazol-4-yl)-8-pyridin-3-yl-4H-pyrazolo[1,5-a]quinazolin-5-one, HCl Salt

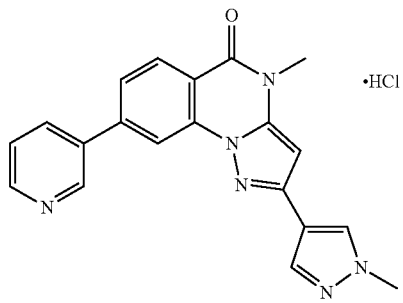 [SMILES: Cn1cc(-c2cc3n(C)c(=O)c4ccc(-c5cccnc5)cc4n3n2)cn1 ; Cl]

Example 126 was obtained according to general procedure IV(vi) starting from compound 106 in presence of 3-pyridineboronic acid. Purification by flash-chromatography (MeOH in CH$_2$Cl$_2$, 0 to 4%) and salt formation according to procedure V(i) afforded example 126 as a beige solid in 76% yield.

$^1$H-NMR (400 MHz, DMSO): 3.57 (s, 3H, N—CH$_3$); 3.92 (s, 3H, N—CH$_3$); 6.55 (s, 1H, Ar); 7.89-7.98 (m, 2H, Ar); 8.02 (dd, J 8.0 Hz, J 5.3 Hz, 1H, Ar); 8.21 (s, 1H, Ar); 8.32 (d, J 8.2 Hz, 1H, Ar); 8.40 (d, J 1.7 Hz, 1H, Ar); 8.79-8.81 (m, 1H, Ar); 8.92 (dd, J 5.3 Hz, J 1.3 Hz, 1H, Ar); 9.33 (m, 1H, Ar). Signal for HCl salt is not observed. M/Z (M+H)$^+$=357.2. MP: >250° C.

Example 127

4-Methyl-2-(1-methyl-1H-pyrazol-4-yl)-8-(2-methyl-pyridin-3-yl)-4H-pyrazolo[1,5-a]quinazolin-5-one, HCl Salt

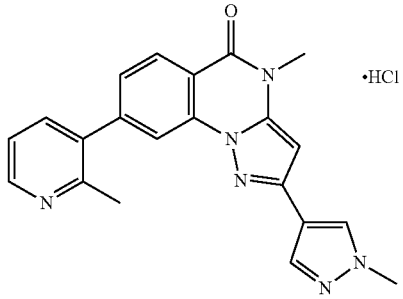 [SMILES: Cc1ncccc1-c1ccc2c(=O)n(C)c3cc(-c4cnn(C)c4)nn3c2c1 ; Cl]

Example 127 was obtained according to general procedure IV(v) starting from compound 106 in presence of 2-methylpyridine-3-boronic acid pinacol ester. Purification by flash-chromatography (MeOH in CH$_2$Cl$_2$, 0 to 5%) and salt formation according to procedure V(i) afforded example 127 as a white solid in 77% yield.

$^1$H-NMR (400 MHz, DMSO): 2.70 (s, 3H, CH$_3$); 3.57 (s, 3H, N—CH$_3$); 3.90 (s, 3H, N—CH$_3$); 6.55 (s, 1H, Ar); 7.59 (dd, J 8.2 Hz, J 1.8 Hz, 1H, Ar); 7.87 (s, 1H, Ar); 8.00 (dd, J 7.7 Hz, J 5.8 Hz, 1H, Ar); 8.13 (d, J 1.8 Hz, 1H, Ar); 8.17 (s, 1H, Ar); 8.30 (d, J 8.2 Hz, 1H, Ar); 8.53 (dd, J 7.7 Hz, J 1.4 Hz, 1H, Ar); 8.87 (dd, J 5.8 Hz, J 1.4 Hz, 1H, Ar). Signal for HCl salt is not observed. M/Z (M+H)$^+$=371.1. MP: 169-187° C.

Example 128

8-(6-Amino-pyridin-3-yl)-4-methyl-2-(1-methyl-1H-pyrazol-4-yl)-4H-pyrazolo[1,5-a]quinazolin-5-one, HCl Salt

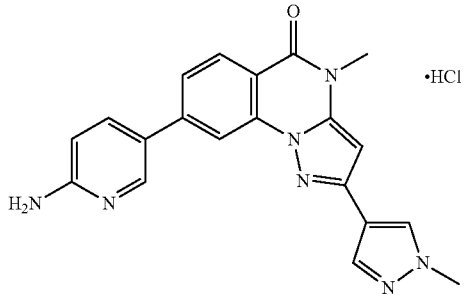 [SMILES: Cn1cc(-c2cc3n(C)c(=O)c4ccc(-c5ccc(N)nc5)cc4n3n2)cn1 ; Cl]

Example 128 was obtained according to general procedure IV(iii) starting from compound 106 in presence of 2-aminopyridine-5-boronic acid pinacol ester. No purification was required. Salt formation according to procedure V(i) afforded example 128 as a white solid in 17% yield.

$^1$H-NMR (400 MHz, DMSO): 3.54 (s, 3H, N—CH$_3$); 3.91 (s, 3H, N—CH$_3$); 6.52 (s, 1H, Ar); 7.17 (d, J 9.3 Hz, 1H, Ar); 7.75 (dd, J 8.5 Hz, J 1.7 Hz, 1H, Ar); 7.90 (s, 1H, Ar); 8.19 (s, 1H, Ar); 8.22-8.24 (m, 2H, Ar); 8.31 (bs, 2H, NH$_2$); 8.44 (dd, J 9.3 Hz, J 2.2 Hz, 1H, Ar); 8.53 (d, J 2.2 Hz, 1H, Ar). Signal for HCl salt is not observed. M/Z (M+H)$^+$=372.1. MP: 217-228° C.

Example 129

4-Methyl-2-(1-methyl-1H-pyrazol-4-yl)-8-pyridin-4-yl-4H-pyrazolo[1,5-a]quinazolin-5-one, HCl Salt

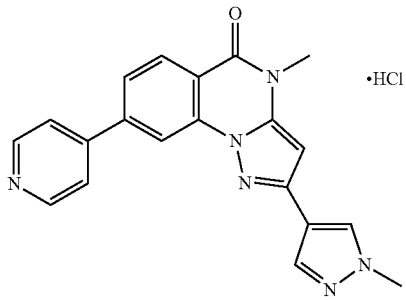 [SMILES: Cn1cc(-c2cc3n(C)c(=O)c4ccc(-c5ccncc5)cc4n3n2)cn1 ; Cl]

Example 129 was obtained according to general procedure IV(iv) starting from compound 106 in presence of 4-pyridineboronic acid. Purification by flash-chromatography (MeOH in $CH_2Cl_2$, 0 to 5%) and salt formation according to procedure V(i) afforded example 129 as a yellow solid in 68% yield.

$^1$H-NMR (400 MHz, DMSO): 3.57 (s, 3H, N—$CH_3$); 3.92 (s, 3H, N—$CH_3$); 6.55 (s, 1H, Ar); 7.92 (s, 1H, Ar); 7.99 (dd, J 8.2 Hz, J 1.8 Hz, 1H, Ar); 8.22 (s, 1H, Ar); 8.34 (d, J 8.2 Hz, 1H, Ar); 8.39-8.40 (m, 2H, Ar); 8.46 (d, J 1.8 Hz, 1H, Ar); 9.00-9.02 (m, 2H, Ar). Signal for HCl salt is not observed. M/Z (M+H)$^+$=357.2. MP: >250° C.

Example 130

8-(2,6-Dimethyl-pyridin-4-yl)-4-methyl-2-(1-methyl-1H-pyrazol-4-yl)-4H-pyrazolo[1,5-a]quinazolin-5-one, HCl Salt

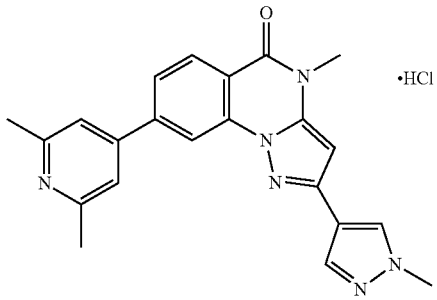

Example 130 was obtained according to general procedure starting from compound 106 in presence of 2,6-dimethylpyridine-4-boronic acid pinacol ester. To a celite pad suspension in a DMSO-MeOH mixture (1-1 (v-v)), Smopex resin (2 equiv. referred to initial Pd quantity) was added. The mixture was stirred for 2 Hrs, filtered off and the solid was washed with a mixture of DMSO-MeOH. The filtrate was concentrated and water was added to the residue. The resulting solid was collected, washed with water and dried under reduced pressure with $P_2O_5$ at 50° C. Salt formation according to procedure V(i) afforded example 130 as a yellow solid in 19% yield.

$^1$H-NMR (400 MHz, DMSO): 2.83 (s, 6H, 2$CH_3$); 3.56 (s, 3H, N—$CH_3$); 3.92 (s, 3H, N—$CH_3$); 6.56 (s, 1H, Ar); 7.92 (s, 1H, Ar); 7.97 (dd, J 8.2 Hz, J 1.7 Hz, 1H, Ar); 8.21 (s, 1H, Ar); 8.27 (s, 2H, Ar); 8.35 (d, J 8.2 Hz, 1H, Ar); 8.47 (d, J 1.7 Hz, 1H, Ar). Signal for HCl salt is not observed. M/Z (M+H)$^+$=385.2. MP: >250° C.

Compound 107

1-Ethyl-1H-pyrazole-4-carboxylic acid ethyl ester

Under anhydrous condition, to a solution of ethyl 4-pyrazolecarboxylate (600 mg) in DMF (21 mL, c=0.1 molL$^{-1}$) cooled by an ice bath, NaH (in mineral oil 60%, 225 mg, 1.3 equiv.) was added in 3 portions (over 5 minutes). The mixture was stirred for 15 minutes, then methyl iodide (410 μL, 1.2 equiv.) was added. The ice bath was removed and the reaction was stirred at room temperature for 1 Hrs. The mixture was hydrolysed with a saturated aqueous solution of $NaHCO_3$ (200 mL) and extracted twice with EtOAc (2*250 mL). The organic layers were combined, washed with brine (400 mL), dried over $MgSO_4$ and concentrated. Purification by flash-chromatography (AcOEt in cyclohexane, 5 to 100%) afforded compound 107 as a colourless oil in 90% yield.

$^1$H-NMR (400 MHz, DMSO): 1.26 (t, J 7.1 Hz, 3H, O—$CH_2$—$CH_3$); 1.38 (t, J 7.3 Hz, 3H, N—$CH_2$—$CH_3$); 4.17 (q, J 7.3 Hz, 2H, N—$CH_2$—$CH_3$); 4.21 (q, J 7.1 Hz, 2H, O—$CH_2$—$CH_3$); 7.84 (s, 1H, Ar); 8.33 (s, 1H, Ar). M/Z (M+H)$^+$=169.0.

Compound 108

3-(1-Ethyl-1H-pyrazol-4-yl)-3-oxo-propionitrile

Compound 108 was obtained according to general procedure VII(i) starting from compound 107. Purification by flash-chromatography (AcOEt in cyclohexane, 25 to 100%) afforded compound 108 as a white solid in 92% yield.

$^1$H-NMR (400 MHz, DMSO): 1.39 (t, J 7.3 Hz, 3H, N—$CH_2$—$CH_3$); 4.19 (q, J 7.3 Hz, 2H, N—$CH_2$—$CH_3$); 4.43 (s, 2H, $CH_2$); 7.99 (s, 1H, Ar); 8.50 (s, 1H, Ar). M/Z (M+H)$^+$=164.1.

Compound 109

8-Bromo-2-(1-ethyl-1H-pyrazol-4-yl)-4H-pyrazolo[1,5-a]quinazolin-5-one

Compound 109 was obtained according to general procedure II(i), starting from compound 1 in presence of compound 108, as a beige solid in 72% yield.

$^1$H-NMR (400 MHz, DMSO): 1.43 (t, J 7.3 Hz, 3H, N—$CH_2$—$CH_3$); 4.18 (q, J 7.3 Hz, 2H, N—$CH_2$—$CH_3$); 6.15 (s, 1H, Ar); 7.63 (dd, J 8.5 Hz, J 1.9 Hz, 1H, Ar); 7.92 (s, 1H, Ar); 8.03 (d, J 8.5 Hz, 1H, Ar); 8.17 (d, J 1.9 Hz, 1H, Ar); 8.29 (s, 1H, Ar); 12.32 (bs, 1H, NH). M/Z (M[$^{79}$Br]+H)$^+$=358.0.

Compound 110

8-Bromo-4-methyl-2-(1-ethyl-1H-pyrazol-4-yl)-4H-pyrazolo[1,5-a]quinazolin-5-one

Compound 110 was obtained according to general procedure III starting from compound 109 in presence of iodomethane. The reaction mixture was stirred at room temperature for 30 min. Compound 110 was obtained as a white solid in 96% yield.

$^1$H-NMR (400 MHz, DMSO): 1.44 (t, J 7.3 Hz, 3H, N—$CH_2$—$CH_3$); 3.51 (s, 3H, N—$CH_3$); 4.20 (q, J 7.3 Hz, 2H, N—$CH_2$—$CH_3$); 6.51 (s, 1H, Ar); 7.64 (dd, J 8.5 Hz, J 1.8 Hz, 1H, Ar); 7.92 (s, 1H, Ar); 8.07 (d, J 8.5 Hz, 1H, Ar); 8.17 (d, J 1.8 Hz, 1H, Ar); 8.27 (s, 1H, Ar). M/Z (M[$^{79}$Br]+H)$^+$=372.1.

Example 131

8-(6-Amino-pyridin-3-yl)-2-(1-ethyl-1H-pyrazol-4-yl)-4-methyl-4H-pyrazolo[1,5-a]quinazolin-5-one, HCl Salt

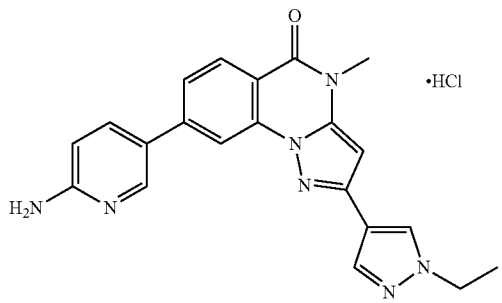 [SMILES: CCn1cc(-c2cc3n(C)c(=O)c4ccc(-c5ccc(N)nc5)cc4n3n2)cn1 ; Cl]

Example 131 was obtained according to general procedure IV(iv) starting from compound 110 in presence of 2-aminopyridine-5-boronic acid pinacol ester. The filtrate was hydrolysed with water (50 DMF volumes) and extracted twice with EtOAc (2*50 DMF volumes). The organic layers were combined, washed with brine, dried over MgSO$_4$ and concentrated. Purification by flash-chromatography (MeOH in CH$_2$Cl$_2$, 0 to 8%) and salt formation according to procedure V(ii) afforded example 131 as a brown solid in 35% yield.

$^1$H-NMR (400 MHz, DMSO): 1.44 (t, J 7.3 Hz, 3H, N—CH$_2$—CH$_3$); 3.55 (s, 3H, N—CH$_3$); 4.22 (q, J 7.3 Hz, 2H, N—CH$_2$—CH$_3$); 6.53 (s, 1H, Ar); 7.18 (d, J 9.3 Hz, 1H, Ar); 7.76 (dd, J 8.5 Hz, J 1.7 Hz, 1H, Ar); 7.92 (s, 1H, Ar); 8.23-8.25 (m, 2H, Ar); 8.25 (s, 1H, Ar); 8.35 (bs, 2H, NH$_2$); 8.45 (dd, J 9.3 Hz, J 2.2 Hz, 1H, Ar); 8.55 (d, J 2.2 Hz, 1H, Ar); 14.21 (bs, 1H, NH). M/Z (M+H)$^+$=386.2. MP: 226-238° C.

Compound 111

3-(2-methyl-pyridin-4-yl)-3-oxo-propionitrile

Compound 111 was obtained according to general procedure VII(ii) starting from ethyl 2-methylpyridine-4-carboxylate. Compound 111 was used in the next step without further purification. M/Z (M+H)$^+$=161.1.

Compound 112

8-Bromo-2-(2-methyl-pyridin-4-yl)-4H-pyrazolo[1,5-a]quinazolin-5-one

Compound 112 was obtained according to general procedure II(iii), starting from compound 1 in presence of compound 111, as a brown solid in 65% yield.

$^1$H-NMR (400 MHz, DMSO): 2.54 (s, 3H, CH$_3$); 6.44 (s, 1H, Ar); 7.65 (dd, J 8.5 Hz, J 1.9 Hz, 1H, Ar); 7.72 (dd, J 5.2 Hz, J 1.2 Hz, 1H, Ar); 7.82 (d, J 1.2 Hz, 1H, Ar); 8.04 (d, J 8.5 Hz, 1H, Ar); 8.28 (d, J 1.9 Hz, 1H, Ar); 8.50 (d, J 5.2 Hz, 1H, Ar). Signal for NH is not observed. M/Z (M[$^{79}$Br]+H)$^+$=355.1.

Compound 113

8-Bromo-2-(2-methyl-pyridin-4-yl)-4-methyl-4H-pyrazolo[1,5-a]quinazolin-5-one

Compound 113 was obtained according to general procedure III starting from compound 112 in presence of iodomethane. The reaction mixture was stirred at room temperature for 60 min. Addition of water did not promote precipitation. Therefore, the reaction mixture was extracted twice with EtOAc. The organic layers were combined, washed with brine, dried over MgSO$_4$ and concentrated. Purification by flash-chromatography (MeOH in CH$_2$Cl$_2$, 0 to 3%) afforded compound 113 as a beige solid in 63% yield. M/Z (M[$^{79}$Br]+H)$^+$=369.1.

Example 132

2-(2-methyl-pyridin-4-yl)-4-methyl-8-(2-methyl-pyridin-3-yl)-4H-pyrazolo[1,5-a]quinazolin-5-one, diHCl Salt

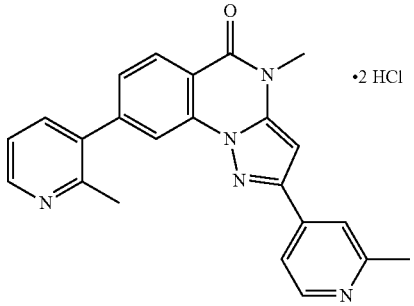 [SMILES: Cc1cc(-c2cc3n(C)c(=O)c4ccc(-c5cccnc5C)cc4n3n2)ccn1 ; "·2 HCl"]

Example 132 was obtained according to general procedure IV(v) starting from compound 113 in presence of 2-methylpyridine-3-boronic acid pinacol ester. Purification by flash-chromatography (MeOH in CH$_2$Cl$_2$, 0 to 5%) and salt formation according to procedure V(i) afforded example 132 as a white solid in 85% yield.

$^1$H-NMR (400 MHz, D$_2$O): 2.72 (s, 3H, CH$_3$); 2.75 (s, 3H, CH$_3$); 3.54 (s, 3H, N—CH$_3$); 6.79 (s, 1H, Ar); 7.57 (d, J 8.2 Hz, 1H, Ar); 7.97 (m, 1H, Ar); 8.13-8.19 (m, 3H, Ar); 8.21 (s, 1H, Ar); 8.51 (d, J 8.0 Hz, 1H, Ar); 8.56 (d, J 6.2 Hz, 1H, Ar); 8.69 (d, J 5.7 Hz, 1H, Ar). M/Z (M+H)+=382.2. MP: >250° C.

Example 133

8-(2,6-Dimethyl-pyridin-4-yl)-4-methyl-2-(2-methyl-pyridin-4-yl)-4H-pyrazolo[1,5-a]quinazolin-5-one, diHCl Salt

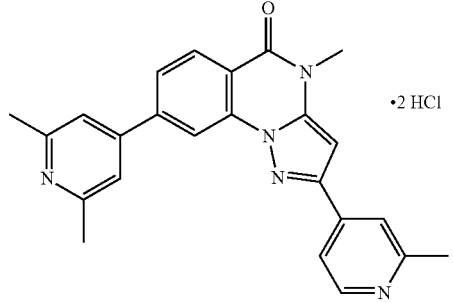

Example 133 was obtained according to general procedure IV(v) starting from compound 113 in presence of 2,6-dimethylpyridine-4-boronic acid pinacol ester. Purification by flash-chromatography (MeOH in $CH_2Cl_2$, 0 to 4%) and salt formation according to procedure V(ii) afforded example 133 as a white solid in 94% yield.

$^1$H-NMR (400 MHz, DMSO): 2.79 (s, 3H, $CH_3$); 2.81 (s, 6H, $2CH_3$); 3.62 (s, 3H, N—$CH_3$); 7.29 (s, 1H, Ar); 8.11 (dd, J 8.3 Hz, J 1.7 Hz, 1H, Ar); 8.25 (s, 2H, Ar); 8.32 (d, J 5.9 Hz, 1H, Ar); 8.40 (s, 1H, Ar); 8.43 (d, J 8.3 Hz, 1H, Ar); 8.69 (d, J 1.7 Hz, 1H, Ar); 8.86 (d, J 5.9 Hz, 1H, Ar). Signals for HCl salt are not observed. M/Z $(M+H)^+$=396.3. MP: >250° C.

Compound 114

8-Bromo-4-methyl-2-pyridin-3-yl-4H-pyrazolo[1,5-a]quinazolin-5-one

Compound 114 was obtained according to general procedure III starting from compound 74 in presence of iodomethane. The reaction mixture was stirred at room temperature for 60 min. Compound 114 was obtained as a yellow solid in 87% yield.

$^1$H-NMR (400 MHz, DMSO): 3.57 (s, 3H, N—$CH_3$); 6.98 (s, 1H, Ar); 7.55 (dd, J 7.4 Hz, J 4.8 Hz, 1H, Ar); 7.72 (dd, J 8.5 Hz, J 1.8 Hz, 1H, Ar); 8.12 (d, J 8.5 Hz, 1H, Ar); 8.34 (d, J 1.8 Hz, 1H, Ar); 8.36-8.39 (m, 1H, Ar); 8.64 (dd, J 4.8 Hz, J 1.5 Hz, 1H, Ar); 9.21 (m, 1H, Ar). M/Z $(M[^{79}Br]+H)^+$=355.1.

Example 134

4-Methyl-8-(2-methyl-pyridin-3-yl)-2-pyridin-3-yl-4H-pyrazolo[1,5-a]quinazolin-5-one, diHCl Salt

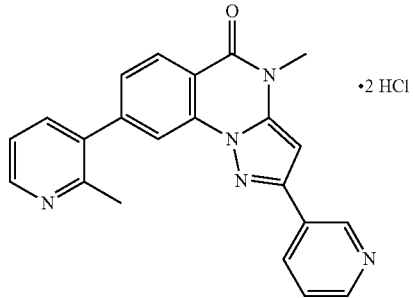 [SMILES: Cc1ncccc1-c1ccc2c(=O)n(C)c3cc(-c4cccnc4)nn3c2c1]

Example 134 was obtained according to general procedure IV(v) starting from compound 114 in presence of 2-methylpyridine-3-boronic acid pinacol ester. Purification by flash-chromatography (MeOH in $CH_2Cl_2$, 0 to 5%) and salt formation according to procedure V(i) afforded example 134 as a white solid in 57% yield.

$^1$H-NMR (400 MHz, DMSO): 2.64 (s, 3H, $CH_3$); 3.64 (s, 3H, N—$CH_3$); 6.96 (s, 1H, Ar); 7.61-7.76 (m, 3H, Ar); 8.21 (d, J 7.1 Hz, 1H, Ar); 8.26 (s, 1H, Ar); 8.35 (d, J 8.0 Hz, 1H, Ar); 8.49 (d, J 7.8 Hz, 1H, Ar); 8.68 (d, J 4.8 Hz, 1H, Ar); 8.74 (d, J 5.3 Hz, 1H, Ar); 9.24 (s, 1H, Ar). Signals for HCl salt are not observed. M/Z $(M+H)^+$=368.2. MP: >250° C.

Compound 115

2-Trifluoromethyl-isonicotinic Acid Methyl Ester

Under inert atmosphere, a mixture of 2-Trifluoromethyl-isonicotinic acid (1.0 equiv.), BOP (1.2 equiv.), DIPEA (1.5 equiv.) in DCM (C=0.1 $molL^{-1}$) and MeOH (C=0.1 $molL^{-1}$) was stirred at RT for 16 h. The reaction mixture was evaporated to dryness. The resulting residue was hydrolysed with HCl 1N and extracted twice with $Et_2O$. The organic layers were combined, washed with a saturated solution of $NaHCO_3$, brine, dried over $MgSO_4$, concentrated to afford the product as transparent oil in a 66% yield.

$^1$H-NMR (400 MHz, DMSO): 3.95 (s, 3H, $CH_3$); 8.16-8.22 (m, 2H, Ar); 9.05 (d, J 5.0 Hz, 1H, Ar); M/Z $(M+H)^+$=206.3.

Compound 116

3-Oxo-3-(2-trifluoromethyl-pyridin-4-yl)-propionitrile

Compound 116 was obtained according to general procedure VII(ii) starting from compound 115 as a red solid in 17% yield.

Compound 117

8-Bromo-2-(2-trifluoromethyl-pyridin-4-yl)-4H-pyrazolo[1,5-a]quinazolin-5-one

Compound 117 was obtained according to general procedure II(iii), starting from compound 1 in presence of compound 116 as a pale green solid in 20% yield.

$^1$H-NMR (400 MHz, DMSO): 6.66 (s, 1H, Ar); 7.64-7.71 (m, 1H, Ar); 8.05 (d, J 8.2 Hz, 1H, Ar); 8.27 (d, J 4.8 Hz, 1H, Ar); 8.32-8.37 (m, 1H, Ar); 8.38-8.43 (m, 1H, Ar); 8.27 (d, J 4.8 Hz, 1H, Ar). M/Z $(M[^{79}Br]+H)^+$=409.0.

Compound 118

8-Bromo-4-methyl-2-(2-trifluoromethyl-pyridin-4-yl)-4H-pyrazolo[1,5-a]quinazolin-5-one Compound 118 was obtained according to general procedure III, starting from compound 117 in presence of iodomethane. The reaction mixture was stirred at room temperature for 120 min. Compound 118 was obtained as a pale green solid in 93% yield.

$^1$H-NMR (400 MHz, DMSO): 3.46 (s, 3H, N—$CH_3$); 7.11 (s, 1H, Ar); 7.66 (dd, J 8.5 Hz, J 1.2 Hz, 1H, Ar); 7.67 (d, J 8.5 Hz, 1H, Ar); 8.16-8.21 (m, 1H, Ar); 8.29 (m, 1H); 8.32 (m, 1H); 8.82 (d, J 5.0 Hz, 1H, Ar). M/Z $(M[^{79}Br]+H)^+$=423.2.

Example 135

4-Methyl-8-(2-methyl-pyridin-3-yl)-2-(2-trifluoromethyl-pyridin-4-yl)-4H-pyrazolo[1,5-a]quinazolin-5-one, HCl Salt

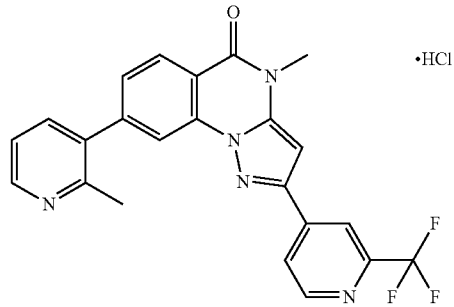 [SMILES: Cc1ncccc1-c1ccc2c(=O)n(C)c3cc(-c4ccnc(C(F)(F)F)c4)nn3c2c1 ; Cl]

Example 135 was obtained according to general procedure IV(vii) starting from compound 118 in presence of 2-methyl-pyridine-3-boronic acid pinacol ester. Purification by flash-chromatography (DCM/MeOH) and salt formation according to procedure V(ii), afforded example 135 as a white solid in 30% yield.

¹H-NMR (400 MHz, DMSO): 2.65 (s, 3H, CH₃); 3.62 (s, 3H, N—CH₃); 7.26 (s, 1H, Ar); 7.67 (dd, J 8.1 Hz, J 1.5 Hz, 1H, Ar); 7.84-7.89 (m, 1H, Ar); 8.27 (dd, J 5.1 Hz, J 0.9 Hz, 1H, Ar); 8.33 (dd, J 1.5 Hz, 1H, Ar); 8.34-8.38 (m, 2H, Ar); 8.39-8.42 (m, 1H, Ar); 8.82 (dd, J 5.5 Hz, J 0.9 Hz, 1H, Ar); 8.90 (d, J 5.1 Hz, 1H, Ar). Signals for HCl salt are not observed. M/Z (M+H)⁺=436.3. MP: >250° C.

Example 136

8-(6-Amino-pyridin-3-yl)-4-methyl-2-(2-trifluoromethyl-pyridin-4-yl)-4H-pyrazolo[1,5-a]quinazolin-5-one, HCl Salt

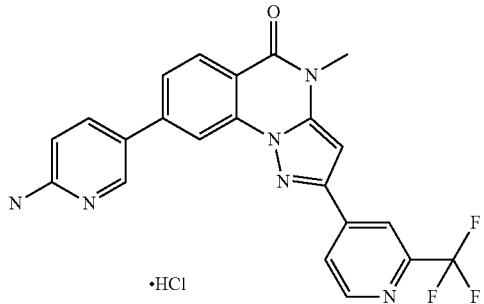 [SMILES: Cn1c(=O)c2ccc(-c3ccc(N)nc3)cc2n2nc(-c3ccnc(C(F)(F)F)c3)cc12 ; Cl]

Example 136 was obtained according to general procedure IV(ix) starting from compound 118 in presence of 2-aminopyridine-5-boronic acid pinacol ester. Purification by flash-chromatography (DCM/MeOH) and salt formation according to procedure V(iii), afforded example 136 as a white solid in 36% yield.

¹H-NMR (400 MHz, DMSO): 3.57 (s, 3H, N—CH₃); 7.13 (d, J 9.2 Hz, 1H, Ar); 7.20 (s, 1H, Ar); 7.84 (dd, J 8.3 Hz, J 1.8 Hz, 2H, Ar); 8.04-8.24 (bs, 2H, NH₂); 8.23-8.29 (m, 2H, Ar); 8.39-8.42 (m, 2H); 8.45 (dd, J 9.2 Hz, J 2.3 Hz, 1H, Ar); 8.58 (d, J 2.3 Hz, 1H, Ar); 8.90 (d, J 5.1 Hz, 1H, Ar). M/Z (M+H)⁺=437.2. MP: >250° C.

Example 137

8-(2-Ethyl-pyridin-3-yl)-4-methyl-2-(2-trifluoromethyl-pyridin-4-yl)-4H-pyrazolo[1,5-a]quinazolin-5-one, HCl Salt

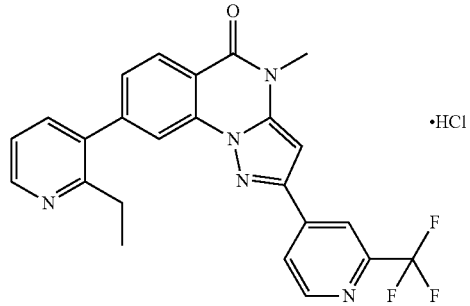 [SMILES: CCc1ncccc1-c1ccc2c(=O)n(C)c3cc(-c4ccnc(C(F)(F)F)c4)nn3c2c1 ; Cl]

Example 137 was obtained according to general procedure IV(ix) starting from compound 118 in presence of 2-ethyl-pyridine-3-boronic acid pinacol ester. Purification by flash-chromatography (DCM/MeOH) and salt formation according to procedure V(iii), afforded example 137 as a white solid in 31% yield.

¹H-NMR (400 MHz, DMSO): 1.18 (t, J 7.3 Hz, 3H, CH₂—CH₃); 2.93 (q, J 7.3 Hz, 2H, CH₂—CH₃); 3.62 (s, 3H, N—CH₃); 7.25 (s, 1H, Ar); 7.65 (dd, J 8.2 Hz, J 1.7 Hz, 1H, Ar); 7.75-7.85 (m, 1H, Ar); 8.22-8.29 (m, 2H, Ar); 8.30 (d, J 1.3 Hz, 1H, Ar); 8.30 (d, J 8.2 Hz, 1H, Ar); 8.38-8.42 (m, 1H, Ar); 7.82 (dd, J 5.2 Hz, J 1.0 Hz, 1H, Ar); 8.89 (d, J 5.2 Hz, 1H, Ar). Signals for HCl salt are not observed. M/Z (M+H)⁺=450.3. MP: >250° C.

Example 138

4-Methyl-8-(2-methyl-pyridin-4-yl)-2-(2-trifluoromethyl-pyridin-4-yl)-4H-pyrazolo[1,5-a]quinazolin-5-one, HCl Salt

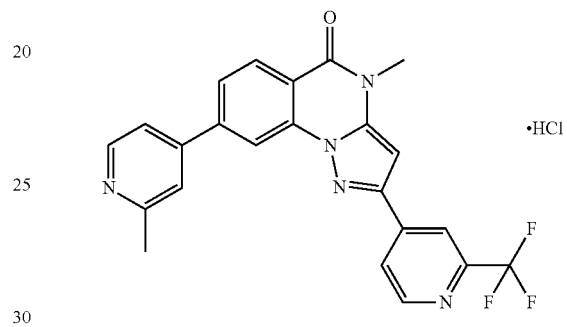

Example 138 was obtained according to general procedure IV(ix) starting from compound 118 in presence of 2-ethyl-pyridine-3-boronic acid pinacol ester. Purification by flash-chromatography (DCM/MeOH) and salt formation according to procedure V(iii), afforded example 138 as a white solid in 19% yield.

¹H-NMR (400 MHz, DMSO): 2.76 (s, 3H, CH₃); 3.61 (s, 3H, N—CH₃); 7.26 (s, 1H, Ar); 8.05 (dd, J 8.3 Hz, J 1.8 Hz, 1H, Ar); 8.14-8.21 (m, 1H, Ar); 8.27-8.31 (m, 1H, Ar); 8.31 (dd, J 5.0 Hz, J 1.0 Hz, 1H, Ar); 8.38 (d, J 8.3 Hz, 1H, Ar); 8.43-8.47 (m, 1H, Ar); 8.65 (d, J 1.5 Hz, 1H, Ar); 8.84 (d, J 5.8 Hz, 1H, Ar); 8.92 (d, J 5.0 Hz, 1H, Ar). Signals for HCl salt are not observed. M/Z (M+H)⁺=436.3. MP: >250° C.

Example 139

4-Methyl-2,8-bis-(2-trifluoromethyl-pyridin-4-yl)-4H-pyrazolo[1,5-a]quinazolin-5-one

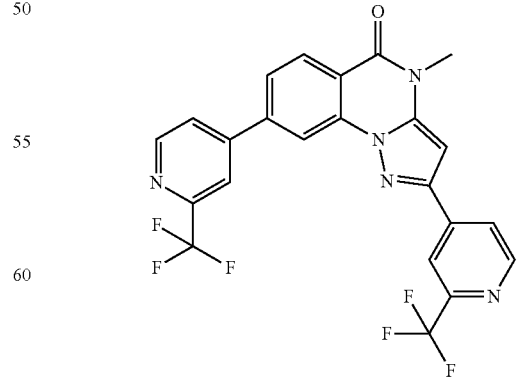

Example 139 was obtained according to general procedure IV(vii) starting from compound 118 in presence of 2-trifluoromethyl-pyridine-4-boronic acid. Purification by flash-chromatography (DCM/MeOH) and trituration in Et₂O afforded example 139 as a white solid in 33% yield.

¹H-NMR (400 MHz, DMSO): 3.59 (s, 3H, N—CH₃); 7.22 (s, 1H, Ar); 8.05 (dd, J 8.3 Hz, J 1.8 Hz, 1H, Ar); 8.29 (dd, J 5.0 Hz, J 1.1 Hz, 1H, Ar); 8.32 (d, J 8.3 Hz, 1H, Ar); 8.35-8.38 (m, 1H, Ar); 8.41-8.44 (m, 1H, Ar); 8.61 (d, J 1.8 Hz, 1H, Ar); 8.89 (d, J 5.0 Hz, 1H, Ar); 8.93 (d, J 5.2 Hz, 1H, Ar). M/Z (M+H)⁺=490.3. MP: >250° C.

Example 140

8-(2-Fluoro-pyridin-4-yl)-4-methyl-2-(2-trifluoromethyl-pyridin-4-yl)-4H-pyrazolo[1,5-a]quinazolin-5-one

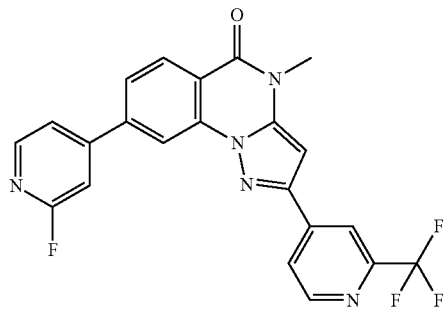 [SMILES: Cn1c(=O)c2ccc(-c3ccnc(F)c3)cc2n2nc(-c3ccnc(C(F)(F)F)c3)cc12]

Example 140 was obtained according to general procedure IV(vii) starting from compound 118 in presence of 2-fluoropyridine-4-boronic acid. Purification by flash-chromatography (DCM/MeOH) and trituration in Et₂O afforded example 140 as a beige solid in 63% yield.

¹H-NMR (400 MHz, DMSO): 3.60 (s, 3H, N—CH₃); 7.24 (s, 1H, Ar); 7.77 (s, 1H, Ar); 7.88-7.94 (m, 1H, Ar); 7.98-8.06 (m, 1H, Ar); 8.29-8.36 (m, 2H, Ar); 8.40-8.48 (m, 2H, Ar); 8.57-8.62 (m, 1H, Ar); 8.91 (d, J 5.0 Hz, 1H, Ar). M/Z (M+H)⁺=440.3. MP: >250° C.

Example 141

8-(6-Fluoro-pyridin-3-yl)-4-methyl-2-(2-trifluoromethyl-pyridin-4-yl)-4H-pyrazolo[1,5-a]quinazolin-5-one

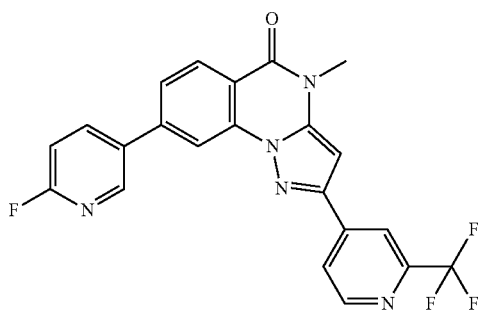 [SMILES: Cn1c(=O)c2ccc(-c3ccc(F)nc3)cc2n2nc(-c3ccnc(C(F)(F)F)c3)cc12]

Example 141 was obtained according to general procedure IV(ix) starting from compound 118 in presence of 2-fluoropyridine-5-boronic acid pinacol ester. Purification by flash-chromatography (DCM/MeOH) and trituration in Et₂O afforded example 141 as a white solid in 51% yield.

¹H-NMR (400 MHz, DMSO): 3.57 (s, 3H, N—CH₃); 7.18 (s, 1H, Ar); 7.38 (dd, J 8.2 Hz, J 2.7 Hz, 1H, Ar); 7.89 (dd, J 8.2 Hz, J 1.8 Hz, 1H, Ar); 8.25 (d, J 8.2 Hz, 1H, Ar); 8.27 (dd, J 5.0 Hz, J 1.1 Hz, 1H, Ar); 8.38-8.42 (m, 1H, Ar); 8.45 (d, J 1.1 Hz, 1H, Ar); 8.52 (dd, J 8.3 Hz, J 2.7 Hz, 1H, Ar);); 8.76 (d, J 2.4 Hz, 1H, Ar); 8.88 (d, J 5.0 Hz, 1H, Ar). M/Z (M+H)⁺=440.2. MP: >250° C.

Example 142

4-Methyl-2-(2-trifluoromethyl-pyridin-4-yl)-8-(2-trifluoromethyl-pyridin-3-yl)-4H-pyrazolo[1,5-a]quinazolin-5-one

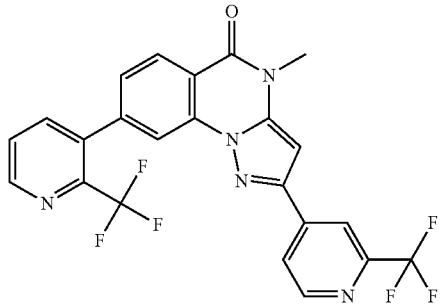 [SMILES: Cn1c(=O)c2ccc(-c3cccnc3C(F)(F)F)cc2n2nc(-c3ccnc(C(F)(F)F)c3)cc12]

Example 142 was obtained according to general procedure IV(ix) starting from compound 118 in presence of 2-trifluoromethyl-pyridine-3-boronic acid pinacol ester. Purification by flash-chromatography (DCM/MeOH) and trituration in Et₂O afforded example 142 as a white solid in 17% yield.

¹H-NMR (400 MHz, DMSO): 3.61 (s, 3H, N—CH₃); 7.25 (s, 1H, Ar); 7.57 (dd, J 8.2 Hz, J 1.3 Hz, 1H, Ar); 7.89 (dd, J 7.8 Hz, J 4.5 Hz, 1H, Ar); 8.10 (dd, J 7.8 Hz, J 0.9 Hz, 1H, Ar); 8.23-8.28 (m, 1H, Ar); 8.32 (d, J 8.2 Hz, 2H, Ar); 8.38-8.42 (m, 1H, Ar); 8.86-8.92 (m, 2H, Ar). M/Z (M+H)⁺= 490.3. MP: >250° C.

Compound 119

4-Methyl-8-(4,4,5,5-tetramethyl-[1,3,2]dioxaborolan-2-yl)-2-(2-trifluoromethyl-pyridin-4-yl)-4H-pyrazolo[1,5-a]quinazolin-5-one Compound 119 was obtained according to general procedure VI starting from compound 118. Trituration of the crude product in Et₂O afforded the pure product as a brown solid in 92% yield.

¹H-NMR (400 MHz, DMSO): 1.38 (s, 12H, CH₃); 7.22 (s, 1H, Ar); 7.81 (d, J 7.6 Hz, 1H, Ar); 8.23 (d, J 8.0 Hz, 1H, Ar); 8.28-8.32 (m, 1H, Ar); 8.37 (s, 1H, Ar); 8.45 (s, 1H, Ar); 8.89 (d, J 5.0 Hz, 1H, Ar). M/Z (M+H)⁺=471.3.

Example 143

8-(2,6-Dimethyl-pyridin-3-yl)-4-methyl-2-(2-trifluoromethyl-pyridin-4-yl)-4H-pyrazolo[1,5-a]quinazolin-5-one, HCl Salt

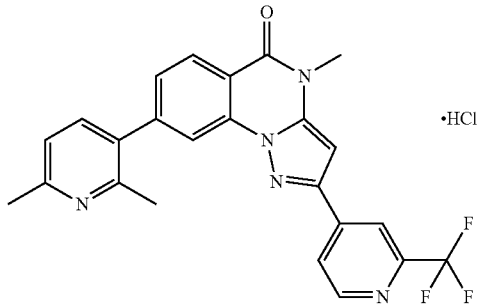 [SMILES: Cc1ccc(-c2ccc3c(=O)n(C)c4cc(-c5ccnc(C(F)(F)F)c5)nn4c3c2)c(C)n1 ; Cl]

Example 143 was obtained according to general procedure IV(viii) starting from compound 119 in presence of 3-Bromo-2,6-dimethyl-pyridine. Purification by flash-chromatography (DCM/MeOH) and salt formation according to procedure V(ii), afforded example 143 as a brown solid in 11% yield.

$^1$H-NMR (400 MHz, DMSO): 2.64 (s, 3H, Ar—CH$_3$); 2.76 (s, 3H, Ar—CH$_3$); 3.62 (s, 3H, N—CH$_3$); 7.26 (s, 1H, Ar); 7.65 (dd, J 8.2 Hz, J 1.7 Hz, 1H, Ar); 7.70-7.82 (m, 1H, Ar); 8.27 (d, J 5.1 Hz, 1H, Ar); 8.28-8.38 (m, 3H, Ar); 8.40-8.43 (m, 1H, Ar); 8.25-8.90 (d, J 5.1 Hz, 1H, Ar). Signals for HCl salt are not observed. M/Z (M+H)$^+$=450.3. MP: >250° C.

Example 144

4-Methyl-8-(4-methyl-pyrimidin-5-yl)-2-(2-trifluoromethyl-pyridin-4-yl)-4H-pyrazolo[1,5-a]quinazolin-5-one, HCl Salt

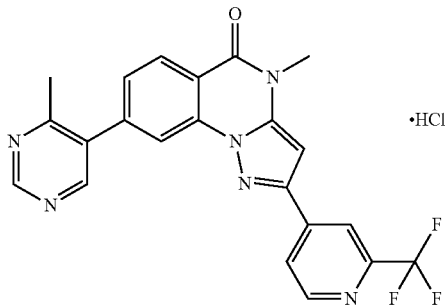 [SMILES: Cc1ncncc1-c1ccc2c(=O)n(C)c3cc(-c4ccnc(C(F)(F)F)c4)nn3c2c1 ; Cl]

Example 144 was obtained according to general procedure IV(viii) starting from compound 119 in presence of 5-Bromo-4-methyl-pyrimidine. Purification by flash-chromatography (DCM/MeOH) and salt formation according to procedure V(ii), afforded example 144 as a beige solid in 5% yield.

$^1$H-NMR (400 MHz, DMSO): 2.50 (s, 3H, Ar—CH$_3$); 3.60 (s, 3H, N—CH$_3$); 7.23 (s, 1H, Ar); 7.67 (dd, J 8.1 Hz, J 1.7 Hz, 1H, Ar); 8.27 (dd, J 5.1 Hz, J 1.1 Hz, 1H, Ar); 8.29-8.34 (m, 2H, Ar); 8.39-8.43 (m, 1H, Ar); 8.76 (s, 1H, Ar); 8.87 (d, J 5.1 Hz, 1H, Ar); 9.14 (s, 1H, Ar). Signals for HCl salt are not observed. M/Z (M+H)$^+$=437.3. MP: >250° C.

Example 145

8-(3,5-Dimethyl-1H-pyrazol-4-yl)-4-methyl-2-(2-trifluoromethyl-pyridin-4-yl)-4H-pyrazolo[1,5-a]quinazolin-5-one

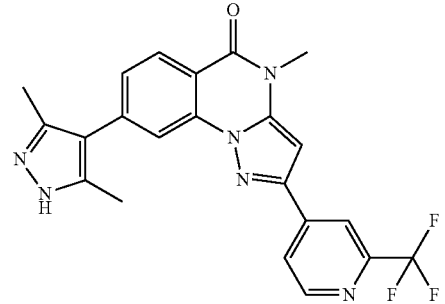 [SMILES: Cc1n[nH]c(C)c1-c1ccc2c(=O)n(C)c3cc(-c4ccnc(C(F)(F)F)c4)nn3c2c1]

Example 145 was obtained according to general procedure IV(viii) starting from compound 118 in presence of 3,5-dimethyl-1H-pyrazol-boronic acid pinacol ester. Purification by flash-chromatography (DCM/MeOH) and trituration in Et$_2$O afforded example 145 as a white solid in 31% yield.

$^1$H-NMR (400 MHz, DMSO): 2.43 (s, 6H, Ar—CH$_3$); 3.71 (s, 3H, N—CH$_3$); 7.32 (s, 1H, Ar); 7.64 (dd, J 8.3 Hz, J 1.8 Hz, 1H, Ar); 8.23 (d, J 1.5 Hz, 1H, Ar); 8.33 (d, J 8.3 Hz, 1H, Ar); 8.41 (d, J 5.1 Hz, 1H, Ar); 8.50-8.53 (m, 1H, Ar); 9.00 (d, J 5.1 Hz, 1H, Ar). M/Z (M+H)'=439.3. MP: >250° C.

Example 146

8-(3,5-Dimethyl-1H-pyrazol-4-yl)-2-(2,6-dimethyl-pyridin-4-yl)-4-methyl-4H-pyrazolo[1,5-a]quinazolin-5-one, HCl Salt

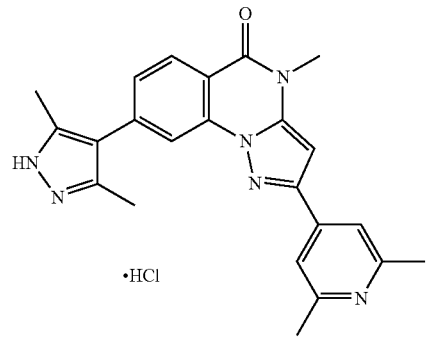 [SMILES: Cc1cc(-c2cc3n(C)c(=O)c4ccc(-c5c(C)n[nH]c5C)cc4n3n2)cc(C)n1 ; Cl]

Example 146 was obtained according to general procedure IV(v) starting from compound 102 in presence of 3,5-dimethylpyrazol-4-boronic acid pinacol ester. Purification by flash-chromatography (MeOH in CH$_2$Cl$_2$, 0 to 8%) and salt formation according to procedure V(iii) afforded example 146 as a white solid in 40% yield.

$^1$H-NMR (400 MHz, DMSO): 2.53 (s, 6H, 2CH$_3$); 2.78 (s, 6H, 2CH$_3$); 3.60 (s, 3H, N—CH$_3$); 7.19 (s, 1H, Ar); 7.57 (dd, J 8.2 Hz, J 1.7 Hz, 1H, Ar); 8.15 (d, J 1.7 Hz, 1H, Ar); 8.25 (d, J 8.2 Hz, 1H, Ar); 8.29 (s, 2H, Ar). Signals for HCl salt and Pyrazol NH are not observed. M/Z (M+H)$^+$=399.3. MP: >250° C.

Example 147

2-(2,6-Dimethyl-pyridin-4-yl)-4-methyl-8-(3-trifluoromethyl-1H-pyrazol-4-yl)-4H-pyrazolo[1,5-a]quinazolin-5-one, HCl Salt

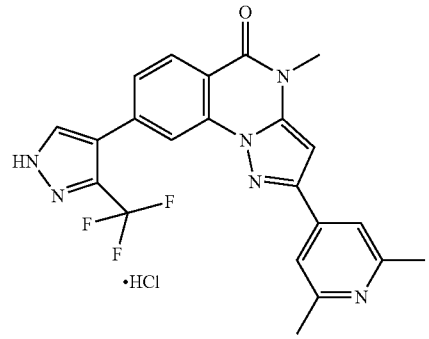 [SMILES: Cc1cc(-c2cc3n(C)c(=O)c4ccc(-c5c[nH]nc5C(F)(F)F)cc4n3n2)cc(C)n1 ; Cl]

Example 147 was obtained according to general procedure IV(v) starting from compound 102 in presence of 3-trifluoromethylpyrazol-4-boronic acid pinacol ester. Purification by flash-chromatography (MeOH in CH$_2$Cl$_2$, 0 to 8%) and salt formation according to procedure V(iii) afforded example 147 as a white solid in 45% yield.

$^1$H-NMR (400 MHz, DMSO): 2.76 (s, 6H, 2CH$_3$); 3.58 (s, 3H, N—CH$_3$); 7.17 (s, 1H, Ar); 7.65 (dd, J 8.4 Hz, J 1.4 Hz, 1H, Ar); 8.17 (s, 2H, Ar); 8.26 (d, J 8.4 Hz, 1H, Ar); 8.29 (d, J 1.4 Hz, 1H, Ar); 8.51 (s, 1H, Ar); 14.01 (s, 1H, NH). Signals for HCl salt are not observed. M/Z (M+H)$^+$=439.3 MP; >250° C.

Example 148

Human mGluR2 Negative Allosteric Modulator Evaluation Using Ca$^{++}$ Functional Assay Compounds of the present invention were tested successively for their agonist and negative allosteric modulator activities on human mGluR2 (hmGluR2) transiently overexpressed in HEK-293 cells. They exert agonist activity if they are able to activate mGluR2 by themselves, i.e., in absence of the endogenous agonist glutamate; and they exert negative allosteric modulator activity if they decrease the action of the endogenous agonist glutamate.

Cell Culture and Transfection

HEK-293 cells were maintained in Modified Eagle's Medium supplemented with 10% Foetal Calf Serum, 1% Penicillin/Streptomycin and 1% nonessential amino acids at 37° C./5% CO$_2$.

Cells were co-transfected by electroporation with two DNA plasmids encoding hmGluR2 and a chimeric Gg protein (Brabet I et al., *Neuropharmacology* 37(8), 1043-51, 1998) allowing redirection of the activation signal toward intracellular calcium pathway. Cells were plated after transfection onto polyornithine coated, clear bottom, black-walled, 96-well plates and cultured for 24 h.

Calcium Assay IC$_{50}$ Determination

Receptor activity was detected by changes in intracellular calcium measured using the fluorescent Ca$^{2+}$ sensitive dye, Fluo4AM (Molecular Probes).

The day of the assay, medium was aspirated and replaced during 3 hours by medium without serum supplemented with 1% Glutamax, 1% Penicillin/Streptomycin and 1% nonessential amino acids. Then, cells were washed with freshly prepared buffer B (HBSS 1× (PAA), Hepes 20 mM, MgSO$_4$-7H$_2$O 1 mM, Na$_2$CO$_3$ 3.3 mM, CaCl$_2$-2H$_2$O 1.3 mM, 0.5% BSA, Probenecid 2.5 mM) and loaded at 37° C./5% CO$_2$ for 1.5 hours with buffer B containing 1 μM Fluo4AM, 0.1 mg/mL Pluronic Acid, 7 μg/mL Glutamate Pyruvate Transaminase and 2 mM sodium pyruvate. Afterwards cells were washed twice with buffer B and 50 μL of this buffer were added to each well. Addition of compounds and intracellular Ca$^{2+}$ measurements (excitation 485 nm, emission 525 nm) were performed by the fluorescence microplate reader FLIPR Tetra (Molecular Devices).

Agonist and negative allosteric modulator activities of compounds were consecutively evaluated on the same cells plate. Agonist activity was first tested during 60 s with the addition of compound alone on the cells. Then, the cells were stimulated by an EC$_{80}$ glutamate concentration and fluorescence was recorded for additional 60 s. EC$_{80}$ glutamate concentration is the concentration giving 80% of the maximal glutamate response. Agonist and/or negative allosteric modulator activity(ies) were evaluated in comparison to basal signal or signal evoked by EC$_{80}$ glutamate alone, respectively.

For potency determination, a dose-response test was performed using 8 concentrations of each compound of the invention. Dose-response curves were fitted using the sigmoidal dose-response (variable slope) analysis in GraphPad Prism program (Graph Pad Inc) and EC$_{50}$ of agonist/IC$_{50}$ of negative allosteric modulator activity was calculated. Dose-response experiments were all performed in duplicate, two times independently.

The compounds of the present invention were found to have no agonist activity on hmGluR2. The IC$_{50}$ of the hmGluR2 negative allosteric modulator compounds of the present invention are preferably 5 μM or less, more preferably 1 μM or less.

The following list represents selected examples of the compounds of the present invention showing mGluR2 negative allosteric modulator activity with an IC$_{50}$<1 μM:

Examples: 1, 2, 3, 6, 8, 10, 14, 15, 16, 17, 18, 19, 20, 21, 24, 25, 26, 27, 29, 30, 31, 32, 34, 35, 36, 37, 38, 39, 40, 42, 43, 44, 45, 46, 47, 48, 49, 50, 51, 52, 53, 55, 63, 64, 65, 66, 67, 68, 69, 70, 71, 74, 75, 76, 77, 78, 79, 80, 81, 82, 83, 84, 85, 86, 88, 89, 92, 93, 95, 96, 97, 100, 101, 102, 103, 104, 106, 107, 108, 109, 110, 111, 112, 113, 114, 115, 116, 117, 118, 119, 121, 122, 124, 126, 128, 129, 130, 131, 132, 133, 135, 136, 137, 138, 139, 140, 141, 143, 144, 145, 146 and 147.

The invention claimed is:
1. A compound of formula (I):

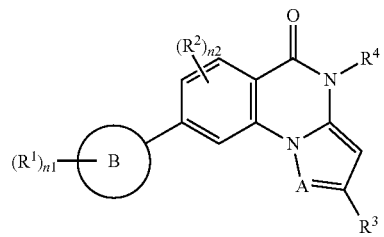

wherein:
A is N or C(H);
B is aryl or heteroaryl;
each R$^1$ is independently selected from R$^5$, halogen, —CF$_3$, —CN, —OR$^5$, —OCF$_3$, —NR$^5$R$^6$, —COOR$^5$, tetrazolyl, —SO$_3$H, —B(OH)$_2$, —CONR$^5$R$^6$, —COR$^5$, —SR$^5$, —SOR$^5$, —SO$_2$R$^5$, —SO$_2$NR$^5$R$^6$, —NR$^5$COR$^6$, —NR$^5$SO$_2$R$^6$ or —OCOR$^5$;
n1 is 1,2 or 3;
each R$^2$ is independently selected from R$^5$, halogen, —CF$_3$, —CN, —OR$^5$, —OCF$_3$, —NR$^5$R$^6$, —COOR$^5$, —CONR$^5$R$^6$, —COR$^5$, —SR$^5$, —SOR$^5$, —SO$_2$R$^5$, SO$_2$NR$^5$R$^6$, —NR$^5$COR$^6$, —NR$^5$SO$_2$R$^6$, or —OCOR$^5$;
n2 is 1, 2 or 3;
R$^3$ is a -L-R$^7$ group, wherein:
L is a bond or C$_1$-C$_4$ alkylene, wherein one or more —CH$_2$— units comprised in said alkylene are each optionally replaced by a group independently selected from —O—, —NR$^5$—, —CO—, —S—, —SO—, or —SO$_2$—; and
R$_7$ is selected from hydrogen, halogen, —CF$_3$, —CN, an optionally substituted C$_1$-C$_4$ alkyl, an optionally substituted cycloalkyl, an optionally substituted heterocycloalkyl, an optionally substituted aryl, or an optionally substituted heteroaryl, wherein said C$_1$-C$_4$ alkyl, said cycloalkyl, said heterocycloalkyl, said aryl or said heteroaryl is optionally substituted with one or more groups independently selected from R$^5$, halogen, —CF$_3$, —CN, —NR$^5$R$^6$, —CONR$^5$R$^6$, —COR$^5$, —OR$^5$, —SR$^5$, —SOR$^5$, —SO$_2$R$^5$, —SO$_2$N R$^5$R$^6$, —NR$^5$COR$^6$, —NR$^5$SO$_2$R$^6$, —OCOR$^5$, —COOR$^5$, tetrazolyl, —SO$_3$H, or —B(OH)$_2$;

R$_4$ is selected from an optionally substituted C$_1$-C$_4$ alkyl, an optionally substituted cycloalkyl, or an optionally substituted heterocycloalkyl, wherein said C$_1$-C$_4$ alkyl is optionally substituted with one or more groups independently selected from cycloalkyl, halogen, —CF$_3$, —CN, —OH or —O(C$_1$-C$_4$ alkyl), and further wherein said cycloalkyl or said heterocycloalkyl is optionally substituted with one or more groups independently selected from C$_1$-C$_4$ alkyl, cycloalkyl, halogen, —CF$_3$, —CN, —OH or —O(C$_1$-C$_4$ alkyl); and each R$_5$ and each R$_6$ is independently selected from hydrogen, an optionally substituted C$_1$-C$_4$ alkyl, an optionally substituted cycloalkyl, or an optionally substituted heterocycloalkyl, wherein said C$_1$-C$_4$ alkyl is optionally substituted with one or more groups independently selected from halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl), and further wherein said cycloalkyl and said heterocycloalkyl are each optionally substituted with one or more groups independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl);

or a pharmaceutically acceptable salt, solvate or prodrug thereof.

2. The compound of claim 1, wherein A is N.

3. The compound of claim 1, wherein A is C(H).

4. The compound of claim 1, wherein B is phenyl or B is a heteroaryl having 5 or 6 ring members and comprising one or more ring heteroatoms independently selected from O, S, or N, and further wherein each R$^1$ is independently selected from C$_1$-C$_4$ alkyl, halogen, —CF$_3$, —CN, —NH$_2$, —NH(C$_1$-C$_4$ alkyl), —N(C$_1$-C$_4$ alkyl)(C$_1$-C$_4$ alkyl), —COOH, —COO (C$_1$-C$_4$ alkyl), tetrazol-5-yl, —SO$_3$H, —CO(C$_1$-C$_4$ alkyl), —SO$_2$(C$_1$-C$_4$ alkyl), —SO$_2$NH$_2$, —SO$_2$NH(C$_1$-C$_4$ alkyl), or —SO$_2$N(C$_1$-C$_4$ alkyl)(C$_1$-C$_4$ alkyl).

5. The compound of claim 1, wherein the moiety —(B)—(R$^1$)$_{n1}$ is selected from phenyl, pyridinyl, pyrazolyl, oxazolyl, tetrazolyl, pyrimidinyl, pyridazinyl, or pyrazinyl, wherein said phenyl, said pyridinyl, said pyrazolyl, said oxazolyl, said tetrazolyl, said pyrimidinyl, said pyridazinyl or said pyrazinyl is substituted with one, two or three groups selected independently from methyl, ethyl, halogen, —CF$_3$, —CN, —NH$_2$, —NH(CH$_3$), —N(CH$_3$)$_2$, —COOH, tetrazol-5-yl, —COCH$_3$, —SO$_2$NH$_2$, —SO$_2$NH(CH$_3$), or —SO$_2$N(CH$_3$)$_2$.

6. The compound of claim 1, wherein n2 is 1 and R$_2$ is hydrogen.

7. The compound of claim 1, wherein L is a bond or C$_1$-C$_4$ alkylene, wherein one —CH$_2$— unit comprised in said alkylene is optionally replaced by —O—, and further wherein R$_7$ is selected from hydrogen, an optionally substituted C$_1$-C$_4$ alkyl, an optionally substituted cycloalkyl, an optionally substituted heterocycloalkyl, an optionally substituted aryl, or an optionally substituted heteroaryl, wherein said C$_1$-C$_4$ alkyl is optionally substituted with one or more groups independently selected from halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl), and further wherein said cycloalkyl, said heterocycloalkyl, said aryl or said heteroaryl is optionally substituted with one or more groups independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl) or —N(C$_1$-C$_4$ alkyl)(C$_1$-C$_4$ alkyl).

8. The compound of claim 1, wherein R$_4$ is selected from an optionally substituted C$_1$-C$_4$ alkyl, a cycloalkyl, or a heterocycloalkyl, wherein said C$_1$-C$_4$ alkyl is optionally substituted with one or more groups independently selected from cycloalkyl, halogen, —CF$_3$, —CN, —OH or —O(C$_1$-C$_4$ alkyl).

9. The compound of claim 1, wherein each R$_5$ and each R$_6$ is independently selected from hydrogen, an optionally substituted C$_1$-C$_4$ alkyl or an optionally substituted heterocycloalkyl, wherein said C$_1$-C$_4$ alkyl is optionally substituted with one or more groups independently selected from halogen or —CF$_3$, and further wherein said heterocycloalkyl is optionally substituted with one or more groups independently selected from C$_1$-C$_4$ alkyl, halogen, or —CF$_3$.

10. The compound of claim 1, wherein said compound is selected from:

8-(6-Amino-pyridin-3-yl)-4-methyl-2-phenyl-4H-pyrazolo[1,5-a]quinazolin-5-one;

8-(4-Amino-phenyl)-4-methyl-2-phenyl-4H-pyrazolo[1,5-a]quinazolin-5-one;

4-Methyl-8-(6-morpholin-4-yl-pyridin-3-yl)-2-phenyl-4H-pyrazolo[1,5-a]quinazolin-5-one;

4-Methyl-2-phenyl-8-(3,4,5,6-tetrahydro-2H-[1,2']bipyridinyl-5'-yl)-4H-pyrazolo[1,5-a]quinazolin-5-one;

4-Methyl-2-phenyl-8-(1H-pyrazol-4-yl)-4H-pyrazolo[1,5-a]quinazolin-5-one;

8-(4-Methoxy-phenyl)-4-methyl-2-phenyl-4H-pyrazolo[1,5-a]quinazolin-5-one;

8-Imidazo[1,2-a]pyridin-6-yl-4-methyl-2-phenyl-4H-pyrazolo[1,5-a]quinazolin-5-one; 8-(3-Methoxymethyl-phenyl)-4-methyl-2-phenyl-4H-pyrazolo[1,5-a]quinazolin-5-one; 4-(4-Methyl-5-oxo-2-phenyl-4,5-dihydro-pyrazolo[1,5-a]quinazolin-8-yl)-benzenesulfonamide;

8-(3-Methoxy-phenyl)-4-methyl-2-phenyl-4H-pyrazolo[1,5-a]quinazolin-5-one;

8-(4-Fluoro-phenyl)-4-methyl-2-phenyl-4H-pyrazolo[1,5-a]quinazolin-5-one;

8-(4-Chloro-phenyl)-4-methyl-2-phenyl-4H-pyrazolo[1,5-a]quinazolin-5-one;

8-(3-Acetyl-phenyl)-4-methyl-2-phenyl-4H-pyrazolo[1,5-a]quinazolin-5-one;

8-(3,5-Dimethyl-1H-pyrazol-4-yl)-4-methyl-2-phenyl-4H-pyrazolo[1,5-a]quinazolin-5-one;

4-Methyl-8-(1-methyl-1H-pyrazol-4-yl)-2-phenyl-4H-pyrazolo[1,5-a]quinazolin-5-one;

4-Methyl-2-phenyl-8-(1H-pyrazol-3-yl)-4H-pyrazolo[1,5-a]quinazolin-5-one;

4-Methyl-8-(3-methyl-1H-pyrazol-4-yl)-2-phenyl-4H-pyrazolo[1,5-a]quinazolin-5-one;

4-Methyl-2-phenyl-8-(3-trifluoromethyl-1H-pyrazol-4-yl)-4H-pyrazolo[1,5-a]quinazolin-5-one;

4-Methyl-8-oxazol-2-yl-2-phenyl-4H-pyrazolo[1,5-a]quinazolin-5-one;

4-Methyl-8-oxazol-5-yl-2-phenyl-4H-pyrazolo[1,5-a]quinazolin-5-one;

4-Methyl-2-phenyl-8-(2H-tetrazol-5-yl)-4H-pyrazolo[1,5-a]quinazolin-5-one;

8-(3-Bromo-phenyl)-4-methyl-2-phenyl-4H-pyrazolo[1,5-a]quinazolin-5-one;

8-(6-Amino-4-methyl-pyridin-3-yl)-4-methyl-2-phenyl-4H-pyrazolo[1,5-a]quinazolin-5-one;

8-(6-Amino-2-methyl-pyridin-3-yl)-4-methyl-2-phenyl-4H-pyrazolo[1,5-a]quinazolin-5-one;

8-(6-Amino-5-methyl-pyridin-3-yl)-4-methyl-2-phenyl-4H-pyrazolo[1,5-a]quinazolin-5-one;
8-(6-Amino-2-ethyl-pyridin-3-yl)-4-methyl-2-phenyl-4H-pyrazolo[1,5-a]quinazolin-5-one;
8-(6-Amino-2,4-dimethyl-pyridin-3-yl)-4-methyl-2-phenyl-4H-pyrazolo[1,5-a]quinazolin-5-one;
8-(6-Amino-pyridazin-3-yl)-4-methyl-2-phenyl-4H-pyrazolo[1,5-a]quinazolin-5-one;
8-(5-Amino-pyrazin-2-yl)-4-methyl-2-phenyl-4H-pyrazolo[1,5-a]quinazolin-5-one;
8-(2-Amino-pyrimidin-5-yl)-4-methyl-2-phenyl-4H-pyrazolo[1,5-a]quinazolin-5-one;
8-(5-Amino-3-methyl-pyrazin-2-yl)-4-methyl-2-phenyl-4H-pyrazolo[1,5-a]quinazolin-5-one;
8-(6-Amino-2-trifluoromethyl-pyridin-3-yl)-4-methyl-2-phenyl-4H-pyrazolo[1,5-a]quinazolin-5-one;
3-(4-Methyl-5-oxo-2-phenyl-4,5-dihydro-pyrazolo[1,5-a]quinazolin-8-yl)-benzoic acid;
3-(4-Methyl-5-oxo-2-phenyl-4,5-dihydro-pyrazolo[1,5-a]quinazolin-8-yl)-benzonitrile;
4-Methyl-2-phenyl-8-[3-(2H-tetrazol-5-yl)-phenyl]-4H-pyrazolo[1,5-a]quinazolin-5-one;
8-(2,6-Dimethyl-pyridin-4-yl)-4-methyl-2-phenyl-4H-pyrazolo[1,5-a]quinazolin-5-one;
N,N-Dimethyl-3-(4-methyl-5-oxo-2-phenyl-4,5-dihydro-pyrazolo[1,5-a]quinazolin-8-yl)-benzenesulfonamide;
N,N-Dimethyl-3-(4-Ethyl-5-oxo-2-phenyl-4,5-dihydro-pyrazolo[1,5-a]quinazolin-8-yl)-benzenesulfonamide;
N,N-Dimethyl-3-(4-propyl-5-oxo-2-phenyl-4,5-dihydro-pyrazolo[1,5-a]quinazolin-8-yl)-benzenesulfonamide;
3-(4-Isobutyl-5-oxo-2-phenyl-4,5-dihydro-pyrazolo[1,5-a]quinazolin-8-yl)-N,N-dimethyl-benzenesulfonamide;
3-(4-Cyclopropylmethyl-5-oxo-2-phenyl-4,5-dihydro-pyrazolo[1,5-a]quinazolin-8-yl)-N,N-dimethyl-benzenesulfonamide;
8-(6-Amino-pyridin-3-yl)-4-ethyl-2-phenyl-4H-pyrazolo[1,5-a]quinazolin-5-one;
8-(6-Amino-pyridin-3-yl)-2-phenyl-4-propyl-4H-pyrazolo[1,5-a]quinazolin-5-one;
8-(6-Amino-pyridin-3-yl)-2-phenyl-4-(2,2,2-trifluoro-ethyl)-4H-pyrazolo[1,5-a]quinazolin-5-one;
8-(6-Amino-pyridin-3-yl)-4-(2,2-difluoro-ethyl)-2-phenyl-4H-pyrazolo[1,5-a]quinazolin-5-one;
8-(6-Amino-pyridin-3-yl)-4-isopropyl-2-phenyl-4H-pyrazolo[1,5-a]quinazolin-5-one;
8-(6-Amino-pyridin-3-yl)-4-cyclobutyl-2-phenyl-4H-pyrazolo[1,5-a]quinazolin-5-one;
8-(6-Amino-pyridin-3-yl)-2-ethyl-4-methyl-4H-pyrazolo[1,5-a]quinazolin-5-one;
8-(6-Amino-pyridin-3-yl)-4-methyl-2-propyl-4H-pyrazolo[1,5-a]quinazolin-5-one;
8-(6-Amino-pyridin-3-yl)-2-isopropyl-4-methyl-4H-pyrazolo[1,5-a]quinazolin-5-one;
8-(6-Amino-pyridin-3-yl)-2-tert-butyl-4-methyl-4H-pyrazolo[1,5-a]quinazolin-5-one;
8-(6-Amino-pyridin-3-yl)-2-(2-methoxy-ethyl)-4-methyl-4H-pyrazolo[1,5-a]quinazolin-5-one;
8-(2,6-Dimethyl-pyridin-4-yl)-2-(2-methoxy-ethyl)-4-methyl-4H-pyrazolo[1,5-a]quinazolin-5-one;
8-(6-Amino-pyridin-3-yl)-2-(2-methoxy-ethyl)-4-methyl(D 3)-4H-pyrazolo[1,5-a]quinazolin-5-one;
8-(2,6-Dimethyl-pyridin-4-yl)-2-(2-methoxy-ethyl)-4-methyl(D 3)-4H-pyrazolo[1,5-a]quinazolin-5-one;
8-(6-Amino-pyridin-3-yl)-4-ethyl-2-(2-methoxy-ethyl)-4H-pyrazolo[1,5-a]quinazolin-5-one;
8-(2,6-Dimethyl-pyridin-4-yl)-4-ethyl-2-(2-methoxy-ethyl)-4H-pyrazolo[1,5-a]quinazolin-5-one;
8-(6-Amino-pyridin-3-yl)-2-(2-methoxy-ethyl)-4-propyl-4H-pyrazolo[1,5-a]quinazolin-5-one;
8-(2,6-Dimethyl-pyridin-4-yl)-2-(2-methoxy-ethyl)-4-propyl-4H-pyrazolo[1,5-a]quinazolin 5-one;
8-(6-Amino-pyridin-3-yl)-2-methoxymethyl-4-methyl-4H-pyrazolo[1,5-a]quinazolin-5-one;
8-(2,6-Dimethyl-pyridin-4-yl)-2-methoxymethyl-4-methyl-4H-pyrazolo[1,5-a]quinazolin-5-one;
8-(6-Amino-pyridin-3-yl)-2-cyclopropyl-4-methyl-4H-pyrazolo[1,5-a]quinazolin-5-one;
8-(6-Amino-pyridin-3-yl)-2-cyclobutyl-4-methyl-4H-pyrazolo[1,5-a]quinazolin-5-one;
8-(6-Amino-pyridin-3-yl)-2-cyclopentyl-4-methyl-4H-pyrazolo[1,5-a]quinazolin-5-one;
2-Cyclopentyl-8-(2,6-dimethyl-pyridin-4-yl)-4-methyl-4H-pyrazolo[1,5-a]quinazolin-5-one;
8-(6-Amino-pyridin-3-yl)-2-cyclopentyl-4-methyl(D 3)-4H-pyrazolo[1,5-a]quinazolin-5-one;
2-Cyclopentyl-8-(2,6-dimethyl-pyridin-4-yl)-4-methyl(D 3)-4H-pyrazolo[1,5-a]quinazolin-5-one;
8-(6-Amino-pyridin-3-yl)-2-cyclopentyl-4-ethyl-4H-pyrazolo[1,5-a]quinazolin-5-one;
2-Cyclopentyl-8-(2,6-dimethyl-pyridin-4-yl)-4-ethyl-4H-pyrazolo[1,5-a]quinazolin-5-one;
8-(6-Amino-pyridin-3-yl)-2-cyclopentyl-4-propyl-4H-pyrazolo[1,5-a]quinazolin-5-one;
2-Cyclopentyl-8-(2,6-dimethyl-pyridin-4-yl)-4-propyl-4H-pyrazolo[1,5-a]quinazolin-5-one;
2-Cyclopentyl-8-(2,6-dimethyl-pyridin-4-yl)-4-(2,2,2-trifluoro-ethyl)-4H-pyrazolo[1,5-a]quinazolin-5-one;
8-(6-Amino-pyridin-3-yl)-2-cyclohexyl-4-methyl-4H-pyrazolo[1,5-a]quinazolin-5-one;
2-Cyclohexyl-4-methyl-8-(3-methyl-1H-pyrazol-4-yl)-4H-pyrazolo[1,5-a]quinazolin-5-one;
8-(6-Amino-pyridin-3-yl)-2-cycloheptyl-4-methyl-4H-pyrazolo[1,5-a]quinazolin-5-one;
2-Cycloheptyl-8-(2,6-dimethyl-pyridin-4-yl)-4-methyl-4H-pyrazolo[1,5-a]quinazolin-5-one;
2-Cycloheptyl-8-(2,6-dimethyl-pyridin-4-yl)-4-ethyl-4H-pyrazolo[1,5-a]quinazolin-5-one;
8-(6-Amino-pyridin-3-yl)-2-benzyl-4-methyl-4H-pyrazolo[1,5-a]quinazolin-5-one;
8-(6-Amino-pyridin-3-yl)-2-(4-fluoro-phenyl)-4-methyl-4H-pyrazolo[1,5-a]quinazolin-5-one;
2-(4-Fluoro-phenyl)-4-methyl-8-(3-methyl-1H-pyrazol-4-yl)-4H-pyrazolo[1,5-a]quinazolin-5-one;
8-(6-Amino-pyridin-3-yl)-2-furan-2-yl-4-methyl-4H-pyrazolo[1,5-a]quinazolin-5-one;
8-(6-Amino-pyridin-3-yl)-4-methyl-2-(tetrahydro-thiopyran-4-yl)-4H-pyrazolo[1,5-a]quinazolin-5-one; 8-(6-Amino-pyridin-3-yl)-2-(1,1-dioxo-tetrahydro-2H-thiopyran-4-yl)-4-methyl-4H-pyrazolo[1,5-a]quinazolin-5-one;
4-Methyl-8-(1-methyl-1H-pyrazol-4-yl)-2-pyridin-3-yl-4H-pyrazolo[1,5-a]quinazolin-5-one;
8-(6-Amino-pyridin-3-yl)-4-methyl-2-(tetrahydro-pyran-4-yl)-4H-pyrazolo[1,5-a]quinazolin-5-one;
4-Methyl-8-(1H-pyrazol-4-yl)-2-(tetrahydro-pyran-4-yl)-4H-pyrazolo[1,5-a]quinazolin-5-one;
3-[4-Methyl-5-oxo-2-(tetrahydro-pyran-4-yl)-4,5-dihydro-pyrazolo[1,5-a]quinazolin-8-yl]-benzonitrile;
4-Methyl-8-pyridin-3-yl-2-(tetrahydro-pyran-4-yl)-4H-pyrazolo[1,5-a]quinazolin-5-one;
4-Methyl-8-pyridin-4-yl-2-(tetrahydro-pyran-4-yl)-4H-pyrazolo[1,5-a]quinazolin-5-one;

4-Methyl-8-oxazol-2-yl-2-(tetrahydro-pyran-4-yl)-4H-pyrazolo[1,5-a]quinazolin-5-one;
4-Methyl-8-(5-methyl-1H-pyrazol-4-yl)-2-(tetrahydro-pyran-4-yl)-4H-pyrazolo[1,5-a]quinazolin-5-one;
4-Methyl-8-(2-methyl-pyridin-4-yl)-2-(tetrahydro-pyran-4-yl)-4H-pyrazolo[1,5-a]quinazolin-5-one;
4-Methyl-8-(2-methyl-pyridin-3-yl)-2-(tetrahydro-pyran-4-yl)-4H-pyrazolo[1,5-a]quinazolin-5-one;
4-Methyl-8-(6-methyl-pyridin-3-yl)-2-(tetrahydro-pyran-4-yl)-4H-pyrazolo[1,5-a]quinazolin-5-one;
4-Methyl-2-(tetrahydro-pyran-4-yl)-8-[3-(2H-tetrazol-5-yl)-phenyl]-4H-pyrazolo[1,5-a]quinazolin-5-one;
8-(2,6-Dimethyl-pyridin-4-yl)-4-methyl-2-(tetrahydro-pyran-4-yl)-4H-pyrazolo[1,5-a]quinazolin-5-one;
8-(6-Amino-pyridazin-3-yl)-4-methyl-2-(tetrahydro-pyran-4-yl)-4H-pyrazolo[1,5-a]quinazolin-5-one;
8-(2,6-Dimethyl-pyridin-3-yl)-4-methyl-2-(tetrahydro-pyran-4-yl)-4H-pyrazolo[1,5-a]quinazolin-5-one;
3-[4-Methyl-5-oxo-2-(tetrahydro-pyran-4-yl)-4,5-dihydro-pyrazolo[1,5-a]quinazolin-8-yl]-benzenesulfonamide;
N-(2-Hydroxy-1,1-dimethyl-ethyl)-3-[4-methyl-5-oxo-2-(tetrahydro-pyran-4-yl)-4,5-dihydro-pyrazolo[1,5-a]quinazolin-8-yl]benzenesulfonamide;
4-(2,2-Difluoro-ethyl)-8-(2,6-dimethyl-pyridin-4-yl)-2-(tetrahydro-pyran-4-yl)-4H-pyrazolo[1,5-a]quinazolin-5-one;
8-(6-Amino-pyridin-3-yl)-4-(2,2-difluoro-ethyl)-2-(tetrahydro-pyran-4-yl)-4H-pyrazolo[1,5-a]quinazolin-5-one;
8-(6-Amino-pyridin-3-yl)-2-(tetrahydro-pyran-4-yl)-4-(2,2,2-trifluoro-ethyl)-4H-pyrazolo[1,5-a]quinazolin-5-one;
8-(2,6-Dimethyl-pyridin-4-yl)-2-(tetrahydro-pyran-4-yl)-4-(2,2,2-trifluoro-ethyl)-4H-pyrazolo[1,5-a]quinazolin-5-one;
8-(2,6-Dimethyl-pyridin-4-yl)-4-methyl-2-(tetrahydro-furan-3-yl)-4H-pyrazolo[1,5-a]quinazolin-5-one;
8-(2,6-Dimethyl-pyridin-4-yl)-4-methyl-2-(tetrahydro-furan-2-yl)-4H-pyrazolo[1,5-a]quinazolin-5-one;
8-(2,6-Dimethyl-pyridin-4-yl)-4-methyl-2-(tetrahydro-pyran-3-yl)-4H-pyrazolo[1,5-a]quinazolin-5-one;
8-(2,6-Dimethyl-pyridin-4-yl)-4-methyl-2-(tetrahydro-pyran-2-yl)-4H-pyrazolo[1,5-a]quinazolin-5-one;
8-(6-Amino-pyridin-3-yl)-4-methyl-2-phenyl-4H-pyrrolo[1,2-a]quinazolin-5-one;
8-(2,6-Dimethyl-pyridin-4-yl)-4-methyl-2-phenyl-4H-pyrrolo[1,2-a]quinazolin-5-one;
8-(6-Amino-pyridin-3-yl)-2-(2,6-dimethyl-pyridin-4-yl)-4-methyl-4H-pyrazolo[1,5-a]quinazolin-5-one;
2-(2,6-Dimethyl-pyridin-4-yl)-4-methyl-8-(2-methyl-pyridin-3-yl)-4H-pyrazolo[1,5-a]quinazolin-5-one;
2,8-Bis-(2,6-dimethyl-pyridin-4-yl)-4-methyl-4H-pyrazolo[1,5-a]quinazolin-5-one;
2-(2,6-Dimethyl-pyridin-4-yl)-4-methyl-8-phenyl-4H-pyrazolo[1,5-a]quinazolin-5-one;
2-(2,6-Dimethyl-pyridin-4-yl)-4-methyl-8-pyridin-3-yl-4H-pyrazolo[1,5-a]quinazolin-5-one;
2-(2,6-Dimethyl-pyridin-4-yl)-4-methyl-8-(6-methyl-pyridin-3-yl)-4H-pyrazolo[1,5-a]quinazolin-5-one;
2-(2,6-Dimethyl-pyridin-4-yl)-4-methyl-8-(5-methyl-pyridin-3-yl)-4H-pyrazolo[1,5-a]quinazolin-5-one,
2-(2,6-Dimethyl-pyridin-4-yl)-4-methyl-8-(4-methyl-pyridin-3-yl)-4H-pyrazolo[1,5-a]quinazolin-5-one;
2-(2,6-Dimethyl-pyridin-4-yl)-8-(2-ethyl-pyridin-3-yl)-4-methyl-4H-pyrazolo[1,5-a]quinazolin-5-one;

2-(2,6-Dimethyl-pyridin-4-yl)-4-methyl-8-(3-methyl-1H-pyrazol-4-yl)-4H-pyrazolo[1,5-a]quinazolin-5-one;
2-(2,6-Dimethyl-pyridin-4-yl)-4-methyl-8-(1-methyl-1H-pyrazol-4-yl)-4H-pyrazolo[1,5-a]quinazolin-5-one;
2-(2,6-Dimethyl-pyridin-4-yl)-4-methyl-8-(2H-pyrazol-3-yl)-4H-pyrazolo[1,5-a]quinazolin-5-one;
4-Methyl-2-(1-methyl-1H-pyrazol-4-yl)-8-phenyl-4H-pyrazolo[1,5-a]quinazolin-5-one;
8-(4-Methoxy-phenyl)-4-methyl-2-(1-methyl-1H-pyrazol-4-yl)-4H-pyrazolo[1,5-a]quinazolin-5-one;
4-Methyl-2-(1-methyl-1H-pyrazol-4-yl)-8-pyridin-3-yl-4H-pyrazolo[1,5-a]quinazolin-5-one;
4-Methyl-2-(1-methyl-1H-pyrazol-4-yl)-8-(2-methyl-pyridin-3-yl)-4H-pyrazolo[1,5-a]quinazolin-5-one;
8-(6-Amino-pyridin-3-yl)-4-methyl-2-(1-methyl-1H-pyrazol-4-yl)-4H-pyrazolo[1,5-a]quinazolin-5-one;
4-Methyl-2-(1-methyl-1H-pyrazol-4-yl)-8-pyridin-4-yl-4H-pyrazolo[1,5-a]quinazolin-5-one;
8-(2,6-Dimethyl-pyridin-4-yl)-4-methyl-2-(1-methyl-1H-pyrazol-4-yl)-4H-pyrazolo[1,5-a]quinazolin-5-one;
8-(6-Amino-pyridin-3-yl)-2-(1-ethyl-1H-pyrazol-4-yl)-4-methyl-4H-pyrazolo[1,5-a]quinazolin-5-one;
2-(2-methyl-pyridin-4-yl)-4-methyl-8-(2-methyl-pyridin-3-yl)-4H-pyrazolo[1,5-a]quinazolin-5-one;
8-(2,6-Dimethyl-pyridin-4-yl)-4-methyl-2-(2-methyl-pyridin-4-yl)-4H-pyrazolo[1,5-a]quinazolin-5-one;
4-Methyl-8-(2-methyl-pyridin-3-yl)-2-pyridin-3-yl-4H-pyrazolo[1,5-a]quinazolin-5-one;
4-Methyl-8-(2-methyl-pyridin-3-yl)-2-(2-trifluoromethyl-pyridin-4-yl)-4H-pyrazolo[1,5-a]quinazolin-5-one;
8-(6-Amino-pyridin-3-yl)-4-methyl-2-(2-trifluoromethyl-pyridin-4-yl)-4H-pyrazolo[1,5-a]quinazolin-5-one;
8-(2-Ethyl-pyridin-3-yl)-4-methyl-2-(2-trifluoromethyl-pyridin-4-yl)-4H-pyrazolo[1,5-a]quinazolin-5-one;
4-Methyl-8-(2-methyl-pyridin-4-yl)-2-(2-trifluoromethyl-pyridin-4-yl)-4H-pyrazolo[1,5-a]quinazolin-5-one;
4-Methyl-2,8-bis-(2-trifluoromethyl-pyridin-4-yl)-4H-pyrazolo[1,5-a]quinazolin-5-one;
8-(2-Fluoro-pyridin-4-yl)-4-methyl-2-(2-trifluoromethyl-pyridin-4-yl)-4H-pyrazolo[1,5-a]quinazolin-5-one;
8-(6-Fluoro-pyridin-3-yl)-4-methyl-2-(2-trifluoromethyl-pyridin-4-yl)-4H-pyrazolo[1,5-a]quinazolin-5-one;
4-Methyl-2-(2-trifluoromethyl-pyridin-4-yl)-8-(2-trifluoromethyl-pyridin-3-yl)-4H-pyrazolo[1,5-a]quinazolin-5-one;
8-(2,6-Dimethyl-pyridin-3-yl)-4-methyl-2-(2-trifluoromethyl-pyridin-4-yl)-4H-pyrazolo[1,5-a]quinazolin-5-one;
4-Methyl-8-(4-methyl-pyrimidin-5-yl)-2-(2-trifluoromethyl-pyridia]quinazolin-5-one;
8-(3,5-Dimethyl-1H-pyrazol-4-yl)-4-methyl-2-(2-trifluoromethyl-pyridin-4-yl)-4H-pyrazolo[1,5-a]quinazolin-5-one;
8-(3,5-Dimethyl-1H-pyrazol-4-yl)-2-(2,6-dimethyl-pyridin-4-yl)-4-methyl-4H-pyrazolo[1,5-a]quinazolin-5-one;
2-(2,6-Dimethyl-pyridin-4-yl)-4-methyl-8-(3-trifluoromethyl-1H-pyrazol-4-yl)-4H pyrazolo[1,5-a]quinazolin-5-one;

or a pharmaceutically acceptable salt, solvate or prodrug thereof.

11. A pharmaceutical composition comprising the compound of claim 1 and a pharmaceutically acceptable excipient.

12. The compound or a pharmaceutical composition comprising the compound of claim 1 and a pharmaceutically acceptable excipient for use in treating a condition associated with altered glutamatergic signalling and/or functions, or a condition which can be affected by alteration of glutamate level or signalling.

13. The compound or the pharmaceutical composition of claim 12, wherein the condition to be treated is selected from: epilepsy; dementias; parkinsonism and movement disorders; motor neuron disease or amyotrophic lateral sclerosis; neurodegenerative and/or hereditary disorders of the nervous system; disorders of the peripheral nervous system; multiple sclerosis and other demyelinating diseases of the nervous system; infantile cerebral palsy; paralytic syndromes including hemiplegia and hemiparesis; cerebrovascular disorders; migraine; headache; myoneural disorders; disorders of the eye and visual pathways; intracranial trauma/injury and their sequels; trauma/injury to nerves and spinal cord and their sequels; poisoning and toxic effects of nonmedicinal substances; accidental poisoning by drugs, medicinal substances and biologicals acting on the central, peripheral and autonomic system; neurological and psychiatric adverse effects of drugs, medicinal and biological substances; disturbance of sphincter control and sexual function; mental disorders; delirium and cognitive disorders; substance related disorders; schizophrenia and psychotic disorders; mood disorders; anxiety disorders; eating disorders; sleep disorders; medication-induced movement disorders; endocrine and metabolic diseases; acute and chronic pain; nausea and vomiting; irritable bowel syndrome; or cancers.

14. The compound or the pharmaceutical composition of claim 13, wherein the condition to be treated is selected from: dementias; parkinsonism and movement disorders; acute or chronic pain; anxiety disorders; schizophrenia; mood disorders; endocrine or metabolic diseases; or cancers;
    and further wherein said dementias are selected from: dementias of the Alzheimer's type (DAT); Alzheimer's disease; Pick's disease; vascular dementias; Lewy-body disease; dementias due to metabolic, toxic and deficiency diseases, including alcoholism, hypothyroidism, and vitamin B12 deficiency; AIDS-dementia complex; Creutzfeld-Jacob disease; or atypical subacute spongiform encephalopathy;
    wherein said parkinsonism and movement disorders are selected from: Parkinson's disease; multiple system atrophy; progressive supranuclear palsy; corticobasal degeneration; hepatolenticular degeneration; chorea, including Huntington's disease and hemiballismus; athetosis; dystonias, including spasmodic torticollis, occupational movement disorder, and Gilles de la Tourette syndrome; tardive or drug induced dyskinesias; tremor; or myoclonus;
    wherein said anxiety disorders are selected from: panic disorders, phobias, obsessive-compulsive disorders, stress disorders, or generalized anxiety disorders;
    wherein said mood disorders are selected from depressive disorders or bipolar disorders;
    wherein said endocrine or metabolic diseases are selected from: diabetes; disorders of the endocrine glands; or hypoglycaemia; and
    wherein said cancers are selected from: gliomas; colorectal cancer; melanoma; or prostate cancer.

15. A method for identifying an agent that binds to metabotropic glutamate receptor 2 (mGluR2) or to metabotropic glutamate receptor 3 (mGluR3), comprising the following steps:
    (a) contacting mGluR2 or mGluR3 with the compound of claim 1, wherein said compound is radio-labeled or fluorescence-labeled, under conditions that permit binding of the compound to mGluR2 or mGluR3, thereby generating bound, labeled compound;
    (b) detecting a signal that corresponds to the amount of bound, labeled compound in the absence of test agent;
    (c) contacting the bound, labeled compound with a test agent;
    (d) detecting a signal that corresponds to the amount of bound labeled compound in the presence of test agent; and
    (e) comparing the signal detected in step (d) to the signal detected in step (b) to determine whether the test agent binds to mGluR2 or mGluR3.

* * * * *